United States Patent
Flynn et al.

(10) Patent No.: US 11,986,463 B2
(45) Date of Patent: May 21, 2024

(54) COMBINATION THERAPY FOR THE TREATMENT OF GASTROINTESTINAL STROMAL TUMOR

(71) Applicant: Deciphera Pharmaceuticals, LLC, Waltham, MA (US)

(72) Inventors: Daniel L. Flynn, Waltham, MA (US); Bryan D. Smith, Waltham, MA (US); Anu Gupta, Waltham, MA (US)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 140 days.

(21) Appl. No.: 16/943,821

(22) Filed: Jul. 30, 2020

(65) Prior Publication Data

US 2021/0145805 A1    May 20, 2021

Related U.S. Application Data

(63) Continuation of application No. PCT/US2019/016148, filed on Jan. 31, 2019.

(60) Provisional application No. 62/624,448, filed on Jan. 31, 2018.

(51) Int. Cl.
*A61K 31/4375* (2006.01)
*A61K 45/06* (2006.01)
*A61P 35/04* (2006.01)

(52) U.S. Cl.
CPC .......... *A61K 31/4375* (2013.01); *A61K 45/06* (2013.01); *A61P 35/04* (2018.01)

(58) Field of Classification Search
CPC .......... A61P 35/04; A61P 35/00; A61P 31/155
See application file for complete search history.

(56) References Cited

U.S. PATENT DOCUMENTS

| | | |
|---|---|---|
| 3,528,980 A | 9/1970 | Islip |
| 3,818,024 A | 6/1974 | Krenzer |
| 3,939,122 A | 2/1976 | Merten et al. |
| 3,949,002 A | 4/1976 | Feasey et al. |
| 4,093,624 A | 6/1978 | Revankar et al. |
| 4,296,237 A | 10/1981 | Cragoe, Jr. et al. |
| 4,366,189 A | 12/1982 | Burdeska et al. |
| 4,432,992 A | 2/1984 | Craqoe, Jr. et al. |

(Continued)

FOREIGN PATENT DOCUMENTS

| | | |
|---|---|---|
| CN | 101528744 A | 9/2009 |
| CN | 101553232 A | 10/2009 |

(Continued)

OTHER PUBLICATIONS

Szucs et al., Promising novel therapeutic approaches in the management of gastrointestinal stromal tumors, Future Oncology, 2017, 13(2), pp. 185-194 (Year: 2017).*

(Continued)

*Primary Examiner* — Savitha M Rao
*Assistant Examiner* — Andrew P Lee
(74) *Attorney, Agent, or Firm* — Goodwin Procter LLP

(57) ABSTRACT

The present disclosure relates to the use of 1-[4-bromo-5-[1-ethyl-7-(methylamino)-2-oxo-1,2-dihydro-1,6-naphthyridin-3-yl]-2-fluorophenyl]-3-phenylurea or 1-(5-(7-amino-1-ethyl-2-oxo-1,2-dihydro-1,6-naphthyridin-3-yl)-4-bromo-2-fluorophenyl)-3-phenylurea, or a pharmaceutically acceptable salt thereof, in combination with a MAPKAP kinase inhibitor for the treatment of cancers, including c-KIT-mediated cancers, such as GIST.

11 Claims, 47 Drawing Sheets

(56) References Cited

U.S. PATENT DOCUMENTS

| | | |
|---|---|---|
| 4,525,450 A | 6/1985 | Itoh et al. |
| 4,816,454 A | 3/1989 | Zoller et al. |
| 5,103,014 A | 4/1992 | Musser et al. |
| 5,162,360 A | 11/1992 | Creswell et al. |
| 5,189,045 A | 2/1993 | Peglion et al. |
| 5,319,099 A | 6/1994 | Kamata et al. |
| 5,494,925 A | 2/1996 | Court et al. |
| 5,514,691 A | 5/1996 | Chan et al. |
| 5,614,532 A | 3/1997 | Carling et al. |
| 5,621,010 A | 4/1997 | Sueda |
| 5,658,924 A | 8/1997 | Matsuura et al. |
| 5,721,231 A | 2/1998 | Moriwaki et al. |
| 5,811,456 A | 9/1998 | Seman et al. |
| 6,020,357 A | 2/2000 | Pinto et al. |
| 6,028,085 A | 2/2000 | Bromidge |
| 6,080,763 A | 6/2000 | Regan et al. |
| 6,123,964 A | 9/2000 | Asgharnejad et al. |
| 6,147,088 A | 11/2000 | Goulet et al. |
| 6,197,599 B1 | 3/2001 | Chin et al. |
| 6,235,786 B1 | 5/2001 | Dai et al. |
| 6,294,573 B1 | 9/2001 | Curtin et al. |
| 6,319,921 B1 | 11/2001 | Cirillo et al. |
| 6,410,254 B1 | 6/2002 | Finer et al. |
| 6,500,628 B1 | 12/2002 | Robison |
| 6,525,046 B1 | 2/2003 | Cirillo et al. |
| 6,645,990 B2 | 11/2003 | Askew et al. |
| 6,763,607 B2 | 7/2004 | Beyerinck et al. |
| 6,916,924 B2 | 7/2005 | Tan et al. |
| 6,973,741 B2 | 12/2005 | Beyerinck et al. |
| 7,071,199 B1 | 7/2006 | Hirst et al. |
| 7,135,550 B2 | 11/2006 | Come et al. |
| 7,144,911 B2 | 12/2006 | Flynn et al. |
| 7,202,257 B2 | 4/2007 | Flynn et al. |
| 7,211,575 B2 | 5/2007 | Moss et al. |
| 7,279,576 B2 | 10/2007 | Flynn et al. |
| 7,342,037 B2 | 3/2008 | Flynn et al. |
| 7,531,566 B2 | 5/2009 | Flynn et al. |
| 7,666,895 B2 | 2/2010 | Flynn et al. |
| 7,737,283 B2 | 6/2010 | Flynn et al. |
| 7,790,756 B2 | 9/2010 | Flynn et al. |
| 7,897,762 B2 | 3/2011 | Flynn et al. |
| 8,143,293 B2 | 3/2012 | Flynn et al. |
| 8,163,756 B2 | 4/2012 | Flynn et al. |
| 8,188,113 B2 | 5/2012 | Flynn et al. |
| 8,278,331 B2 | 10/2012 | Flynn et al. |
| 8,343,550 B2 | 1/2013 | Beyerinck et al. |
| 8,461,179 B1 | 6/2013 | Flynn et al. |
| 8,486,951 B2 | 7/2013 | Flynn et al. |
| 8,569,319 B2 | 10/2013 | Flynn et al. |
| 8,586,565 B2 | 11/2013 | Flynn et al. |
| 8,637,672 B2 | 1/2014 | Flynn et al. |
| 8,669,289 B2 | 3/2014 | Li |
| 8,741,911 B2 | 6/2014 | Allgeier et al. |
| 8,828,443 B2 | 9/2014 | Beyerinck et al. |
| 8,921,565 B2 | 12/2014 | Flynn et al. |
| 8,940,756 B2 | 1/2015 | Flynn et al. |
| 9,012,635 B2 | 4/2015 | Flynn et al. |
| 9,133,183 B2 | 9/2015 | Flynn et al. |
| 9,181,223 B2 | 11/2015 | Kaufman et al. |
| 9,187,474 B2 | 11/2015 | Flynn et al. |
| 9,193,719 B2 | 11/2015 | Flynn et al. |
| 9,248,584 B2 | 2/2016 | Friesen et al. |
| 9,265,731 B2 | 2/2016 | Ray et al. |
| 9,309,224 B2 | 4/2016 | Flynn et al. |
| 9,334,267 B2 | 5/2016 | Flynn et al. |
| 9,339,467 B2 | 5/2016 | Beyerinck et al. |
| 9,382,228 B2 | 7/2016 | Flynn et al. |
| 9,387,202 B2 | 7/2016 | Flynn et al. |
| 9,457,019 B2 | 10/2016 | Flynn et al. |
| 9,545,407 B2 | 1/2017 | Shu et al. |
| 9,724,664 B2 | 8/2017 | Friesen et al. |
| 10,300,443 B2 | 5/2019 | Friesen et al. |
| 10,383,941 B2 | 8/2019 | Beyerinck et al. |
| 10,675,602 B2 | 6/2020 | Friesen et al. |
| 10,966,966 B2 | 4/2021 | Soto et al. |
| 11,103,507 B2 | 8/2021 | Flynn et al. |
| RE48,731 E | 9/2021 | Flynn et al. |
| 11,185,535 B2 | 11/2021 | Kaufman et al. |
| 11,266,635 B2 | 3/2022 | Soto et al. |
| 11,344,536 B1 | 5/2022 | Soto et al. |
| 11,395,818 B2 | 7/2022 | Kaufman et al. |
| 11,426,390 B2 | 8/2022 | Soto et al. |
| 11,433,056 B1 | 9/2022 | Soto et al. |
| 11,529,336 B2 | 12/2022 | Soto et al. |
| 11,534,432 B2 | 12/2022 | Soto et al. |
| 11,576,903 B2 | 2/2023 | Kaufman et al. |
| 11,576,904 B2 | 2/2023 | Soto et al. |
| 11,612,591 B2 | 3/2023 | Kaufman et al. |
| 2002/0058678 A1 | 5/2002 | Cirillo et al. |
| 2002/0077486 A1 | 6/2002 | Scarborough et al. |
| 2002/0165394 A1 | 11/2002 | Dumas et al. |
| 2002/0193405 A1 | 12/2002 | Askew |
| 2003/0060455 A1 | 3/2003 | Moss et al. |
| 2003/0105139 A1 | 6/2003 | Gaster et al. |
| 2003/0144278 A1 | 7/2003 | Riedl et al. |
| 2003/0181442 A1 | 9/2003 | Riedl et al. |
| 2003/0207870 A1 | 11/2003 | Dumas et al. |
| 2003/0216396 A1 | 11/2003 | Dumas et al. |
| 2003/0232865 A1 | 12/2003 | Cirillo et al. |
| 2004/0043388 A1 | 3/2004 | Come et al. |
| 2004/0067938 A1 | 4/2004 | Zhang et al. |
| 2004/0102636 A1 | 5/2004 | Miller et al. |
| 2004/0157827 A1 | 8/2004 | Pevarello et al. |
| 2004/0167224 A1 | 8/2004 | Ozaki et al. |
| 2004/0171075 A1 | 9/2004 | Flynn et al. |
| 2004/0180906 A1 | 9/2004 | Flynn et al. |
| 2004/0229937 A1 | 11/2004 | Dumas et al. |
| 2005/0014753 A1 | 1/2005 | Ding et al. |
| 2005/0148605 A1 | 7/2005 | Grotzfeld et al. |
| 2005/0165024 A1 | 7/2005 | Milanov et al. |
| 2005/0165031 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0192314 A1 | 9/2005 | Mehta et al. |
| 2005/0197371 A1 | 9/2005 | Milanov et al. |
| 2005/0256174 A1 | 11/2005 | Wood et al. |
| 2005/0261315 A1 | 11/2005 | Mehta et al. |
| 2005/0267182 A1 | 12/2005 | Milanov et al. |
| 2005/0288286 A1 | 12/2005 | Flynn et al. |
| 2006/0229337 A1 | 10/2006 | Brittelli et al. |
| 2006/0247186 A1 | 11/2006 | Carter et al. |
| 2007/0037794 A1 | 2/2007 | Ungashe et al. |
| 2007/0078121 A1 | 4/2007 | Flynn et al. |
| 2007/0155764 A1 | 7/2007 | Lang et al. |
| 2007/0179130 A1 | 8/2007 | Bannen |
| 2007/0191336 A1 | 8/2007 | Flynn et al. |
| 2007/0244120 A1 | 10/2007 | Dumas et al. |
| 2007/0293685 A1 | 12/2007 | Fritch et al. |
| 2008/0009527 A1 | 1/2008 | Dumas et al. |
| 2008/0045531 A1 | 2/2008 | Flynn et al. |
| 2008/0045706 A1 | 2/2008 | Flynn et al. |
| 2008/0064717 A1 | 3/2008 | Iyengar et al. |
| 2008/0090856 A1 | 4/2008 | Flynn et al. |
| 2008/0113967 A1 | 5/2008 | Flynn et al. |
| 2008/0114006 A1 | 5/2008 | Flynn et al. |
| 2008/0132506 A1 | 6/2008 | Flynn et al. |
| 2008/0176846 A1 | 7/2008 | Chianelli et al. |
| 2008/0187978 A1 | 8/2008 | Flynn et al. |
| 2008/0194836 A1 | 8/2008 | Gharbaoui et al. |
| 2008/0200530 A1 | 8/2008 | Unett et al. |
| 2008/0207699 A1 | 8/2008 | Hoelzemann et al. |
| 2008/0214545 A1 | 9/2008 | Lee et al. |
| 2008/0220497 A1 | 9/2008 | Flynn et al. |
| 2008/0221192 A1 | 9/2008 | Wan et al. |
| 2008/0248487 A1 | 10/2008 | Flynn et al. |
| 2008/0248548 A1 | 10/2008 | Flynn et al. |
| 2008/0300281 A1 | 12/2008 | Dumas et al. |
| 2009/0069310 A1 | 3/2009 | Flynn et al. |
| 2009/0075986 A1 | 3/2009 | Flynn et al. |
| 2009/0093526 A1 | 4/2009 | Miller et al. |
| 2009/0099190 A1 | 4/2009 | Flynn et al. |
| 2009/0105230 A1 | 4/2009 | Flynn et al. |
| 2009/0124633 A1 | 5/2009 | Jonczyk et al. |

(56) References Cited

U.S. PATENT DOCUMENTS

| | | |
|---|---|---|
| 2009/0137021 A1 | 5/2009 | Flynn et al. |
| 2009/0192307 A1 | 7/2009 | Michelotti et al. |
| 2009/0215799 A1 | 8/2009 | Stieber et al. |
| 2009/0281089 A1 | 11/2009 | Gunzner et al. |
| 2009/0312349 A1 | 12/2009 | Flynn et al. |
| 2009/0325945 A1 | 12/2009 | Niculescu-Duvaz et al. |
| 2010/0075971 A1 | 3/2010 | Dumas et al. |
| 2010/0160292 A1 | 6/2010 | Whitney et al. |
| 2010/0209420 A1 | 8/2010 | Lamb et al. |
| 2010/0286215 A1 | 11/2010 | Pelcman et al. |
| 2010/0298290 A1 | 11/2010 | Anand et al. |
| 2011/0077240 A1 | 3/2011 | Mannion et al. |
| 2011/0092461 A1 | 4/2011 | Gunzner et al. |
| 2011/0098293 A1 | 4/2011 | Mannion et al. |
| 2011/0112193 A1 | 5/2011 | Nilsson et al. |
| 2011/0124640 A1 | 5/2011 | Liu et al. |
| 2011/0136760 A1 | 6/2011 | Flynn et al. |
| 2011/0136809 A1 | 6/2011 | Lee et al. |
| 2011/0183997 A1 | 7/2011 | Chianelli et al. |
| 2011/0195110 A1 | 8/2011 | Smith et al. |
| 2011/0237563 A1 | 9/2011 | Costantini |
| 2012/0094980 A1 | 4/2012 | Gunzner et al. |
| 2012/0114605 A1 | 5/2012 | Li |
| 2012/0214808 A1 | 8/2012 | Bloxham et al. |
| 2012/0225057 A1 | 9/2012 | Flynn et al. |
| 2012/0270878 A1 | 10/2012 | Miller et al. |
| 2012/0289540 A1 | 11/2012 | Flynn et al. |
| 2013/0071403 A1 | 3/2013 | Rolland et al. |
| 2013/0225581 A1 | 8/2013 | Furuta et al. |
| 2013/0296326 A1 | 11/2013 | Pollock |
| 2014/0088075 A1 | 3/2014 | Flynn et al. |
| 2014/0107100 A1 | 4/2014 | Rice et al. |
| 2014/0147415 A1 | 5/2014 | Moussy et al. |
| 2014/0179632 A1 | 6/2014 | Mannion et al. |
| 2014/0296248 A1 | 10/2014 | Bernards et al. |
| 2014/0296267 A1 | 10/2014 | Fry et al. |
| 2014/0336210 A1 | 11/2014 | Christopher et al. |
| 2015/0031648 A1 | 1/2015 | Le Tiran et al. |
| 2015/0073141 A1 | 3/2015 | Teegarden et al. |
| 2015/0105550 A1 | 4/2015 | Gunzner et al. |
| 2015/0111879 A1 | 4/2015 | Gunzner et al. |
| 2015/0133462 A1 | 5/2015 | Singh et al. |
| 2015/0218652 A1 | 8/2015 | Doebele et al. |
| 2015/0225369 A1 | 8/2015 | Wucherer-Plietker et al. |
| 2015/0246033 A1 | 9/2015 | Flynn et al. |
| 2015/0275306 A1 | 10/2015 | Bernards et al. |
| 2015/0320759 A1 | 11/2015 | Flynn et al. |
| 2016/0009709 A1 | 1/2016 | Cheve et al. |
| 2016/0045532 A1 | 2/2016 | Roberts et al. |
| 2016/0152569 A1 | 6/2016 | Gunzner-Toste et al. |
| 2016/0166679 A1 | 6/2016 | Low et al. |
| 2016/0222012 A1 | 8/2016 | Ruan |
| 2016/0243150 A1 | 8/2016 | Wood et al. |
| 2016/0289663 A1 | 10/2016 | Kiyokawa et al. |
| 2016/0374990 A1 | 12/2016 | Teegarden et al. |
| 2017/0015627 A1 | 1/2017 | Gunzner-Toste et al. |
| 2017/0121321 A1 | 5/2017 | Crews et al. |
| 2017/0174750 A1 | 6/2017 | Lim et al. |
| 2017/0349880 A1 | 12/2017 | Doucey et al. |
| 2017/0360791 A1 | 12/2017 | Joshi-Hangal et al. |
| 2018/0000771 A1 | 1/2018 | Inoue et al. |
| 2018/0071302 A1 | 3/2018 | Abella et al. |
| 2018/0071303 A1 | 3/2018 | Abella et al. |
| 2019/0091217 A1 | 3/2019 | Flynn et al. |
| 2020/0129489 A1 | 4/2020 | Flynn et al. |
| 2020/0253973 A1 | 8/2020 | Flynn et al. |
| 2020/0352920 A1 | 11/2020 | Flynn et al. |
| 2020/0354346 A1 | 11/2020 | Flynn et al. |
| 2020/0354352 A1 | 11/2020 | Flynn et al. |
| 2021/0015801 A1 | 1/2021 | Flynn et al. |

FOREIGN PATENT DOCUMENTS

| | | |
|---|---|---|
| CN | 102731385 A | 10/2012 |
| CN | 105461699 A | 4/2016 |
| CN | 106573002 A | 4/2017 |
| CN | 106822128 A | 6/2017 |
| CN | 108379591 A | 8/2018 |
| CN | 111328283 A | 6/2020 |
| CN | 114902895 A | 8/2022 |
| DE | 1115350 B | 10/1961 |
| DE | 4343831 A1 | 6/1995 |
| EP | 0021228 A1 | 1/1981 |
| EP | 0025232 A1 | 3/1981 |
| EP | 0154190 A1 | 9/1985 |
| EP | 0661276 A1 | 7/1995 |
| EP | 0692483 A4 | 11/1995 |
| EP | 0739884 A2 | 10/1996 |
| EP | 0867435 A1 | 9/1998 |
| EP | 0927555 A1 | 7/1999 |
| EP | 928790 A1 | 7/1999 |
| EP | 0956855 A1 | 11/1999 |
| EP | 1281399 A2 | 2/2003 |
| EP | 2858646 A1 | 4/2015 |
| EP | 2827900 B1 | 3/2018 |
| FR | 2337554 A1 | 8/1977 |
| FR | 2396549 A2 | 2/1979 |
| GB | 971307 A | 9/1964 |
| GB | 1410279 A | 10/1975 |
| GB | 2220206 A | 1/1990 |
| JP | 59-177557 A | 8/1984 |
| JP | 9221476 | 8/1997 |
| JP | 2000275886 A | 10/2000 |
| JP | 20012687 A | 1/2001 |
| JP | 2010-506948 A | 3/2010 |
| JP | 2015-520186 A | 7/2015 |
| JP | 59-15247 B2 | 5/2016 |
| KR | 20130065368 A | 6/2013 |
| WO | 1991/19708 A1 | 12/1991 |
| WO | 1992/08693 A1 | 5/1992 |
| WO | 1994/18176 A1 | 8/1994 |
| WO | 1994/21617 | 9/1994 |
| WO | 1994/24095 A1 | 10/1994 |
| WO | 1995/006044 A1 | 3/1995 |
| WO | 1995/15954 A1 | 6/1995 |
| WO | 1995/29902 A1 | 11/1995 |
| WO | 1995/34540 A1 | 12/1995 |
| WO | 1996/16046 A2 | 5/1996 |
| WO | 1996/19477 A1 | 6/1996 |
| WO | 1996/023783 A1 | 8/1996 |
| WO | 1997/34900 A1 | 9/1997 |
| WO | 1997/037989 A2 | 10/1997 |
| WO | 1997/40028 A1 | 10/1997 |
| WO | 1997/045400 A1 | 12/1997 |
| WO | 1998/22103 A1 | 5/1998 |
| WO | 1998/52558 A1 | 11/1998 |
| WO | 1999/15164 A1 | 4/1999 |
| WO | 1999/23091 A1 | 5/1999 |
| WO | 1999/23093 A1 | 5/1999 |
| WO | 1999/32106 | 7/1999 |
| WO | 1999/32110 A1 | 7/1999 |
| WO | 1999/32111 | 7/1999 |
| WO | 1999/32455 | 7/1999 |
| WO | 1999/37622 A1 | 7/1999 |
| WO | 1999/59959 A1 | 11/1999 |
| WO | 2000/06550 A1 | 2/2000 |
| WO | 2000/07980 A1 | 2/2000 |
| WO | 2000/18738 A1 | 4/2000 |
| WO | 2000/21927 A2 | 4/2000 |
| WO | 2000/41698 A1 | 7/2000 |
| WO | 2000/042012 A1 | 7/2000 |
| WO | 2000/43384 A1 | 7/2000 |
| WO | 2000/55139 A2 | 9/2000 |
| WO | 2000/59506 A1 | 10/2000 |
| WO | 2000/071515 A2 | 11/2000 |
| WO | 2001/12621 A1 | 2/2001 |
| WO | 2001/14372 A2 | 3/2001 |
| WO | 2001/74771 A1 | 10/2001 |
| WO | 2001/96298 A2 | 12/2001 |
| WO | 2002/00647 A1 | 1/2002 |
| WO | 2002/014291 A1 | 2/2002 |
| WO | 2002/014311 A2 | 2/2002 |
| WO | 2002/026712 A2 | 4/2002 |
| WO | 2002/028835 A1 | 4/2002 |

(56) References Cited

FOREIGN PATENT DOCUMENTS

| | | |
|---|---|---|
| WO | 2002/034727 A2 | 5/2002 |
| WO | 2002/060869 A2 | 8/2002 |
| WO | 2002/060876 A1 | 8/2002 |
| WO | 2002/062763 A2 | 8/2002 |
| WO | 2002/070662 A2 | 9/2002 |
| WO | 2003/005999 A2 | 1/2003 |
| WO | WO-2003/002114 A2 | 1/2003 |
| WO | 2003/047579 A1 | 6/2003 |
| WO | 2003/053368 A2 | 7/2003 |
| WO | 2003/059373 A2 | 7/2003 |
| WO | 2003/068223 A1 | 8/2003 |
| WO | 2003/068229 A1 | 8/2003 |
| WO | 2003/072577 A1 | 9/2003 |
| WO | 2003/084539 A2 | 10/2003 |
| WO | 2004/004720 A1 | 1/2004 |
| WO | 2004/056783 A1 | 7/2004 |
| WO | 2004/060305 A2 | 7/2004 |
| WO | 2004/060306 A2 | 7/2004 |
| WO | 2004/061084 A2 | 7/2004 |
| WO | 2004/078128 A2 | 9/2004 |
| WO | 2004/078746 A2 | 9/2004 |
| WO | 2004/113352 A1 | 12/2004 |
| WO | 2005/002673 A1 | 1/2005 |
| WO | 2005/012254 A1 | 2/2005 |
| WO | 2005/024755 A2 | 3/2005 |
| WO | 2005/034869 A2 | 4/2005 |
| WO | 2005/048948 A2 | 6/2005 |
| WO | 2005/103011 A1 | 11/2005 |
| WO | 2005/110994 A2 | 11/2005 |
| WO | 2006/014290 A2 | 2/2006 |
| WO | 2006/014325 A2 | 2/2006 |
| WO | 2006/018662 A2 | 2/2006 |
| WO | 2006/028958 A2 | 3/2006 |
| WO | 2006/039718 A2 | 4/2006 |
| WO | 2006/040056 A1 | 4/2006 |
| WO | 2006/046552 A1 | 5/2006 |
| WO | 2006/052936 A2 | 5/2006 |
| WO | 2006/062984 A2 | 6/2006 |
| WO | 2006/071940 A2 | 7/2006 |
| WO | 2006/072589 A2 | 7/2006 |
| WO | 2006/078610 A1 | 7/2006 |
| WO | 2006/081034 A2 | 8/2006 |
| WO | 2006/081335 A2 | 8/2006 |
| WO | 2006/099075 A2 | 9/2006 |
| WO | 2006/105844 A1 | 10/2006 |
| WO | 2007/008917 A2 | 1/2007 |
| WO | 2007/042321 A2 | 4/2007 |
| WO | 2007/064872 A2 | 6/2007 |
| WO | 2007/076473 A2 | 7/2007 |
| WO | 2007/081690 A2 | 7/2007 |
| WO | 2007/115670 A1 | 10/2007 |
| WO | 2007/125330 A1 | 11/2007 |
| WO | 2007/136465 A2 | 11/2007 |
| WO | 2007/137107 A2 | 11/2007 |
| WO | 2008/033858 A2 | 3/2008 |
| WO | 2008/033999 A2 | 3/2008 |
| WO | 2008/034008 A2 | 3/2008 |
| WO | 2008/046003 A2 | 4/2008 |
| WO | 2008/051757 A1 | 5/2008 |
| WO | 2008/131227 A1 | 10/2008 |
| WO | 2008/131253 A1 | 10/2008 |
| WO | 2008/140895 A1 | 11/2008 |
| WO | 2009/030887 A2 | 3/2009 |
| WO | 2009/076454 A2 | 6/2009 |
| WO | 2009/109035 A1 | 9/2009 |
| WO | 2009/126863 A2 | 10/2009 |
| WO | 2009/127822 A2 | 10/2009 |
| WO | 2009/138758 A2 | 11/2009 |
| WO | 2010/011837 A1 | 1/2010 |
| WO | 2010/051373 A1 | 5/2010 |
| WO | 2010/124283 A2 | 10/2010 |
| WO | 2010/135524 A1 | 11/2010 |
| WO | 2011/067306 A1 | 6/2011 |
| WO | 2011/123788 A1 | 10/2011 |
| WO | 2011/137342 A1 | 11/2011 |
| WO | 2011/139891 A1 | 11/2011 |
| WO | 2011/150198 A1 | 12/2011 |
| WO | 2012/008563 A1 | 1/2012 |
| WO | 2012/019015 A2 | 2/2012 |
| WO | 2012/035131 A1 | 3/2012 |
| WO | 2012/071519 A1 | 5/2012 |
| WO | 2012/097021 A1 | 7/2012 |
| WO | 2012/138783 A2 | 10/2012 |
| WO | 2013/036232 A2 | 3/2013 |
| WO | 2013/043569 A1 | 3/2013 |
| WO | 2013/066440 A1 | 5/2013 |
| WO | 2013/078295 A2 | 5/2013 |
| WO | 2013/134243 A1 | 9/2013 |
| WO | 2013/134252 A1 | 9/2013 |
| WO | 2013/134298 A1 | 9/2013 |
| WO | 2013/177420 A2 | 11/2013 |
| WO | 2013/184119 A1 | 12/2013 |
| WO | 2014/015056 A2 | 1/2014 |
| WO | 2014/032755 A2 | 3/2014 |
| WO | 2014/036387 A2 | 3/2014 |
| WO | 2014/037480 A1 | 3/2014 |
| WO | 2014/040242 A1 | 3/2014 |
| WO | 2014/040549 A1 | 3/2014 |
| WO | 2014/058317 A1 | 4/2014 |
| WO | 2014/102376 A1 | 7/2014 |
| WO | 2014/102377 A1 | 7/2014 |
| WO | 2014/139458 A1 | 9/2014 |
| WO | 2014/145004 A1 | 9/2014 |
| WO | 2014/145015 A2 | 9/2014 |
| WO | 2014/145023 A1 | 9/2014 |
| WO | 2014/145025 A2 | 9/2014 |
| WO | 2014/145028 A2 | 9/2014 |
| WO | 2014/145029 A2 | 9/2014 |
| WO | 2014/160183 A1 | 10/2014 |
| WO | 2014/182643 A2 | 11/2014 |
| WO | 2015/011399 A1 | 1/2015 |
| WO | WO-2015/051252 A1 | 4/2015 |
| WO | 2015/069217 A1 | 5/2015 |
| WO | 2015/069266 A1 | 5/2015 |
| WO | 2015/076213 A1 | 5/2015 |
| WO | 2015/092423 A1 | 6/2015 |
| WO | 2015/106292 A1 | 7/2015 |
| WO | 2015/106294 A1 | 7/2015 |
| WO | 2015/148620 A2 | 10/2015 |
| WO | 2015/184443 A1 | 12/2015 |
| WO | 2016/061228 A1 | 4/2016 |
| WO | 2016/061231 A1 | 4/2016 |
| WO | 2016/096903 A1 | 6/2016 |
| WO | 2016/103223 A1 | 6/2016 |
| WO | 2016/114322 A1 | 7/2016 |
| WO | 2016/135046 A1 | 9/2016 |
| WO | 2016/154524 A1 | 9/2016 |
| WO | 2016/196141 A1 | 12/2016 |
| WO | 2017/013160 A1 | 1/2017 |
| WO | 2017/042944 A1 | 3/2017 |
| WO | WO-2017/033113 A1 | 3/2017 |
| WO | 2017/079267 A1 | 5/2017 |
| WO | 2017/117182 A1 | 7/2017 |
| WO | 2017/146794 A1 | 8/2017 |
| WO | 2017/146795 A1 | 8/2017 |
| WO | 2017/214514 A1 | 12/2017 |
| WO | 2018/005737 A1 | 1/2018 |
| WO | 2018/052053 A1 | 3/2018 |
| WO | 2018/053189 A2 | 3/2018 |
| WO | 2018/106595 A1 | 6/2018 |
| WO | 2018/195450 A1 | 10/2018 |
| WO | 2018/222173 A1 | 12/2018 |
| WO | 2018/222644 A1 | 12/2018 |
| WO | WO-2019/084462 A1 | 5/2019 |
| WO | WO-2020/185812 A1 | 9/2020 |

OTHER PUBLICATIONS

Kwong, et al., "A General, Efficient, and Inexpensive Catalyst System for the Coupling Aryl Iodides and Thiols", Orqanic Letters, 4(20):3517-3520 (2002).

Laskowski, "SURFNET: A Program for Visualizing Molecular Surfaces, Cavities, and Intermolecular Interactions", Journal of Molecular Graphics, 13:323-330 (1995).

(56) References Cited

OTHER PUBLICATIONS

Leca, et al., "A New Practical One-Pot Access to Sulfonimidates", Organic Letters, 4(23):4093-4095 (2002).
Lefevre, et al., "Roles of Stem Cell Factor/c-Kit and Effects of Glivec®/STI571 in Human Uveal Melanoma Cell Turmorigenesis", Journal of Biological Chemistry, 279(30):31769-31779 (2004).
Lesort, et al., "Insulin Transiently Increases Tau Phosphorylation: Involvement of Glycogen Synthase Kinase-3f3 and Fyn Tyrosine Kinase", Journal of Neurochemistry, 72(2):576-584 (1999).
Leung, et al., "The Difluoromethylensulfonic Acid Groups as a Monoanionic Phosphate Surrogate for Obtaining PTP1B Inhibitors", Bioorganic & Medicinal Chemistry, 10:2309-2323 (2002).
Li, et al., "Targeting Serine/Threonine Protein Kinase B/Akt and Cell-cycle Checkpoint Kinases for Treating Cancer", Current Topics in Medicinal Chemistry, 2:939-971 (2002).
Li, et al., "The P190, {210, and P230 Forms of the BCR/ABL Oncogene Induce a Similar Chronic Myeloid Leukemia-like Syndrome in Mice but Have Different Lymphoid Leukemogenic Activity", J. Exp. Med., 189(9):1399-1412 (1999).
Lim et al., "Current research and treatment for gastrointestinal stromal tumors" World Journal of Gastroenterology (2017), 23(27), 4856-4866 Publisher: Baishideng Publishing Group Inc.
Link, et al., "Synthesis of 8-Substituted 5-Deazaflavins", J. Heterocyclic Chem, 22:841-848 (1985).
Lipinski, et al., "Experimental and Computational Approaches to Estimate Solubility and Permeability in Drug Discovery and Development Settings", Advanced Drug Delivery Reviews, 23:3-25 (1997).
Longley et al., "Somatic c-KIT activating mutation in urticaria pigmentosa and aggressive mastocytosis: establishment of clonality in a human mast cell neoplasm," Nature Genetics, 12(3):312-314 (1996).
Loren, et al., "NH-1,2,3-Triazoles from Azidomethyl Pivalate and Carbamates: Base-Labile N-Protecting Groups", SYNLETT, 18:2847-2850 (2005).
Lorenzi, et al., "Amino Acid Ester Prodrugs of 2-Bromo-5, 6-dichloro-1-([3-D-ribofuranosyl)benzimidazole Enhance Metabolic Stability In Vitro and In Vivo," The Journal of Phannaco/ogy and Experimental Therapeutics (2005) vol. 314, No. 2 pp. 883-890.
Lowinger, et al., "Design and Discovery of Small Molecules Targeting Raf-1 Kinase", Current Pharmaceutical Design, 8:2269-2278 (2002).
Ma, et al., "c-MET Mutational Analysis in Small Cell Lung Cancer: Novel Juxtamembrane Domain Mutations Regulating Cytoskeletal Functions", Cancer Research, 63:6272-6281 (2003).
Ma, et al., "c-Met: Structure, Functions and Potential for Therapeutic Inhibition", Cancer and Metastasis Reviews, 22:309-325 (2003).
Magnuson, et al, "The Raf-I serine/threonine protein kinase," Seminars in Cancer Biology. (1994) 5: 247-253.
Mallakpour, et al., "Uncatalyzed Polymerization of Bistriazolinediones with Electron-Rich Aromatic Compounds via Electrophilic Aromatic Substitution", Journal of Polymer Science: Part A: Polymer Chemistry, 27:217-235 (1989).
Mamaev, et al., "Synthesis of 2,5'-Bipyrimidines from Substituted 5-Cyanopyrimidines", Khimiya Geterotsiklicheskikh Soedinenni, 24(3):371-375—(1988).
March's Advanced Organic Chemisto.::: Reactions Mechanisms and Structure Fifth Edition, Smith and March Editors, Wiley-Interscience Publication (2001).
March, et al., "Tautomerism", from March's Advanced Organic Chemisto.::, 4th Edition, WileyInterscience, pp. 69-74.
Martinez, et al., "First Non-ATP Competitive Glycogen Synthase Kinase 313 (GSK-313) Inhibitors: Thiadizolidinones (TDZD) as Potential Drugs for the Treatment of Alzheimers Disease", J. Med. Chem., 45(2002)1292-1299 (2002).
Mattsson, et al., "Six X-Linked Agammaglobulinemia-Causing Missense Mutations in the Src Homology 2 Domain of Bruton's Tyrosine Kinase: Phosphotyrosine-Binding and Circular Dichroism Analysis", Journal of Immunoloav, pp. 4170-4177 (2000).

Mazzieri, R et al., Targeting The ANG2/TIE2 Axis Inhibits Tumor Growth And Metastasis By impairing Angiogenesis And Disabling Rebounds Of Proangiogenic Myeloid Cells. Cell. Apr. 12, 2001, vol. 19, pp. 512-526; DOI: 10.1016/j.ccr.2001.02.005.
McPherson, "Current Approaches to Macromolecular Crystallization", Eur. J. Biochem, 189:1-23 (1990).
Medebielle, et al., "A Convenient Synthesis of Perfluoroalkylated and Fluorinated-Aryl Nitrogen Bases by Electrochemically Induced SRN1 Substitution", J. Org. Chem., 61:1331-1340 (1996).
Medebielle, et al., "A New Convenient Synthesis of 5-Aryl Uracils Using SRN1 Aromatic Nucleophilic Substitution", Tetrahedron Letters, 34(21 ):3409-3412 (1993).
Mikhaleva, et al., "Relative Reactivities of the Chlorine Atoms of 2,2',4-Trichloro-4',5-Dipyrimidinyl in its Reaction with Piperidine", Khimiya Geterotsiklicheskikh Soedinenii, 6:821-826 (1979).
Mol, "Structural Basis for the Autoinhibition and STI-571 Inhibition of c-Kit Tyrosine Kinase," The Journal Of Biological Chemistry, 279(30):31655-31663 (2004).
Morris, et al., "Automated Docking of Flexible Ligands to Macromolecules", AutoDock Website, www.scripps.edu/mb/olson/doc/autodock/, printed Mar. 3, (2005).
Morris, et al., "Automated Docking Using a Lamarckian Genetic Algorithm and an Empirical Binding Free Energy Function", Journal of Computational Chemistry, 19(14):1639-1662 (1998).
Morstyn, et al., "Stem Cell Factor Is a Potent Synergistic Factor in Hematopoiesis", Oncology, 51 :205-214 (1994).
Moss, et al., "Basic Terminology of Stereochemistry", Pure & Appl. Chem., 6812):2193-2222 (1996).
Muller, "Glossary of Terms Used in Physical Organic Chemistry", Pure & Appl. Chem., 66(5):1077-1184 (1994).
Muller, et al., "A General Synthesis of 4-Substituted 1, 1-Dioxo-1,2,5-thiadiazolidin-3-ones Derived from a-Amino Acids", J. Org. Chem., 54:4471-473 (1989).
Murayama, et al., "JNK (c-Jun NH2 Terminal Kinase) and p38 During Ischemia Reperfusion Injury in the Small Intestine" Transplantation, 81(9): 1325-1330 (2006).
Mutlib, et al., "Disposition of 1-[3-(Aminomethyl)phenyl]-N-[3-fluoro-2'-(methylsulfonyl)-[1, 1 '-biphenyl]-4-yl]-3(trifluomethyl)-1 H-pyrazole-5-carboxamide (DPC 423) by Novel Metabolic Pathways. Characterization of Unusual Metabolites by Liquid Chromatography/Mass Spectrometry and NMR", Chem. Res. Toxicol., 15:48-62 (2002).
Mutlib, et al., "P450-Mediated Metabolism of 1-[3-(Aminomethyl)phenyl]-N-[3-fluoro-2'-(methylsulfonyl)-[1, 1 '-biphenyl]-4-yl]-3(trifluomethyl)-1 H-pyrazole-5-carboxamide (DCP 423) and Its Analogues to Aldoximes. Characterization of Glutathione Conjugates of Postulated Intermediates Derived from Aloximes", Chem. Res. Toxicol., 15:63-75 (2002).
Nagano, M. et al., "Studies on Organic Sulfur Compounds. XIV. The Reaction of N-alkoxycarbonyl-N'-(2-thiazolyl)thioureas with some oxidants." Chemical and Pharmaceutical Bulletin. vol. 21, No. 11, pp. 2408-2416. ISSN: 0009-2363. Nov. 1973.
Nagar, et al., "Crystal Structures of the Kinase Domain of c-Abl in Complex with the Small Molecule Inhibitors PD173955 and Imatinib (STI-571 )", Cancer Research, 62:4236-4243 (2002).
Nagata, et al., "Identification of a point mutation in the catalytic domain of the protooncogene c-kit in peripheral blood mononuclear cells of patients who have mastocytosis with an associated hematologic disorder," Proc. Natl. Acad. Sci. USA, 92(23):10560-10564 (1995).
Nager, et al., "Structural Basis for the Autoinhibition of c-Abl Tyrosine Kinase," Cell (Mar. 21, 2003) vol. 112, pp. 859-871.
Nakopoulou, et al., "c-Met Tyrosine Kinase Receptor Expression is Associated with Abnormal !3-catenin Expression and Favourable Prognostic Factors in Invasive Breast Carcinoma", Histopatholoav, 36:313-325 (2000).
Nantaka-Namirski, et al., "Condensation Reaction of Ethyl (4-Uracil)-Acetate with Ethyl Orthoformate", ACTA Polon. Pharm XXVII, 28(5):455-463 (1971).
National Academy of Sciences, "Abstracts of Papers Presented at the Autumn Meeting, Nov. 14-16, 1960", Science, 132:1488-1501 (1960).

(56) References Cited

OTHER PUBLICATIONS

Nicolaou, et al., "Molecular Design and Chemical Synthesis of a Highly Potent Epothilone", ChemMedChem, 1:41-44 (2006).
Nikolaev, et al., "Solubility Polytherm in the System HNO3—H2O—(C4H9O)PO(C4H9)2", Dokladv Akademii Nauk SSSR, 160(4):841-844 (1965).
Ning, et al., "Activating Mutations of c-Kit at Codon 816 Confer Drug Resistance in Human Leukemia Cells," Leukemia and Lymphoma, 41(5-6):513-522 (2001).
Nofal, et al., "Synthesis of Novel Uracil-5-Sulphonamide Derivatives of Possible Biological Activity", Egypt J. Chem., 33(4):375-380 (1990).
"A Safety, Tolerability and PK Study of DCC-2618 in Patients With Advanced Malignancies," ClinicalTrials.gov, Jan. 12, 2018, pp. 1-11. Retrieved from the Internet: URL: <https://clinicaltrials.gov/ct2/show/NC>.
"NHLBI LBC Computational Biophysics Scetion", CHARMM Documentation Index, http://www.lobos.nih.gov/Charmm/chmdoc.html, printed Mar. 4, 2005.
"Trilateral Project WM4—Comparative Studies in New Technologies: Report on Comparative Study on Protein 3-Dimensional Structure Related Claims—ANNEX 3: Comments of the USPTO", Vienna, Austria, Nov. 4-8, pp. 58-79 (2002).
Additions and Corrections, Journal of Medicinal Chemistry, 32(12):2583 (1989).
Aklilu, et al., "Increased PTHRP Production by a Tyrosine Kinase Oncogene, Tpr-Met: Rose of the Ras Signaling Pathway", The American Physiological Society, pp. E277-E283 (1996).
Albericio, et al., "Synthesis of a Sulfaydantion Library", J. Comb. Chem., 3:290-300 (2001).
Almerico, et al., "On the Preparation of 1-aryl-2-heteroaryl- and 2-aryl-1-heteroaryl-pyrroles as Useful Building Blocks for Biologically Interesting Heterocycles", ARKIVOC, Rudy Abramovitch Issue, pp. 129-142 (2001).
Antonescu, et al., "Acquired Resistance to Imatinib in Gastrointestinal Stromal Tumor Occurs Through Secondary Gene Mutation," Clinical cancer research : an official journal of the American Association for Cancer Research, 11(11):4182-4190 (2005).
Anzai, et al., "Alkyl- and Arylthiation of Uracil and Indole", J. Heterocyclic Chem., 16:567-569 (1979).
Askew, et al., "Molecular Recognition with Convergent Functional Groups: 6. Synthetic and Structural Studies with a Model Receptor for Nucleic Acid Components", J. Am. Chem., 111:1082-1090 (1989).
Avruch, J. et al., "Ras Activation of the Raf Kinase: Tyrosine Kinase Recmitment of the MAP Kinase Cascade," Recent Prag Harm. Res. (2001) 56: 127-155.
Bai et al., "Targeting the KITactivating switch control pocket: a novel mechanism to inhibit neoplastic mast cell proliferation and mast cell activation," Leukemia (2013), vol. 27, pp. 278-285.
Bais, et al., "Inhibition of Endogenous Wxalate Production: Biochemical Consideration of the Roles of Glycollate Oxidase and Lactate Dehydrogenase", Clinical Science, 76:303-309 (1989).
Baker, et al., "Irreversible Enzyme Inhibitors. 188. Inhibition of Mammalian Thymidine Phosphorylase", Journal of Medicinal Chemistry, 14:612-616 (1971).
Barker, et al., "Characterization of pp60c-src Tyrosine Kinase Activities Using a Continuous Assay: Autoactivation of the Enzyme is an Intermolecular Autophosphorylation Process", Biochemist, 35:14843-14851 (1995).
Barvian, et al, "Pyrido[2,3-d]pyrimidin-7-one Inhibitors of Cyclin-Dependent Kinases," J Med Chem. (2000) 43: 4606-4616.
Bausch, et al., "Proton-Transfer Chemistry of Urazoles and Related Imides, and Diacyl H drazides", J. Org. Chem., 56:5643-5651 (1991).
Beghini, et al., "C-kit mutations in core binding factor leukemias," Blood Journal, 95(2):726-727 (2000).
Benvenuti, et al., "Crystallization of Soluble Proteins in Vapor Diffusion for X-Ray Crystallography", Nature Protocols, 2(7):1633-1651 (2007).

Blay, et al., "Ripretinib in patients with advanced gastrointestinal stromal tumours (INVICTUS): a double-blind, randomised, placebo-controlled, phase 3 trial", Lancet Oncology, 21:923-934 (2020).
Bolton, et al, "Chapter 17. Ras Oncogene Directed Approaches in Cancer Chemotherapy," Ann. Rep. Med. Chem. (1994) 29: 165-174.
Bosca, et al., "Circular Dichroism Analysis of Ligand-Induced Conformational Changes in Protein Kinase C", Biochem J., 290:827-832 (1993).
Boschelli, et al., "4-Anilino-3-quinolinecarbonitriles: An Emerging Class of Kinase Inhibitors", Current Topics in Medicinal Chemist, 2:1051-1063 (2002).
Bourdon NEC, et al., "Synthesis and Pharmacological Evaluation of New Pyrazolidine-3,5-diones as AT 1 Angiotensin II Receptor Antagonists", J. Med. Chem., 43:2685-2697 (2000).
Boyer, "Small Molecule Inhibitors of KDR (VEGFR-2) Kinase: An Overview of Structure Activit Relationships", Current Topics in Medicinal Chemist, 2:973-1000 (2002).
Brady, et al., "Fast Prediction and Visualization of Protein Binding Pockets with PASS". Journal of Computer-Aided Molecular Desi n, 14:383-401 (2000).
Branford, et al., "High Frequency of Point Mutations Clustered Within the Adenosine Triphosphate-binding Region of BCR/ABL in Patients With Chronic Myeloid Leukemia or Ph-positive Acute Lymphoblastic Leukemia Who Develop Imatinib (ST1571)resistance," Blood (2002) vol. 99, pp. 3472-3475.
Brasher, et al., "C-Abul has High Intrinsic Tyrosine Kinase Activity that is Stimulated by Mutation of the Src Homology 3 Domain and by Autophosphorylation at Two Distinct Re ulator T rosines", Journal of Biolo ical Chemistr, 275:35631-35637 (2000).
Bullock, et al., "Prospects for Kinase Activity Modulators in the Treatment of Diabetes and Diabetic Complications", Current Topics in Medicinal Chemistr, 2:915-938 (2002).
Byron, et al., "The Synthesis of some Substituted Biphenyl-4-carboxylic Acids, 4-Biphenylylacetic Acids, and 4-Aminobiphenyls", J. Chem. Soc. (C), Organic, pp. 840-845 (1966).
Cardillo, et al., "Su lie 1,2-difenil-3.5-dichetopirazolidine", Gazz. Chim., Ital., 9:973-985 (1966).
Carr, J. B., et al., "Isoxazolc Anthelmintics,".J /'vied. Chem (1977) vol. 20, No. 7, pp. 934-939.
Chan, "Promotion of Reaction of N—H Bonds with Triarylbismuth and Cupric Acetate," Tetrahedron Letters (1996) vol. 37, No. 50, pp. 9013-9016.
Chan, et al, "New N- and O-Arylations with Phenylboronic Acids and Cupric Acetate," Tetrahedron Lett. (1998) 39: 2933-2936.
Chan, et al., "Copper Promoted C—N and C—O Bond Crosscoupling With Phenyl and Pyridylboronates," Tetrahedron Letters (2003) vol. 44, pp. 3863-3865.
Chen, et al., "Biochemical Evidence for the Autophosphorylation and Transphosphorylation of Transforming Growth Factor 13 Receptor Kinases", Proc. Natl. Acad. Sci. USA, 92:1565-1569 (1995).
Cheng, et al., "Novel Solution Phase Strategy for the Synthesis of Chemical Libraries Containing Small Orqanic Molecules", J. Am. Chem. Soc., 118:2567-2573 (1996).
Cheng, et al., "Synthesis and SAR of Heteroaryl-phenyl-substituted Pyrazole Derivatives as Highly Selective and Potent Canine COX-2 Inhibitors", Bioorganic & Medicinal Chemistry Letters, 16:2076-2080 (2006).
Chu, et al., "Using Affinity Capillary Electrophoresis to Determine Binding Stoichiometries of Protein-Ligand Interactions", Biochemistry, 33:10616-10621 (1994).
Cirillo, et al., "The Non-Diaryl Heterocycle Classes of p38 MAP Kinase Inhibitors", Current Topics in Medicinal Chemistry, 2:1021-1035 (2002).
Clincial trial NCT02571036—A Safety, Tolerability and PK Study of DCC-2618 in Patients With Advanced Malignancies—clinicaltrials.gov—May 25, 2017.
Clincial trial NCT02571036—A Safety, Tolerability and PK Study of DCC-2618 in Patients With Advanced Malignancies—clinicaltrials.gov—Oct. 8, 2015.
Clincial trial NCT02571036—A Safety, Tolerability and PK Study of DCC-2618 in Patients With Advanced Malignancies—clinicaltrials.gov—Sep. 17, 2018.

(56) References Cited

OTHER PUBLICATIONS

Clinical trial NCT03353753 Phase 3 Study of DCC-2618 vs Placebo in Advanced GIST Patients Who Have Been Treated With Prior Anticancer Therapies (invictus)—clinicaltrials.gov—Nov. 27, 2017.
Clinical trial NCT03353753 Phase 3 Study of DCC-2618 vs Placebo in Advanced GIST Patients Who Have Been Treated With Prior Anticancer Therapies (invictus)—clinicaltrials.gov—Nov. 21, 2018.
Closier, et al., "Nitrofuryl Heterocyclics. 1", Journal of Medicinal Chemistry, 13(4):638-640 (1970).
Cockerill, et al., "Small Molecule Inhibitors of the Class 1 Receptor Tyrosine Kinase Family", Current Topics in Medicinal Chemistry, 2:1001-1010 (2002).
Col Ton, et al., "Affinity Capillary Electrophoresis: A Physical-Organic Tool for Studying Interactions in Biomolecular Recognition", Electrophoresis, 19:367-382 (1998).
Corless, et al., "Biology of Gastrointestinal Stromal Tumors," Journal of Clinical Oncology, 22(18):3813-3825 (2004).
Cortes, et al., "Results of Imatinib Mesylate Therapy in Patients with Refractory or Recurrent Acute Myeloid Leukemia, High-Risk Myelodysplastic Syndrime, and Mveloproliferative Disorders", Cancer, 97(11 ):2760-2766 (2003).
Cortes, Javier, et al., "Eribulin Monotherapy Versus Treatment of Physician's Choice in Patients With Metastatic Breast Cancer (EMBRACE): A Phase 3 Open-label Randomised Study", The Lancet, vol. 377, No. 9769, Mar. 1, 2011 (Mar. 1, 2011), pp. 914-923, ISSN: 0140-6736, DOI: 10.1016/S0140-6736(11)60070-6.
Cross, et al., "Inhibition of Glycogen Synthase Kinase-3 by Insulin Mediated by Protein Kinase B", Nature, 378:785-789 (1995).
Cudney, "Preface: Protein Crystallization and Dumb Luck", The Rigaku Journal, 16(1): 1-7 (1999).
Dajani, et al., "Crystal Structur of Glycogen Synthase Kinas 3j3: Structural Basis for Phosphate-Primed Substrate Specificity and Autoinhibition", Cell, 105:721-732 (2001).
Dajani, et al., "Structural Basis for Recruitment of Glycogen Synthase Kinase 313 to the Axin-APC Scaffold Complex", EMBO, 22(3):494-501 (2003).
Daley, et al., "Induction of Chronic Myelogenous Leukemia in Mice by the P21 otcriat, Gene of the Philadelphia Chromosome," Science (Feb. 16, 1990) vol. 247, pp. 824-830.
Database Registry [Online] Chemical Abstracts Service, Columbus, Ohio, US; May 27, 2010, XP002777425, retrieved from STN accession No. 1225278-16-9 RN (2 pages).
Davies, H. et al., "Mutations of the BRAF gene in human cancer," Nature (Jun. 2002) 41 7: 949-954.
Davis, et al., "Iterative Size-Exclusion Chromatography Coupled with Liquid Chromatography Mass Spectrometry to Enrich and Identify Tight-Binding Ligands from Complex Mixtures", Tetrahedron, 55:11653-11667 (1999).
De Boer, et al., "Synthesis and Characterization of Conjugated Mono- and Dithiol Oligomers and Characterization of Their Self-Assembled Monolayers", Langmuir, 19:4272-4284 (2003).
De Palma et al., "Angiopoietin-2 TIEs Up Macrophages in Tumor Angiogenesis" Clin Cancer Res; 17(16) Aug. 15, 2011.
De Silva, et al., "Gastrointestinal Stromal Tumors (GIST): C-kin Mutations, CD117 Expression, Differential Diagnosis and Targeted Cancer Therapy with Imatinib", Pathology Oncology Research, 9(1 ):13-19 (2003).
Debiec-Rychter, et al., "Mechanisms of Resistance to Imatinib Mesylate in Gastrointestinal Stromal Tumors and Activity of the PKC412 Inhibitor Against Imatinib-Resistant Mutants," Gastroenterology, 128(2):270-279 (2005).
Decipera Pharmaceuticals LLC, "DCC-2618, a small molecule inhibitor of normal and mutant KIT kinase for treatment of refractory gastrointestinal stromal tumors (GIST)" (Presented on Sep. 24, 2011 at GIST Summit 2011 on "Gastrointestinal stromal tumors.").
Deciphera Pharmaceuticals LLC, "Deciphera Pharmaceuticals announces positive top-line results from INVICTUS pivotal phase 3 clinical study of Ripretinib in patients with advanced gastrointestinal stromal tumors", 1-3 (2019).
Deciphera Pharmaceuticals LLC, "Deciphera Pharmaceuticals Initiates Pivotal Phase 3 Clinical Study of Ripretinib (DCC-2618) in Second-line Patients with Gastrointestinal Stromal Tumors ("INTRIGUE" Study)", 1-2 (2018).
Deciphera Pharmaceuticals LLC, "Qinlock Full Prescribing Information", 1-18 (2020).
Deng, et al., "Expression, Characterization, and Crystallization of the Pyrophosphate-Dependent Phosphofructo-1-Kinase of Borrelia Burgdorferi", Archives of Biochemistry and Biophysics, 371(2):326-331 (1999).
Dess, et al., "A Useful 12-1-5 Triacetoxyperiodiane (the Dess-Martin Periodiane) for Selective Oxidation of Primary or Secondary Alcohols and a Variety of Related 12-1-5 Species", J. Am. Chem., Soc., 113:7277-7287 (1991).
Dong, J., Overcoming Resistance TO BRAF And MEK inhibitors By Simultaneous Suppression Of CDK4. InTech. Jan. 30, 2013. Melanoma—From Early Detection to Treatment, Chapter 1; abstract; p. 7, second paragraph; p. 9, figure 4; DOI: 10.5772/53620.
Dumas, "Preface", Current Topics in Medicinal Chemistry (2002).
Dumas, "Protein Kinase Inhibitors: Emerging Pharmacophores", Exp. Opin. Ther. Patent, 11 :405-429 (2001).
Dumas, et al., "Discovery of a New Class of p38 Kinase Inhibitors", Bioorganic & Medicinal Chemistry Letters, 10:2047-2050 (2000).
Dumas, et al., "Recent Developments in the Discovery of Protein Kinase Inhibitors From the Urea Ciass," Current Opinion in Drug Discovery & Development (2004) vol. 7, No. 5, pp. 600-616.
Ettmayer, et al., "Lessons Learned from Marketed and Investigational Prodrugs," Journal of Medicinal Chemistry (May 6, 2004) vol. 47, No. 10, pp. 2393-2404.
Ewing, "Critical Evaluation of Search Algorithms for Automated Molecular Docking and Database Screening", Journal of Computational Chemistry, 18(9):1175-1189 (1997).
Examination Report in Indian Patent App. No. 11241/DELNP/2014 dated Apr. 1, 2019.
Faderl, et al., "The Biology of Chronic Myeloid Leukemia," The New England Journal of Medicine (Jul. 15, 1999) vol. 341. No. 3, pp. 164-172.
Farooqui, et al., "Interactions Between Neural Membrane Glycerophospholipid and Sphingolipid Mediators: A Recipe for Neural Cell Survival or Suicide", Journal of Neuroscience Research, 85:1834-1850 (2007).
Fathalla, "Synthesis of New Pyrazolo[1,5-a]pyrimidine Derivative Using 5-Aminouracil and Ketene Dithiacetal", Arch Pharm Res, 22(6):571-574 (1999).
Fathalla, et al., "Synthesis of New Uracil-5-Sulfonamide Derivatives and Immuno-Stimulatory Effect of a Chemically Modified Hemolymph of Biomphalaria Alexandrina on Schistosoma Manosi Infected Mice", Arch Pharm Res., 26(5):358-366 (2003).
Fathalla, et al., "Synthesis of New Uracil-5-Sulphonamide-p-Phenyl Derivatives and Their Effect on Biomphalaria Alexandrina Snail's Nucleoproteins", Arch. Pharm. Res., 23(2):128-138 (2000).
Flatt, et al., "Synthesis of Thiol Substituted Oligoanilines for Molecular Device Candidates", Tetrahedron Letters, 44:6699-6702 (2003).
Fletcher, et al., "Diagnosis of Gastrointestinal Stromal Tumors: A Consensus Approach", 33(5):459-465 (2002).
Fletcher, et al., "KIT Mutations in GIS, Current Opinion in Genetics & Development," Science Direct, p. 3-7 (2007).
Frame, et al., "A Common Phosphate Binding Site Explains the Unique Substrate Specificity of GSK3 and Its Inactivation by Phosphorylation", Molecular Cell, 7:1321-1327 (2001).
Furyua, et al., "Addition of 4-Ethoxyimidazoles to Dimethyl Acetylenedicarboxylate and Transformation of the Adducts to Pyrimidian-5-yl Acetates", Chem. Pharm. Bull., 36(5):1669-1675 (1988).
Gajiwala, et al., "KIT kinase mutants show unique mechanisms of drug resistance to imatinib and sunitinib in gastrointestinal stromal tumor patients," Proceedings of the National Academy of Sciences of the USA 106(5):1542-1547 (2009).
Garcia-Tellado, et al., "Molecular Recognition in the Solid Waste State: Controlled Assembly of Hydrogen-Bonded Molecular Sheets", J. Am. Chem. Soc., 113:9265-9269 (1991).

(56) References Cited

OTHER PUBLICATIONS

George, et al., "Initial Results of Phase 1 Study of DCC-2618, a Broad-Spectrum Kit and PDGFRA Inhibitor, in Patients (PTS) with Gastrointestinal Stromal Tumor (GIST) by Number of Prior Regimes", European Society for Medical Oncology, 1-13 (2018).

Gishizky, et al., "Efficient transplantation of BCR-ABL-induced Chronic Myelogenous Leukemia-like Syndrome in Mice," Proc. Natl. Acad. Sci. (Apr. 1993) vol. 90, pp. 3755-3759.

Gorre, et al., "Clinical Resistance to STI-571Cancer Therapy Caused by BCR-ABL Gene Mutation or Amplification," Science (Aug. 3, 2001) vol. 293, pp. 876-880.

Greene, et al., "Chapter 7: Protection for the Amino Group", in Protective Groups in Organic Synthesis, Third Edition, pp. 494-653 (1999).

Griffith, et al., "TPAP: Tetra-n-propylammonium Perruthenate, A Mild and Convenient Oxidant for Alcohols", Aldrichimica Acta, 23(1):13-19 (1990).

Guzel, "Investigation of the Relationship Between the Inhibitory Activity of Glycolic Acid Oxidase (GAO) and its Chemical Structure: Electron-Topological Approach", Journal of Molecular Structure, 366:131-137 (1996).

Haar, et al., "Structure of GSK313 Reveals a Primed Phosphorylation Mechanism", Nature Structural Bioloav, 8(7):593-596 (2001).

Hackler, et al., "The Syntheses of 5-Amino-3- t-butylisothiazole and 3-Amino-5- t-butylisothiazole," J. Heterocyclic Chem. (Nov.-Dec. 1989) vol. 26, pp. 1575-1578.

Haesslein, et al., "Recent Advances in Cyclin-Dependent Kinase Inhibition. Purine-Based Derivatives as Anti- Cancer Agents. Roles and Perspectives for the Future", Current Topics in Medicinal Chemistry, 2:1037-1050 (2002).

Hearing Notice in Indian Patent App. No. 11241/DELNP/2014 mailed Jan. 24, 2020.

Heegaard, et al., "Affinity Capillary Electrophoresis: Important Application Areas and Some Recent Developments", Journal ofChromatography B, 715:29-54 (1998).

Heinrich, et al., "Molecular Correlates of Imatinib Resistance in Gastrointestinal Stromal Tumors," Journal of Clinical Oncology, 24(29):4764-4774 (2006).

Heinrich, et al., "Primary and Secondary Kinase Genotypes Correlate With the Biological and Clinical Activity of Sunitinib in Imatinib-Resistant Gastrointestinal Stromal Tumor," Journal of Clinical Oncology, 26(33):5352-5359 (2008).

Honda, et al., "Determination of the Association Constant of Monovalent Mode Protein-Sugar Interaction by Capillary Zone Electrophoresis", Journal of Chromatography, 597:377-382 (1992).

Hu, et al., "Capillary Electrophoresis for the Analysis of Biopolymers", Anal., Chem., 74:2833-2850 (2002).

Huang, et al., "Inhibition of Nucleoside Transport by Protein Kinase Inhibitors", The Journal of Pharmacolo and Experimental Therapeutics, 304 2 :753-760 (2003).

Hubbard, "Crystal Structure of the Activated Insulin Receptor Tyrosine Kinase in Complex with Peptide Substrate and ATP Analo", EMBO, 16(18):5573-5581 (1997).

Hubbard, et al., "Crystal Structure of the Tyrosine Kinase Domain of the Human Insulin Receptor", Nature, 374:746-754 (1994).

Hughes, et al., "Modulation of the Glycogen Synthase Kinase-3 Family by Tyrosine Phosphor lation", EMBO, 122 :803-808 (1993).

Huse, et al., "Crystal Structure of the Cytoplasmic Domain of the Type I TGFl3 Receptor in Complex with FKBP12", Cell, 96:425-436 (1999).

Huse, et al., "The Conformational Plasticity of Protein Kinases," Cell (May 3, 2002) vol. 109, pp. 275-282.

Huse, et al., "The TGFl3 Receptor Activation Process: An Inhibitor-to Substrate-Binding Switch", Molecular Cell, 8:671-682 (2001).

Igarashi, et al., "Antimicrobial Activities of 2-arylthio-N-alkylmaleimides", Journal of Industrial Microbiolo, 9:91-96 (1992).

International Human Genome Sequencing Consortium, "Initial Sequencing and Analysis of the Human Genome", Nature, 409:860-921 (2001).

International Search Report and Written Opinion from PCT/US2012/041378, dated Sep. 17, 2012.

International Search Report and Written Opinion from PCT/US2017/035005, dated Feb. 22, 2018.

International Search Report and Written Opinion from PCT/US2019/016148, dated Apr. 17, 2019.

International Search Report and Written Opinion from PCT/US2019/016161, dated Apr. 23, 2019.

International Search Report and Written Opinion from PCT/US2020/045876, dated Oct. 22, 2020.

International Search Report and Written Opinion from WO2008/034008 A3, dated Apr. 11, 2008.

International Search Report issued for PCT/US2008/060833, dated Sep. 30, 2008.

International Search Report issued for PCT/US2008/060867, dated Sep. 29, 2008.

International Search Report issued for PCT/US2008/060896, dated Sep. 29, 2008.

Ishida, et al., "Molecular Arrangement and Electrical Conduction of Self-Assembled Monola ers Made from Terphen I Thiols", Surface Sciences, 514:187-193 (2002).

Islip, et al., "Nitrofuryl Heterocyclics 3", Journal of Medicinal Chemistry, 16(11 ): 1309-1310 (1973).

Jackson, et al., "N-Terminal Mutations Activate the Leukemogenic Potential of the M risto lated form of c-abl", EMBO, 8(2):449-456 (1989).

Jackson, et al., "Pyridinylimidazole Based p38 MAP Kinase Inhibitors", Current Topics in Medicinal Chemist, 2:1011-1020 (2002).

Janku Filip et al., "Pharmacokinetic-driven phase I study of DCC-2618 a pan-KIT and PDGFR inhibitor in patients (pts) with gastrointestinal stromal tumor (GIST) and other solid tumors," J. Clin. Oncol. (2017) No. 15, Suppl 2515.

Janku, et al., "Abstract CT058: Ripretinib (DCC-2618) pharmacokinetics (PK) in a Phase I study in patients with gastroinestinal stromal tumors (GIST) and other advanced malignancies: A retrospective evaluation of the PK effects of proton pump inhibitors (PPIs)", American Association for Cancer Research, 79(13):1-4 (2019).

Jiang, et al., "Soft Docking": Matching of Molecular Surface Cubes, J. Mol. Biol., 219:79-102 (1991).

Jiang, et al., "Synthesis and SAR Investigations for Novel Melanin-Concentrating Hormone 1 Receptor (MCH1) Antagonists Part 1. The Discovery of Arylacetamides as Viable Replacements for the Dihydropyrimidione Moiety of an HTS Hit", J. Med. Chem., 50:3870-3882 (2007).

Johnson, "Circular Dichroism Spectroscopy and The Vacuum Ultraviolet Region", Ann. Rev. Phys. Chem., 29:93-114 (1978).

Johnson, "Protein Secondary Structure and Circular Dichroism: A Practical Guide", PROTEINS: Structure, Function, and Genetics, 7:205-214 (1990).

Johnson, et al., "An Evaluation of the Effect of Light Stabilisers on the Exterior Durability of Polyester Powder Coatings for the Architectural Market", Surface Coatings International, 3:134-141 (1999).

Johnson, et al., "The Stereochemistry of Oxidation at Sulfur Oxidation of 2-Thiabicyclo[2.2.1 ]Hpetane", Tetrahedron, 25:5649-5653 (1969).

Katritzky, et al., "Novel Chromophoric Heterocycles Based on Maleimide and Naphthoquinone", J. Heterocyclic Chem., 26:885-892 (1989).

Kern, et al., "Synthese von Makromolekeln einheitlicher Brol3e. II Mitt: Syntheses neuer Diololigo-urethane nach dem Duplikationsverfahren", Makromolekulara Chemie, 16:89-107 (1955).

Kettle et al., "Discovery of N-(4-{[5-Fluoro-7-(2-methoxyethoxy)quinazolin-4-yl]amino}phenyl)-2-[4-(propan-2-yl)-1H-1,2,3-triazol-1-yl]acetamide (AZD3229), a Potent Pan-KIT Mutant Inhibitor for the Treatment of Gastrointestinal Stromal Tumors" Journal of Medicinal Chemistry (2018), 61(19), 8797-8810.

Kim, et al., "Solid Phase Synthesis of Benzamidine and Butylamine-Derived Hydantoin Libraries", Molecular Diversity, 3:129-132 (1998).

Klayman, et al., "The Reaction of S-Methiodide Derivatives of Activated Thioureas with Hydroxylic Compounds. A Novel Synthesis of Mercaptans", J. Org. Chem., 37(10):1532-1537 (1972).

(56) References Cited

OTHER PUBLICATIONS

Kleywegt, et al., "Detection, Delineation, Measurement and Display of Cavities in Macromolecular Structures", Acta Cryst, D50:178-185 (1994).
Koch, et al., "QSAR and Molecular Modelling for a Series of Isomeric X-Sulfanilamido-1-phenylpyrazoles", Quant. Struct. Act. Relat., 12:373-382 (1993).
Kolch, W., "Meaningful relationships: the regulation of the Ras/Raf/MEKJERK pathway by protein interactions," Biochemn. J (2000) 351: 289-305.
Konopka, et al., "Cell Lines and Clinical Isolates Derived From Ph-positive Chronic Myelogenous Leukemia Patients Express c-abl Proteins With A Common Structural Alteration," Proc. Natl. Acad. Sci. (Mar. 1985) vol. 82, pp. 1810-1814.
Krasovitskii, et al., "Synthesis and Spectral-Luminescence Properties of Hetarylethylene Derivatives of 2,5-Diphenyloxazole and 2,5-Diphenyl-1,3,4-Oxadiazole", Khimiya Geterotsiklicheskikh Soedinenii, 5:617-621 (1982).
Kuhn, et al., "The Genesis of High-Throughput Structure-Based Drug Discovery using Protein Crystallography", Analytical Techniques, Current Opinion in Chemical Biology, 6:704-710 (2002).
Kumar, et al., "P38 Map Kinases: Key Signalling Molecules as Therapeutic Targets for Inflammatory Diseases", Nature Reviews Drug Discovery, 2:717-726 (2003).
Kundrot, "Which Strategy for a Protein Crystallization Project", CMLS, Cell. Mol. Life Sci., 61 :525-536 (2004).
Kundu, et al., "Depropargylation Under Palladium-Copper Catatlysis: Synthesis of Diaryl Sulfides", Tetrahedron, 57:5885-5895 (2001).
Kurogi, et al., "Discovery of Novel Mesangial Cell Proliferation Inhibitors Using a Three-Dimensional Database Searching Method", J. Med. Chem., 44:2304-2307 (2001).
Kuse, et al., Synthesis of azide-fluoro-dehydrocoelentcrazine analog as a photoaffinitylabeling probe and photolysis of azide-fluoro-coelenterazine; Tetrahedron Lett. (2005) 61: 5754-5762.
Shah, et al., "Overriding Imatinib Resistance with a Novel ABL Kinase Inhibitor," Science (Jul. 16, 2004) vol. 305, pp. 399-401.
Shi, et al., "Abnormal Diels-Alder Reaction of 5-Alkoxythiazoles with Highly Reactive Dienophiles; 4-Phenyl-3H-1,2,4-triazole-3,5(4H)-dione, Diethyl Azodicarboxylate, and Diethyl Oxomalonate", Bull. Chem. Soc. Jpn., 65:3315-3321 (1992).
Shinkai, et al., "Coenzyme Models, Part 45. Synthesis of Atropisomeric Flavins and their Novel Redox-induced Racemisation", J. Chem. Soc. Perkin Trans., pp. 313-319 (1988).
Shiozaki, et al., "Impaired Differentiation of Endocrine and Exocrine Cells of the Pancreas in Transgenic Mouse Expressing the Truncated Type II Activin Receptor", Biochimica et Biophysica Acta, 1450:1-11 (1999).
Sihto, et al., "KIT and Platelet-Derived Growth Factor Receptor Alpha Tyrosine Kinase Gene 1-30 Mutations and KIT Amplifications in Human Solid Tumors," Journal of Clinical Oncology, 23(1):49-57 (2005).
Sircar, et al., "Synthesis of 4-Hydroxy-N-[5-{hydroxymethyl}-3-isoxazolyl]2-methyl-2H-1,2-bsnzo-thiazine-3-carboxamide 1, 1-Dioxide and [(5-Methyl-3-isoxazolyl)amino]oxoacetic Acid. Major Metabolites of Isoxicam," J. Org. Chem. (1985) vol. 50, pp. 5723-5727.
Smith et al., "Ripretinib (DCC-2618) is a switch control kinase inhibitor of a broad spectrum of oncogenic and drug-resistant KIT and PDGFRA variants," Cancer Cell (2019), vol. 35, No. 5, pp. 738-759.
Stout, et al., "High-Throughput Structural Biology in Drug Discovery: Protein Kinases", Current Pharmaceutical Design, 10:1069-1082 (2004).
Sugden, et al., ""Stress-Responsive" Mitogen-Activated Protein Kinases (c-Jun N-Terminal Kinases and p38 Mitogen-Activated Protein Kinases) in the Myocardium", Circulation Research—Journal of the American Heart Association, 83:345-352 (1998).
Tanis, et al., "Two Distinct Phosphorylation Pathways Have Additive Effects on Abl Family Kinase Activation", Molecular and Cellular Bioloav, 23(11 ):3884-3896 (2003).

Tarn, et al., "Analysis of KIT Mutations in Sporadic and Familial Gastrointestinal Stromal Tumors: Therapeutic Implications through Protein Modeling," Clinical cancer research : an official journal of the American Association for Cancer Research, 11(10):3668-3677 (2005).
Teague, "Implications of Protein Flexibility for Drug Discovery", Nature Reviews, 2:527-541 (2003).
Tian, et al., "Activating c-kit Gene Mutations in Human Germ Cell Tumors," American Journal of Pathology, 154(6):1643-1647 (1999).
Tominaga, et al., "General model for Estimation of the Inhibition of Protein Kinases Using Monte Carlo Simulations", J. Med. Chem., 47:2534-2549 (2004).
Tremblay, et al., "Efficient Solid-Phase Synthesis of Sulfahydantoins", J. Comb. Chem., 4:429-435 (2002).
Tsuzuki, et al., "Synthesis and Structure-Activity Relationships of Novel ?-Substituted 1,4-Dihydro-4-oxo-1-(2-thiazolyl)-1,8-napthyridine-3-carboxylic Acids as Antitumor Agents. Part 2", J. Med. Chem., 47:2097-2109 (2004).
Van Etten, "Cycling, Stressed-out and Nervous: Ceiiuiar Functions of c-Abi," Trends in Cell Biology (May 1999) vol. 9, pp. 179-186.
Venter, et al., "The Sequence of the Human Genome", Science, 291:1304-1351, Feb. 16, 2001; Erratum, Jun. 8, 2001.
Von Bubnoff, et al., "BCR-ABL gene mutations in relation to clinical resistance of Philadelphia-chromosome-positive leukemia to STI571. a prospective study," The Lancet (Feb. 9, 2002) vol. 359, pp. 487-491.
Waetzig, et al., "Review Article: Mitogen-Activated Protein Kinases in Chronic Intestinal Inflammation—Targeting Ancient Pathways to Treat Modern Diseases", Aliment Pharmacol Ther, 18:17-32 (2003).
Wan, et al., "Mechanism of Activation of the RAF-ERK Signaling Pathway by Oncogenic Mutations of B-RAF," Cell (Mar. 19, 2004) vol. 116, pp. 855-867.
Wardelmann, "Acquired resistance to imatinib in gastrointestinal stromal tumours caused by multiple KIT mutations," The Lancet Oncology, 6(4):249-251 (2005).
Welker, et al., "Glucocorticoid-Induced Modulation of Cytokine Secretion from Normal and Leukemic Human Myelomonocytic Cells", Int. Arch. Allergy Immunol, 109:110-115 (1996).
Wentland, et al., "3-Quinolinecarboxamides. A Series of Novel Orally-Active Antiherpetic Agents", J. Med. Chem., 36:1580-1596 (1993).
Wilson, et al., "The Structural Basis for the Specificity of Pyridinylimidazole Inhibitors of p38 MAP Kinase", Chemistry & Biology, 4(6):423-431 (1997).
Wilson, et el., "Laser-Jet Delayed Trapping: Electron-Transfer Trapping of the Photoenol from 2-Methylbenzophenone", J. Am. Chem. Soc., 109:4743-4745 (1987).
Wolter, et al., "Copper-Catalyzed Coupling of Aryl Iodides with Aliphatic Alcohols", Organic Letters, 4(6):973-976 (2002).
Wrana, et al., "Mechanism of Activation of the TGF-B Receptor", Nature, 370:341-347 (1994).
Wu, et al., "Discovery of a Novel Family of CDK Inhibitors with the Program LIDAEUS:Structual Basis for Ligand-Induced Disordering of the Acivation Loop", Structure, 11:399-410 (2003).
Yang, et al., "Molecular Mechanism for the Regulation of Protein Kinase B/Akt by Hydrophobic Motif Phosphorylation", Molecular Cell, 9:1227-1240 (2002).
Yang, et al., "Palladium-Catalyzed Amination of Arly Halides and Sulfonates", Journal of Organometallic Chemistry, 576:125-146 (1999).
Yarden, et al., "Human Proto-oncogene c-kit: a New Cell Surface Receptor Tyrosine Kinase for an Unidentified Ligand", The EMBO Journal, 6(11):3341-3351 (1987).
Yoneda, et al., "A New Synthesis of Purines", J.C.S. Chem. Comm., pq. 551 (1974).
Yonezawa, et al., "Synthesis of Sequentially Controlled Isomeric, Wholly aromatic Polyketones Composed of 2-trifluoromethylbiphenylene and 2,2'-dimethoxybiphenylene Units", Reactive & Functional Polymers, 52:19-30 (2002).
Yoshimoto, et al., "Correlation Analysis of Baker's Studies on Enzyme Inhibition. 2. Chymotrypsin, Trypsin, Thymidine Phosphorylase, Uridine Phosphorylase, Thimidylate Synthetase, Cytosine Nucleoside Deaminase, Dihodrofolate Dehydrogenase,

(56) References Cited

OTHER PUBLICATIONS

Glutamate Dehydrogenase, Lactate Dehydrogenase, and Glyceraldehydephosphate Reductase, Malate Dehydrogenase", Journal of Medicinal Chemistry, 19(1 ):71-98 (1976).

Yoshino, et al., "Organic Phosphorous Compounds. 2. Synthesis and Coronary Vasodilator Activity of (Benzothiazolybenzyl) Phosphonate Derivatives", J. Med. Chem., 32:1528-1532 (1989).

Yu, et al., "Frequency of TPR-MET Rearrangement in Patients with Gastric Carcinoma and in First-Degree Relatives", Cancer, 88(8):1801-1806 (2000).

Zaidi, et al., "New Anti-Mycobacterial Hydantoins", Pharmazie, 35:755-756 (1980).

Zhen, et al., "Structural and Functional Domains Critical for Constitutive Activation of the HGF-Receptor (Met)", Oncogene, 9(6):1691-1697 (1994).

Zinner, et al., "Zur Weiteren Kenntnis Bicyclischer 3.5-Dioxopyrazolidine", Die Pharmazie, 25(5):309-312 (1970).

Zvilichovsky, et al., "Aminolysis and Polymerization of 3-(p-Toluenesulfonoxy) Hydantoin", Israel Journal of Chemistry, 7:547-554 (1969).

Nowell, et al., "A Minute Chromosome in Human Chronic Granulocytic Leukemia," Science (Nov. 18, 1960) vol. 132, p. 1497.

O'Dell, et al., "Treatment of Rheumatoid Arthritis with Methotrexate Alone, Sulfasalazine and Hydroxychloroquine, or a Combination of All Three Medications", New England J. Med., 334(20):1287-1291 (1996).

O'Neill, "Targeting Signal Transduction as a Strategy to Treat Inflammatory Diseases", Nature Review Drug Discovery, Published Online Jun. 9, 2006, www.nature.com/reviews/druqdisc.

Okano, et al., "o-Bromophenylzinc Compound: A Readily Available and Efficient Synthetic Equivalent of o-Phenylene 1-Anion 2-Cation", Tetrahedron Letters 39:3001-3004 (1998).

Okishio, et al., "Differential Ligand Recognition by the Src and Phosphatidylinositol 3-Kinase Src Homology 3 Domains: Circular Dichroism and Ultraviolet Resonance Raman Studies", Biochemistry, 42:208-216 (2003).

Okishio, et al., "Identification of Tyrosine Residues Involved in Ligand Recognition by the Phosphatidylinositol 3-Kinase Src Homology 3 Domain: Circular Dichroism and UV Resonance Raman Studies", Biochemistry, 40:15797-15804 (2001).

Okishio, et al., "Role of the Conserved Acidic Residue Asp21 in the Structure of Phosphatidylinositol 3-Kinase Src Homolgy 3 Domain: Circular Dichroism and Nuclear Magnetic Resonance Studies", Biochemistry 40:119-129 (2001).

Okram, Barun et al: "A General Strategy for Creating "Inactive-Conformation" Abl Inhibitors" Chemistry&Biology (Cambridge, MA, US), 13(7), 779-786 CODEN: CBOLE2; ISSN: 1074-5521, 2006, XP002469183 table 1 the whole document.

Palmer, Brian, B. et al: "Structure-Activity Relationships For 2-Anilino-6-Phenylpyrido[2,3-d]Pyrimidin-7(8H)-Ones As Inhibitors of the Cellular Checkpoint Kinase Wee1" Bioorganic & Medicinal Chemistry Letters, 15(7), 1931-1935 CODEN: BMCLE8; ISSN: 0960-894X, 2005, XP004789411 p. 1933.

Parang, et al., "Mechanism-based Design of a Protein Kinase Inhibitor", Nature Structural Bioloav, 8( 1 ):37-41 (2001).

Pargellis, et al., "Inhibition of p38 MAP Kinase by Utilizing a Novel Allosteric Binding Site", Nature Structural Bioloav, 9(4 ):268-272 (2002).

Park, et al., "Mechanism of met Oncogene Activation", Cell, 45:895-904 (1986).

Pearlman, et al., "Assisted Model Building with Energy Refinement", Amber Home Page, amber.scripts.edu.

Pedersen, "The Preparation of Some N-Methyl-1,2,3-Triazoles", Acta Chimica Scandinavica, 13(5):888-892 (1959).

Peng, et al., "Identification of Novel Inhibitors of BCR-ABL Tyrosine Kinase via Virtual Screening", Bioorganic & Medicinal Chemistry Letters, 13:3693-3699 (2003).

Pereira, et al., "The Role of c-kit and Imatinib Mesylate in Uveal Melanoma", Journal of Carcinogenesis, 4:19 (2005), downloaded from www.carcinogenesis.com/content/4/1/19, Sep. 3, 2008.

Peyssonnaux, C. et al, "The RaflMEK/ERK pathway: new concepts of activation," Biol. Cell (2001) 93: 53-62.

Picard, et al., Inhibitors of Acyl-CoA: Cholesterol O-Acyltrasferase. 17. Structure-Activity Relationships of Several Series of Compounds.

Pierrat, et al, "Solid Phase Synthesis of Pyridine-Based Derivatives from a 2-Chloro-5-Bromopyridine Scaffold," .J Comb. Chem. (2005) 7 (6): 879-886.

Pluk, et al., "Autoinhibition of c-Abl," Cell (Jan. 25, 2002) vol. 108, pp. 247-259.

Ponzetto, et al., "A Novel Recognition Motif for Phosphatidylinositol 3-Kinase Binding Mediates Its Association with the Hepatocyte Growth Factor/Scatter Factor Receptor", Molecular and Cellular Bioloav, 13(8):4600-4608 (1993).

Raimbaul T, et al., "Effects of pH and KCl on the Conformations of Creatine Kinase from Rabbit Muscle", Eur. J. Biochem., 234:570-578 (1995).

Ranatunge, et al, "Synthesis and Selective Cyclooxygenase-2 Inhibitory Activity of a Series of Novel, Nitric Oxide Donor-Containing Pyrazoles," J Med Chem. (2004) 47: 2180-2193.

Rebek, et al. "Convergent Functional Groups: Synthetic and Structural Studies", J. Am. Chem. Soc., 107:7476-7481 (1985).

Rebek, et al., "Convergent Functional Groups. 2. Structure and Selectivity in Olefin Epoxidation with Peracids", J. Org. Chem., 51:1649-1653 (1986).

Reed, et al., "Circular Dichroic Evidence for an Ordered Sequence Ligand/Binding Site Interactions in the Catalytic Reaction of the cAMP-Dependent Protein Kinase", Biochemistry, 24:2967-2973 (1985).

Regan, et al., "Pyrazole Urea-Based Inhibitors of p38 MAP Kinase: From Lead Compound to Clinical Candidate", J. Med. Chem., 45:2994-3008 (2002).

Regan, et al., "Structure-Activity Relationships of the p38a MAP Kinase Inhibitor 1-(5-tert-Butyl-2-p-tolyl-2H-pyrazol-3-yl )-3-[4-(2-morpholi n-4-yl-ethoxy)naph-thalen-1-yl]urea (BI RB 796)", J. Med. Chem., 46:4676-4686 (2003).

Rooney, et al., "Inhibitors of Gylcolic Acid Oxidase. 4-Substituted 3-Hydroxy-1 H-pyrrole-2,5-dione Derivatives", J. Med. Chem., 26(5):700-714 (1983).

Roux, et al., "ERK and p38 MAPK-Activated Protein Kinases: a Family of Protein Kinases with Diverse Biological Functions", Microbiology and Molecular Biology Reviews, 68(2):320-344 (2004).

Rowley, "A New Consistent Chromosomal Abnormality in Chronic Myelogenous Leukaemia identified by Quinacrine Flourescence and Giemsa Staining," Nature (Jun. 1, 1973) vol. 243, pp. 290-293.

Rubin, et al., "Gastrointestinal stromal tumour," The Lancet Oncology, 369(9574):1731-1741 (2007).

Russell, et al., "3-[3-(Piperdin-1-yl)propyl]indoles as Highly Selective h5-HT1D Receptor", J. Med. Chem., 42:4981-5001 (1999).

Rutkowski, et al., "Gastrointestinal stromal tumours (GIST)—2018", Oncology in Clinical Practice, 14(6):399-407 (2019).

Saiga, et al., "Consecutive Cross-Coupling of o-Phenylenedizinc Compound with Acyl and/or Aryl Halides in the Presence of Pd(0)-tris(2,4,6-trimethoxyphenyl)phosphine", Tetrahedron Letters, 41 :4629-4632 (2000).

Sakamoto, et al., "Condensed Heteroaromatic Ring Systems. XIX. Synthesis and Reactions of 5-(Tributylstannyl)soxazoles", Tetrahedron, 4 7(28):5111-5118 (1991).

Sakuma, et al., "c-kit Gene Mutations in Intracranial Germinomas", Cancer Sci, 95(9):716-720 (2004).

Salgia, "Studies on c-Kit and c-Met in Lung Cancer with Similarities to Stem Cells," Microscopy Society of America, 11(2):1-30 (2005).

Satsangi, et al., "1-(4-Substituted-thiazol-2-yl)hydatoins as Anti-inflammatory and CNS Active Agents", Pharmazie, 38:341-342 (1983).

Sawyers, "Chronic Myeloid Leukemia," The New England Journal of Medicine (Apr. 29, 1999) vol. 340, No. 17, pp. 1330-1340.

Schindler, et al., "Structural Mechanism for STI-571 Inhibition of Abelson Tyrosine Kinase." Science (Sep. 15, 2000) vol. 289, pp. 1938-1942.

(56) References Cited

OTHER PUBLICATIONS

Schlosser, et al., "Regiochemically Flexible Substitutions of Di-, Tri-, and Tetrahalopy ridines: The Trialkylsily Trick," J Org. Chem. (2005) 70: 2494-2502.

Schmidt, et al., "Germline and Somatic Mutations in the Tyrosine Kinase Domain of the MET proto-oncogene in Papillary Renal Carcinomas", Nature Genetics, 16:68-73 (1997).

Schmidt, et al., "Novel Mutations of the MET Proto-oncogene in Papillary Renal Carcinomas", Oncogene, 18:2343-2350 (1999).

Schneeweiss Mathias, et al., "The KIT and PDGFRA switch-control inhibitor DCC-2618 blocks growth and survival of multiple neoplastic cell types in advanced mastocytosis," Haematologica (2018) vol. 103, No. 5, pp. 799-809.

Schneeweiss Mathias, et al., "The Multi-Kinase Inhibitor DCC-2618 Inhibits Proliferation and Survival of Neoplastic Mast Cells and Other Cell Types Involved in Systemic Mastocytosis," Blood (2016) vol. 128, No. 22, pp. 1965.

Seimiya, et al., "Telomere Shortening and Growth Inhibition of Human Cancer Cells by Novel Synthetic Telomerase Inhibitors MST-312, MST-295, and MST-199", Molecular Cancer Therapeutics, 1:657-665 (2002).

Seminario, et al., "Theoretical Study of a Molecular Resonant Tunneling Diode", J. Am. Chem. Soc., 122:3015-3020 (2000).

Seto, et al. "2-Substituted-4-aryl-6, 7 ,8,9-tetrahydro-5/ 1-p)'Timido [ 4, 5-b] [ 1,5 Joxazocin-5-oneasastructurallynewNK1 antagonist," Biorg Nied Chem. Tea. (2005) 15: 1485-1488.

Shah, et al., "Circular Dichroic Studies of Protein Kinase C and its Interactions with Calcium and Lipid Vesicles", Biochimica et Biophysica Acta, 1119:19-26 (1992).

Banks et al., Discovery and pharmacological characterization of AZD3229, a potent KIT/PDGFR inhibitor fortreatment of gastrointestinal stromal tumors, Sci. Transl. Med. 12, (2020).

Clinical trial NCT02571036—A Safety, Tolerability and PK Study of DCC-2618 in Patients With Advanced Malignancies—clinicaltrials.gov—Dec. 16, 2015.

Clinical trial NCT02571036—A Safety, Tolerability and PK Study of DCC-2618 in Patients With Advanced Malignancies—clinicaltrials.gov—Feb. 10, 2016.

Clinical trial NCT02571036—A Safety, Tolerability and PK Study of DCC-2618 in Patients With Advanced Malignancies—clinicaltrials.gov—Nov. 3, 2015.

Clinical trial NCT02571036—A Safety, Tolerability and PK Study of DCC-2618 in Patients With Advanced Malignancies—clinicaltrials.gov—Oct. 29, 2015.

International Search Report and Written Opinion from PCT/US2020/067557, dated Apr. 23, 2021.

International Search Report and Written Opinion from PCT/US2020/067560, dated Apr. 23, 2021.

Janku F. et al, "DCC-2618, a pan KIT and PDGFR switch control inhibitor, achieves proof-of-concept in a first-in-human study," Late Breaking Abstracts, Plenary Session 6, Dec. 1, 2016, p. s4.

Lu Jiade et al., "Advanced in the targeted therapy of cancer: multi targeted Raf kinase inhibitor," China Oncology, vol. 17, No. 1, (Dec. 31, 2007), pp. 1-7.

Procenko, S.A., "Targeted Therapy in Melanoma, Gastrointestinal Stromal Tumors, Dermatofibrosarcoma Protuberans", Practical Oncology, vol. 11, No. 3, https://practical-oncology.ru/articles/196.pdf, (2010), pp. 162-170.

Reardon, D. et al., "Effect of CYP3A-inducing anti-epileptics on sorafenib exposure: results of a phase II study of sorafenib plus daily temozolomide in adults with recurrent gliosblastoma", J. Neurooncol. (2011), 101: pp. 57-66.

Reis, R. et al., "Molecular characterization of PDGFR-α/PDGF-A and c-KIT/SCF in gliosarcomas", Cellular Oncology, 2005; 27: pp. 319-326.

Remington, The Science and Practice of Pharmacy, Nineteenth Edition—1995, pp. 710-712.

STN Registry Database RN 1225278-16-9.

Tanno, F. et al., "Evaluation of Hypromellose Acetate Succinate (HPMCAS) as a Carrier in Solid Dispersions", Journal of Drug Development and Industrial Pharmacy, vol. 30, No. 1, pp. 9-17 (2004).

Vladimirova, L.U., "Usage of MEK Inhibitors in Oncology: Results and Perspectives", Modern Natural Science Successes, No. 3, https://s.natural-sciences.m/pdf/2015/3/34730.pdf., (2015), pp. 18-30.

Zustovich, F. et al., "Sorafenib plus Daily Low-dose Temozolomide for Relapsed Glioblastoma: A Phase II Study", Anticancer Research (2013), 33: pp. 3487-3494.

* cited by examiner

Fig. 1A  GIST T1 cells - 24 hr
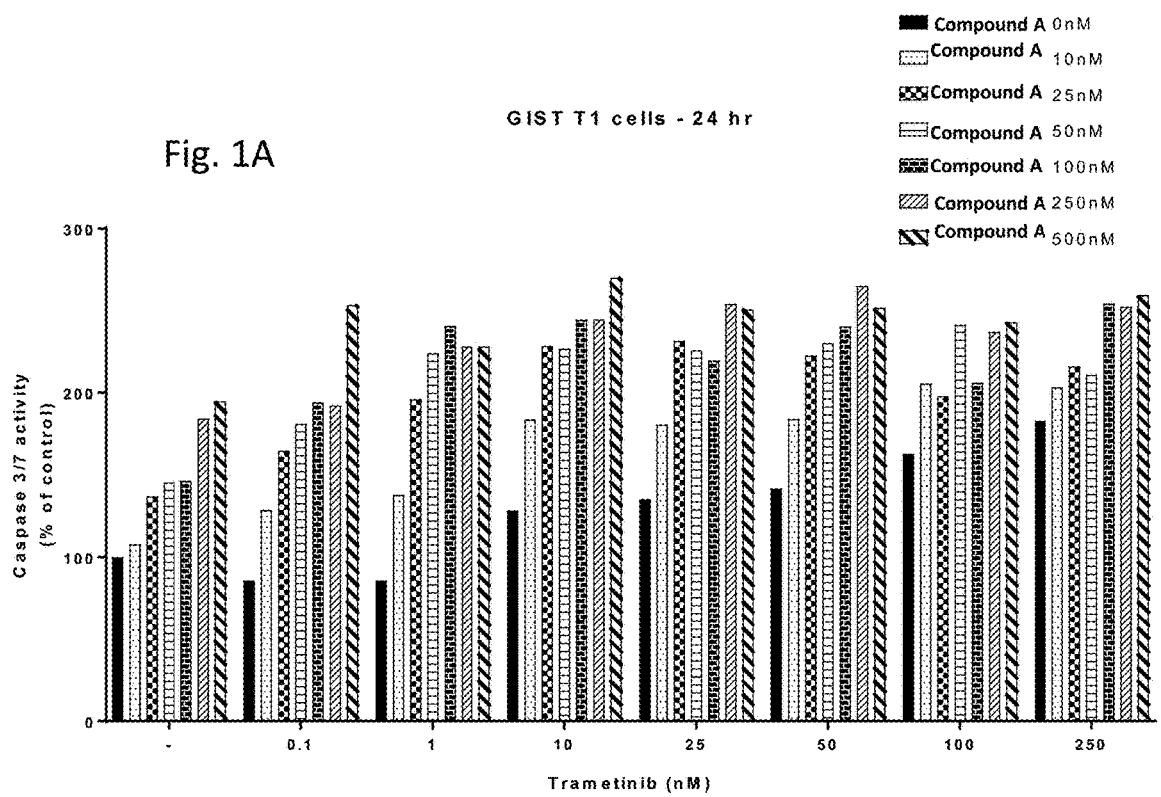
Fig. 1B  Combination index by Chou Talalay analysis
CI<1 = synergy
CI=1 = additive effect
CI>1 = antagonism
| CI | Compound A 10nM | Compound A 25nM | Compound A 50nM | Compound A 100nM | Compound A 250nM | Compound A 500nM |
|---|---|---|---|---|---|---|
| Trametinib 0.1nM | 0.41635 | 0.20181 | 0.18684 | 0.19377 | 0.53669 | 0.01446 |
| Trametinib 1nM | 0.32337 | 0.04483 | 0.01746 | 0.00975 | 0.06517 | 0.13033 |
| Trametinib 10nM | 0.04689 | 0.00672 | 0.01463 | 0.00706 | 0.01761 | 0.0012 |
| Trametinib 25nM | 0.08445 | 0.00557 | 0.01592 | 0.0473 | 0.00679 | 0.01911 |
| Trametinib 50nM | 0.1024 | 0.01154 | 0.01213 | 0.01019 | 0.00149 | 0.01747 |
| Trametinib 100nM | 0.03211 | 0.0835 | 0.00501 | 0.12226 | 0.03448 | 0.0413 |
| Trametinib 250nM | 0.07868 | 0.03424 | 0.07228 | 0.00273 | 0.00836 | 0.007 |
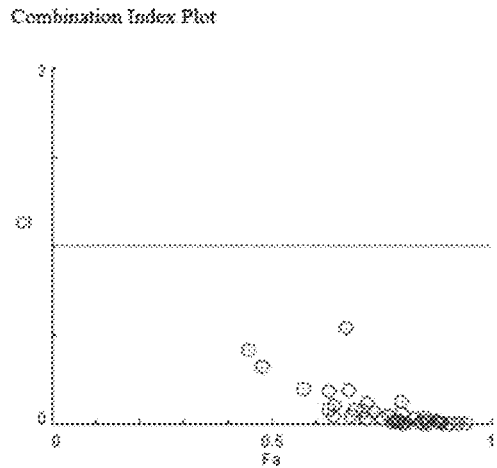

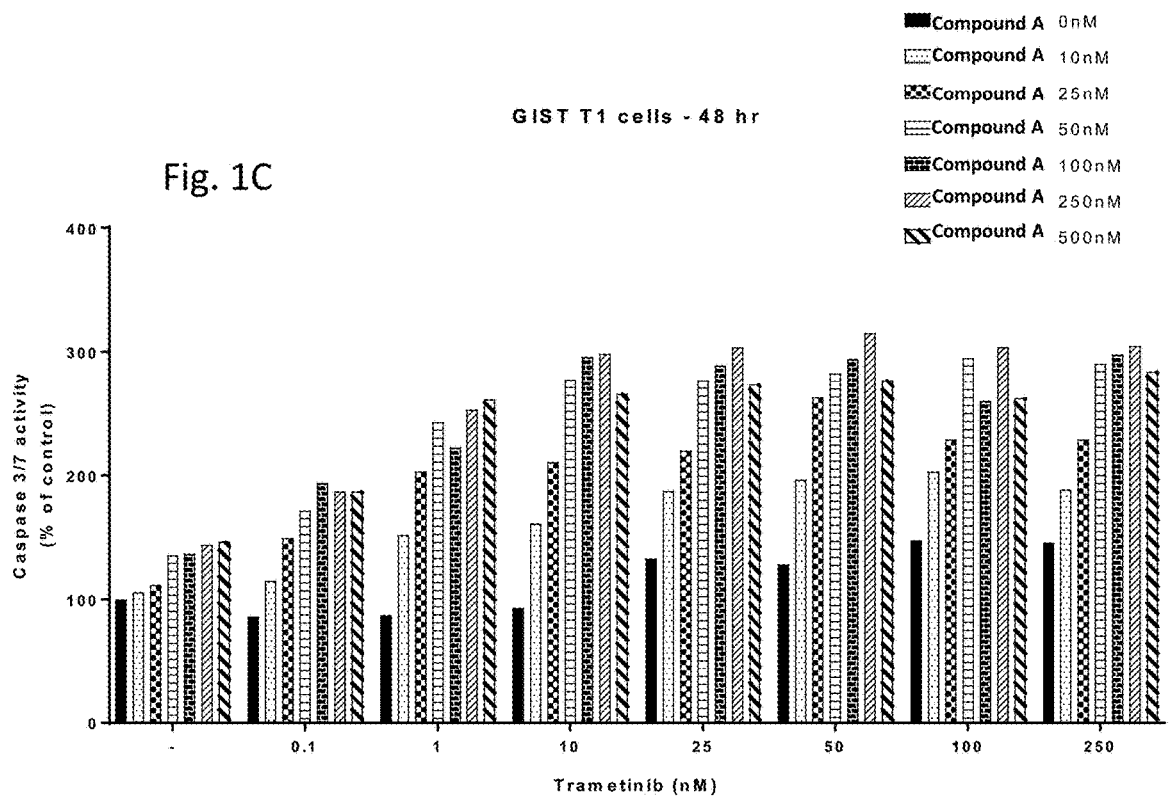
Fig. 1C
Fig. 1D Combination index by Chou Talalay analysis
| CI | Compound A 10nM | Compound A 25nM | Compound A 50nM | Compound A 100nM | Compound A 250nM | Compound A 500nM |
|---|---|---|---|---|---|---|
| Trametinib 0.1nM | 0.544 | 0.06109 | 0.01804 | 0.00494 | 0.02246 | 0.04491 |
| Trametinib 1nM | 0.02154 | 5.23E-04 | 1.55E-05 | 3.09E-04 | 2.10E-05 | 1.29E-05 |
| Trametinib 10nM | 0.01666 | 2.97E-04 | 7.82E-08 | 9.90E-10 | 9.00E-10 | 6.44E-06 |
| Trametinib 25nM | 0.0022 | 1.33E-04 | 8.55E-08 | 9.57E-09 | 5.70E-11 | 1.63E-06 |
| Trametinib 50nM | 0.00133 | 6.05E-07 | 2.55E-08 | 1.79E-09 | 1.10E-21 | 8.28E-07 |
| Trametinib 100nM | 0.00116 | 8.38E-05 | 7.50E-10 | 3.55E-06 | 5.70E-11 | 1.09E-05 |
| Trametinib 250nM | 0.01223 | 1.51E-04 | 4.04E-09 | 5.00E-10 | 3.10E-11 | 1.69E-07 |
CI<1 = synergy
CI=1 = additive effect
CI>1 = antagonism
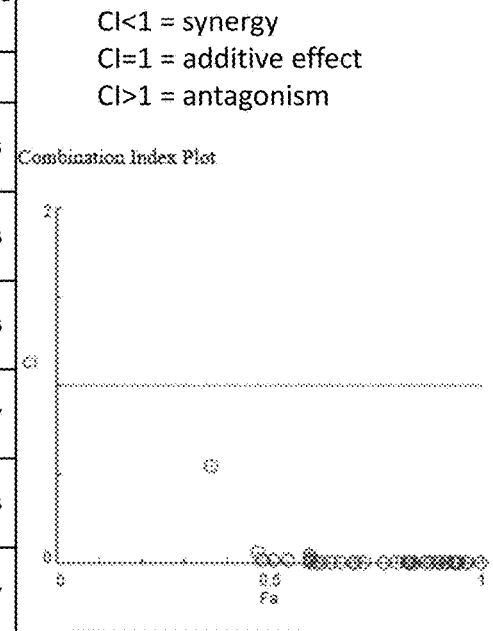

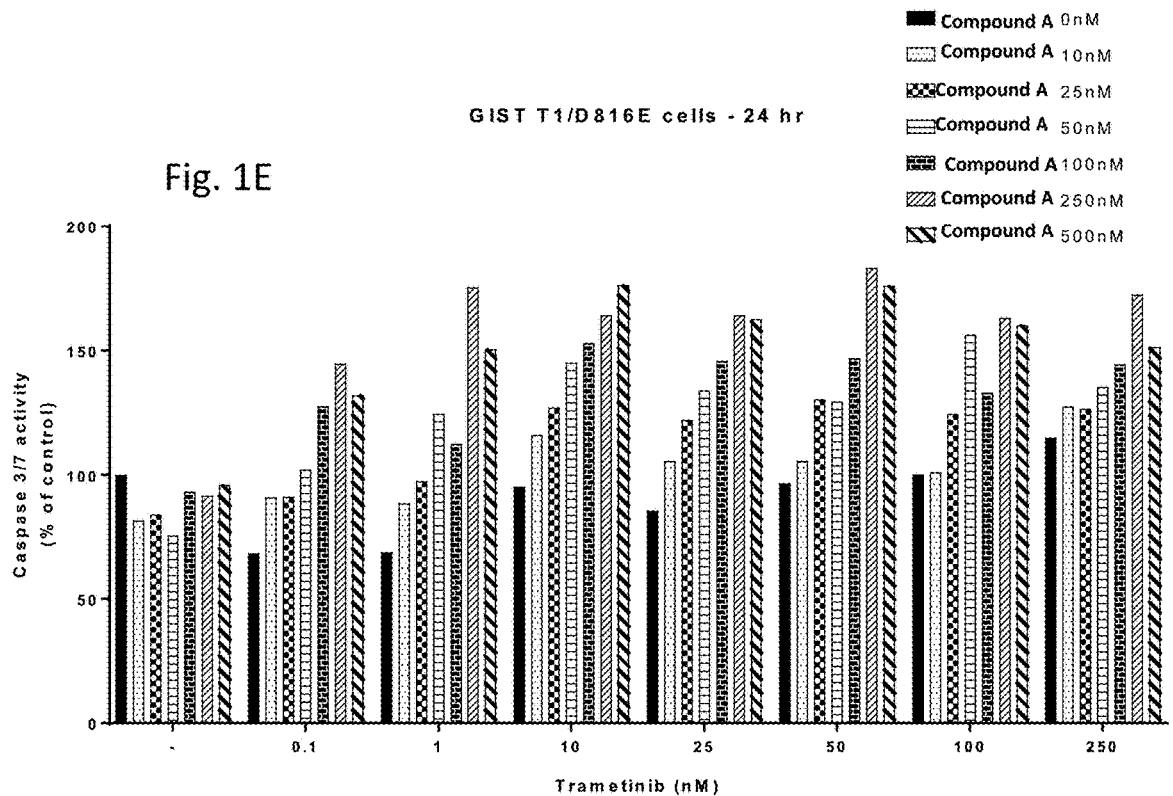
Fig. 1E
Fig. 1F  Combination index by Chou Talalay analysis
CI<1 = synergy
CI=1 = additive effect
CI>1 = antagonism
| CI index | Compound A 10nM | Compound A 25nM | Compound A 50nM | Compound A 100nM | Compound A 250nM | Compound A 500nM |
|---|---|---|---|---|---|---|
| Trametinib 0.1nM | 0.05427 | 0.11928 | 0.0195 | 0.000143 | 8.28E-06 | 0.000253 |
| Trametinib 1nM | 0.18113 | 0.0469 | 0.02853 | 0.00535 | 7.11E-08 | 8.34E-06 |
| Trametinib 10nM | 0.01105 | 0.00199 | 0.000117 | 3.21E-05 | 5.07E-06 | 5.61E-07 |
| Trametinib 25nM | 0.14462 | 0.01078 | 0.00166 | 0.000258 | 1.26E-05 | 1.64E-05 |
| Trametinib 50nM | 0.28757 | 0.00592 | 0.00668 | 0.000438 | 7.57E-07 | 2.91E-06 |
| Trametinib 100nM | 1.18272 | 0.02898 | 0.000185 | 0.00772 | 5.94E-05 | 9.92E-05 |
| Trametinib 250nM | 0.04532 | 0.05299 | 0.01351 | 0.00313 | 0.000029 | 0.00106 |
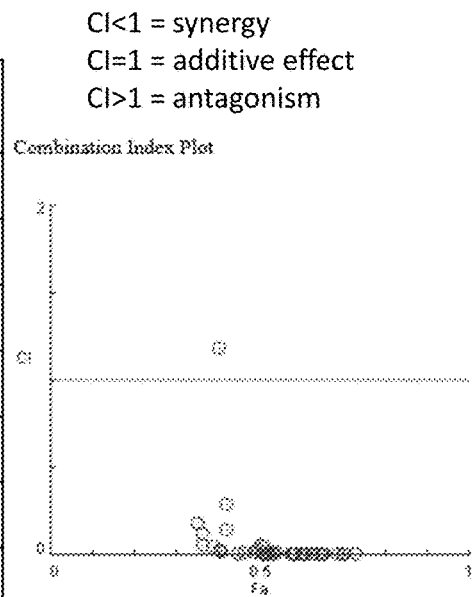

Fig. 1H  Combination index by Chou Talalay analysis

CI<1 = synergy
CI=1 = additive effect
CI>1 = antagonism

Combination Index Plot

| CI | Compound A 10nM | Compound A 25nM | Compound A 50nM | Compound A 100nM | Compound A 250nM | Compound A 500nM | Compound A 1000nM |
|---|---|---|---|---|---|---|---|
| Trametinib 1 nM | 0.89607 | 1.05715 | 1.20054 | 0.54408 | 0.42371 | 0.03244 | 0.00155 |
| Trametinib 10 nM | 1.04701 | 0.8501 | 0.32966 | 0.07514 | 0.0131 | 5.13E-04 | 1.32E-04 |
| Trametinib 25 nM | 0.74569 | 0.19466 | 0.13966 | 0.04476 | 0.01521 | 0.00128 | 3.14E-04 |
| Trametinib 50 nM | 0.63181 | 0.12923 | 0.05747 | 0.02767 | 0.00618 | 8.94E-04 | 3.39E-04 |
| Trametinib 100 nM | 0.0564 | 0.03232 | 0.01456 | 0.00513 | 0.00183 | 5.78E-05 | 4.17E-04 |
| Trametinib 250 nM | 0.05133 | 0.02117 | 0.00447 | 0.00255 | 0.00425 | 2.46E-04 | 2.20E-04 |

Compound B and trametinib in GIST-T1

Fig. 2B  Combination index by Chou Talalay analysis

| CI Index | Compound B 10nM | Compound B 25nM | Compound B 50nM | Compound B 100nM | Compound B 250nM | Compound B 500nM |
|---|---|---|---|---|---|---|
| Trametinib 1nm | 1.39845 | 0.30024 | 0.01632 | 2.30138 | 0.10126 | 0.064 |
| Trametinib 10nm | 0.02443 | 0.00825 | 6.55E-04 | 2.14E-04 | 4.87E-05 | 1.10E-04 |
| Trametinib 25nm | 0.04489 | 0.00449 | 9.92E-04 | 0.00355 | 3.69E-04 | 5.99E-04 |
| Trametinib 50nm | 0.014 | 0.0184 | 0.00206 | 7.38E-04 | 0.00246 | 7.39E-04 |
| Trametinib 100nm | 0.03929 | 0.00411 | 0.00137 | 0.00631 | 4.00E-04 | 3.70E-04 |
| Trametinib 500nm | 0.06136 | 0.00435 | 0.00244 | 4.54E-04 | 2.94E-04 | 2.15E-04 |

CI<1 = synergy
CI=1 = additive effect
CI>1 = antagonism

Fig. 2D  Combination index by Chou Talalay analysis

CI<1 = synergy
CI=1 = additive effect
CI>1 = antagonism

| CI | Compound B 10nM | Compound B 25nM | Compound B 50nM | Compound B 100nM | Compound B 250nM | Compound B 500nM |
|---|---|---|---|---|---|---|
| Trametinib 1nM | 665.864 | 0.12785 | 26.2251 | 0.45772 | 0.00161 | 0.04969 |
| Trametinib 10nM | 0.54776 | 1.20639 | 0.00454 | 4.57E-04 | 6.01E-06 | 1.07E-04 |
| Trametinib 25nM | 0.03782 | 0.0046 | 4.67E-05 | 8.93E-06 | 2.92E-06 | 2.39E-04 |
| Trametinib 50nM | 0.01217 | 4.63E-05 | 2.61E-04 | 1.36E-07 | 2.74E-08 | 9.66E-07 |
| Trametinib 100nM | 0.00188 | 0.00445 | 0.0033 | 3.10E-04 | 8.20E-08 | 3.44E-06 |
| Trametinib 500nM | 0.04614 | 0.00446 | 5.99E-04 | 4.82E-05 | 1.36E-06 | 1.23E-07 |

Fig. 2F  Combination index by Chou Talalay analysis

CI<1 = synergy
CI=1 = additive effect
CI>1 = antagonism

| CI | Compound B 1nM | Compound B 5nM | Compound B 10nM | Compound B 25nM | Compound B 50nM | Compound B 100nM | Compound B 200nM |
|---|---|---|---|---|---|---|---|
| Trametinib 1 nM | 1.14152 | 0.68225 | 1.61409 | 0.98075 | 1.71864 | 0.29552 | 0.03118 |
| Trametinib 10 nM | 2.69122 | 0.75205 | 0.55106 | 0.43683 | 0.16308 | 0.04278 | 0.0037 |
| Trametinib 25 nM | 5.2964 | 0.89005 | 0.48271 | 0.20367 | 0.05226 | 0.01535 | 7.67E-04 |
| Trametinib 50 nM | 1.55676 | 0.48782 | 0.13831 | 0.09887 | 0.02177 | 0.00642 | 6.93E-04 |
| Trametinib 100 nM | 0.95619 | 0.29266 | 0.19773 | 0.06368 | 0.01283 | 0.00935 | 0.00127 |
| Trametinib 200 nM | 0.72063 | 0.27355 | 0.09362 | 0.05242 | 0.04964 | 0.02614 | 0.0108 |

Fig. 3B  Combination index by Chou Talalay analysis

CI<1 = synergy
CI=1 = additive effect
CI>1 = antagonism

| CI | Compound A 0nM | Compound A 5nM | Compound A 10nM | Compound A 25nM | Compound A 50nM | Compound A 100nM | Compound A 250nM |
|---|---|---|---|---|---|---|---|
| Binimetinib 50 nM | 0.33162 | 0.11367 | 0.01361 | 0.03539 | 0.08336 | 0.05317 | 0.0021 |
| Binimetinib 100 nM | 0.13977 | 0.03047 | 0.02054 | 0.04202 | 0.00686 | 0.0182 | 0.00352 |
| Binimetinib 250 nM | 0.2221 | 0.00601 | 0.00355 | 0.0046 | 0.00416 | 5.34E-04 | 0.00246 |
| Binimetinib 500 nM | 0.00186 | 0.00463 | 2.11E-05 | 1.03E-05 | 1.45E-05 | 5.78E-05 | 2.16E-05 |
| Binimetinib 1000 nM | 0.00584 | 0.0022 | 4.83E-04 | 5.74E-05 | 2.16E-05 | 9.19E-07 | 5.62E-08 |
| Binimetinib 2000 nM | 0.00526 | 0.00249 | 1.18E-05 | 1.11E-04 | 1.39E-05 | 3.10E-04 | 0.00447 |
| Binimetinib 5000 nM | 0.00224 | 4.19E-04 | 3.22E-05 | 1.09E-04 | 2.53E-04 | 3.75E-05 | 2.22E-04 |

Combination Index Plot

Fig. 3D    Combination index by Chou Talalay analysis

CI<1 = synergy
CI=1 = additive effect
CI>1 = antagonism

| CI | Compound A 5nM | Compound A 10nM | Compound A 25nM | Compound A 50nM | Compound A 100nM | Compound A 250nM | Compound A 500nM |
|---|---|---|---|---|---|---|---|
| Binimetinib 50 nM | 1.44226 | 0.18041 | 0.04953 | 0.18041 | 0.04533 | 0.00368 | 2.70E-04 |
| Binimetinib 100 nM | 0.00887 | 0.04581 | 0.018 | 0.01068 | 3.28E-04 | 3.65E-04 | 9.10E-04 |
| Binimetinib 250 nM | 0.27864 | 0.16365 | 0.02359 | 0.01571 | 6.58E-04 | 2.18E-04 | 1.05E-04 |
| Binimetinib 500 nM | 0.25046 | 0.19724 | 0.0189 | 0.00118 | 2.38E-04 | 1.70E-04 | 1.06E-04 |
| Binimetinib 1000 nM | 0.19128 | 0.05539 | 0.03323 | 0.0011 | 1.63E-04 | 5.17E-04 | 0.00294 |
| Binimetinib 2000 nM | 0.91612 | 0.0148 | 0.00181 | 7.43E-05 | 3.72E-04 | 5.74E-05 | 8.87E-06 |
| Binimetinib 5000 nM | 0.4718 | 0.01468 | 0.01892 | 1.25E-05 | 7.15E-05 | 6.91E-07 | 2.20E-07 |

Combination Index Plot

Fig. 3F  Combination index by Chou Talalay analysis

CI<1 = synergy
CI=1 = additive effect
CI>1 = antagonism

| CI | Compound A 5nM | Compound A 10nM | Compound A 25nM | Compound A 50nM | Compound A 100nM | Compound A 250nM | Compound A 500nM |
|---|---|---|---|---|---|---|---|
| Binimetinib 50 nM | 0.26759 | 0.19769 | 0.97922 | 0.09229 | 0.1009 | 0.02216 | 0.00492 |
| Binimetinib 100 nM | 0.37303 | 0.26335 | 0.28329 | 0.31079 | 0.07363 | 0.01588 | 0.00691 |
| Binimetinib 250 nM | 0.27979 | 0.27979 | 0.21379 | 0.05549 | 0.02307 | 0.0121 | 0.00751 |
| Binimetinib 500 nM | 0.2403 | 0.14108 | 0.0946 | 0.04058 | 0.02056 | 0.00922 | 0.00547 |
| Binimetinib 1000 nM | 0.40206 | 0.1466 | 0.06912 | 0.01474 | 0.01722 | 0.00394 | 0.00588 |
| Binimetinib 2000 nM | 0.21654 | 0.01366 | 0.00386 | 4.15E-04 | 0.0012 | 0.00506 | 0.00572 |
| Binimetinib 5000 nM | 0.10041 | 0.05372 | 0.01007 | 3.42E-04 | 1.38E-04 | 0.00104 | 0.00569 |

Combination Index Plot

Fig. 4A

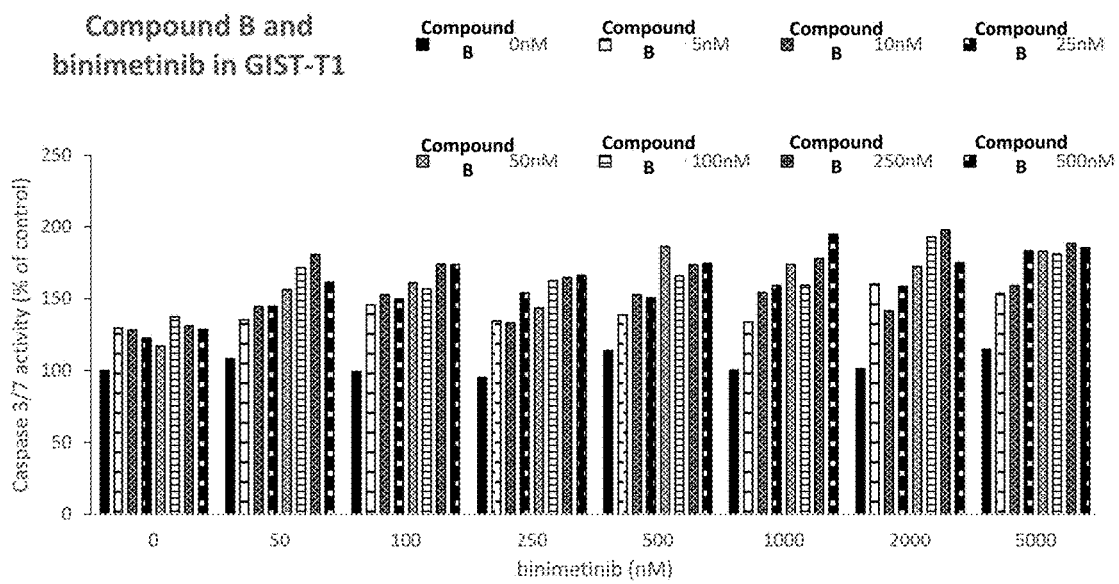

Combination index by Chou Talalay analysis

Fig. 4B

CI<1 = synergy
CI=1 = additive effect
CI>1 = antagonism

| CI | Compound B 5nM | Compound B 10nM | Compound B 25nM | Compound B 50nM | Compound B 100nM | Compound B 250nM | Compound B 500nM |
|---|---|---|---|---|---|---|---|
| Binimetinib 50 nM | 4.65E-06 | 1.70E-11 | 3.20E-11 | 4.90E-19 | 7.80E-28 | 2.00E-34 | 5.50E-22 |
| Binimetinib 100 nM | 1.40E-12 | 4.60E-17 | 1.40E-14 | 1.10E-21 | 3.70E-19 | 4.30E-29 | 5.80E-29 |
| Binimetinib 250 nM | 1.39E-05 | 1.87E-04 | 1.80E-17 | 3.80E-10 | 4.30E-22 | 4.00E-23 | 5.50E-24 |
| Binimetinib 500 nM | 4.02E-08 | 5.20E-17 | 2.20E-17 | 4.50E-39 | 1.40E-23 | 4.00E-28 | 8.40E-29 |
| Binimetinib 1000 nM | 4.15E-05 | 1.80E-17 | 7.80E-20 | 5.80E-28 | 6.50E-20 | 3.80E-31 | 4.10E-54 |
| Binimetinib 2000 nM | 5.10E-20 | 1.44E-09 | 3.00E-19 | 7.20E-27 | 3.00E-49 | 7.20E-68 | 1.80E-28 |
| Binimetinib 5000 nM | 1.30E-16 | 4.80E-19 | 4.90E-35 | 1.20E-34 | 5.80E-33 | 7.00E-41 | 3.70E-37 |

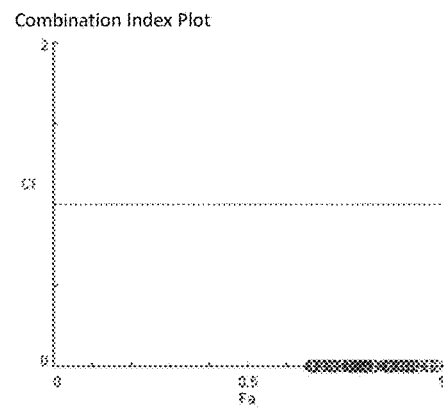

Combination Index Plot

Fig. 4C

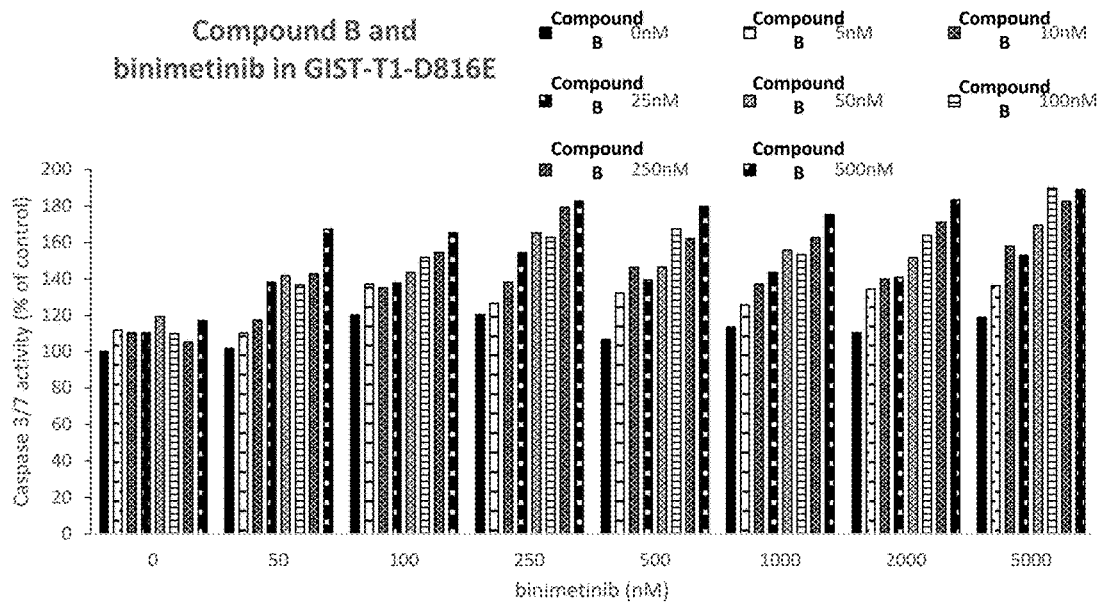

Fig. 4D  Combination index by Chou Talalay analysis

CI<1 = synergy
CI=1 = additive effect
CI>1 = antagonism

| CI | Compound B 5nM | Compound B 10nM | Compound B 25nM | Compound B 50nM | Compound B 100nM | Compound B 250nM | Compound B 500nM |
|---|---|---|---|---|---|---|---|
| Binimetinib 50 nM | 1606.78 | 0.00356 | 9.50E-11 | 3.40E-12 | 3.40E-10 | 1.10E-12 | 9.80E-25 |
| Binimetinib 100 nM | 4.70E-10 | 2.81E-09 | 2.70E-10 | 1.20E-12 | 2.60E-16 | 1.60E-17 | 3.19E-23 |
| Binimetinib 250 nM | 9.63E-06 | 4.80E-10 | 3.90E-17 | 1.00E-22 | 1.80E-21 | 6.80E-33 | 3.20E-36 |
| Binimetinib 500 nM | 1.64E-07 | 4.10E-13 | 3.20E-10 | 3.30E-13 | 9.80E-24 | 1.00E-20 | 5.80E-33 |
| Binimetinib 1000 nM | 8.87E-05 | 4.71E-09 | 1.20E-11 | 3.30E-17 | 5.90E-16 | 9.50E-21 | 6.10E-29 |
| Binimetinib 2000 nM | 9.56E-08 | 8.80E-10 | 2.90E-10 | 6.50E-15 | 4.00E-21 | 1.40E-25 | 5.70E-36 |
| Binimetinib 5000 nM | 4.83E-08 | 1.70E-17 | 4.50E-15 | 4.00E-24 | 3.00E-44 | 6.30E-35 | 6.30E-43 |

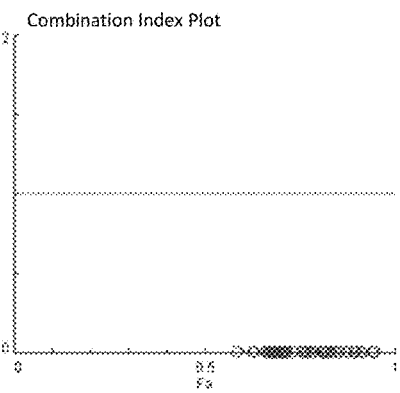

Combination Index Plot

Fig. 4F  Combination index by Chou Talalay analysis

CI<1 = synergy
CI=1 = additive effect
CI>1 = antagonism

| CI | Compound B 5nM | Compound B 10nM | Compound B 25nM | Compound B 50nM | Compound B 100nM | Compound B 250nM | Compound B 500nM |
|---|---|---|---|---|---|---|---|
| Binimetinib 50 nM | 0.34963 | 0.16862 | 0.17353 | 1.08713 | 0.15037 | 0.00828 | 4.63E-04 |
| Binimetinib 100 nM | 0.0904 | 0.03897 | 0.10661 | 0.07671 | 0.06878 | 0.00101 | 3.34E-04 |
| Binimetinib 250 nM | 0.13837 | 0.10561 | 0.07858 | 0.01969 | 0.00238 | 3.25E-04 | 2.35E-05 |
| Binimetinib 500 nM | 0.0897 | 0.02509 | 0.00754 | 0.00476 | 1.96E-04 | 1.17E-05 | 3.46E-05 |
| Binimetinib 1000 nM | 0.06371 | 0.00878 | 0.00298 | 2.52E-04 | 7.39E-06 | 2.35E-06 | 2.08E-05 |
| Binimetinib 2000 nM | 0.02182 | 0.00631 | 8.43E-05 | 2.32E-05 | 6.49E-06 | 3.90E-06 | 8.47E-06 |
| Binimetinib 5000 nM | 1.21E-04 | 1.26E-04 | 4.19E-05 | 7.69E-07 | 1.09E-07 | 3.77E-07 | 5.71E-06 |

Combination Index Plot

Fig. 5B  Combination index by Chou Talalay analysis

CI<1 = synergy
CI=1 = additive effect
CI>1 = antagonism

| CI | Compound A 1nM | Compound A 10nM | Compound A 25nM | Compound A 50nM | Compound A 100nM | Compound A 200nM | Compound A 500nM | Compound A 1000nM |
|---|---|---|---|---|---|---|---|---|
| Cobimetinib 1 nM | 0.79708 | 1.31592 | 0.55315 | 0.75613 | 0.30708 | 0.04872 | 0.09745 | 0.42662 |
| Cobimetinib 10 nM | 0.0855 | 0.0977 | 0.01338 | 0.02833 | 0.00855 | 0.0069 | 0.02772 | 0.00822 |
| Cobimetinib 25 nM | 3.4939 | 0.09192 | 0.01338 | 0.08493 | 0.0949 | 0.04362 | 0.03441 | 0.06882 |
| Cobimetinib 50 nM | 0.50545 | 0.00754 | 0.00461 | 0.00363 | 0.00107 | 0.00621 | 0.00138 | 0.00249 |
| Cobimetinib 100 nM | 0.34962 | 0.0678 | 0.01067 | 9.52E-04 | 0.00223 | 2.74E-04 | 3.13E-04 | 4.17E-04 |
| Cobimetinib 250 nM | 0.08223 | 8.55E-04 | 8.95E-05 | 5.31E-06 | 2.27E-05 | 3.37E-04 | 3.47E-04 | 0.00122 |
| Cobimetinib 500 nM | 0.04575 | 0.00305 | 4.76E-04 | 4.33E-04 | 1.04E-04 | 0.00135 | 0.00271 | 4.62E-04 |

Combination Index Plot

Fig. 5D  Combination index by Chou Talalay analysis

CI<1 = synergy
CI=1 = additive effect
CI>1 = antagonism

| CI | Compound A 1nM | Compound A 10nM | Compound A 25nM | Compound A 50nM | Compound A 100nM | Compound A 200nM | Compound A 500nM | Compound A 1000nM |
|---|---|---|---|---|---|---|---|---|
| Cobimetinib 1 nM | 0.18534 | 438.696 | 4.76549 | 0.02461 | 0.03479 | 0.00915 | 0.02461 | 0.08008 |
| Cobimetinib 10 nM | 0.23568 | 0.04233 | 0.03138 | 0.00324 | 0.00193 | 3.04E-04 | 1.35E-04 | 3.08E-05 |
| Cobimetinib 25 nM | 1.17886 | 0.94861 | 0.0607 | 0.00882 | 0.00598 | 4.44E-04 | 0.00129 | 3.77E-05 |
| Cobimetinib 50 nM | 2.46263 | 0.79943 | 1.28476 | 0.00963 | 0.00227 | 0.01361 | 0.00259 | 0.01248 |
| Cobimetinib 100 nM | 10.3649 | 1.46703 | 0.09078 | 0.00705 | 4.08E-04 | 0.00675 | 0.01549 | 0.00135 |
| Cobimetinib 250 nM | 2.28677 | 0.60705 | 1.15264 | 0.15427 | 0.09612 | 0.25807 | 0.04413 | 0.06806 |
| Cobimetinib 500 nM | 5.42979 | 11.784 | 0.20954 | 1.11463 | 0.33621 | 0.30855 | 0.56228 | 0.30855 |

Combination Index Plot

Fig. 5E

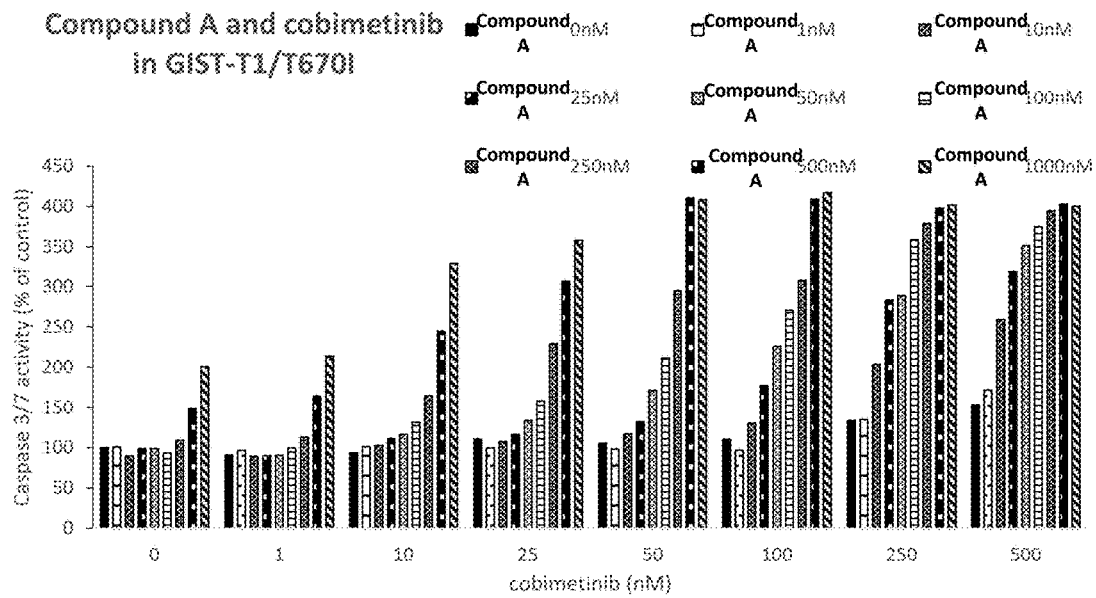

Fig. 5F

Combination index by Chou Talalay analysis

| CI | Compound A 1nM | Compound A 10nM | Compound A 25nM | Compound A 50nM | Compound A 100nM | Compound A 200nM | Compound A 500nM | Compound A 1000nM |
|---|---|---|---|---|---|---|---|---|
| Cobimetinib 1 nM | 0.26554 | 2.67726 | 5.76653 | 10.5467 | 7.71672 | 4.89163 | 0.13285 | 0.0072 |
| Cobimetinib 10 nM | 0.9985 | 1.33769 | 0.84391 | 0.86036 | 0.39351 | 0.06559 | 4.54E-04 | 2.51E-06 |
| Cobimetinib 25 nM | 2.8673 | 1.43276 | 0.75657 | 0.22264 | 0.04996 | 6.46E-04 | 6.27E-06 | 2.47E-07 |
| Cobimetinib 50 nM | 6.77934 | 0.90654 | 0.2524 | 0.01232 | 0.00104 | 7.27E-06 | 8.00E-10 | 1.99E-09 |
| Cobimetinib 100 nM | 16.1737 | 0.4255 | 0.00853 | 2.79E-04 | 1.89E-05 | 3.10E-06 | 9.50E-10 | 7.40E-10 |
| Cobimetinib 250 nM | 0.62392 | 0.0019 | 5.23E-06 | 4.56E-06 | 3.00E-08 | 1.07E-08 | 3.20E-09 | 4.13E-09 |
| Cobimetinib 500 nM | 0.04617 | 5.14E-05 | 5.56E-07 | 4.53E-08 | 1.19E-09 | 2.52E-09 | 1.94E-09 | 5.19E-09 |

CI<1 = synergy
CI=1 = additive effect
CI>1 = antagonism

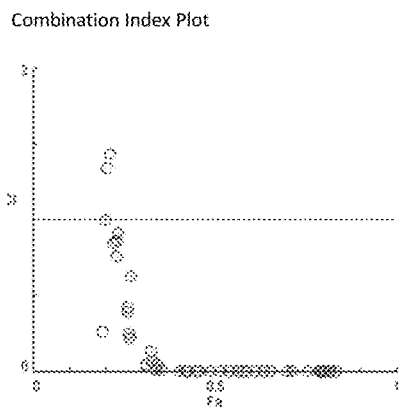

Combination Index Plot

Combination index by Chou Talalay analysis

CI<1 = synergy
CI=1 = additive effect
CI>1 = antagonism

| CI | Compound B 1nM | Compound B 10nM | Compound B 25nM | Compound B 50nM | Compound B 100nM | Compound B 200nM | Compound B 500nM |
|---|---|---|---|---|---|---|---|
| Cobimetinib 10nM | 0.56205 | 1.23447 | 0.95172 | 0.33923 | 0.8499 | 0.57466 | 0.05953 |
| Cobimetinib 25nM | 0.37301 | 0.08307 | 0.01254 | 0.01607 | 0.000825 | 0.00764 | 0.00181 |
| Cobimetinib 50nM | 1.76547 | 0.06105 | 0.00477 | 0.01282 | 0.000975 | 0.00158 | 0.0002 |
| Cobimetinib 100nM | 0.17549 | 0.00644 | 0.0073 | 0.000551 | 0.00193 | 1.34E-05 | 2.54E-05 |
| Cobimetinib 200nM | 0.3168 | 0.01266 | 0.000656 | 0.000703 | 0.00317 | 0.00249 | 0.000126 |
| Cobimetinib 500nM | 0.00186 | 0.000613 | 4.14E-06 | 0.000144 | 0.000251 | 0.000131 | 8.3E-07 |

Combination index by Chou Talalay analysis

CI<1 = synergy
CI=1 = additive effect
CI>1 = antagonism

| CI | Compound B 1nM | Compound B 10nM | Compound B 25nM | Compound B 50nM | Compound B 100nM | Compound B 200nM | Compound B 500nM |
|---|---|---|---|---|---|---|---|
| Cobimetinib 10 nM | 1.78658 | 1.4423 | 33.0169 | 1.15037 | 7.15955 | 0.03569 | 0.000619 |
| Cobimetinib 25 nM | 0.37205 | 0.54877 | 0.09771 | 7.19E-05 | 0.000137 | 0.000781 | 3.5E-07 |
| Cobimetinib 50 nM | 0.12042 | 0.36756 | 0.0391 | 8.29E-05 | 2.14E-07 | 6.79E-06 | 7.2E-10 |
| Cobimetinib 100 nM | 0.24051 | 0.09661 | 2.61E-05 | 1.04E-05 | 4.2E-10 | 2.11E-08 | 1.07E-09 |
| Cobimetinib 200 nM | 1.00074 | 0.03502 | 3.02E-05 | 1.47E-05 | 1.8E-11 | 3.89E-08 | 2.34E-09 |
| Cobimetinib 500 nM | 0.1855 | 0.000379 | 4.48E-05 | 1.86E-08 | 4.1E-12 | 1.8E-10 | 3.97E-09 |

Combination Index Plot

Combination index by Chou Talalay analysis

CI<1 = synergy
CI=1 = additive effect
CI>1 = antagonism

| CI | Compound B 1nM | Compound B 5nM | Compound B 10nM | Compound B 25nM | Compound B 50nM | Compound B 100nM | Compound B 200nM |
|---|---|---|---|---|---|---|---|
| Cobimetinib 1nM | 0.41369 | 3.735 | 1.55347 | 21.4235 | 6.74637 | 0.24978 | 0.00783 |
| Cobimetinib 10nM | 1.03215 | 0.85167 | 0.54699 | 0.59718 | 0.05047 | 0.00877 | 6.73E-05 |
| Cobimetinib 25nM | 1.09419 | 0.2284 | 0.22022 | 0.04847 | 0.0152 | 3.62E-04 | 1.23E-07 |
| Cobimetinib 50nM | 3.39319 | 0.55609 | 0.29001 | 0.01725 | 0.00105 | 8.66E-07 | 3.52E-09 |
| Cobimetinib 100nM | 1.04878 | 0.40707 | 0.02628 | 5.35E-04 | 9.31E-06 | 8.64E-08 | 5.25E-09 |
| Cobimetinib 200nM | 1.33157 | 0.00418 | 9.39E-05 | 5.03E-06 | 2.57E-07 | 1.63E-08 | 6.70E-09 |
| Cobimetinib 500nM | 0.10996 | 4.48E-04 | 1.11E-05 | 9.15E-08 | 2.16E-06 | 5.98E-08 | 8.60E-10 |

Combination Index Plot

Combination index by Chou Talalay analysis

CI<1 = synergy
CI=1 = additive effect
CI>1 = antagonism

| CI | Compound A 5nM | Compound A 5nM | Compound A 10nM | Compound A 25nM | Compound A 50nM | Compound A 100nM | Compound A 200nM | Compound A 500nM | Compound A 1000nM |
|---|---|---|---|---|---|---|---|---|---|
| Ulixertinib 50nM | 397033 | 12152.7 | 0.29353 | 2.00594 | 3.73337 | 2.73202 | 6.357 | 0.83994 | 0.143 |
| Ulixertinib 100nM | 15.0853 | 1.23598 | 7.30524 | 4.9472 | 4.97932 | 12.3642 | 0.67675 | 0.13312 | 0.57025 |
| Ulixertinib 250nM | 1.3E+11 | 1.29932 | 1.48118 | 4.60126 | 9.20222 | 16.5094 | 1.16864 | 0.67302 | 0.1129 |
| Ulixertinib 500nM | 0.14288 | 0.18202 | 0.0261 | 0.44394 | 0.06984 | 0.60244 | 0.12257 | 0.0243 | 0.00367 |
| Ulixertinib 1000nM | 0.05213 | 0.92137 | 0.30425 | 0.6357 | 0.13049 | 0.16799 | 0.10139 | 0.02333 | 6.50E-04 |
| Ulixertinib 2000nM | 9233.7 | 1.87274 | 70.9971 | 0.84709 | 3.23328 | 1.15347 | 0.03718 | 1.43611 | 0.00291 |
| Ulixertinib 5000nM | 0.7266 | 0.43113 | 274131 | 1.73715 | 3.87011 | 0.50263 | 0.67675 | 1.12708 | 0.0448 |

Combination Index Plot

Fig. 7D Combination index by Chou Talalay analysis

CI<1 = synergy
CI=1 = additive effect
CI>1 = antagonism

| CI | Compound A 5nM | Compound A 10nM | Compound A 25nM | Compound A 50nM | Compound A 100nM | Compound A 200nM | Compound A 500nM |
|---|---|---|---|---|---|---|---|
| Ulixertinib 50nM | 1.31834 | 3.57672 | 2.90308 | 5.56256 | 3.88493 | 1.36233 | 0.3461 |
| Ulixertinib 100nM | 1.10711 | 3.91925 | 1.11824 | 5.40429 | 0.75024 | 0.75332 | 0.00559 |
| Ulixertinib 250nM | 17.7013 | 8.33131 | 4.13239 | 2.71447 | 0.87632 | 0.19479 | 9.19E-04 |
| Ulixertinib 500nM | 175.181 | 27.9521 | 1.87828 | 0.83106 | 0.68648 | 0.11088 | 0.00217 |
| Ulixertinib 1000nM | 87.5534 | 27.0813 | 11.9376 | 3.57 | 0.14557 | 0.013 | 1.83E-04 |
| Ulixertinib 2000nM | 2.74177 | 0.20886 | 3.54357 | 0.1633 | 0.01821 | 0.00135 | 6.21E-05 |
| Ulixertinib 5000nM | 0.02425 | 0.00614 | 0.01896 | 0.01184 | 0.00199 | 2.93E-04 | 9.86E-06 |

Combination Index Plot

GIST-T1

2 wk drug treatment, 9 day recovery

GIST-T1/D816E 2 wk drug treatment, 10 day recovery

Imatinib/Compound A in GIST-T1/D816E cells

GIST-T1/D816E

Fig. 8D    GIST-T1/T670I 2 wk drug treatment, 10 day recovery

Fig. 9B    GIST-T1/D816E
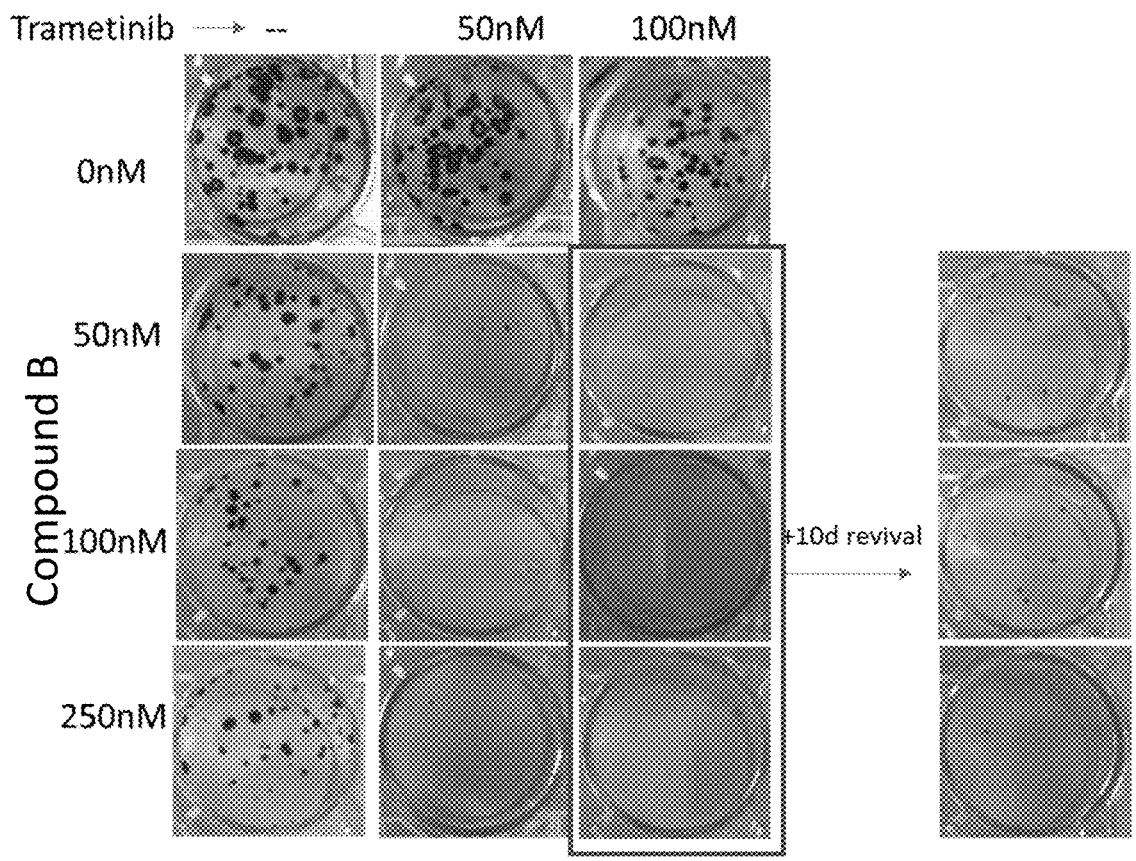
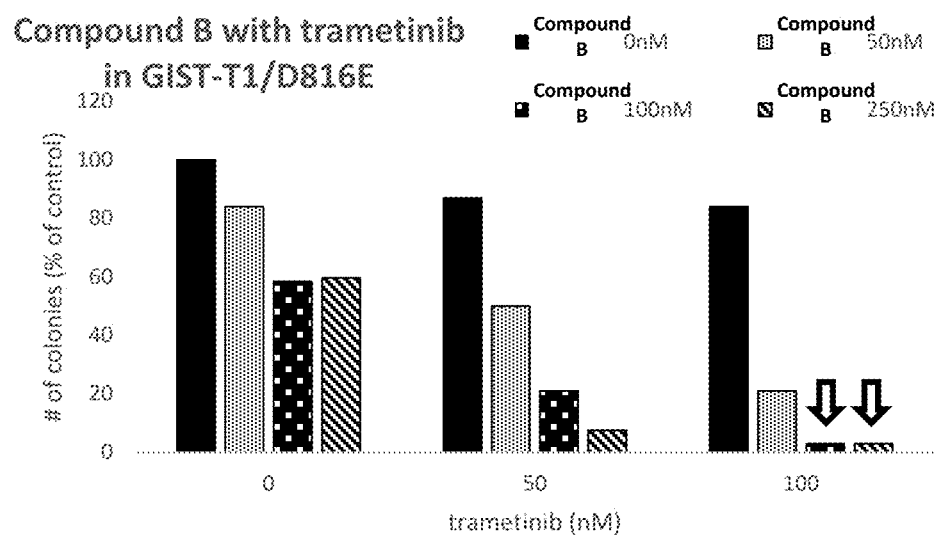

GIST-T1/T670I

Fig. 11C  GIST-T1/T670I
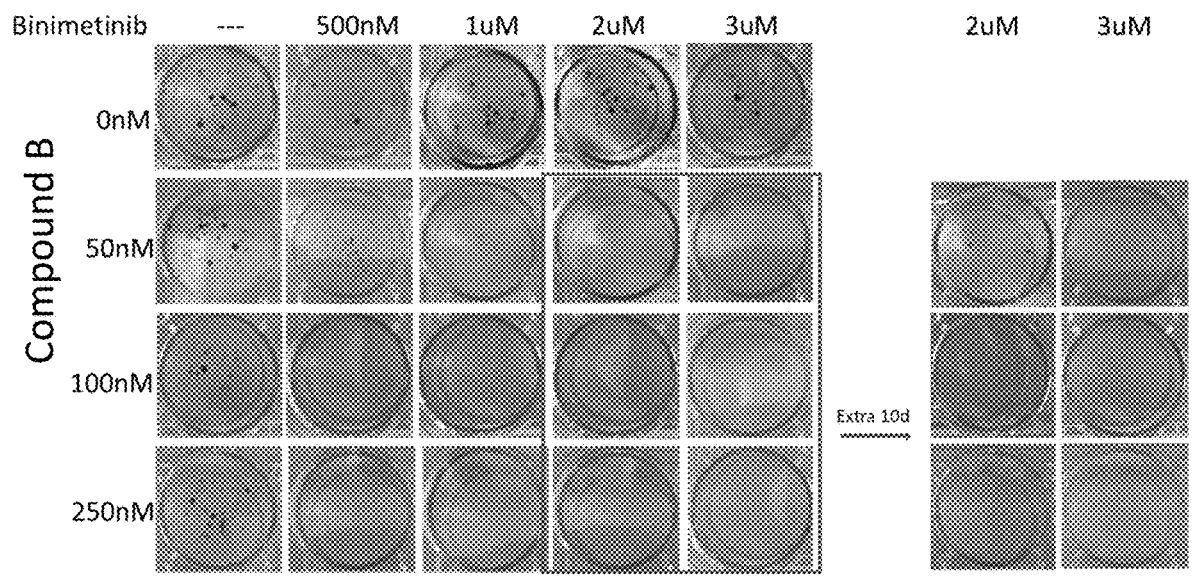
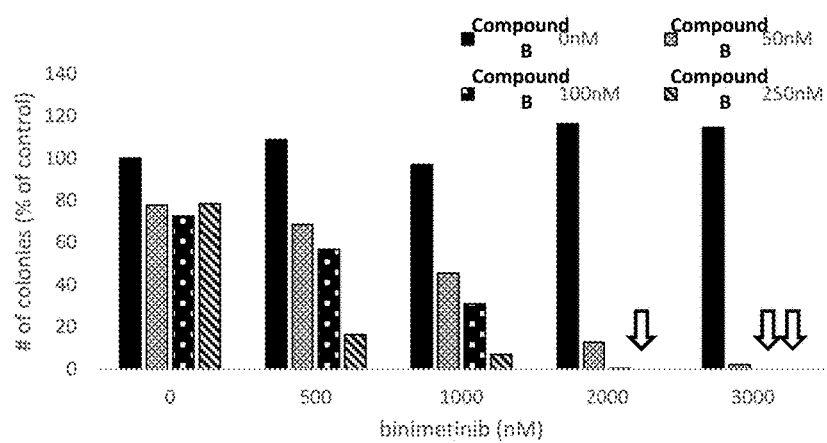
Compound B and binimetinib in GIST-T1/T670I Fig. 13B      GIST-T1/D816E
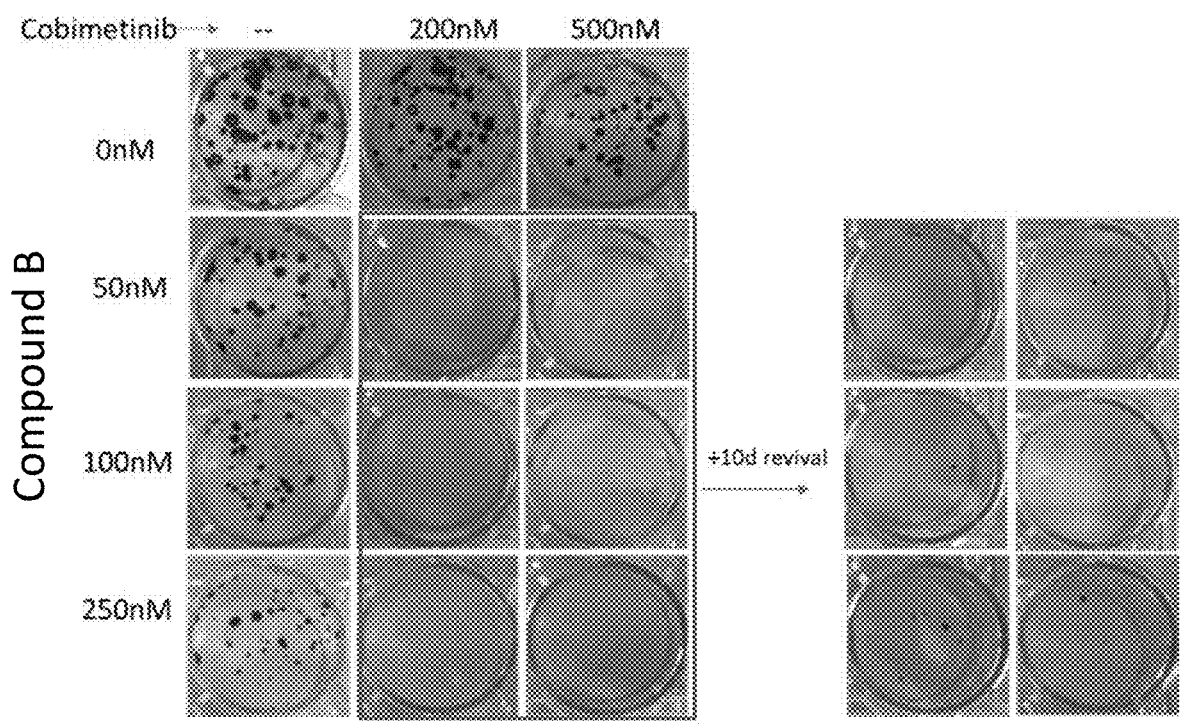
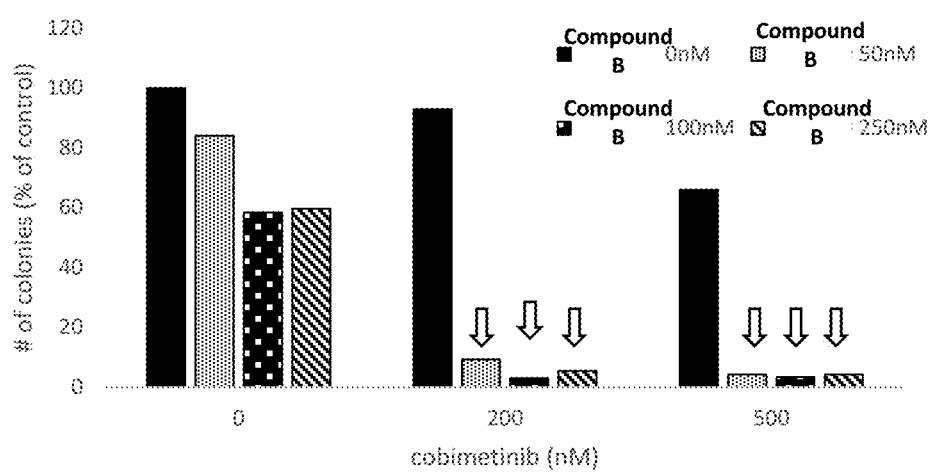

GIST-T1/T670I

Fig. 16D
Fig. 16E
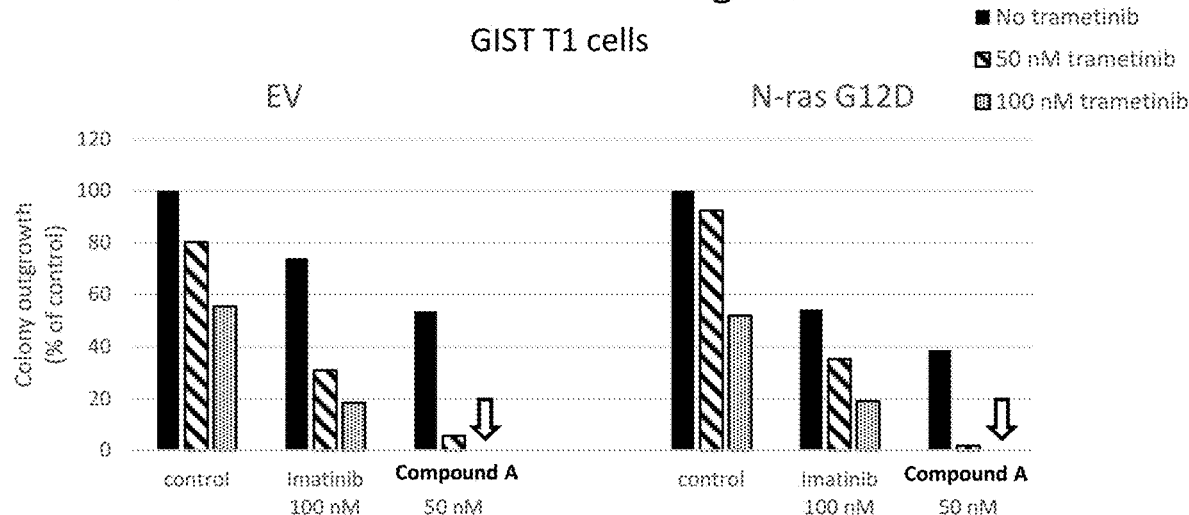
Fig. 16F
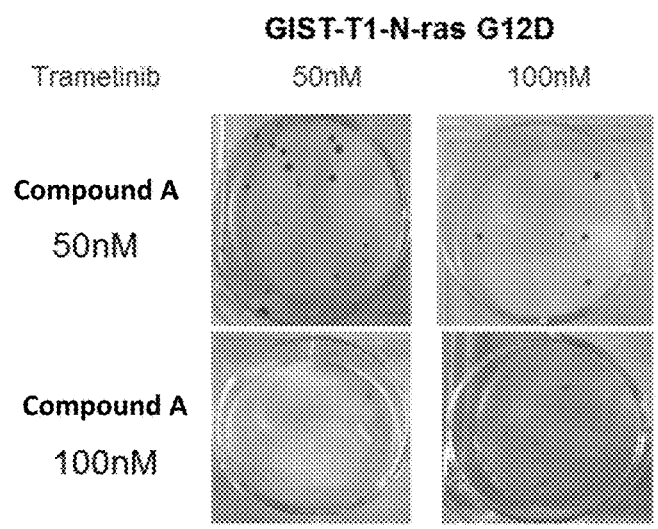

COMBINATION THERAPY FOR THE TREATMENT OF GASTROINTESTINAL STROMAL TUMOR

CROSS-REFERENCE TO RELATED APPLICATIONS

This application is a continuation of International Application Number PCT/US2019/016148 filed Jan. 31, 2019, which claims priority to U.S. Ser. No. 62/624,448 filed Jan. 31, 2018, the contents of which are incorporated herein by reference in their entirety.

BACKGROUND c-KIT (also known as KIT, CD117, and stem cell factor receptor) is a 145 kDa transmembrane tyrosine kinase protein that acts as a type-III receptor. The c-KIT proto-oncogene, located on chromosome 4q11-21, encodes the c-KIT receptor, whose ligand is the stem cell factor (SCF, steel factor, kit ligand, mast cell growth factor). The receptor has tyrosine-protein kinase activity, and binding of the ligand SCF leads to the autophosphorylation of c-KIT and its association with substrates such as phosphatidylinositol 3-kinase (PI3K). Tyrosine phosphorylation by protein tyrosine kinases is of particular importance in cellular signaling and can mediate signals for major cellular processes, such as proliferation, survival, differentiation, apoptosis, attachment, invasiveness and migration.

The role of c-KIT expression and activity has been studied in hematologic and solid tumors, such as acute leukemias and gastrointestinal stromal tumors (GISTs). Most GISTs have primary activating mutations in the genes encoding the closely related RTKs c-KIT (75-80% of GIST) or PDGFRα (8% of the non-c-KIT mutated GIST), and gain-of-function mutations of the c-KIT gene and the expression of constitutively phosphorylated c-KIT are found in many GIST. The majority of primary GIST-causing c-KIT mutations affect the juxtamembrane (JM) region of the protein encoded by exon 11 and consist of in-frame deletions or insertions, or missense mutations (i.e., V560D). c-KIT exon 11 mutations have been identified as primary mutations in approximately 65% of GISTs. Such JM domain mutations disrupt the autoinhibition mechanism of c-KIT kinase, leading to constitutive kinase activity and cell-transforming events causative of GIST. Other primary GIST-causing c-KIT mutations are located in exon 9 (AY501-502 duplication/insertion, 8%), exon 13 (mutation, 1%), and exon 17 (mutation, 1%).

The clinical importance of c-KIT expression in malignant tumors was demonstrated in studies with Gleevec® (imatinib mesylate, STI571 (signal transduction inhibitor number 571), Novartis Pharma AG Basel, Switzerland), which specifically inhibits tyrosine kinase receptors. Moreover, a clinically relevant breakthrough has been the finding of anti-tumor effects of this compound in GIST, a group of tumors regarded as being generally resistant to conventional chemotherapy. However, while major responses were seen after first-line treatment of GIST with Gleevec®, an inhibitor of c-KIT, and a substantial number of patients with metastatic and/or inoperable GIST benefit from treatment with Gleevec®, complete tumor remissions are rare, and about 50% of patients experience disease recurrence within two years of treatment. It has also been reported that a combination of the c-KIT inhibitor imatinib and the MEK kinase inhibitor MEK162 resulted in an increased growth suppression in vitro and tumor regression in vivo in various GIST cancer cell lines compared to treatment with either single agent.

GIST most often become Gleevec® resistant, and molecularly targeted small molecule therapies that target c-KIT secondary mutations remain elusive. GIST patients who relapse after treatment with Gleevec® or Sutent® have disease still driven by c-KIT mutations. These secondary mutations occur on the same alleles as the primary JM-region mutation, and thus represent even more aggressive activated forms of c-KIT than the original primary mutation. These secondary mutants of c-KIT identified in GIST lead to acquired drug resistance. Secondary mutations are found in the ATP binding pocket (exon 13, i.e. K642E, V654A; exon 14, i.e. T670I), and activation loop (exon 17, i.e. N822K, D816H, D816V, D820A; exon 18 A829P). These various secondary c-KIT mutations have been reported: Sunitinib malate (Sutent™, Pfizer) is an inhibitor of multiple RTKs, notably in this context, c-KIT and PDGFRα, and has been shown to be effective against certain imatinib-resistant c-KIT mutants, such as the ATP-binding pocket mutants V654A and T670I. Certain Gleevec®-resistant mutants are also resistant to sunitinib, such as D816H and D816V which are located in the activation loop of the c-KIT catalytic domain encoded by exon 17. Median survival after progression due to Gleevec®-resistance remains relatively short.

It has been demonstrated that complex, multiple secondary c-KIT mutations can arise and vary within individual patients, such variation in mutational status of c-KIT being demonstrated by biopsy samples obtained from different progressing metastases within each patient. The complex c-KIT mutational heterogeneity within individual patients underscores an unmet medical need to identify inhibitors of c-KIT kinase that are effective across a broad spectrum of c-KIT primary and secondary mutations. In addition, there is a need to identify therapies that are cytotoxic, or cytocidal, to c-KIT-mediated GISTs, as opposed to merely being cytostatic, and which result in disease remission and/or reduced disease recurrence.

SUMMARY

The instant disclosure is drawn to the combination of the c-KIT inhibitor Compound A or the c-KIT inhibitor Compound B with an inhibitor of the MAPKAP kinase signaling pathway. Herein, the MAPKAP pathway is defined as the signaling through the kinases RAF→MEK→ERK. It has been unexpectedly demonstrated that combination of the c-KIT inhibitor Compound A or Compound B with a MEK inhibitor, including trametinib, an ERK inhibitor including ulixertinib, or a RAF inhibitor including LY3009120 leads to cell death, apoptosis, or prolonged cell stasis of GIST cells, enhanced GIST tumor regression in vivo, or eradication of GIST cells in colony formation assays as compared to a combination of imatinib with a MEK inhibitor or to single agent treatment with Compound A, imatinib, or a MEK inhibitor. Additionally it has been demonstrated that combination of the c-KIT inhibitor Compound A with a MEK inhibitor leads to enhanced cell death or apoptosis and eradication of GIST cancer cell lines that are resistant to imatinib in combination with a MEK inhibitor. In colony outgrowth studies in GIST cells, Compound A exhibited superior synergy in combination with a MEK inhibitor compared to imatinib in combination with a MEK inhibitor. This disclosure, in part, relates to methods of treating tumors in patients using Compound A as described herein or a pharmaceutically acceptable salt thereof.

For example, described herein is a method of treating a tumor having one or more c-KIT mutations in a patient in need thereof, comprising administering to the patient: an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof; and an effective amount of a mitogen-activated protein kinase inhibitor (MEK inhibitor) and/or an effective amount of an extracellular signal regulated kinase inhibitor (ERK inhibitor).

This disclosure also provides a method of treating a solid tumor in an imatinib resistant patient, comprising: administering to the patient an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof; and administering to the patient an effective amount of a MEK or ERK inhibitor selected from the group consisting of trametinib, binimetinib, cobimetinib, and ulixertinib wherein the solid tumor is selected from the group consisting of of lung adenocarcinoma, squamous cell lung cancer, glioblastoma, pediatric glioma, astrocytoma, sarcoma, gastrointestinal stromal tumor (GIST), and melanoma.

A method of treating an imatinib resistant gastrointestinal stromal tumor or imatinib resistant melanoma in a patient in need thereof is also contemplated herein, comprising administering to the patient an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof; and administering to the patient an effective amount of a MEK or ERK inhibitor selected from the group consisting of trametinib, binimetinib, cobimetinib, and ulixertinib.

This disclosure also provides a method of treating a solid tumor in a patient in need thereof, comprising: administering to the patient an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof; and administering to the patient an effective amount of a MEK or ERK inhibitor selected from the group consisting of trametinib, binimetinib, cobimetinib, and ulixertinib wherein the solid tumor is selected from the group consisting of of lung adenocarcinoma, squamous cell lung cancer, glioblastoma, pediatric glioma, astrocytoma, sarcoma, gastrointestinal stromal tumor (GIST), and melanoma.

A method of treating an gastrointestinal stromal tumor or melanoma in a patient in need thereof is also contemplated herein, comprising administering to the patient an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof; and administering to the patient an effective amount of a MEK or ERK inhibitor selected from the group consisting of trametinib, binimetinib, cobimetinib, and ulixertinib.

Additionally contemplated herein is a method of treating a solid tumor in a patient need thereof, comprising administering to the patient an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof; and administering to the patient an effective amount of a RAF inhibitor.

BRIEF DESCRIPTION OF THE DRAWINGS

FIG. 1A shows a graphical representation of Caspase activity following various treatments with Compound A and trametinib for 24 hours in GIST-T1 cells.

FIG. 1B provides a synergy matrix chart based on the combination index method for various treatments with Compound A and trametinib for 24 hours in GIST-T1 cells and a Combination Index Plot demonstrating synergy graphed as combination index (CI) on the y-axis and Fraction affected (Fa) on the x-axis.

FIG. 1C shows a graphical representation of Caspase activity following various treatments with Compound A and trametinib for 48 hours in GIST-T1 cells.

FIG. 1D provides a synergy matrix chart based on the combination index method for various treatments with Compound A and trametinib for 48 hours in GIST-T1 cells and a Combination Index Plot demonstrating synergy graphed as combination index (CI) on the y-axis and Fraction affected (Fa) on the x-axis.

FIG. 1E shows a graphical representation of Caspase activity following various treatments with Compound A and trametinib for 24 hours in GIST-T1/D816E imatinib resistant cells.

FIG. 1F provides a synergy matrix chart based on the combination index method for various treatments with Compound A and trametinib for 24 hours in GIST-T1/D816E imatinib resistant cells and a Combination Index Plot demonstrating synergy graphed as combination index (CI) on the y-axis and Fraction affected (Fa) on the x-axis.

FIG. 1H provides a synergy matrix chart based on the combination index method for various treatments with Compound A and trametinib for 24 hours in GIST-T1/T670I imatinib resistant cells and a Combination Index Plot demonstrating synergy graphed as combination index (CI) on the y-axis and Fraction affected (Fa) on the x-axis.

FIG. 2B provides a synergy matrix chart based on the combination index method for various treatments with Compound B and trametinib for 24 hours in GIST-T1 cells and a Combination Index Plot demonstrating synergy graphed as combination index (CI) on the y-axis and Fraction affected (Fa) on the x-axis.

FIG. 2D provides a synergy matrix chart based on the combination index method for various treatments with Compound B and trametinib for 24 hours in GIST-T1/D816E imatinib resistant cells and a Combination Index Plot demonstrating synergy graphed as combination index (CI) on the y-axis and Fraction affected (Fa) on the x-axis.

FIG. 2F provides a synergy matrix chart based on the combination index method for various treatments with Compound B and trametinib for 24 hours in GIST-T1/T670I imatinib resistant cells and a Combination Index Plot demonstrating synergy graphed as combination index (CI) on the y-axis and Fraction affected (Fa) on the x-axis.

FIG. 3B provides a synergy matrix chart based on the combination index method for various treatments with Compound A and binimetinib for 24 hours of GIST-T1 cells and a Combination Index Plot demonstrating synergy graphed as combination index (CI) on the y-axis and Fraction affected (Fa) on the x-axis.

FIG. 3D provides a synergy matrix chart based on the combination index method for various treatments with Compound A and binimetinib for 24 hours in GIST-T1/D816E imatinib resistant cells and a Combination Index Plot demonstrating synergy graphed as combination index (CI) on the y-axis and Fraction affected (Fa) on the x-axis.

FIG. 3F provides a synergy matrix chart based on the combination index method for various treatments with Compound A and binimetinib for 24 hours in GIST-T1/T670I imatinib resistant cells and a Combination Index Plot demonstrating synergy graphed as combination index (CI) on the y-axis and Fraction affected (Fa) on the x-axis.

FIG. 4A shows a graphical representation of Caspase activity following various treatments with Compound B and binimetinib for 24 hours in GIST-T1 cells.

FIG. 4B provides a synergy matrix chart based on the combination index method for various treatments with Compound B and binimetinib for 24 hours in GIST-T1 cells and a Combination Index Plot demonstrating synergy graphed as combination index (CI) on the y-axis and Fraction affected (Fa) on the x-axis.

FIG. 4C shows a graphical representation of Caspase activity following various treatments with Compound B and binimetinib for 24 hours in GIST-T1/D816E imatinib resistant cells.

FIG. 4D provides a synergy matrix chart based on the combination index method for various treatments with Compound B and binimetinib for 24 hours in GIST-T1/D816E imatinib resistant cells and a Combination Index Plot demonstrating synergy graphed as combination index (CI) on the y-axis and Fraction affected (Fa) on the x-axis.

FIG. 4F provides a synergy matrix chart based on the combination index method for various treatments with Compound B and binimetinib for 24 hours in GIST-T1/T670I imatinib resistant cells and a Combination Index Plot demonstrating synergy graphed as combination index (CI) on the y-axis and Fraction affected (Fa) on the x-axis.

FIG. 5B provides a synergy matrix chart based on the combination index method for various treatments with Compound A and cobimetinib for 24 hours in GIST-T1 cells and a Combination Index Plot demonstrating synergy graphed as combination index (CI) on the y-axis and Fraction affected (Fa) on the x-axis.

FIG. 5D provides a synergy matrix chart based on the combination index method for various treatments with Compound A and cobimetinib for 24 hours in GIST-T1/D816E imatinib resistant cells and a Combination Index Plot demonstrating synergy graphed as combination index (CI) on the y-axis and Fraction affected (Fa) on the x-axis.

FIG. 5E shows a graphical representation of Caspase activity following various treatments with Compound A and cobimetinib for 24 hours in GIST-T1/T670I imatinib resistant cells.

FIG. 5F provides a synergy matrix chart based on the combination index method for various treatments with Compound A and cobimetinib for 24 hours in GIST-T1/T670I imatinib resistant cells and a Combination Index Plot demonstrating synergy graphed as combination index (CI) on the y-axis and Fraction affected (Fa) on the x-axis.

FIG. 7D provides a synergy matrix chart based on the combination index method for various treatments with Compound A and ulixertinib for 24 hours in GIST-T1/T670I imatinib resistant cells

FIG. 8D shows images of representative culture plates and a graphical representation of the number of GIST-T1/T670I colonies counted following various treatments with Compound A, imatinib, and trametinib for 2 weeks followed by a 10 day recovery period.

FIG. 9B shows images of representative culture plates and a graphical representation of the number of GIST-T1/D816E colonies counted following various treatments with Compound B and trametinib for 2 weeks followed by a 10 day recovery period. The right upper panel shows representative culture plates after additional 10 days of recovery.

FIG. 11C shows images of representative culture plates showing the number of GIST-T1/D816E colonies counted following various treatments with Compound B and binimetinib for 2 weeks followed by a 10 day recovery period. The right upper panel shows representative culture plates after additional 10 days of recovery.

FIG. 13B shows images of representative culture plates and a graphical representation of the number of GIST-T1/D816E colonies counted following various treatments with Compound B and cobimetinib for 2 weeks followed by a 10 day recovery period. The right upper panel shows representative culture plates after additional 10 days of recovery.

FIG. 16D shows a graphical representation of the number of vector control transfected GIST-T1 colonies counted following various treatments treatments with Compound A, imatinib, and trametinib and a subsequent 10 day recovery period.

FIG. 16E shows a graphical representation of the number of N-ras G12D transfected GIST-T1 colonies counted following various treatments treatments with Compound A, imatinib, and trametinib and a subsequent 10 day recovery period.

FIG. 16F shows images of representative culture plates of N-ras G12D transfected GIST-T1 colonies following various treatments with Compound A and trametinib and a subsequent extended 21 day recovery period.

DETAILED DESCRIPTION

Figure 1G:
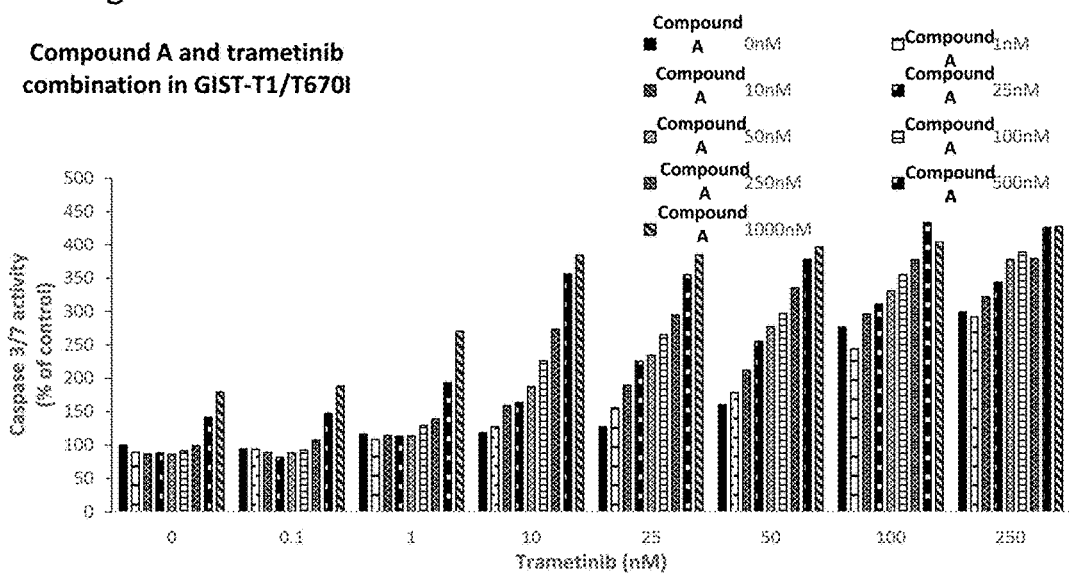
FIG. 1G shows a graphical representation of Caspase activity following various treatments with Compound A and trametinib for 24 hours in GIST-T1/T670I imatinib resistant cells.
Figure 1G:
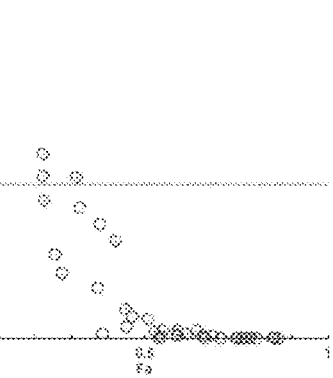

It has been found that the combination of 1-[4-bromo-5-[1-ethyl-7-(methylamino)-2-oxo-1,2-dihydro-1,6-naphthyridin-3-yl]-2-fluorophenyl]-3-phenylurea (Compound A) and a MAPKAP kinase pathway inhibitor, e.g., trametinib, unexpectedly synergizes to lead to cell death, apoptosis, or prolonged cell stasis of GIST cells, to induce eradication of tumor cells, to induce tumor regression, to reduce tumor volume, to inhibit tumor regrowth, and/or to lead to enhanced cell death, apoptosis, cell stasis or eradication of GIST cancer cell lines that are resistant to imatinib in combination with a MEK inhibitor in the accompanying Examples. In addition, the combination therapy methods disclosed herein appear to be cytocidal as opposed to merely cytostatic.

Without wishing to be bound to any particular theory, it is believed that many c-KIT inhibitors only inhibit certain mutant forms of c-KIT, such as the prominent exon 11 mutation observed in GIST. Other mutant forms of c-KIT appear resistant to many c-KIT inhibitors, and these often arise as secondary mutations in exons 13, 14, 17 and 18 that render a tumor resistant to treatment with c-KIT inhibitors. The present disclosure provides methods of treating tumors, e.g., c-KIT-mediated tumors such as GIST, by inhibiting both c-KIT and a MAPKAP pathway kinase using a c-KIT inhibitor disclosed herein as Compound A or a pharmaceutically acceptable salt thereof or Compound B or a pharmaceutically acceptable salt thereof. Surprisingly, Compound A and Compound B (and pharmaceutically acceptable salts thereof) synergize with a MEK inhibitor, a ERK inhibitor, or a RAF inhibitor to induce cell death, apoptosis, or prolonged cell stasis of GIST cells, to induce eradication of tumor cells to the limit of detection, to reduce tumor volume, to inhibit tumor regrowth and/or to lead to enhanced cell death, apoptosis, cell stasis, or eradication to the limit of detection, of GIST cancer cell lines that are resistant to imatinib in combination with a MAPKAP kinase inhibitor. Compound A exhibits superior potency and synergy in combination with MEK inhibition compared to imatinib in combination with MEK inhibition in GIST cells containing c-KIT resistance mutations. Further, the level of potency and synergy and the degree of GIST tumor cell prolonged cell stasis or eradication of Compound A in combination with MEK inhibition is superior to that of imatinib in combination with MEK inhibition even in cell lines known to be sensitive to imatinib. Again without wishing to be bound to any particular theory, it is believed that Compound A is able to inhibit a wider range of mutant forms of c-KIT than previous c-KIT inhibitors, including imatinib, in GIST cells possibly through mechanisms that include the inhibition of drug efflux pumps, including the BCRP efflux pump, within tumor cells, e.g., GIST cells. Imatinib is a substrate for the BCRP efflux pump, leading to lower intracellular concentrations in tumor cells where this efflux pump is present (Eechoute, K, et al, Clin Cancer Res. 2015, 17, 406-15). GIST tumors have been demonstrated to have overexpression of the BCRP efflux pump in 93% (42/45) of GIST patient tumors evaluated (Feldman, R, et al. J Clin Oncol. 2015, 33, 58). Compound A is a potent inhibitor of the BCRP efflux transporter, exhibiting an $IC_{50}$ value of 40 nM.

Accordingly, in certain embodiments, the present disclosure provides methods for inducing prolonged tumor cell stasis, inducing cell death, inducing apoptosis of tumor cells, inducing eradication of tumor cells, inducing tumor regression, reducing tumor volume, inhibiting tumor regrowth, or inhibiting the growth of resistant tumor cells, the methods comprising administering to a patient in need thereof an effective amount of: (i) 1-[4-bromo-5-[1-ethyl-7-(methylamino)-2-oxo-1,2-dihydro-1,6-naphthyridin-3-yl]-2-fluorophenyl]-3-phenylurea or a pharmaceutically acceptable salt thereof, or 1-(5-(7-amino-1-ethyl-2-oxo-1,2-dihydro-1,6-naphthyridin-3-yl)-4-bromo-2-fluorophenyl)-3-phenylurea or a pharmaceutically acceptable salt thereof; and (ii) a MAPKAP kinase inhibitor, e.g., the MEK inhibitor trametinib, binimetinib, or cobimetinib; the ERK inhibitor ulixertinib, or a RAF inhibitor. In particular embodiments of any of the methods disclosed herein, the tumor is a c-KIT-mediated solid tumor, e.g., a c-KIT-mediated GIST or melanoma.

Definitions

Compounds A and B as used herein refer to 1-[4-bromo-5-[1-ethyl-7-(methylamino)-2-oxo-1,2-dihydro-1,6-naphthyridin-3-yl]-2-fluorophenyl]-3-phenylurea and 1-(5-(7-amino-1-ethyl-2-oxo-1,2-dihydro-1,6-naphthyridin-3-yl)-4-bromo-2-fluorophenyl)-3-phenylurea, respectively. Pharmaceutically acceptable salts, tautomers, hydrates, and solvates, of Compounds A and B are also contemplated in this disclosure. The structures of Compounds A and B are represented below:

(Compound A)

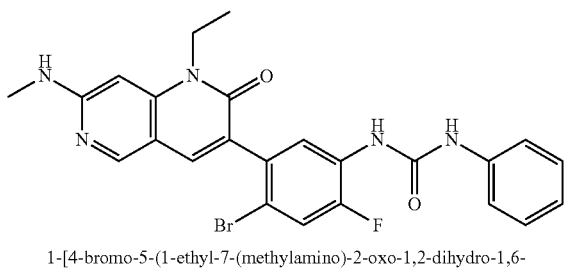

1-[4-bromo-5-(1-ethyl-7-(methylamino)-2-oxo-1,2-dihydro-1,6-naphthyridin-3-yl)-2-fluorophenyl)-3-phenylurea 1-[4-bromo-5-[1-ethyl-7-(methylamino)-2-oxo-1,2-dihydro-1,6-naphthyridin-3-yl]-2-fluorophenyl]-3-phenylurea (Compound A)

(Compound B)

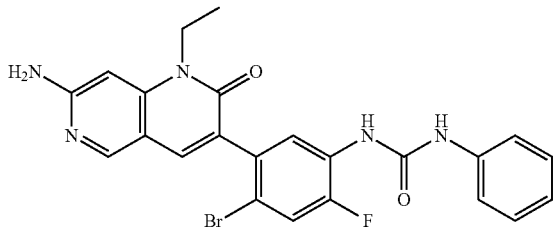

1-(5-(7-amino-1-ethyl-2-oxo-1,2-dihydro-1,6-naphthyridin-3-yl)-4-bromo-2-fluorophenyl)-3-phenylurea 1-(5-(7-amino-1-ethyl-2-oxo-1,2-dihydro-1,6-naphthyridin-3-yl)-4-bromo-2-fluorophenyl)-3-phenylurea (Compound B)

Methods of making Compound A and Compound B are disclosed in U.S. Pat. No. 8,461,179B1 the contents of which are incorporated herein by reference.

Illustrative methods and materials are now described. In the specification and the appended claims, the singular forms also include the plural unless the context clearly dictates otherwise. Unless defined otherwise, all technical and scientific terms used herein have the same meaning as commonly understood by one of ordinary skill in the art.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes acid addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

A "pharmaceutical composition" refers to a formulation of a compound described herein, e.g., Compound A or a pharmaceutically acceptable salt thereof, and a medium generally accepted in the art for the delivery of the biologically active compound to mammals, e.g., humans. Such a medium includes all pharmaceutically acceptable carriers, diluents or excipients therefor.

Subjects or patients "in need of treatment" with a combination therapy of the present disclosure, e.g., Compound A in combination with a MEK inhibitor, include patients with diseases and/or conditions that can be treated with a combination disclosed herein to achieve a beneficial therapeutic result, e.g., a GIST patient. A beneficial outcome includes an objective response, increased progression free survival, increased survival, prolongation of stable disease, and/or a decrease in the severity of symptoms or delay in the onset of symptoms. In certain embodiments, a patient in need of treatment is suffering from a tumor growth or tumor progression; the patient is suffering from, but not limited to, lung adenocarcinoma, squamous cell lung cancer, glioblastoma, pediatric glioma, astrocytomas, sarcomas, melanoma or gastrointestinal stromal tumors.

The term "effective amount" when used in connection with a compound or other therapeutic agent disclosed herein, refers to an amount of the therapeutic agent, e.g., Compound A or a MEK inhibitor, alone or in combination, that is useful to treat or prevent a disease or disorder. The effective amount of therapeutic agents used in a combination therapy is the amount of each of the therapeutic agents that is useful for treating or preventing a disease or disorder when used in the combination therapy, even if the amount of one or both of the therapeutic agents, in the absence of the other therapeutic agent, is ineffective to treat or prevent the disease or disorder. In certain embodiments, an effective amount is a quantity that results in prolonged cell stasis of GIST cells, cytocidal GIST cell killing, apoptosis of GIST cells, eradication of GIST cells, regression of a GIST, reduction of GIST tumor volume, inhibition of GIST regrowth, and/or leads to enhanced cell stasis, cell death, apoptosis, or eradication to the limit of detection, of GIST cancer cell lines that are resistant to imatinib in combination with a MEK inhibitor, and/or a leads to a beneficial clinical outcome of the condition being treated with the compound compared with the absence of treatment. The "effective amount" can vary depending upon the mode of administration, specific locus of the disease or disorder, and the age, body weight, and general health of the subject. The amount of the compounds administered will depend on the degree, severity, and type of the disease or condition, the amount of therapy desired, and the release characteristics of the pharmaceutical formulation(s). It will also depend on the subject's health, size, weight, age, sex and tolerance to drugs. Typically, the compounds are administered for a sufficient period of time to achieve the desired therapeutic effect.

The terms "treatment," "treat," and "treating," are meant to include the full spectrum of intervention in patients with "cancer" with the intention to induce prolonged cell stasis of GIST cells, to induce cytocidal GIST cell killing, to induce apoptosis of GIST cells, to induce eradication of GIST tumor cells to the limit of visual detection as determined by 5× objective microscopy, to cause regression of a GIST tumor in a patient, to reduce GIST tumor volume, to inhibit GIST regrowth, and/or to inhibit the growth of resistant GIST cells on a given treatment, such as administration of a combination therapy disclosed herein to alleviate, slow or reverse one or more of the symptoms and to induce regression of the GIST even if the GIST is not actually eliminated. In some embodiments, treatment includes eliminating the disease or disorder, e.g., GISTs, entirely. Treating can be curing, improving, or at least partially ameliorating the disorder.

"Cancer" as defined herein refers to a new growth which has the ability to invade surrounding tissues, metastasize (spread to other organs) and which may eventually lead to the patient's death if untreated. In certain embodiments, a cancer" can be a solid tumor.

"Tumor" as used herein refers to a mass. This is a term that may refer to benign (generally harmless) or malignant (cancerous) growths. Malignant growth can originate from a solid organ or the bone marrow.

"Tumor growth" as defined herein refers to growth of a mass caused by genomic alterations of a c-KIT gene, which may alter c-KIT protein expression and/or activity.

"Tumor progression" as defined herein refers to growth of an existing c-KIT dependent tumor, e.g., a GIST, wherein such growth of an existing mass may be caused by further genomic alterations of c-KIT resistant to a treatment.

"Tumor regression", "complete response" and "partial response" as defined herein refer to a reduction in tumor size as determined by weight or volume as determined by RECIST 1.1 or Choi criteria.

Eradication of an existing c-KIT-mediated tumor, e.g., a c-KIT-mediated GIST, is defined as a "complete cytocidal cell killing" of a tumor to the limit of detection as determined by 5× objective microscopy for in vitro evaluations, or as defined as a complete response as determined by RECIST 1.1 or Choi criteria for in vivo preclinical or clinical evaluations without the possibility of regrowth of the tumor under preclinical or clinical conditions. Accordingly, "eradication of a c-KIT-mediated tumor" indicates that all cells of the c-KIT-mediated tumor are killed or removed to the limit of detection without the possibility of regrowth of the c-KIT-mediated tumor.

"Tumor regrowth" as used herein refers to growth of a tumor that previously halted growth or regressed following a treatment, e.g., treatment with Gleevec® or Sutent®. In certain embodiments, tumor regrowth occurs due to the introduction of a c-Kit secondary mutation in a tumor cell. In other embodiments, tumor regrowth occurs due to the activation or mutation of a different signaling pathway, including but not limited to activation of the MAPKAP signaling pathway, which includes signaling through MEK kinases.

"Cell stasis" as used herein refers to cells ceasing to divide and remaining in a dormant non-replicative state.

"Apoptosis" as used herein refers to programmed cell death. Features of apoptosis detectable by histologic and histochemical methods include cell shrinkage; increased membrane permeability; nuclear and cytoplasmic condensation; endolytic cleavage of nuclear DNA into oligonucleosomal fragments; and ultimately formation of apoptotic bodies, which are absorbed and removed by macrophages. Apoptosis is primarily medated by the caspases, which are aspartate-specific serine proteases. Apoptosis can be induced via intrinsic genetic programming in response to various conditions, e.g., DNA damage or growth factor withdrawal, or apoptosis can be induced by extrinsic factors, such as injury to cellular DNA by irradiation and some cytotoxic agents used to treat cancer. It can be suppressed by naturally occurring factors (for example, cytokines) and by some drugs (for example, protease inhibitors). Apoptosis typically does not occur or is compromised in malignant cells. In particular embodiments, apoptosis refers to programmed cell death as determined by increases in cleaved and activated caspase 3 and caspase 7.

A "combination therapy" is a treatment that includes the administration of two or more therapeutic agents, e.g., Compound A and a MEK inhibitor, to a patient. The two or more therapeutic agents may be delivered at the same time, e.g., in separate pharmaceutical compositions or in the same pharmaceutical composition, or they may be delivered at different times. For example, they may be delivered concurrently or during overlapping time periods, and/or one therapeutic agent may be delivered before or after the other therapeutic agent(s). Treatment with a combination of a KIT inhibitor such as Compound A and a MEK inhibitor optionally includes treatment with either single agent, preceded or followed by a period of concurrent treatment with both agents. However, it is contemplated that during some time period, effective amounts of the two or more therapeutic agents are present within the patient.

A "MAPKAP pathway inhibitor" is an inhibitor of the MAP kinase signaling pathway. Inhibitors of this pathway include RAS inhibitors, RAF inhibitors (e.g. dabrafenib, vemurafenib, LY3009120), MEK inhibitors (e.g. trametinib, binimetinib, cobimetinib), and ERK inhibitors (e.g. ulixertinib). The terms "MAPKAP pathway inhibitor" and "MAPKAP kinase inhibitor are used interchangeably herein.

Methods of Treatment

The compounds and compositions described herein can be used to treat tumors in a patient in need thereof. For example, provided herein is a method of treating a tumor having one or more c-KIT mutations in patient in need thereof, comprising administering to the patient: an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof; and an effective amount of one or more MAPKAP kinase inhibitors. In one embodiment, the MAPKAP kinase inhibitor is selected from the group consisting of a mitogen-activated protein kinase inhibitor (MEK inhibitor) and an effective amount of an extracellular signal regulated kinase inhibitor (ERK inhibitor).

The c-KIT mutation can be a primary mutation in exon 9, exon 11, exon 13, or exon 17 of the c-KIT gene. In another embodiment, the c-KIT mutation is a deletion mutation.

Furthermore, the tumor can have one or more secondary resistance mutations in the c-KIT gene. In some embodiments, the secondary resistance mutation is in exon 13, exon 14, exon 17, or exon 18 of the c-KIT gene. In some embodiments, the secondary resistance mutation is in exon 17 of the c-KIT gene. In some embodiments, the secondary resistance mutation is the substitution of aspartic acid in codon 816 or the substitution of asparagine in codon 822. In some embodiments, the secondary resistance mutation is one of D816V, D816E, D816H, D820A, T670I, or N822V. In some embodiments, the secondary resistance mutation was acquired after previous administration of imatinib, sunitib or regorafenib, or a pharmaceutically acceptable salt thereof to the patient.

Such a disclosed method further comprises determining if the tumor has the c-KIT secondary mutation. In some embodiments, determining if the tumor has the c-KIT secondary mutation comprises identifying mutations in DNA extracted from a tumor sample. In some embodiments, determining if the tumor has the c-KIT secondary mutation comprises identifying mutations in circulating tumor DNA. In another embodiment, the tumor was been resistant to treatment with imatinib mesylate, sunitinib malate, or regorafenib.

Furthermore, the tumor can be selected from the group consisting of lung adenocarcinoma, squamous cell lung cancer, glioblastoma, pediatric glioma, astrocytoma, sarcoma, gastrointestinal stromal tumor (GIST), and melanoma. In some embodiments, the tumor is melanoma. In some embodiments, the tumor is GIST.

The method may further comprise administering to the patient a cancer targeted therapeutic agent, cancer-targeted biological, immune checkpoint inhibitor, and/or chemotherapeutic agent. The method may also further comprise administering a RAF inhibitor to the patient.

In another embodiment, the 1-[4-bromo-5-[1-ethyl-7-(methylamino)-2-oxo-1,2-dihydro-1,6-naphthyridin-3-yl]-2-fluorophenyl]-3-phenylurea, or the pharmaceutically acceptable salt thereof, and the MAPKAP kinase inhibitor is administered substantially concurrently or sequentially.

The MEK inhibitor in this disclosed method can be selected from the group consisting of trametinib, selumetinib, cobimetinib, and binimetinib. In some embodiments, the MEK inhibitor is binimetinib. In some embodiments, the MEK inhibitor is trametinib. In some embodiments, the ERK inhibitor is selected from the group consisting of ulixertinib, SCH772984, and LY3214996.

Administration for two weeks or more in accordance with such a disclosed method can result in the patient having partial reduction in tumor volume of at least 30%. In some embodiments, the treatment results in a complete reduction in tumor volume.

The disclosed method may further comprise determining if the tumor or tumor cells comprise a primary c-KIT gene mutation. In some embodiments, the primary mutation is in exon 11 of the c-KIT gene. In some embodiments, the primary mutation is in exon 9 of the c-KIT gene. In some embodiments, the primary mutation is a deletion mutation. In some embodiments, the primary mutation is V560D. In other embodiments, one or more additional secondary mutations c-KIT mutations are present.

Also provided by the disclosure is a method of treating a solid tumor in an imatinib resistant patient, comprising: administering to the patient an effective amount of 1-[4-bromo-5-[1[1-ethyl-7-(methylamino)-2-oxo-1,2-dihydro-1,6-naphthyridin-3-yl]-2-fluorophenyl]-3-phenylurea, or a pharmaceutically acceptable salt thereof; and administering to the patient an effective amount of a MAPKAP kinase inhibitor selected from the group consisting of trametinib, binimetinib, cobimetinib, and ulixertinib, wherein the solid tumor is selected from the group consisting of of lung adenocarcinoma, squamous cell lung cancer, glioblastoma, pediatric glioma, astrocytoma, sarcoma, gastrointestinal stromal tumor (GIST), and melanoma. In some embodiments, the method further comprises administering a RAF inhibitor. In some embodiments, the RAF inhibitor is a pan-RAF inhibitor.

Also provided herein is a method of treating an imatinib resistant gastrointestinal stromal tumor or imatinib resistant melanoma in a patient in need thereof, comprising administering to the patient an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof; and administering to the patient an effective amount of a MAPKAP kinase inhibitor selected from the group consisting of trametinib, binimetinib, cobimetinib, and ulixertinib.

In some embodiments, the method further comprises determining whether the tumor has a mutation of the c-KIT gene. In some embodiments, the mutation is in exon 17 of the c-KIT gene. In some embodiments, the c-KIT mutation is the substitution of aspartic acid in codon 816 or the substitution of asparagine in codon 822. In some embodiments, the mutation is one of D816V, D816E, D816H, D820A, T670I, or N822V.

Additionally provided is a method of treating a solid tumor in a patient need thereof, comprising administering to the patient an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof; and administering to the patient an effective amount of a RAF inhibitor.

In such a disclosed method, the solid tumor can be selected from the group consisting of lung adenocarcinoma, squamous cell lung cancer, GIST, and melanoma. In some embodiments, the solid tumor has one or more mutations of the c-KIT gene.

Furthermore, the RAF inhibitor can be a pan-RAF inhibitor. In another embodiment, the RAF inhibitor is dabrafenib, vemurafenib, or LY3009120.

Also provided by the disclosure is a method of treating a solid tumor in a patient in need thereof, comprising: administering to the patient an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof; and administering to the patient an effective amount of a MAPKAP kinase inhibitor selected from the group consisting of trametinib, binimetinib, cobimetinib, and ulixertinib, wherein the solid tumor is selected from the group consisting of of lung adenocarcinoma, squamous cell lung cancer, glioblastoma, pediatric glioma, astrocytoma, sarcoma, gastrointestinal stromal tumor (GIST), and melanoma. In some embodiments, the method further comprises administering a RAF inhibitor. In some embodiments, the RAF inhibitor is a pan-RAF inhibitor.

Also provided herein is a method of treating a gastrointestinal stromal tumor or melanoma in a patient in need thereof, comprising administering to the patient an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof; and administering to the patient an effective amount of a MAPKAP kinase inhibitor selected from the group consisting of trametinib, binimetinib, cobimetinib, and ulixertinib.

In some embodiments, the method further comprises determining whether the tumor has a mutation of the c-KIT gene. In some embodiments, the mutation is in exon 17 of the c-KIT gene. In some embodiments, the c-KIT mutation is the substitution of aspartic acid in codon 816 or the substitution of asparagine in codon 822. In some embodiments, the mutation is one of D816V, D816E, D816H, D820A, T670I, or N822V.

In one embodiment, the present disclosure provides methods of treating or preventing a tumor in a patient, optionally a c-KIT-mediated tumor, e.g., a GIST, comprising administering to a patient in need thereof an effective amount of Compound A, or a pharmaceutically acceptable salt thereof, in combination with an effective amount of a MEK inhibitor, e.g., trametinib. In a related embodiment, the present disclosure provides methods of treating or preventing a tumor in a patient, optionally a c-KIT-mediated tumor, e.g., a GIST, comprising administering to a patient in need thereof an effective amount of Compound B, or a pharmaceutically acceptable salt thereof, in combination with an effective amount of a MEK inhibitor, e.g., trametinib.

In specific embodiments, these methods include methods for: inducing prolonged stasis of tumor cells, e.g., GIST cells; killing of tumor cells, e.g., GIST cells; inducing apoptosis of tumor cells, e.g., GIST cells; inducing tumor cell eradication to the limit of detection, e.g., GIST cells; inducing tumor regression, e.g., GIST regression; reducing tumor volume, e.g., GIST tumor volume; inhibiting tumor regrowth, e.g., GIST regrowth. In another specific embodiment, these methods include methods for inducing prolonged stasis of tumor cells, e.g., GIST cells. In another specific embodiment, these methods include methods killing of tumor cells, e.g., GIST cells. In another specific embodiment, these methods include methods inducing apoptosis of tumor cells, e.g., GIST cells. In another specific embodiment, these methods include methods for inducing tumor cell eradication to the limit of detection, e.g., GIST cells. In another specific embodiment, these methods include methods for inducing tumor regression, e.g., GIST regression. In another specific embodiment, these methods include methods for reducing tumor volume, e.g., GIST tumor volume. In another specific embodiment, these methods include methods for inhibiting tumor regrowth, e.g., GIST regrowth. In another specific embodiment, these methods include methods for inhibiting the growth of drug-resistant tumor cells, e.g., drug-resistant GIST cells. In certain embodiments, the methods encompass methods for eradicating a tumor to the limit of detection, e.g., a GIST, in a subject. In particular embodiments of any of the methods disclosed herein, tumor growth or tumor progression in the patient is caused by c-KIT overexpression, constitutive phosphorylation of c-KIT, increased c-KIT activity, oncogenic c-KIT missense mutations, oncogenic deletion c-KIT mutations, oncogenic nucleotide duplications/insertions, oncogenic c-KIT gene rearrangements leading to c-KIT fusion proteins, c-KIT intragenic in-frame deletions, and/or oncogenic c-KIT gene amplification. In one embodiment, the tumor growth or tumor progression is caused by constitutive phosphorylation of c-KIT. In particular embodiments, the tumor comprises one or more of the primary activating c-KIT mutations and/or secondary c-KIT mutations disclosed herein. In another particular embodiment, the tumor comprises one or more mutations in genes other then c-KIT that cause tumor growth by signaling through the MAPKAP pathway involving RAF, MEK, or ERK kinase activation.

Where the methods described herein refer to treatment with Compound A or a pharmaceutically acceptable salt thereof, or Compound B or a pharmaceutically acceptable salt thereof, it is meant that only one of Compound A or a pharmaceutically acceptable salt thereof, or Compound B or a pharmaceutically acceptable salt thereof is required. However, it is understood that these methods encompass administering to a patient both Compound A or a pharmaceutically acceptable sale thereof, and Compound B or a pharmaceutically acceptable salt thereof, in combination with a MEK inhibitor, ERK inhibitor, or RAF inhibitor. Furthermore, it is understood that upon administration of Compound A in combination with a MEK inhibitor, ERK inhibitor, or a RAF inhibitor to a subject, some amount of the Compound A is metabolized in vivo to Compound B, and that an in vivo mixture of Compound A and Compound B may also be used to effectively treat a subject in combination with the MEK inhibitor, the ERK inhibitor or the RAF inhibitor.

Illustrative MEK inhibitors that may be used according to the disclosed methods and compositions include, but are not limited to, trametinib, selumetinib, cobimetinib, and binimetinib.

Illustrative ERK inhibitors that may be used according to the disclosed methods and compositions include, but are not limited to, ulixertinib, SCH772984, LY3214996, ravoxertinib, and VX-Ile.

Illustrative RAF inhibitors that may be used according to the disclosed methods and compositions include, but are not limited to, LY3009120, dabrafenib, and vemurafenib.

In one embodiment, Compound A or a pharmaceutically acceptable salt thereof and a MEK inhibitor, e.g., trametinib, are administered to a patient with a c-KIT-mediated tumor, e.g., a GIST. In another embodiment, Compound B or a pharmaceutically acceptable salt thereof and a MEK inhibitor, e.g., trametinib, are administered to a patient with a c-KIT-mediated tumor, e.g., a GIST.

In a related embodiment, Compound A or a pharmaceutically acceptable salt thereof and a MEK inhibitor, e.g., trametinib, are administered to a patient with a tumor, e.g., a patient having a GIST, wherein tumor growth or tumor progression is caused by a primary activating c-KIT mutation and/or a secondary c-KIT mutation. In another embodiment, Compound B or a pharmaceutically acceptable salt thereof and a MEK inhibitor, e.g., trametinib, are administered to a patient with a tumor, e.g., a patient having a GIST, wherein tumor growth or tumor progression is caused by a primary activating c-KIT mutation and/or a secondary c-KIT mutation. In certain embodiments, the primary activating c-KIT mutation is an exon 11 mutation (e.g., a 57 base pair exon 11 deletion). In certain embodiments, the primary activating c-KIT mutation is an exon 9 A-Y 502-503 duplication. In certain embodiments, the primary activating c-KIT mutation is an exon 13 mutation. In certain embodiments, the primary activating c-KIT mutation is an exon 17 mutation. In certain embodiments, the secondary c-KIT mutation is any disclosed resistance mutation herein, e.g., a T670I mutation or a D816E mutation. In certain embodiments, multiple secondary c-KIT resistance mutations coexist in a subject.

In certain embodiments, Compound A or a pharmaceutically acceptable salt thereof and a MEK inhibitor, e.g., trametinib, are administered to a cancer patient. In certain embodiments, Compound B or a pharmaceutically acceptable salt thereof and a MEK inhibitor, e.g., trametinib, are administered to a cancer patient. In particular embodiments of any of the methods disclosed herein, the tumor or cancer is lung adenocarcinoma, squamous cell lung cancer, glioblastoma, pediatric glioma, astrocytomas, sarcomas, melanoma, or gastrointestinal stromal tumors (GIST). In one embodiment, the cancer is melanoma. In another embodiment, the tumor or cancer is a gastrointestinal stromal tumor (GIST). In particular embodiments of any of these methods, the tumor or cancer is a c-KIT-mediated cancer, e.g., a c-KIT-mediated GIST or melanoma.

Treatment with Compound A or a pharmaceutically acceptable salt thereof, or Compound B or a pharmaceutically acceptable salt thereof, in combination with a MEK inhibitor, e.g., trametinib, encompasses administering Compound A or a pharmaceutically acceptable salt thereof, or Compound B or a pharmaceutically acceptable salt thereof, before, after, simultaneous with, or during an overlapping time period with administering the MEK inhibitor. It is understood that an effective amount of any of Compound A or a pharmaceutically acceptable salt thereof, Compound B or a pharmaceutically acceptable salt thereof, or a MEK inhibitor, e.g., trametinib, may be different when used in the combinations disclosed herein as compared to when any of these agents is used by itself for the same purpose, e.g., to treat or prevent a tumor. In particular embodiments, an effective amount of Compound A or a pharmaceutically acceptable salt thereof, or of Compound B or a pharmaceutically acceptable salt thereof, is a lower amount when administered as a combination therapy with a MEK inhibitor, e.g., trametinib, as compared to when it is administered as a monotherapy, e.g., to treat or prevent a GIST. In particular embodiments, an effective amount of a MEK inhibitor, e.g., trametinib, is a lower amount when administered in a combination therapy with Compound A or a pharmaceutically acceptable salt thereof, or when administered in a combination therapy with Compound B or a pharmaceutically acceptable salt thereof, e.g., to treat or prevent a GIST.

Any of the methods disclosed herein may further include determining that the tumor being treated has one or more c-KIT gene mutations. Such a determination may be made by routine methods for determining the presence of a gene mutation in a biological sample, e.g., a tumor sample, a blood sample, or a plasma sample obtained from the patient. In addition, such a determination may be made by reviewing the results of tests performed to determine the presence of one or more c-KIT gene mutations in a biological sample, e.g., a tumor sample, blood sample, or plasma sample obtained from the patient. In certain embodiments of any of the methods disclosed herein, the methods are performed on patients wherein the tumor has been identified as having one or more c-KIT gene mutations. The c-KIT gene mutations include but are not limited to any of those specifically described herein.

In various aspects of any of the methods disclosed herein, treatment with either Compound A or a pharmaceutically acceptable salt thereof, or Compound B or a pharmaceutically acceptable salt thereof, in combination with a MEK inhibitor, e.g., trametinib: induces prolonged cell stasis of tumor cells, e.g. GIST cells; induces killing of tumor cells, e.g., GIST cells; induces apoptosis of tumor cells, e.g., GIST cells; induces tumor cell eradication to the limit of detection, e.g., GIST cells; induces tumor regression, e.g., GIST tumor; reduces tumor weight or volume; e.g., GIST tumor; inhibits tumor regrowth, e.g., GIST tumor. In another aspect of any of the methods disclosed herein, treatment with either Compound A or a pharmaceutically acceptable salt thereof, or Compound B or a pharmaceutically acceptable salt thereof, in combination with a MEK inhibitor, e.g., trametinib: induces prolonged cell stasis of tumor cells, e.g. GIST cells; induces killing of tumor cells, e.g., GIST cells; induces apoptosis of tumor cells, e.g., GIST cells; induces tumor cell eradication to the limit of detection, e.g., GIST cells; induces tumor regression, e.g., GIST tumor; reduces tumor weight or volume; e.g., GIST tumor; inhibits tumor regrowth, e.g., GIST tumor in a drug resistant tumor, e.g. drug-resistant GIST. In another aspect of any of the methods disclosed herein, treatment with either Compound A or a pharmaceutically acceptable salt thereof, or Compound B or a pharmaceutically acceptable salt thereof, in combination with a MEK inhibitor, e.g., trametinib: eradicates a tumor to the limit of detection, in a patient being treated, e.g., a GIST patient. Methods for measuring or determining amounts of tumor cell stasis, tumor cell death, apoptosis of tumor cells, tumor regression, tumor weight or volume, tumor regrowth, growth of resistant tumor cells, and eradication of tumors are known in the art and include any methods described herein.

In particular embodiments, treatment with a combination of: Compound A or a pharmaceutically acceptable salt thereof, or Compound B or a pharmaceutically acceptable salt thereof; and a MEK inhibitor, e.g., trametinib, results in an increased amount of tumor cell stasis, killing of tumor cells or apoptosis of tumor cells, e.g., GIST cells, as compared to the amount of stasis, cell killing or apoptosis of tumor cells of the same type or same tumor type either untreated or treated with only a MEK inhibitor, e.g., trametinib, or with only a c-KIT inhibitor, e.g., imatinib, or with a combination of a MEK inhibitor, e.g., trametinib, with the c-KIT inhibitor imatinib. For example, cell stasis, cell killing or apoptosis may be increased by at least 10%, at least 20%, at least 30%, at least 40%, at least 50%, at least 60%, at least 70%, at least 80%, at least 90%, at least two-fold, at least three-fold, at least four-fold, at least five-fold, at least 10-fold, or at least 20-fold. In certain embodiments, amounts of apoptosis are determined by measuring caspase activity of tumor cells.

In particular embodiments, treatment with a combination of: Compound A or a pharmaceutically acceptable salt thereof, or Compound B or a pharmaceutically acceptable salt thereof; and a MEK inhibitor, e.g., trametinib, results in increased tumor regression or decreased tumor size or volume (e.g., a GIST), as compared to the size, e.g., weight or volume of a tumor of the same type or the same tumor either untreated or treated with only a MEK inhibitor, e.g., trametinib, or with only a c-KIT inhibitor, e.g., imatinib. For example, tumor weight or volume may be decreased by at least 10%, at least 20%, at least 30%, at least 40%, at least 50%, at least 60%, at least 70%, at least 80%, or at least 90%.

In particular embodiments, treatment with a combination of: Compound A or a pharmaceutically acceptable salt thereof, or Compound B or a pharmaceutically acceptable salt thereof; and a MEK inhibitor, e.g., trametinib, inhibits the amount of tumor growth or regrowth, e.g., GIST growth or regrowth, to a greater extent as compared to the amount of growth or regrowth the same type or the same tumor either untreated or treated with only a MEK inhibitor, e.g., trametinib, or with only a c-KIT inhibitor, e.g., imatinib. For example, tumor growth or regrowth may be inhibited by at least 10%, at least 20%, at least 30%, at least 40%, at least 50%, at least 60%, at least 70%, at least 80%, or at least 90%.

In particular embodiments, treatment with a combination of: Compound A or a pharmaceutically acceptable salt thereof, or Compound B or a pharmaceutically acceptable salt thereof; and a MEK inhibitor, e.g., trametinib, inhibits the growth of resistant tumor cells, e.g., resistant GIST cells, to a greater extent as compared to the amount of growth of resistant tumor cells of the same type or the same tumor either untreated or treated with only a MEK inhibitor, e.g., trametinib, or with only a c-KIT inhibitor, e.g., imatinib, or with a combination of a MEK inhibitor, e.g., trametinib and a c-KIT inhibitor, e.g., imatinib. For example, the amount of growth or number of resistant tumor cells may be inhibited by at least 10%, at least 20%, at least 30%, at least 40%, at least 50%, at least 60%, at least 70%, at least 80%, or at least 90%. In particular embodiments, resistant tumor cells are resistant to treatment with a c-KIT inhibitor, e.g., imatinib, and/or a MEK inhibitor, e.g., trametinib. In certain embodiments, the resistant tumor cells comprise a c-KIT secondary mutation. In certain embodiments, the c-KIT secondary mutation is a mutation of any of the following amino acid residues of c-KIT: V654, N655, T670, L783, D816, D820, N822, Y823, A829, and/or T847, including but not limited to any of the amino acid substitutions depicted in the accompanying figures. In particular embodiments, the resistant tumor cells comprise an activated MAPKAP kinase pathway, and in certain embodiments, they comprise a mutation in a mutation in a RAS gene, e.g., an N-RAS or K-RAS gene, a Fibloblast Growth Factor Receptor (FGFR) gene, and/or a Neurofibromin-1 (NF1) gene. In certain embodiments, the mutation is an N-RAS G12D mutation.

In particular embodiments, treatment with a combination of: either Compound A or a pharmaceutically acceptable salt thereof, or Compound B or a pharmaceutically acceptable salt thereof; in combination with a MEK inhibitor, e.g., trametinib, results in eradication of a tumor to the limit of detection, e.g., a GIST. In particular embodiments, eradication of a tumor means there is no longer any detectable tumor in the patient to the limit of detection. In particular embodiments, there is no detectable tumor in the patient for at least six months, at least one year, at least two years, at least five years, or at least 10 years following eradication of the tumor, e.g., GIST, by a combination therapy disclosed herein. Tumor eradication may be determined by photon emission tomography (PET), CT scans, absence of circulating cell free DNA (cfDNA) containing a c-KIT mutation, absence of circulating tumor cells (CTCs) present in the vasculature of a subject, or absence of a cancer cell biomarker within the circulating blood vasculature of a subject.

In various aspects of any of the methods disclosed herein, treatment with either Compound A or a pharmaceutically acceptable salt thereof, or Compound B or a pharmaceutically acceptable salt thereof, in combination with a ERK inhibitor, e.g., ulixertinib: induces prolonged cell stasis of tumor cells, e.g. GIST cells; induces killing of tumor cells, e.g., GIST cells; induces apoptosis of tumor cells, e.g., GIST cells; induces tumor cell eradication to the limit of detection, e.g., GIST cells; induces tumor regression, e.g., GIST tumor; reduces tumor weight or volume; e.g., GIST tumor; inhibits tumor regrowth, e.g., GIST tumor. In another aspect of any of the methods disclosed herein, treatment with either Compound A or a pharmaceutically acceptable salt thereof, or Compound B or a pharmaceutically acceptable salt thereof, in combination with a ERK inhibitor, e.g., ulixertinib: induces prolonged cell stasis of tumor cells, e.g. GIST cells; induces killing of tumor cells, e.g., GIST cells; induces apoptosis of tumor cells, e.g., GIST cells; induces tumor cell eradication to the limit of detection, e.g., GIST cells; induces tumor regression, e.g., GIST tumor; reduces tumor weight or volume; e.g., GIST tumor; inhibits tumor regrowth, e.g., GIST tumor in a drug resistant tumor, e.g. drug-resistant GIST. In another aspect of any of the methods disclosed herein, treatment with either Compound A or a pharmaceutically acceptable salt thereof, or Compound B or a pharmaceutically acceptable salt thereof, in combination with a ERK inhibitor, e.g., ulixertinib: eradicates a tumor to the limit of detection, in a patient being treated, e.g., a GIST patient. Methods for measuring or determining amounts of tumor cell stasis, tumor cell death, apoptosis of tumor cells, tumor regression, tumor weight or volume, tumor regrowth, growth of resistant tumor cells, and eradication of tumors are known in the art and include any methods described herein.

In particular embodiments, treatment with a combination of: Compound A or a pharmaceutically acceptable salt thereof, or Compound B or a pharmaceutically acceptable salt thereof; and a ERK inhibitor, e.g., ulixertinib, results in an increased amount of tumor cell stasis, killing of tumor cells or apoptosis of tumor cells, e.g., GIST cells, as compared to the amount of stasis, cell killing or apoptosis of tumor cells of the same type or same tumor type either untreated or treated with only a ERK inhibitor, e.g., ulixertinib, or with only a c-KIT inhibitor, e.g., imatinib, or with a combination of a ERK inhibitor, e.g., ulixertinib, with the c-KIT inhibitor imatinib. For example, cell stasis, cell killing or apoptosis may be increased by at least 10%, at least 20%, at least 30%, at least 40%, at least 50%, at least 60%, at least 70%, at least 80%, at least 90%, at least two-fold, at least three-fold, at least four-fold, at least five-fold, at least 10-fold, or at least 20-fold. In certain embodiments, amounts of apoptosis are determined by measuring caspase activity of tumor cells.

In particular embodiments, treatment with a combination of: Compound A or a pharmaceutically acceptable salt thereof, or Compound B or a pharmaceutically acceptable salt thereof; and a ERK inhibitor, e.g., ulixertinib, results in increased tumor regression or decreased tumor size or volume (e.g., a GIST), as compared to the size, e.g., weight or volume of a tumor of the same type or the same tumor either untreated or treated with only a ERK inhibitor, e.g., ulixertinib, or with only a c-KIT inhibitor, e.g., imatinib. For example, tumor weight or volume may be decreased by at least 10%, at least 20%, at least 30%, at least 40%, at least 50%, at least 60%, at least 70%, at least 80%, or at least 90%.

In particular embodiments, treatment with a combination of: Compound A or a pharmaceutically acceptable salt thereof, or Compound B or a pharmaceutically acceptable salt thereof; and a ERK inhibitor, e.g., ulixertinib, inhibits the amount of tumor growth or regrowth, e.g., GIST growth or regrowth, to a greater extent as compared to the amount of growth or regrowth the same type or the same tumor either untreated or treated with only a ERK inhibitor, e.g., ulixertinib, or with only a c-KIT inhibitor, e.g., imatinib. For example, tumor growth or regrowth may be inhibited by at least 10%, at least 20%, at least 30%, at least 40%, at least 50%, at least 60%, at least 70%, at least 80%, or at least 90%.

In particular embodiments, treatment with a combination of: Compound A or a pharmaceutically acceptable salt thereof, or Compound B or a pharmaceutically acceptable salt thereof; and a ERK inhibitor, e.g., ulixertinib, inhibits the growth of resistant tumor cells, e.g., resistant GIST cells, to a greater extent as compared to the amount of growth of resistant tumor cells of the same type or the same tumor either untreated or treated with only a ERK inhibitor, e.g., ulixertinib, or with only a c-KIT inhibitor, e.g., imatinib, or with a combination of a ERK inhibitor, e.g., ulixertinib and a c-KIT inhibitor, e.g., imatinib. For example, the amount of growth or number of resistant tumor cells may be inhibited by at least 10%, at least 20%, at least 30%, at least 40%, at least 50%, at least 60%, at least 70%, at least 80%, or at least 90%. In particular embodiments, resistant tumor cells are resistant to treatment with a c-KIT inhibitor, e.g., imatinib, and/or a ERK inhibitor, e.g., ulixertinib. In certain embodiments, the resistant tumor cells comprise a c-KIT secondary mutation. In certain embodiments, the c-KIT secondary mutation is a mutation of any of the following amino acid residues of c-KIT: V654, N655, T670, L783, D816, D820, N822, Y823, A829, and/or T847, including but not limited to any of the amino acid substitutions depicted in the accompanying figures. In particular embodiments, the resistant tumor cells comprise an activated MAPKAP kinase pathway, and in certain embodiments, they comprise a mutation in a mutation in a RAS gene, e.g., an N-RAS or K-RAS gene, a Fibloblast Growth Factor Receptor (FGFR) gene, and/or a Neurofibromin-1 (NF1) gene. In certain embodiments, the mutation is an N-RAS G12D mutation.

In particular embodiments, treatment with a combination of: either Compound A or a pharmaceutically acceptable salt thereof, or Compound B or a pharmaceutically acceptable salt thereof; in combination with a ERK inhibitor, e.g., ulixertinib, results in eradication of a tumor to the limit of detection, e.g., a GIST. In particular embodiments, eradication of a tumor means there is no longer any detectable tumor in the patient to the limit of detection. In particular embodiments, there is no detectable tumor in the patient for at least six months, at least one year, at least two years, at least five years, or at least 10 years following eradication of the tumor, e.g., GIST, by a combination therapy disclosed herein. Tumor eradication may be determined by photon emission tomography (PET), CT scans, absence of circulating cell free DNA (cfDNA) containing a c-KIT mutation, absence of circulating tumor cells (CTCs) present in the vasculature of a subject, or absence of a cancer cell biomarker within the circulating blood vasculature of a subject.

In various aspects of any of the methods disclosed herein, treatment with either Compound A or a pharmaceutically acceptable salt thereof, or Compound B or a pharmaceutically acceptable salt thereof, in combination with a RAF inhibitor, e.g., dabrafenib: induces prolonged cell stasis of tumor cells, e.g. GIST cells; induces killing of tumor cells, e.g., GIST cells; induces apoptosis of tumor cells, e.g., GIST cells; induces tumor cell eradication to the limit of detection, e.g., GIST cells; induces tumor regression, e.g., GIST tumor; reduces tumor weight or volume; e.g., GIST tumor; inhibits tumor regrowth, e.g., GIST tumor. In another aspect of any of the methods disclosed herein, treatment with either Compound A or a pharmaceutically acceptable salt thereof, or Compound B or a pharmaceutically acceptable salt thereof, in combination with a RAF inhibitor, e.g., dabrafenib: induces prolonged cell stasis of tumor cells, e.g. GIST cells; induces killing of tumor cells, e.g., GIST cells; induces apoptosis of tumor cells, e.g., GIST cells; induces tumor cell eradication to the limit of detection, e.g., GIST cells; induces tumor regression, e.g., GIST tumor; reduces tumor weight or volume; e.g., GIST tumor; inhibits tumor regrowth, e.g., GIST tumor in a drug resistant tumor, e.g. drug-resistant GIST. In another aspect of any of the methods disclosed herein, treatment with either Compound A or a pharmaceutically acceptable salt thereof, or Compound B or a pharmaceutically acceptable salt thereof, in combination with a RAF inhibitor, e.g., dabrafenib: eradicates a tumor to the limit of detection, in a patient being treated, e.g., a GIST patient. Methods for measuring or determining amounts of tumor cell stasis, tumor cell death, apoptosis of tumor cells, tumor regression, tumor weight or volume, tumor regrowth, growth of resistant tumor cells, and eradication of tumors are known in the art and include any methods described herein.

In particular embodiments, treatment with a combination of: Compound A or a pharmaceutically acceptable salt thereof, or Compound B or a pharmaceutically acceptable salt thereof; and a RAF inhibitor, e.g., dabrafenib, results in an increased amount of tumor cell stasis, killing of tumor cells or apoptosis of tumor cells, e.g., GIST cells, as compared to the amount of stasis, cell killing or apoptosis of tumor cells of the same type or same tumor type either untreated or treated with only a RAF inhibitor, e.g., dabrafenib, or with only a c-KIT inhibitor, e.g., imatinib, or with a combination of a RAF inhibitor, e.g., dabrafenib, with the c-KIT inhibitor imatinib. For example, cell stasis, cell killing or apoptosis may be increased by at least 10%, at least 20%, at least 30%, at least 40%, at least 50%, at least 60%, at least 70%, at least 80%, at least 90%, at least two-fold, at least three-fold, at least four-fold, at least five-fold, at least 10-fold, or at least 20-fold. In certain embodiments, amounts of apoptosis are determined by measuring caspase activity of tumor cells.

In particular embodiments, treatment with a combination of: Compound A or a pharmaceutically acceptable salt thereof, or Compound B or a pharmaceutically acceptable salt thereof; and a RAF inhibitor, e.g., dabrafenib, results in increased tumor regression or decreased tumor size or volume (e.g., a GIST), as compared to the size, e.g., weight or volume of a tumor of the same type or the same tumor either untreated or treated with only a RAF inhibitor, e.g., dabrafenib, or with only a c-KIT inhibitor, e.g., imatinib. For example, tumor weight or volume may be decreased by at least 10%, at least 20%, at least 30%, at least 40%, at least 50%, at least 60%, at least 70%, at least 80%, or at least 90%.

In particular embodiments, treatment with a combination of: Compound A or a pharmaceutically acceptable salt thereof, or Compound B or a pharmaceutically acceptable salt thereof; and a RAF inhibitor, e.g., dabrafenib, inhibits the amount of tumor growth or regrowth, e.g., GIST growth or regrowth, to a greater extent as compared to the amount of growth or regrowth the same type or the same tumor either untreated or treated with only a RAF inhibitor, e.g., dabrafenib, or with only a c-KIT inhibitor, e.g., imatinib. For example, tumor growth or regrowth may be inhibited by at least 10%, at least 20%, at least 30%, at least 40%, at least 50%, at least 60%, at least 70%, at least 80%, or at least 90%.

In particular embodiments, treatment with a combination of: Compound A or a pharmaceutically acceptable salt thereof, or Compound B or a pharmaceutically acceptable salt thereof; and a RAF inhibitor, e.g., dabrafenib, inhibits the growth of resistant tumor cells, e.g., resistant GIST cells, to a greater extent as compared to the amount of growth of resistant tumor cells of the same type or the same tumor either untreated or treated with only a RAF inhibitor, e.g., dabrafenib, or with only a c-KIT inhibitor, e.g., imatinib, or with a combination of a RAF inhibitor, e.g., dabrafenib and a c-KIT inhibitor, e.g., imatinib. For example, the amount of growth or number of resistant tumor cells may be inhibited by at least 10%, at least 20%, at least 30%, at least 40%, at least 50%, at least 60%, at least 70%, at least 80%, or at least 90%. In particular embodiments, resistant tumor cells are resistant to treatment with a c-KIT inhibitor, e.g., imatinib, and/or a RAF inhibitor, e.g., dabrafenib. In certain embodiments, the resistant tumor cells comprise a c-KIT secondary mutation. In certain embodiments, the c-KIT secondary mutation is a mutation of any of the following amino acid residues of c-KIT: V654, N655, T670, L783, D816, D820, N822, Y823, A829, and/or T847, including but not limited to any of the amino acid substitutions depicted in the accompanying figures. In particular embodiments, the resistant tumor cells comprise an activated MAPKAP kinase pathway, and in certain embodiments, they comprise a mutation in a mutation in a RAS gene, e.g., an N-RAS or K-RAS gene, a Fibloblast Growth Factor Receptor (FGFR) gene, and/or a Neurofibromin-1 (NF1) gene. In certain embodiments, the mutation is an N-RAS G12D mutation.

In particular embodiments, treatment with a combination of: either Compound A or a pharmaceutically acceptable salt thereof, or Compound B or a pharmaceutically acceptable salt thereof; in combination with a RAF inhibitor, e.g., dabrafenib, results in eradication of a tumor to the limit of detection, e.g., a GIST. In particular embodiments, eradication of a tumor means there is no longer any detectable tumor in the patient to the limit of detection. In particular embodiments, there is no detectable tumor in the patient for at least six months, at least one year, at least two years, at least five years, or at least 10 years following eradication of the tumor, e.g., GIST, by a combination therapy disclosed herein. Tumor eradication may be determined by photon emission tomography (PET), CT scans, absence of circulating cell free DNA (cfDNA) containing a c-KIT mutation, absence of circulating tumor cells (CTCs) present in the vasculature of a subject, or absence of a cancer cell biomarker within the circulating blood vasculature of a subject.

The present disclosure describes combination therapies that involve the administration of either Compound A or a pharmaceutically acceptable salt thereof, or Compound B or a pharmaceutically acceptable salt thereof, and one or more MAPKAP kinase inhibitors, e.g., a MEK inhibitor, ERK inhibitor, or RAF inhibitor. The combination therapies described herein can be used by themselves, or in further combination with one or more additional therapeutic agents (e.g., one or more additional therapeutic agents described below). For example, either Compound A or a pharmaceutically acceptable salt thereof, or Compound B or a pharmaceutically acceptable salt thereof, and a MEK inhibitor, can be administered together with a cancer targeted therapeutic agent, a cancer-targeted biological, an immune checkpoint inhibitor, or a chemotherapeutic agent. In another embodiment Compound A or Compound B and a MEK inhibitor are administered without any other therapeutic agent. The therapeutic agents can be administered together with or sequentially with another therapeutic agent described herein in a combination therapy.

Combination therapy can be achieved by administering two or more therapeutic agents, each of which is formulated and administered separately, or by administering two or more therapeutic agents in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X-Y-X, X-X-Y, Y-X-Y, Y-Y-X, X-X-Y-Y, etc.

The one or more additional therapeutic agents that may be administered according to the present disclosure include, but are not limited to, cytotoxic agents, cisplatin, doxorubicin, etoposide, irinotecan, topotecan, paclitaxel, docetaxel, the epothilones, tamoxifen, 5-fluorouracil, methotrexate, temozolomide, cyclophosphamide, lonafarib, tipifarnib, 4-((5-((4-(3-chlorophenyl)-3-oxopiperazin-1-yl)methyl)-1H-imidazol-1-yl)methyl)benzonitrile hydrochloride, (R)-1-((1H-imidazol-5-yl)methyl)-3-benzyl-4-(thiophen-2-ylsulfonyl)-2,3,4,5-tetrahydro-1H-benzo diazepine-7-carbonitrile, cetuximab, imatinib, interferon alfa-2b, pegylated interferon alfa-2b, aromatase combinations, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, leucovorin, oxaliplatin, pentostatine, vinblastine, vincristine, vindesine, bleomycin, dactinomycin, daunorubicin, epirubicin, idarubicin, mithramycin, deoxycoformycin, mitomycin-C, L-asparaginase, teniposide 17α-ethinyl estradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, 17α-hydroxyprogesterone, aminoglutethimide, estramustine, medroxyprogesterone acetate, leuprolide acetate, flutamide, toremifene citrate, goserelin acetate, carboplatin, hydroxyurea, amsacrine, procarbazine, mitotane, mitoxantrone, levamisole, vinorelbine, anastrazole, letrozole, capecitabine, raloxifene, droloxafine, hexamethylmelamine, bevacizumab, trastuzumab, tositumomab, bortezomib, ibritumomab tiuxetan, arsenic trioxide, porfimer sodium, cetuximab, thioTEPA, altretamine, fulvestrant, exemestane, rituximab, alemtuzumab, dexamethasone, bicalutamide, chlorambucil, and valrubicin.

The one or more additional therapeutic agents that can be administered may include, without limitation, an AKT inhibitor, alkylating agent, all-trans retinoic acid, antiandrogen, azacitidine, BCL2 inhibitor, BCL-XL inhibitor, BCR- ABL inhibitor, BTK inhibitor, BTK/LCK/LYN inhibitor, CDK1/2/4/6/7/9 inhibitor, CDK4/6 inhibitor, CDK9 inhibitor, CBP/p300 inhibitor, EGFR inhibitor, endothelin receptor antagonist, RAF inhibitor, MEK inhibitor, ERK inhibitor, farnesyltransferase inhibitor, FLT3 inhibitor, glucocorticoid receptor agonist, HDM2 inhibitor, histone deacetylase inhibitor, IKKβ inhibitor, immunomodulatory drug (IMiD), ingenol, ITK inhibitor, JAK1/JAK2/JAK3/TYK2 inhibitor, MTOR inhibitor, PI3 kinase inhibitor, dual PI3 kinase/MTOR inhibitor, proteasome inhibitor, protein kinase C agonist, SUV39H1 inhibitor, TRAIL, VEGFR2 inhibitor, Wnt/β-catenin signaling inhibitor, decitabine, and anti-CD20 monoclonal antibody.

In certain embodiments, the additional therapeutic agent is an immunomodulatory agentis selected from the group consisting of CTLA4 inhibitors such as, but not limited to ipilimumab and tremelimumab; PD1 inhibitors such as, but not limited to pembrolizumab, and nivolumab; PDL1 inhibitors such as, but not limited to atezolizumab (formerly MPDL3280A), durvalumab (formerly MEDI4736), avelumab, PDR001; 4 1BB or 4 1BB ligand inhibitors such as, but not limited to urelumab and PF-05082566; OX40 ligand agonists such as, but not limited to MEDI6469; GITR agents such as, but not limited to TRX518; CD27 inhibitors such as, but not limited to varlilumab; TNFRSF25 or TL1A inhibitors; CD40 agonists such as, but not limited to CP-870893; HVEM or LIGHT or LTA or BTLA or CD160 inhibitors; LAG3 inhibitors such as, but not limited to BMS-986016; TIM3 inhibitors; Siglecs inhibitors; ICOS or ICOS ligand agonists; B7 H3 inhibitors such as, but not limited to MGA271; B7 H4 inhibitors; VISTA inhibitors; HHLA2 or TMIGD2 inhibitors; inhibitors of Butyrophilins, including BTNL2 inhibitors; CD244 or CD48 inhibitors; inhibitors of TIGIT and PVR family members; KIRs inhibitors such as, but not limited to lirilumab; inhibitors of ILTs and LIRs; NKG2D and NKG2A inhibitors such as, but not limited to IPH2201; inhibitors of MICA and MICB; CD244 inhibitors; CSF1R inhibitors such as, but not limited to emactuzumab, cabiralizumab, pexidartinib, ARRY382, BLZ945; IDO inhibitors such as, but not limited to INCB024360; thalidomide, lenalidomide, TGFβ inhibitors such as, but not limited to galunisertib; adenosine or CD39 or CD73 inhibitors; CXCR4 or CXCL12 inhibitors such as, but not limited to ulocuplumab and (3S,6S,9S,12R,17R,20S,23S,26S,29S,34aS)-N—((S)-1-amino-5-guanidino-1-oxopentan-2-yl)-26,29-bis(4-aminobutyl)-17-((S)-2-((S)-2-((S)-2-(4-fluorobenzamido)-5-guanidinopentanamido)-5-guanidinopentanamido)-3-(naphthalen-2-yl)propanamido)-6-(3-guanidinopropyl)-3,20-bis(4-hydroxybenzyl)-1,4,7,10,18,21,24,27,30-nonaoxo-9,23-bis(3-ureidopropyl)triacontahydro-1H,16H-pyrrolo[2,1-p][1,2]dithia[5,8,11,14,17,20,23,26,29]nonaazacyclodotriacontine-12-carboxamide BKT140; phosphatidylserine inhibitors such as, but not limited to bavituximab; SIRPA or CD47 inhibitors such as, but not limited to CC-90002; VEGF inhibitors such as, but not limited to bevacizumab; and neuropilin inhibitors such as, but not limited to MNRP1685A.

Pharmaceutical Compositions

Aspects of the present disclosure are directed to methods of treatment involving the administration of a combination of compounds disclosed herein, or one or more pharmaceutical compositions comprising such compounds and a pharmaceutically acceptable diluent, excipient or carrier. In particular embodiments, the methods disclosed herein involve administering a first pharmaceutical composition comprising either Compound A or a pharmaceutically acceptable salt thereof thereof and a pharmaceutically acceptable diluent, excipient or carrier, and a second pharmaceutical composition comprising a MEK inhibitor, e.g., trametinib, a ERK inhibitor, e.g. ulixertinib, a RAF inhibitor, e.g. LY3009120, or pharmaceutically acceptable salts thereof, and a pharmaceutically acceptable diluent, excipient or carrier. In particular embodiments, the methods disclosed herein involve administering a first pharmaceutical composition comprising Compound B or a pharmaceutically acceptable salt thereof and a pharmaceutically acceptable diluent, excipient or carrier, and a second pharmaceutical composition comprising a MEK inhibitor, e.g., trametinib, a ERK inhibitor, e.g. ulixertinib, a RAF inhibitor, e.g. LY3009120, or pharmaceutically acceptable salts thereof, and a pharmaceutically acceptable diluent, excipient or carrier. In particular embodiments, the methods disclosed herein involve administering a pharmaceutical composition comprising Compound A or a pharmaceutically acceptable salt thereof, a MEK inhibitor, e.g., trametinib, and a pharmaceutically acceptable diluent, excipient or carrier. In particular embodiments, the methods disclosed herein involve administering a pharmaceutical composition comprising Compound B or a pharmaceutically acceptable salt thereof, a MEK inhibitor, e.g., trametinib, and a pharmaceutically acceptable diluent, excipient or carrier.

In particular embodiments, the methods disclosed herein involve administering a pharmaceutical composition comprising Compound A or a pharmaceutically acceptable salt thereof, a ERK inhibitor, e.g., ulixertinib, and a pharmaceutically acceptable diluent, excipient or carrier. In particular embodiments, the methods disclosed herein involve administering a pharmaceutical composition comprising Compound B or a pharmaceutically acceptable salt thereof, a ERK inhibitor, e.g., ulixertinib, and a pharmaceutically acceptable diluent, excipient or carrier.

In particular embodiments, the methods disclosed herein involve administering a pharmaceutical composition comprising Compound A or a pharmaceutically acceptable salt thereof, a RAF inhibitor, e.g., LY3009120, and a pharmaceutically acceptable diluent, excipient or carrier. In particular embodiments, the methods disclosed herein involve administering a pharmaceutical composition comprising Compound B or a pharmaceutically acceptable salt thereof, a RAF inhibitor, e.g., LY3001290, and a pharmaceutically acceptable diluent, excipient or carrier.

In using the pharmaceutical compositions of the compounds described herein, pharmaceutically acceptable carriers can be either solid or liquid. Solid forms include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa, which is hereby incorporated by reference in its entirety.

Liquid form preparations include solutions, suspensions and emulsions. For example, water or water-propylene glycol solutions for parenteral injection or addition of sweeteners and opacifiers for oral solutions, suspensions and emulsions. Liquid form preparations may also include solutions for intranasal administration.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Aerosol preparations suitable for inhalation may also be used. These preparations may include solutions and solids in powder form, which may be in combination with a pharmaceutically acceptable carrier, such as an inert compressed gas, e.g., nitrogen.

Also contemplated for use are solid form preparations that are intended to be converted, shortly before use, to liquid form preparations for either oral or parenteral administration. Such liquid forms include solutions, suspensions and emulsions.

Dosage

In some embodiments where Compound A or Compound B (or pharmaceutically acceptable salts thereof) is used in combination with a MEK inhibitor (e.g., trametinib) for a treatment protocol, the two therapeutics may be administered together or in a "dual-regimen" wherein the two therapeutics are dosed and administered separately. When the Compound A or B (or pharmaceutically acceptable salts thereof) and the MEK inhibitor are dosed separately, the typical dosage of Compound A or Compound B (or pharmaceutically acceptable salts thereof) administered to the subject in need of the treatment is typically from about 5 mg per day to about 5000 mg per day and, in other embodiments, from about 50 mg per day to about 1000 mg per day. Other dosages may be from about 10 mmol up to about 250 mmol per day, from about 20 mmol to about 70 mmol per day or even from about 30 mmol to about 60 mmol per day. Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. A typical recommended daily dosage regimen for oral administration can range from about 1 mg/day to about 500 mg/day or 1 mg/day to 200 mg/day, in a single dose, or in two to four divided doses. In one embodiment, the typical daily dose regimen is 150 mg.

In certain embodiments, the dosage of MEK inhibitors is consistent with previously disclosed dosages and/or dosages approved for use by the Food and Drug Administration. In other embodiments, the dosage of MEK inhibitor is less than previously approved dosages, e.g., about 20%, about 50% or about 80% of an approved dosage. In certain embodiments, the dosage of trametinib is about 0.5 mg to 20 mg orally daily, e.g., about 1 mg daily or about 2 mg daily. In certain embodiments, the dosage of cobimetinib is about 10 mg to 200 mg daily, e.g., about 30 mg or about 60 mg daily. In certain embodiments, the dosage of binimetinib is about 10 mg to about 200 mg twice daily, e.g., about 25 mg or about 45 mg twice daily. In certain embodiments, the dosage of selumetinib is about 10 mg to 200 mg daily, e.g., about 30 mg or about 75 mg twice daily.

The amount and frequency of administration of the compounds described herein and/or the pharmaceutically acceptable salts thereof, and other therapeutic agents, will be regulated according to the judgment of the attending clinician considering such factors as age, condition and size of the patient as well as severity of the symptoms being treated.

Compounds of the present disclosure (e.g., Compound A or Compound B (and pharmaceutically acceptable salts thereof), MEK inhibitors, and other therapeutic agents) may be administered by any suitable route. The compounds can be administrated orally (e.g., dietary) in capsules, suspensions, tablets, pills, dragees, liquids, gels, syrups, slurries, and the like. Methods for encapsulating compositions (such as in a coating of hard gelatin or cyclodextran) are known in the art (Baker, et al., "Controlled Release of Biological Active Agents", John Wiley and Sons, 1986, which is hereby incorporated by reference in its entirety). The compounds can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers are biocompatible, i.e., non-toxic, non-inflammatory, non-immunogenic and devoid of other undesired reactions at the administration site.

Illustrative pharmaceutical compositions are tablets and gelatin capsules comprising a compound described herein and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

If formulated as a fixed dose, such combination products employ the compounds described herein within the dosage range described herein, or as known to those skilled in the art.

Since the compounds described herein (e.g., Compounds A and B and MAPKAP kinase inhibitors including MEK inhibitors) are intended for use in pharmaceutical compositions a skilled artisan will understand that they can be provided in substantially pure forms for example, at least 60% pure, at least 75% pure, at least 85% pure, and at least 98% pure (w/w). The pharmaceutical preparation may be in a unit dosage form. In such form, the preparation is subdivided into suitably sized unit doses containing appropriate quantities of compounds A or B, e.g., an effective amount to achieve the desired purpose as described herein.

EXAMPLES

It is found that treatment of c-KIT-mediated tumor cells with a combination of either Compound A or a pharmaceutically acceptable salt thereof in combination with a MEK inhibitor or an ERK inhibitor, or a RAF inhibitor unexpectedly and synergistically induces apoptosis of the tumor cells. In addition, this combination therapy prevents growth of tumor cells, including tumor cells having a secondary mutation conferring resistance to other c-KIT inhibitors and/or MEK, ERK or RAF inhibitors. Furthermore, the combination therapy disclosed herein appeared to have a prolonged effect on tumor cell stasis, as opposed to rapid tumor regrowth in the absence of drug combination treatment. Furthermore, the combination therapy disclosed herein appeared to have a cytotoxic effect on tumor cells, as opposed to merely a cytostatic effect. Furthermore, the combination therapy disclosed herein appeared to eradicate GIST tumor cells to the limit of detection, with no tumor cell colony outgrowth after removal of combination therapy including drug-free recovery periods of up to 21 days. Characterization of this unexpected finding was undertaken in biochemical assays and cellular assays, including those described herein.

The disclosure is thus further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1. Combination Treatment of Compound a with Trametinib Induces Apoptosis in GIST-T1, GIST-T/D816E Imatinib-Resistant Cells and GIST-T1/T670I Imatinib Resistant Cells A study was performed which demonstrates that combination treatment with Compound A and trametinib induces apoptosis in GIST-T1 (57 bp exon 11 deletion) imatinib sensitive cells, GIST-T1/D816E imatinib resistant cells and GIST-T1/T670I) imatinib resistant cells. Assays were conducted in 96 well plates with 10,000 GIST-T1, GIST-T1/D816E or GIST-T1/T670I cells seeded per well. Cells were treated with vehicle control, Compound A, trametinib, or combinations thereof at varying concentrations, and the cells were allowed to grow for 24 and 48 hours in the presence of the drug treatments. Apoptosis was assessed by measuring Caspase 3/7 activity.

FIG. 1A and FIG. 1C are graphical representations showing the relative percentage of caspase activity (compared to vehicle control set at 100%) determined for various treatments of GIST-T1 cells. FIG. 1B and FIG. 1D are matrix synergy charts and combination index plots based on the combination index (CI) method described by Chou and Talalay (1984) and the computer software of Chou and Martin (2005). CI<1 indicates synergism, CI=1 indicates additive effect, and CI>1 indicates antagonism. Combination treatments for 24 hours (FIG. 1A, FIG. 1B) and 48 hours (FIG. 1C, FIG. 1D) with Compound A and trametinib showed strong synergy for inducing apoptosis in GIST-T1 cells.

FIG. 1E is a graphical representation showing caspase activity from various treatments of GIST-T1/D816E imatinib resistant cells. FIG. 1F is a matrix synergy chart and combination index plot based on the combination index (CI) method described by Chou and Talalay (1984) and the computer software of Chou and Martin (2005). CI<1 indicates synergism, CI=1 indicates additive effect, and CI>1 indicates antagonism. Combination treatments for 24 hours with Compound A and trametinib showed strong synergy for inducing apoptosis of GIST-T1/D816E imatinib resistant cells.

FIG. 1G is a graphical representation showing caspase activity from various treatments of GIST-T1/T670I imatinib resistant cells. FIG. 1H is a matrix synergy chart and combination index plot based on the combination index (CI) method described by Chou and Talalay (1984) and the computer software of Chou and Martin (2005). CI<1 indicates synergism, CI=1 indicates additive effect, and CI>1 indicates antagonism. Combination treatments for 24 hours with Compound A and trametinib showed strong synergy for inducing apoptosis of GIST-T1/T670I imatinib resistant cells.

Figure 2A:
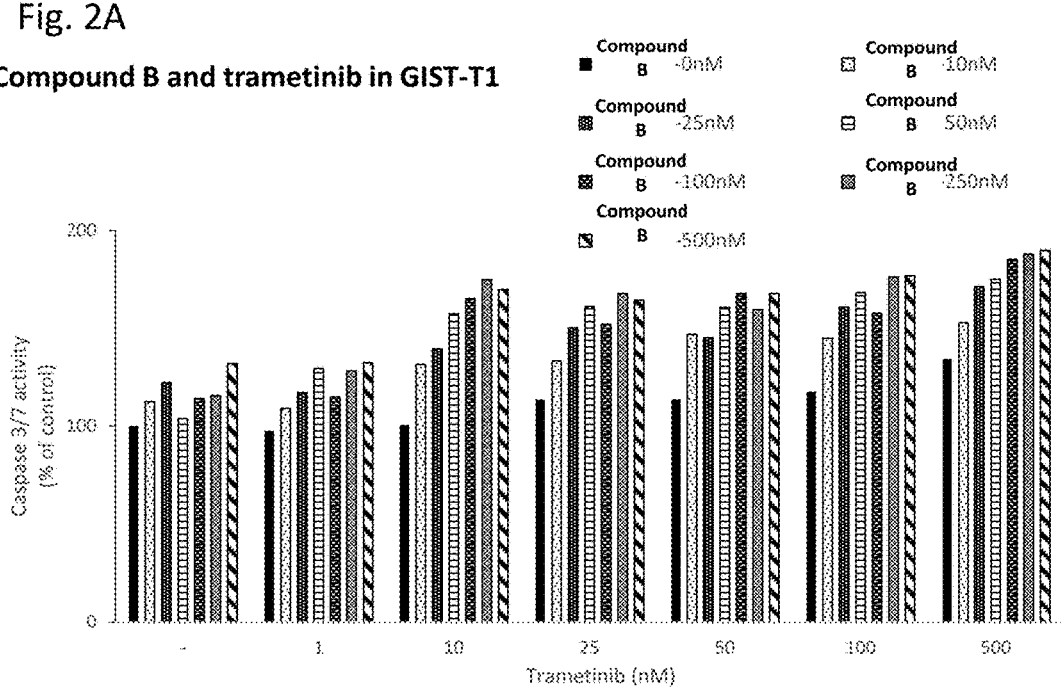
FIG. 2A shows a graphical representation of Caspase activity following various treatments with Compound B and trametinib for 24 hours in GIST-T1 cells.
Figure 2A:
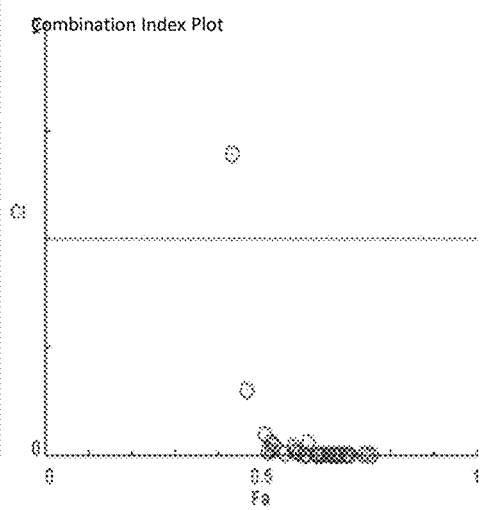

Example 2. Combination Treatment of Compound B with Trametinib Induces Apoptosis in GIST-T1, GIST-T/D816E Imatinib-Resistant Cells and GIST-T/T670I Imatinib Resistant Cells FIG. 2A is a graphical representations showing the relative percentage of caspase activity (compared to vehicle control set at 100%) determined for various treatments of GIST-T1 cells. FIG. 2B is a matrix synergy charts and combination index plots as described in example 1 Combination treatments for 24 hours (FIG. 2A, FIG. 2B) with Compound B and trametinib showed strong synergy for inducing apoptosis in GIST-T1 cells.

Figure 2C:
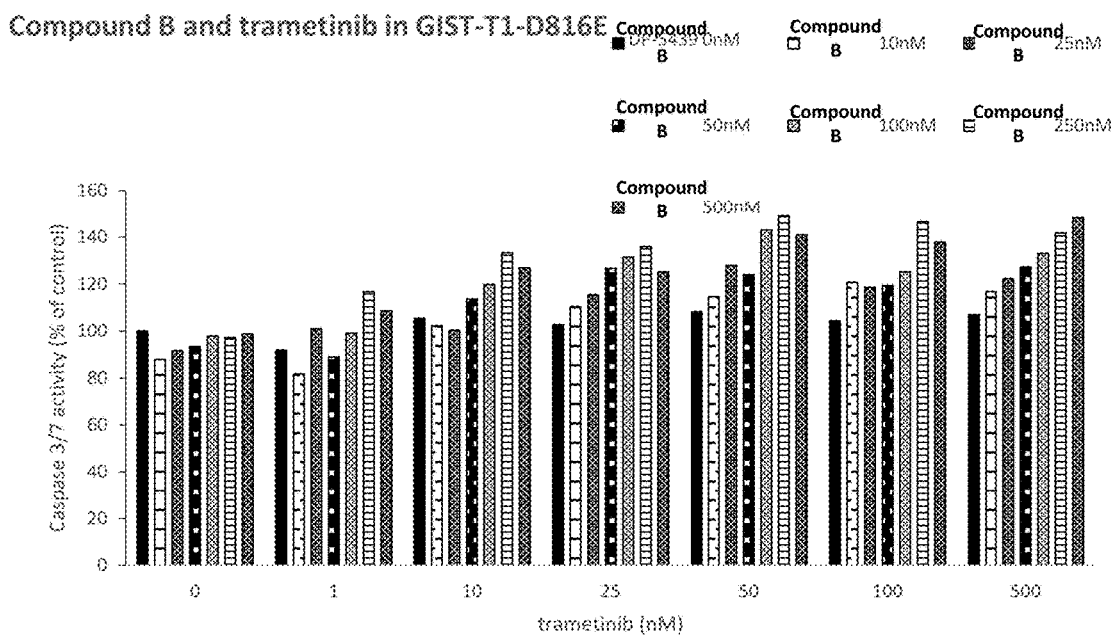
FIG. 2C shows a graphical representation of Caspase activity following various treatments with Compound B and trametinib for 24 hours in GIST-T1/D816E imatinib resistant cells.
Figure 2C:
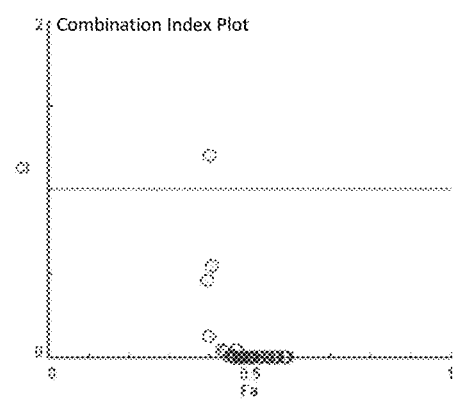

FIG. 2C is a graphical representation showing caspase activity from various treatments of GIST-T1/D816E imatinib resistant cells. FIG. 2D is a matrix synergy chart and combination index plot. Combination treatments for 24 hours with Compound B and trametinib showed strong synergy for inducing apoptosis of GIST-T1/D816E imatinib resistant cells.

Figure 2E:
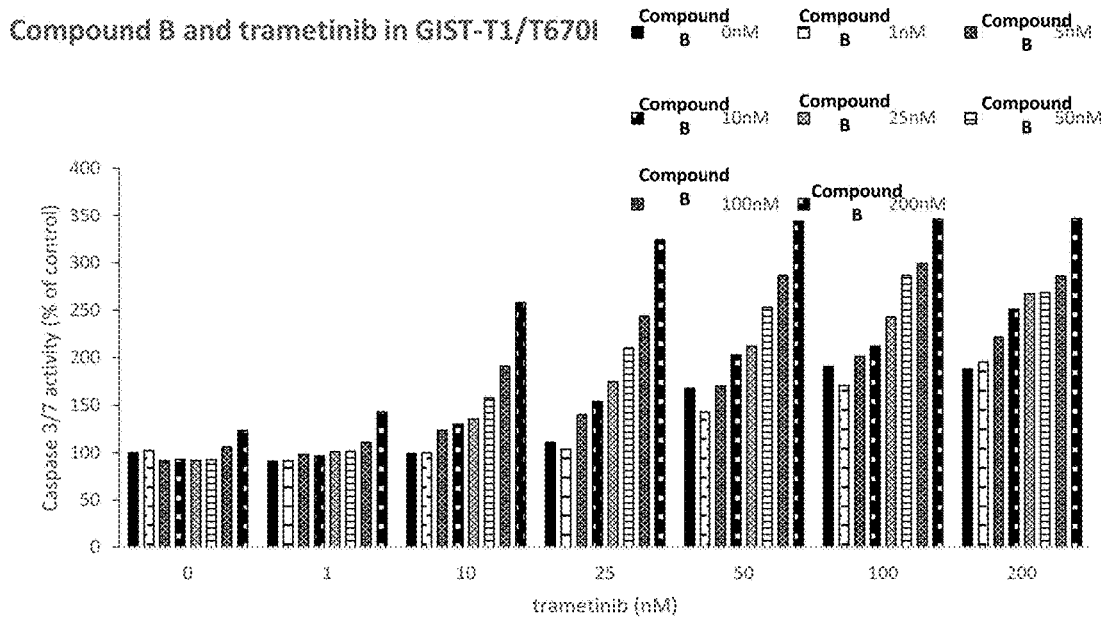
FIG. 2E shows a graphical representation of Caspase activity following various treatments with Compound B and trametinib for 24 hours in GIST-T1/T670I imatinib resistant cells.
Figure 2E:
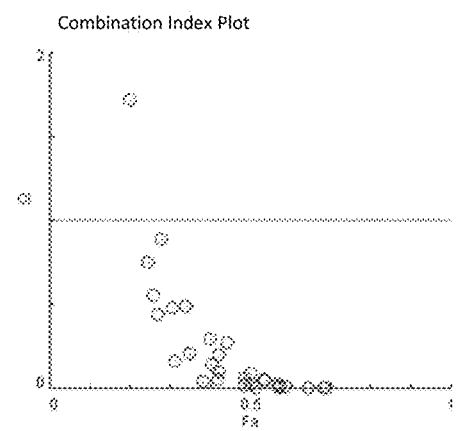

FIG. 2E is a graphical representation showing caspase activity from various treatments of GIST-T1/T670I imatinib resistant cells. FIG. 2F is a matrix synergy chart and combination index plot. Combination treatments for 24 hours with Compound B and trametinib showed strong synergy for inducing apoptosis of GIST-T1/T670I imatinib resistant cells.

Figure 3A:
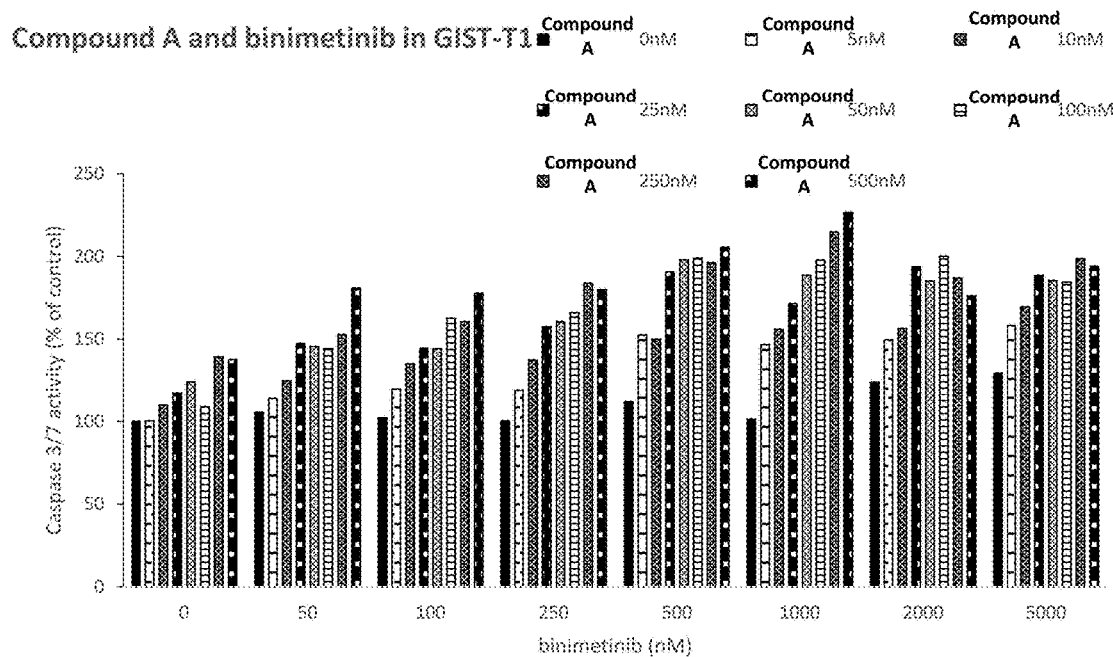
FIG. 3A shows a graphical representation of Caspase activity following various treatments with Compound A and binimetinib for 24 hours in GIST-T1 cells.
Figure 3A:
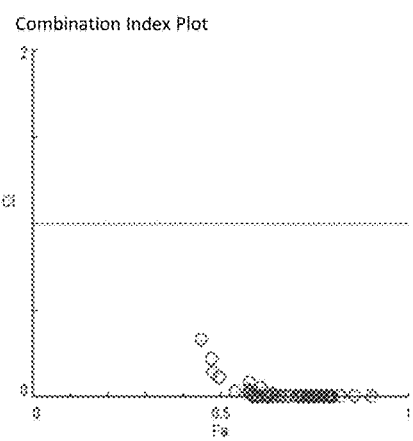

Example 3. Combination Treatment of Compound a with Binimetinib Induces Apoptosis in GIST-T1 and GIST-T/D816E Imatinib-Resistant Cells and GIST-T1/T670I Imatinib Resistant Cells FIG. 3A is graphical representations showing the relative percentage of caspase activity (compared to vehicle control set at 100%) determined for various treatments of GIST-T1 cells. FIG. 3B shows matrix synergy charts and combination index plots based on the combination index (CI) method as described in example 1. Combination treatments for 24 hours (FIG. 3A, FIG. 3B) with Compound A and binimetinib showed strong synergy for inducing apoptosis in GIST-T1 cells.

Figure 3C:
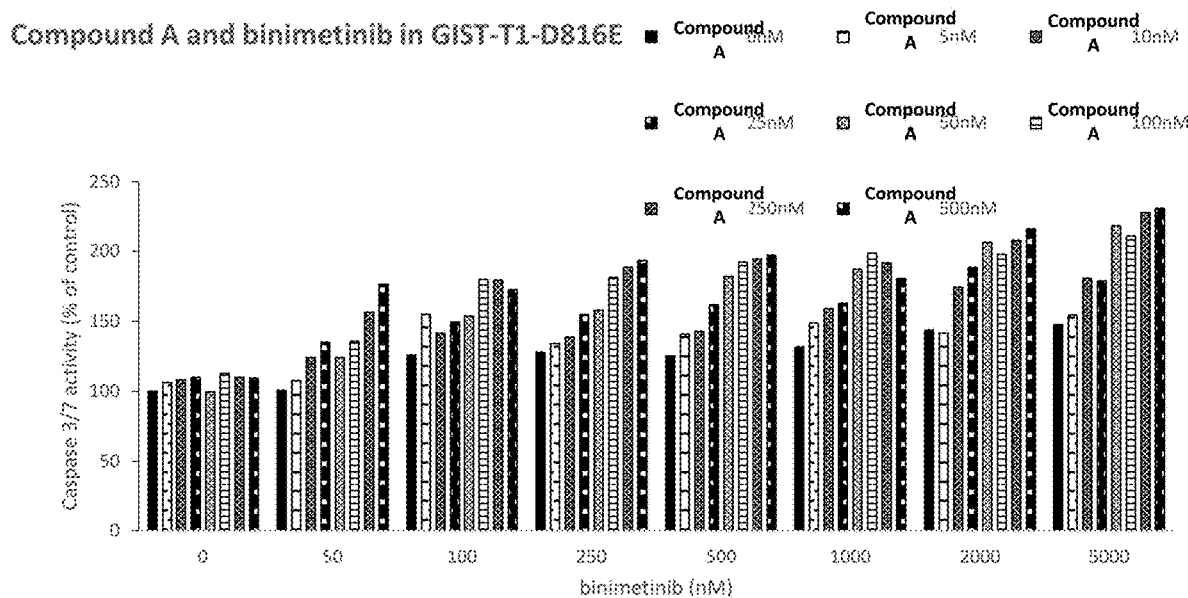
FIG. 3C shows a graphical representation of Caspase activity following various treatments with Compound A and binimetinib for 24 hours in GIST-T1/D816E imatinib resistant cells.
Figure 3C:
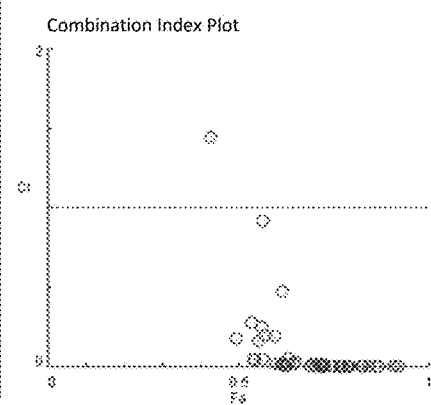

FIG. 3C is a graphical representation showing caspase activity from various treatments of GIST-T1/D816E imatinib resistant cells. FIG. 3D is a matrix synergy chart and combination index plot based on the combination index (CI) as described in example 1. Combination treatments for 24 hours with Compound A and binimetinib showed strong synergy for inducing apoptosis of GIST-T1/D816E imatinib resistant cells.

Figure 3E:
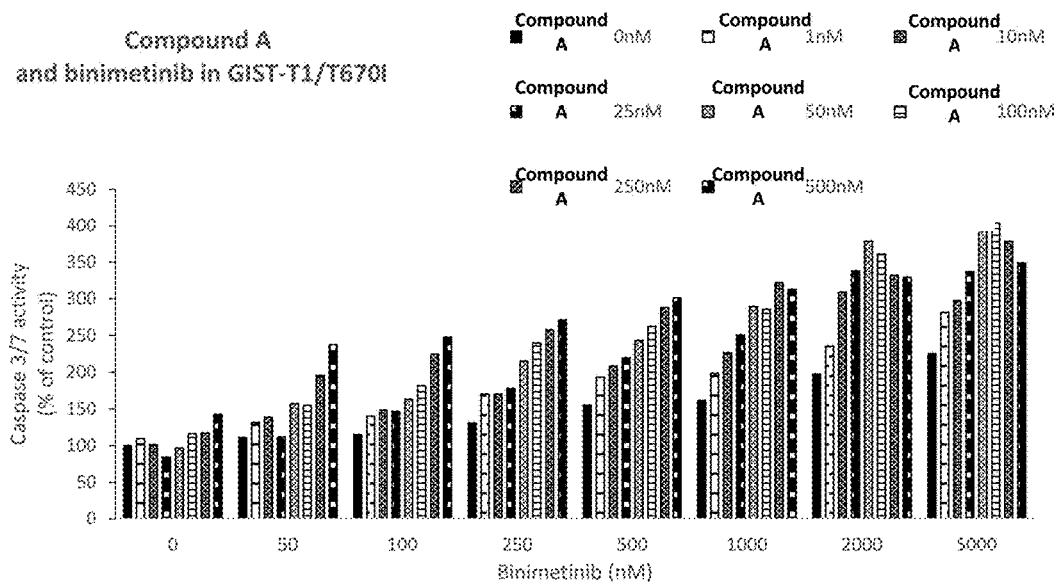
FIG. 3E shows a graphical representation of Caspase activity following various treatments with Compound A and binimetinib for 24 hours in GIST-T1/T670I imatinib resistant cells.
Figure 3E:
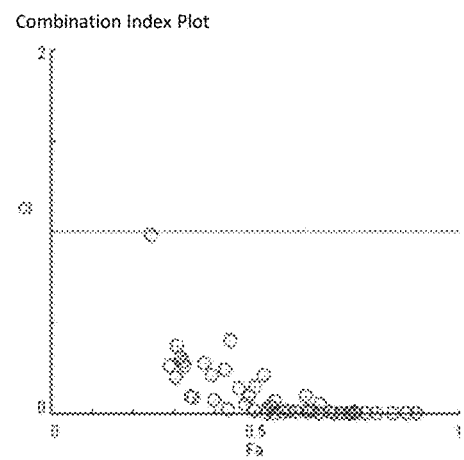

FIG. 3E is a graphical representation showing caspase activity from various treatments of GIST-T1/T670I imatinib resistant cells. FIG. 3F is a matrix synergy chart and combination index plot. Combination treatments for 24 hours with Compound A and binimetinib showed strong synergy for inducing apoptosis of GIST-T1/T670I imatinib resistant cells.

Example 4. Combination Treatment of Compound B with Binimetinib Induces Apoptosis in GIST-T1, GIST-T/D816E Imatinib-Resistant Cells and GIST-T/T670I Imatinib Resistant Cells FIG. 4A is a graphical representations showing the relative percentage of caspase activity (compared to vehicle control set at 100%) determined for various treatments of GIST-T1 cells. FIG. 4B is a matrix synergy charts and combination index plots based on the combination index (CI) method described by Chou and Talalay (1984). Combination treatments for 24 hours (FIG. 4A, FIG. 4B) with Compound B and binimetinib showed strong synergy for inducing apoptosis in GIST-T1 cells.

FIG. 4C is a graphical representation showing caspase activity from various treatments of GIST-T1/D816E imatinib resistant cells. FIG. 4D is a matrix synergy chart and combination index plot. Combination treatments for 24 hours with Compound B and binimetinib showed strong synergy for inducing apoptosis of GIST-T1/D816E imatinib resistant cells.

Figure 4E:
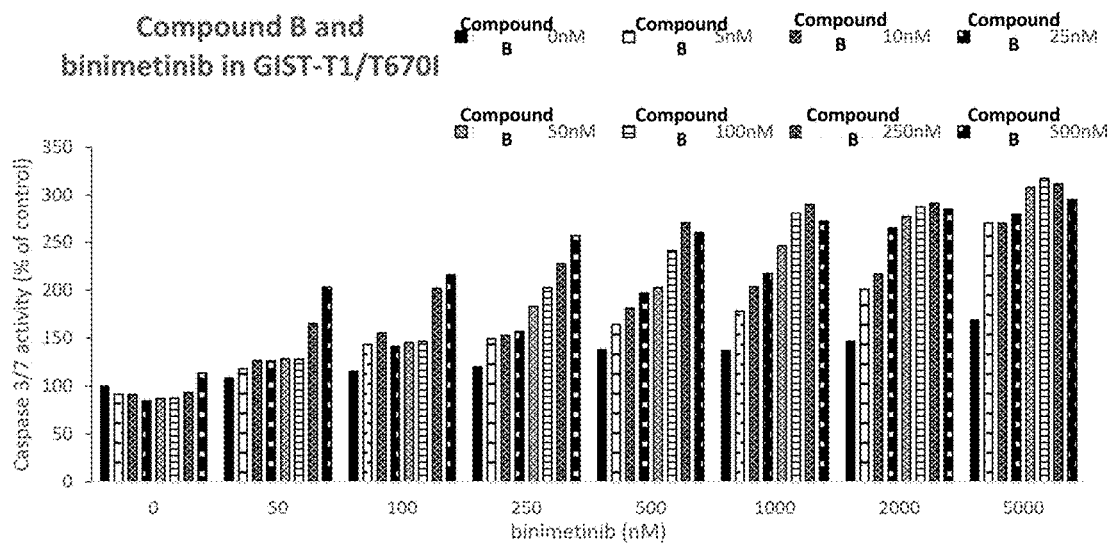
FIG. 4E shows a graphical representation of Caspase activity following various treatments with Compound B and binimetinib for 24 hours in GIST-T1/T670I imatinib resistant cells.
Figure 4E:
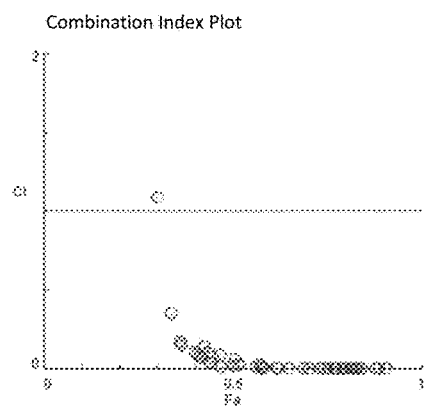

FIG. 4E is a graphical representation showing caspase activity from various treatments of GIST-T1/T670I imatinib resistant cells. FIG. 4F is a matrix synergy chart and combination index plot. Combination treatments for 24 hours with Compound B and binimetinib showed strong synergy for inducing apoptosis of GIST-T1/T670I imatinib resistant cells.

Figure 5A:
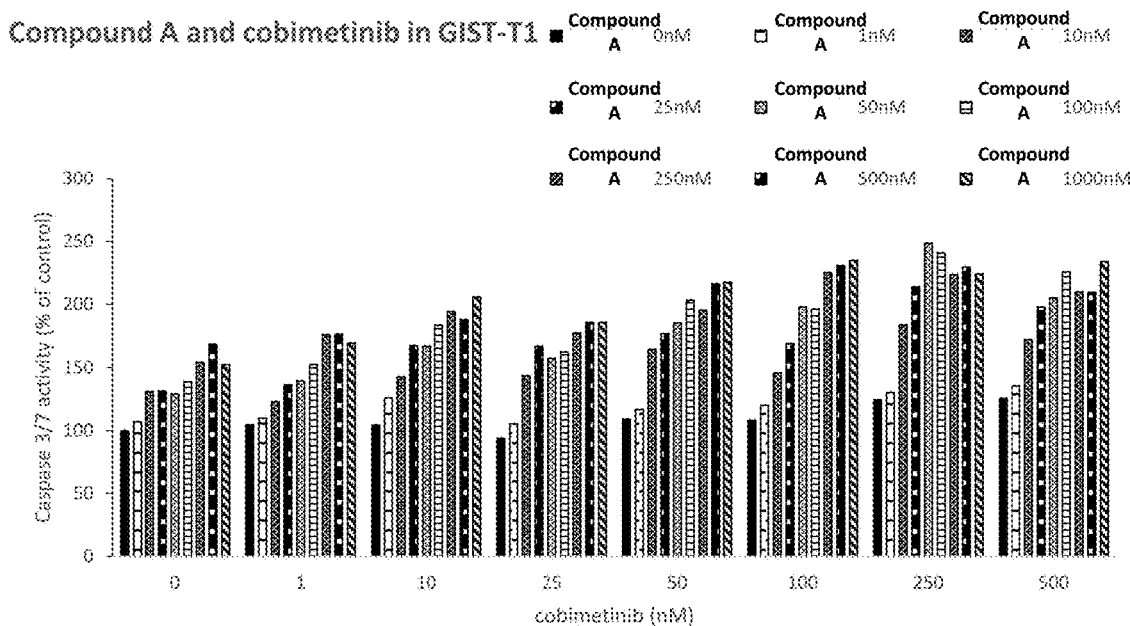
FIG. 5A shows a graphical representation of Caspase activity following various treatments with Compound A and cobimetinib for 24 hours in GIST-T1 cells.
Figure 5A:
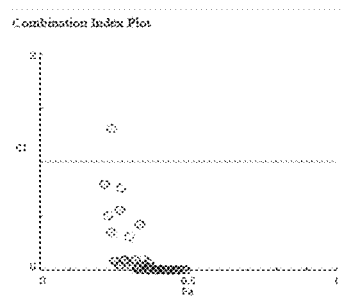

Example 5. Combination Treatment of Compound a with Cobimetinib Induces Apoptosis in GIST-T1 Imatinib Sensitive Cells, GIST-T/D816E Imatinib-Resistant Cells and GIST-T1/T670I Imatinib Resistant Cells FIG. 5A is graphical representations showing the relative percentage of caspase activity (compared to vehicle control set at 100%) determined for various treatments of GIST-T1 cells. FIG. 5B shows matrix synergy charts and combination index plots based on the combination index (CI) method as described in example 1. Combination treatments for 24 hours (FIG. 5A, FIG. 5B) with Compound A and cobimetinib showed strong synergy for inducing apoptosis in GIST-T1 cells.

Figure 5C:
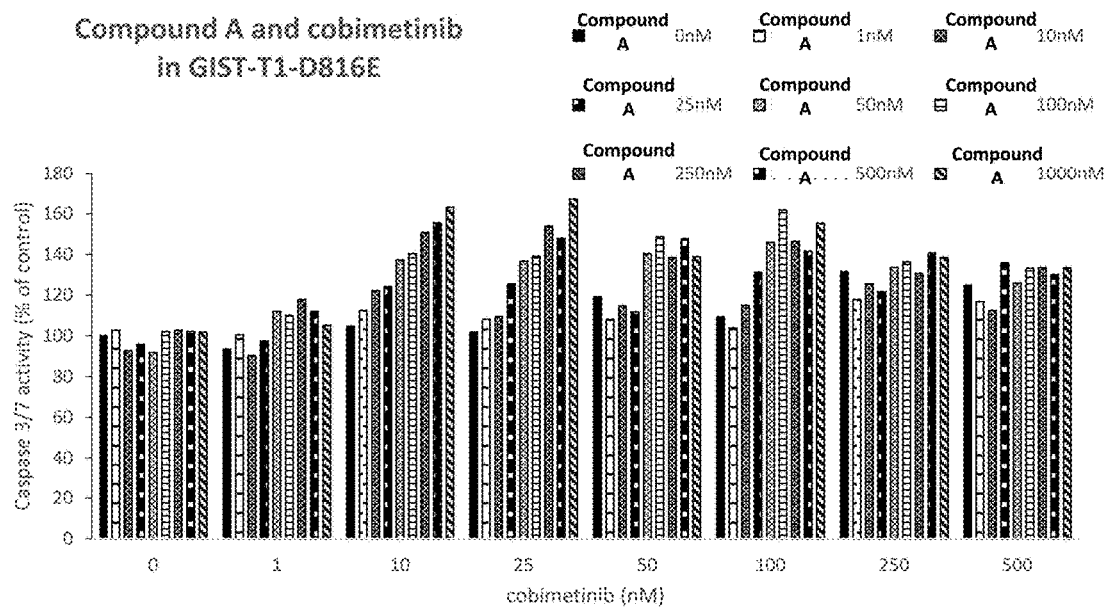
FIG. 5C shows a graphical representation of Caspase activity following various treatments with Compound A and cobimetinib for 24 hours in GIST-T1/D816E imatinib resistant cells.
Figure 5C:
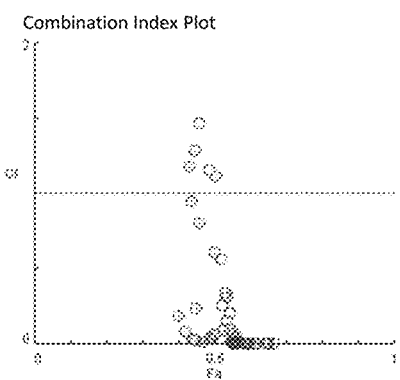

FIG. 5C is a graphical representation showing caspase activity from various treatments of GIST-T1/D816E imatinib resistant cells. FIG. 5D is a matrix synergy chart and combination index plot based on the combination index (CI) as described in example 1. Combination treatments for 24 hours with Compound A and cobimetinib showed strong synergy for inducing apoptosis of GIST-T1/D816E imatinib resistant cells.

FIG. 5E is a graphical representation showing caspase activity from various treatments of GIST-T1/T670I imatinib resistant cells. FIG. 5F is a matrix synergy chart and combination index plot based on the combination index (CI) as described in example 1. Combination treatments for 24 hours with Compound A and cobimetinib showed strong synergy for inducing apoptosis of GIST-T1/T670I imatinib resistant cells.

Figure 6A:
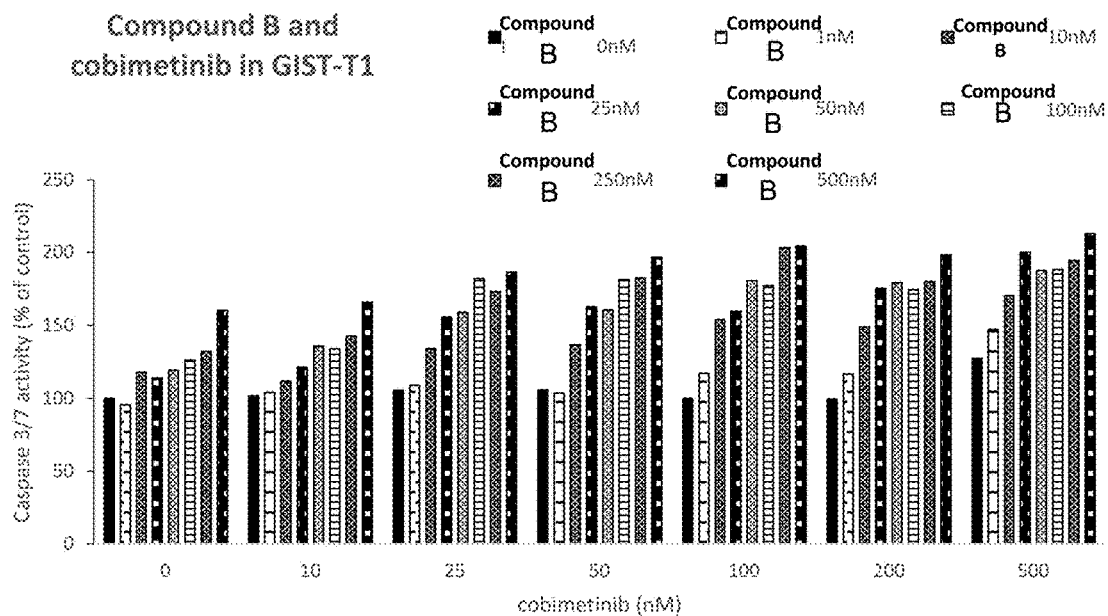
FIG. 6A shows a graphical representation of Caspase activity following various treatments with Compound B and cobimetinib for 24 hours in GIST-T1 cells.
Figure 6B:
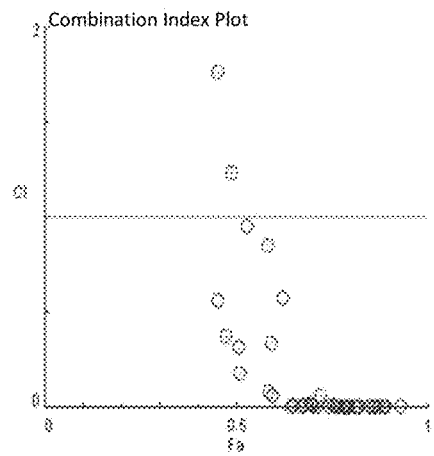
FIG. 6B provides a synergy matrix chart based on the combination index method for various treatments with Compound B and cobimetinib for 24 hours of GIST-T1 cells and a Combination Index Plot demonstrating synergy graphed as combination index (CI) on the y-axis and Fraction affected (Fa) on the x-axis.

Example 6. Combination Treatment of Compound B with Cobimetinib Induces Apoptosis in GIST-T1, GIST-T/D816E Imatinib-Resistant Cells and GIST-T1/T670I Imatinib Resistant Cells FIG. 6A is a graphical representations showing the relative percentage of caspase activity (compared to vehicle control set at 100%) determined for various treatments of GIST-T1 cells. FIG. 6B is a matrix synergy charts and combination index plot. Combination treatments for 24 hours (FIG. 6A, FIG. 6B) with Compound B and cobimetinib showed strong synergy for inducing apoptosis in GIST-T1 cells.

Figure 6C:
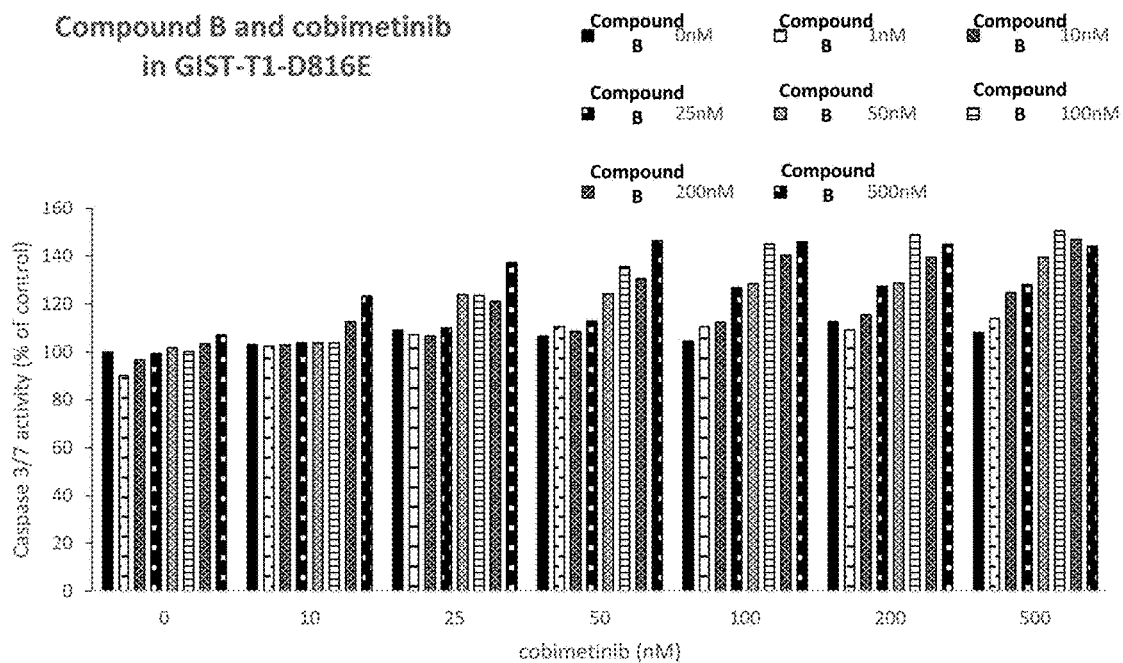
FIG. 6C shows a graphical representation of Caspase activity following various treatments with Compound B and cobimetinib for 24 hours in GIST-T1/D816E imatinib resistant cells.
Figure 6D:
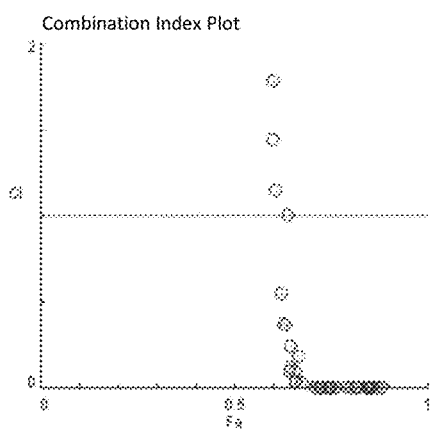
FIG. 6D provides a synergy matrix chart based on the combination index method for various treatments with Compound B and cobimetinib for 24 hours in GIST-T1/D816E imatinib resistant cells and a Combination Index Plot demonstrating synergy graphed as combination index (CI) on the y-axis and Fraction affected (Fa) on the x-axis.

FIG. 6C is a graphical representation showing caspase activity from various treatments of GIST-T1/D816E imatinib resistant cells. FIG. 6D is a matrix synergy chart and combination index plot. Combination treatments for 24 hours with Compound B and cobimetinib showed strong synergy for inducing apoptosis of GIST-T1/D816E imatinib resistant cells.

Figure 6E:
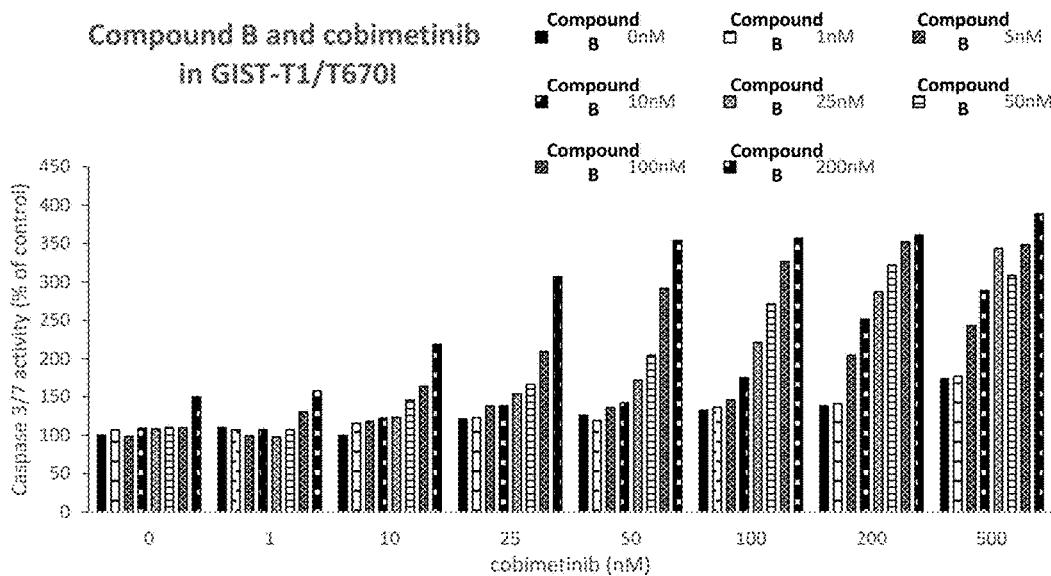
FIG. 6E shows a graphical representation of Caspase activity following various treatments with Compound B and cobimetinib for 24 hours in GIST-T1/T670I imatinib resistant cells.
Figure 6F:
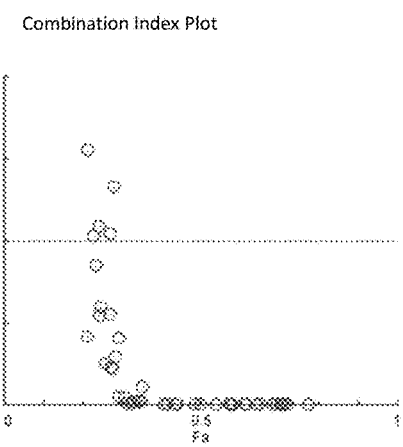
FIG. 6F provides a synergy matrix chart based on the combination index method for various treatments with Compound B and cobimetinib for 24 hours in GIST-T1/T670I imatinib resistant cells and a Combination Index Plot demonstrating synergy graphed as combination index (CI) on the y-axis and Fraction affected (Fa) on the x-axis.

FIG. 6E is a graphical representation showing caspase activity from various treatments of GIST-T1/T670I imatinib resistant cells. FIG. 6F is a matrix synergy chart and combination index plot. Combination treatments for 24 hours with Compound B and cobimetinib showed strong synergy for inducing apoptosis of GIST-T1/T670I imatinib resistant cells.

Figure 7A:
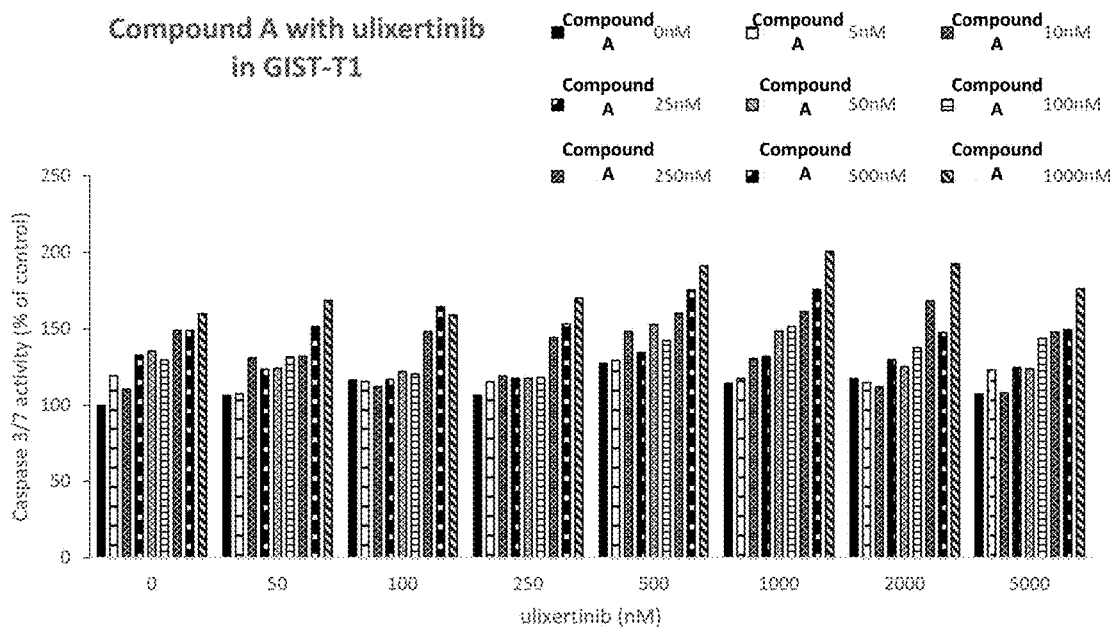
FIG. 7A shows a graphical representation of Caspase activity following various treatments with Compound A and the ERK inhibitor ulixertinib for 24 hours in GIST-T1 cells.
Figure 7B:
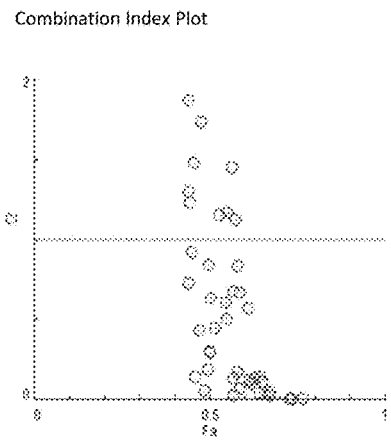
FIG. 7B provides a synergy matrix chart based on the combination index method for various treatments with Compound A and ulixertinib for 24 hours in GIST-T1 cells and a Combination Index Plot demonstrating synergy graphed as combination index (CI) on the y-axis and Fraction affected (Fa) on the x-axis.

Example 7. Combination Treatment of Compound a with Ulixertinib (BVD-523) Induces Apoptosis in GIST-T1, and GIST-T1/T670I Imatinib Resistant Cells FIG. 7A is graphical representations showing the relative percentage of caspase activity (compared to vehicle control set at 100%) determined for various treatments of GIST-T1 cells. FIG. 7B shows matrix synergy charts and combination index plots based on the combination index (CI) method as described in example 1. Combination treatments for 24 hours (FIG. 7A, FIG. 7B) with Compound A and ulixertinib showed strong synergy for inducing apoptosis in GIST-T1 cells at higher concentrations.

Figure 7C:
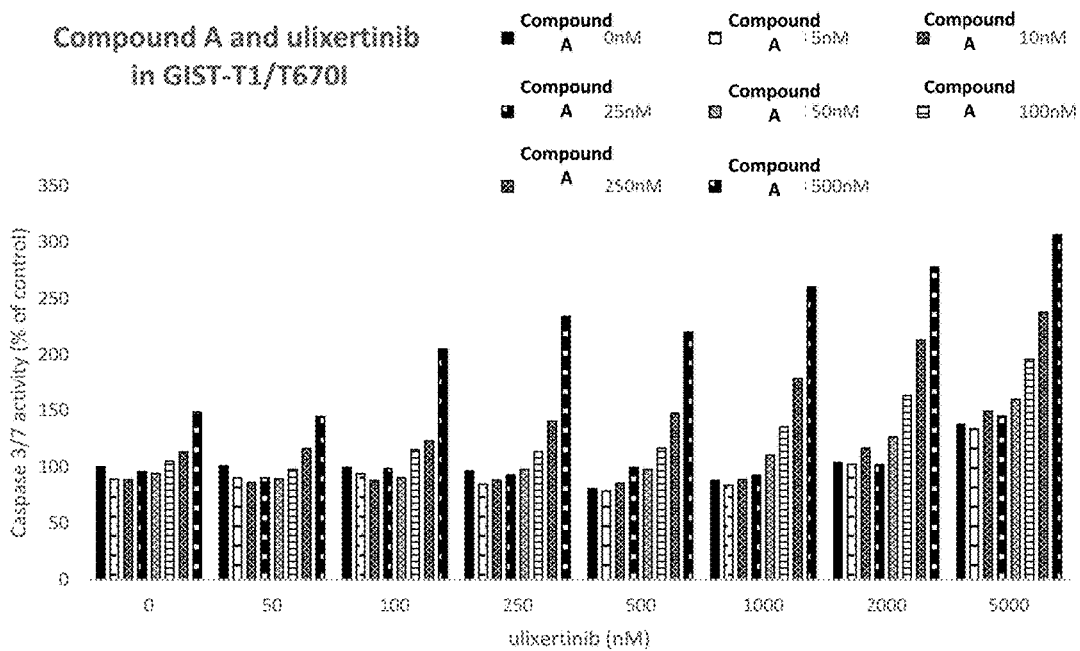
FIG. 7C shows a graphical representation of Caspase activity following various treatments with Compound A and ulixertinib for 24 hours in GIST-T1/T670I imatinib resistant cells.
Figure 7C:
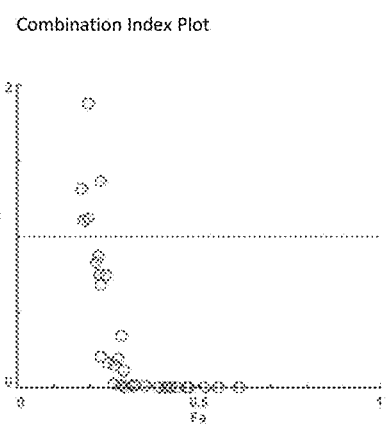

FIG. 7C is a graphical representation showing caspase activity from various treatments of GIST-T1/T670I imatinib resistant cells. FIG. 7D is a matrix synergy chart and combination index plot based on the combination index (CI) as described in example 1. Combination treatments for 24 hours with Compound A and ulixertinib showed strong synergy for inducing apoptosis of GIST-T1/T670I imatinib resistant cells.

Example 8. Combination Treatment of Compound B with Ulixertinib (Bvd-523) Induces Apoptosis in GIST-T1, and GIST-T1/T670I Imatinib Resistant Cells Synergy charts and combination index plots for caspase activity can be used to show for synergy for Compound B and ulixertinib combination in inducing apoptosis in GIST-T1, GIST-T1/D816E imatinib resistant cells and GIST-T1/T670I Imatinib resistant cells.

Example 9. Combination Treatment of Compound a with SCH772984 Induces Apoptosis in GIST-T1, GIST-T1/D816E Imatinib-Resistant Cells and GIST-T1/T670I Imatinib Resistant Cells Synergy charts and combination index plots for caspase activity can be used to show for synergy for Compound A and SCH772984 combination in inducing apoptosis in GIST-T1, GIST-T1/D816E imatinib resistant cells and GIST-T1/T670I imatinib resistant cells.

Example 10. Combination Treatment of Compound B with SCH772984 Induces Apoptosis in GIST-T1, GIST-T1/D816E Imatinib-Resistant Cells and GIST-T1/T670I Imatinib Resistant Cells Synergy charts and combination index plots for caspase activity can be used to show for synergy for Compound B and SCH772984 combination in inducing apoptosis in GIST-T1, GIST-T1/D816E imatinib resistant cells and GIST-T1/T670I imatinib resistant cells.

Example 11. Combination Treatment of Compound a with LY3009120 Induces Apoptosis in GIST-T1, GIST-T1/D816E Imatinib-Resistant Cells and GIST-T1/T670I Imatinib Resistant Cells Synergy charts and combination index plots for caspase activity can be used to show for synergy for Compound A and LY3009120 combination in inducing apoptosis in GIST-T1, GIST-T1/D816E imatinib resistant cells and GIST-T1/T670I imatinib resistant cells.

Example 12. Combination Treatment of Compound B with LY3009120 Induces Apoptosis in GIST-T1, GIST-T1/D816E Imatinib-Resistant Cells and GIST-T1/T670I Imatinib Resistant Cells Synergy charts and combination index plots for caspase activity can be used to show for synergy for Compound B and LY3009120 combination in inducing apoptosis in GIST-T1, GIST-T1/D816E imatinib resistant cells and GIST-T1/T670I Imatinib resistant cells.

Example 13. Combination Treatment of Compound a with Dabrafenib Induces Apoptosis in GIST-T1, GIST-T1/D816E Imatinib-Resistant Cells and GIST-T1/T670I Imatinib Resistant Cells Synergy charts and combination index plots for caspase activity can be used to show for synergy for Compound A and dabrafenib combination in inducing apoptosis in GIST-T1, GIST-T1/D816E imatinib resistant cells and GIST-T1/T670I Imatinib resistant cells.

Example 14. Combination Treatment of Compound B with Dabrafenib Induces Apoptosis in GIST-T1, GIST-T1/D816E Imatinib-Resistant Cells and GIST-T1/T670I Imatinib Resistant Cells Synergy charts and combination index plots for caspase activity can be used to show for synergy for Compound B and dabrafenib combination in inducing apoptosis in GIST-T1, GIST-T1/D816E imatinib resistant cells and GIST-T1/T670I Imatinib resistant cells.

Example 15. Combination Treatment Prevents Colony Outgrowth in GIST-T1, GIST-T1/D816E and GIST-T1/T670I) Imatinib Resistant Cells Studies were performed which demonstrate that combination treatment with Compound A and trametinib prevents colony outgrowth in GIST-T1 (57 bp exon 11 deletion) imatinib sensitive cells, GIST-T1/D816E imatinib resistant cells and GIST-T1/T670I imatinib resistant cells. Assays were conducted in 6 well plates with 100 cells seeded per well. Cells were treated with vehicle control, Compound A, trametinib, imatinib (IM), or combinations thereof at varying concentrations, and the cells were cultured for 2 weeks. Post-treatment, the drug was washed out, and the cells were cultured in normal media for 1-3 weeks. The outgrown cell colonies were stained with crystal violet and counted.

Figure 8A:
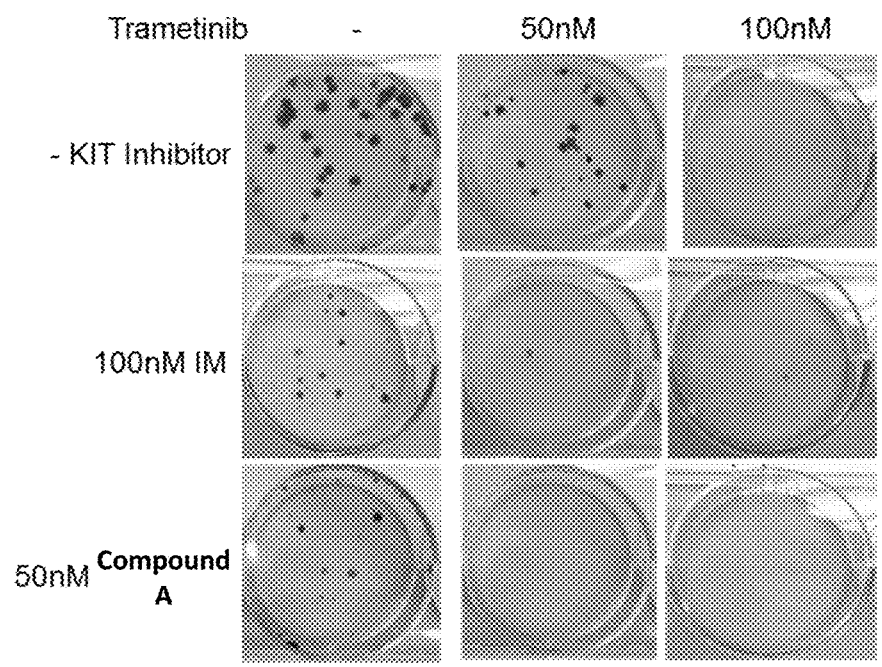
FIG. 8A shows images of representative culture plates and a graphical representation of the number of GIST-T1 colonies counted following various treatments with Compound A, imatinib, and trametinib for 2 weeks followed by a 9 day recovery period.
Figure 8A:
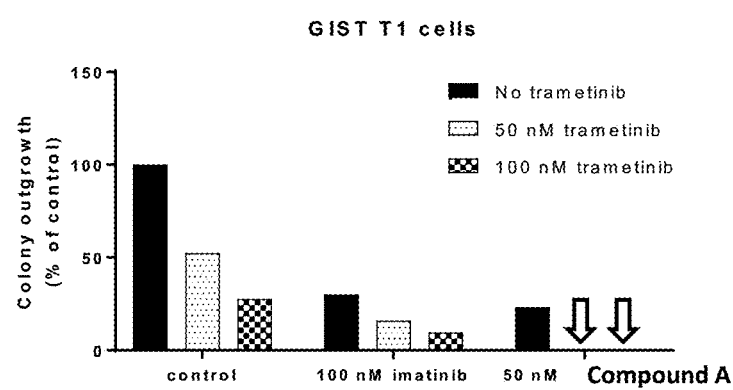

FIG. 8A shows images of representative culture plates and a graphical representation of the number of GIST-T1 colonies counted from various treatments. GIST T1 cells are sensitive to imatinib and Compound A as single agents. It is noted that each of imatinib and Compound A as single agents demonstrate approximately a similar reduction of GIST T1 colony outgrowth to 23-30% of vehicle control. Combination treatment for 2 weeks with 50 nM Compound A and either 50 nM or 100 nM trametinib unexpectedly led to complete cell stasis or eradication of GIST T1 colony outgrowth to the limit of detection as visualized with 5× objective microscopy, with no detectable colonies after removal of combination therapy for 9 days (note arrows in FIG. 8A). In contrast, combination treatment for 2 weeks with 100 nM imatinib and either 50 nM or 100 nM trametinib did not lead to complete tumor cell stasis or eradication after removal of combination therapy for 9 days.

Figure 8B:
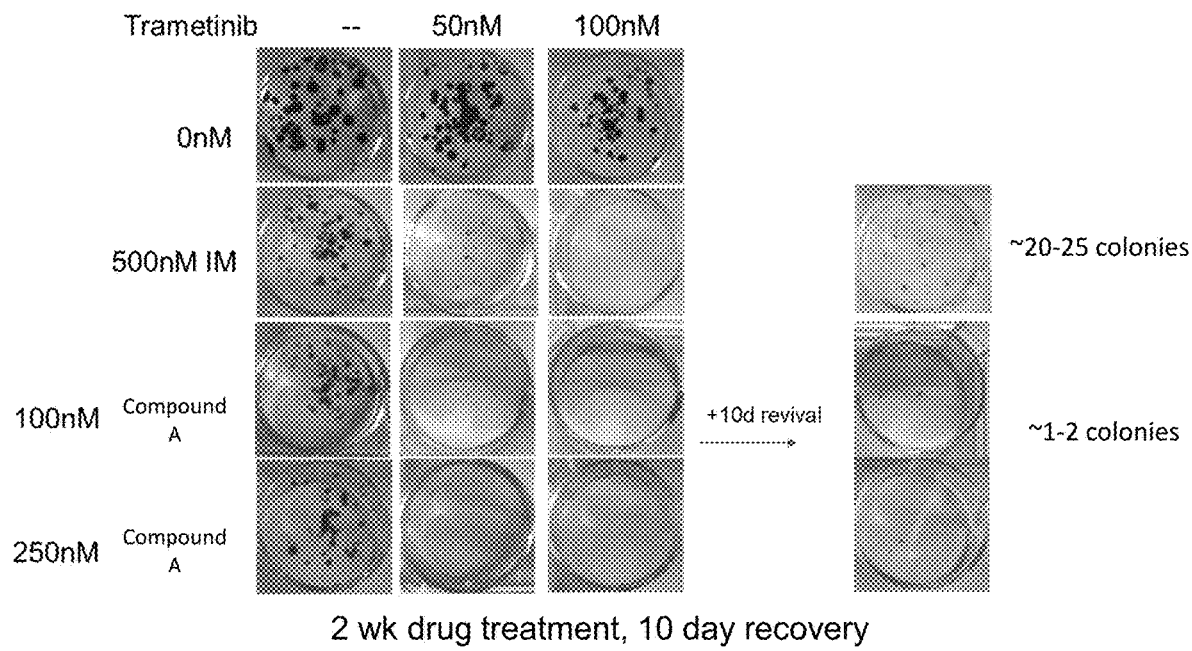
FIG. 8B shows images of representative culture plates and a graphical representation of the number of GIST-T1/D816E colonies counted following various treatments with Compound A, imatinib, and trametinib for 2 weeks followed by a 10 day recovery period. The right upper panel shows representative culture plates after additional 10 days of recovery.
Figure 8B:
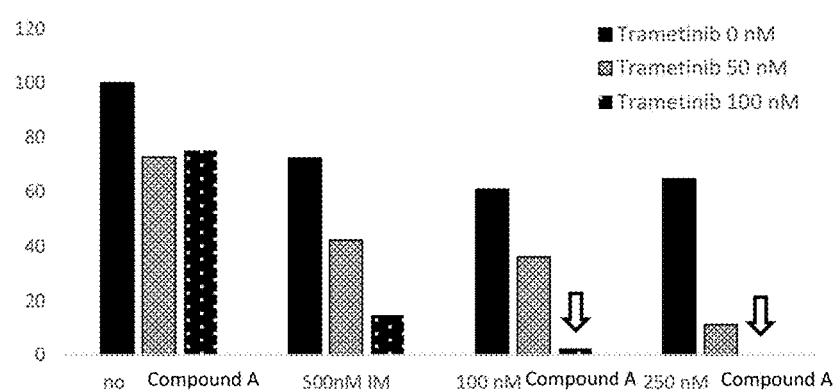
Figure 8C:
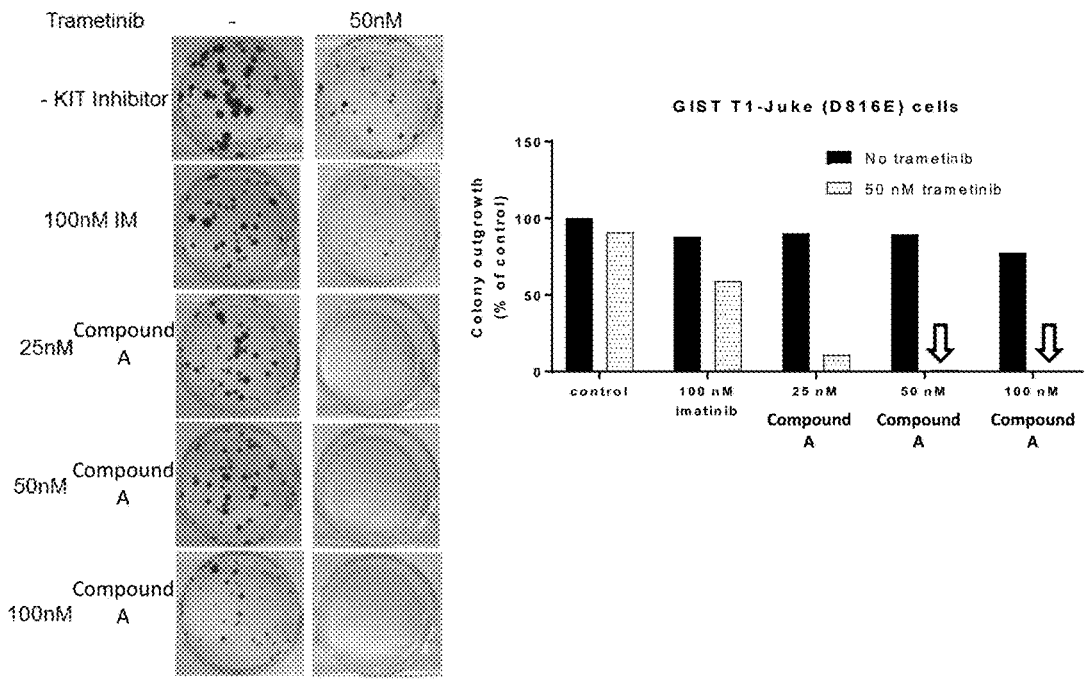
FIG. 8C shows images of representative culture plates and a graphical representation of the number of GIST-T1/D816E colonies counted following various treatments with Compound A, imatinib (IM), and trametinib for 2 weeks followed by a 10 day recovery period.
Figure 8C:
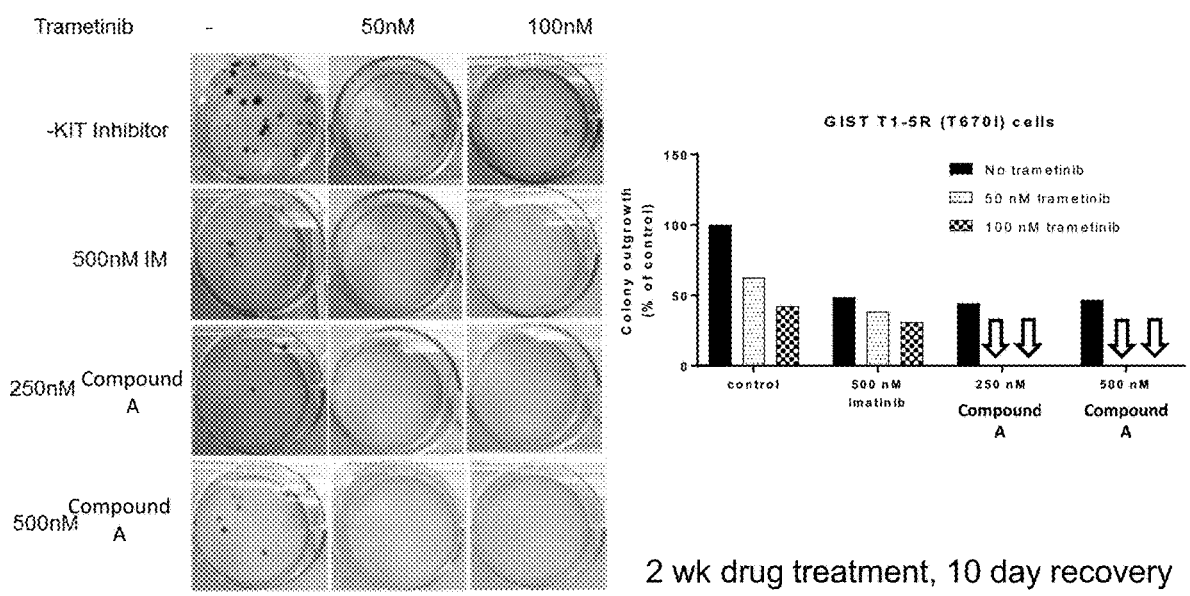

FIG. 8B shows images of representative culture plates and graphical representation of the number of GIST-T1/D816E colonies counted from various treatments. It is noted that each of imatinib (500 nM) and Compound A (100 nM or 250 nM) as single agents demonstrate approximately a similar lack of cytocidal efficacy of GIST T1/D816E with colony outgrowth of approximately 61-72% of vehicle control (FIG. 8B). Combination treatment for 2 weeks with Compound A (100 nM or 250 nM) and trametinib (100 nM) led to almost complete cell stasis with Compound A (100 nM) and complete cell stasis or eradication of colony outgrowth in GIST-T1/D816E cells with combination of trametinib (100 nM) and Compound A (250 nM) to the limit of detection as visualized with 5× objective microscopy, following ten days of recovery (see arrows, FIG. 8B), whereas combination treatment for 2 weeks with imatinib (500 nM) and trametinib (50 nM or 100 nM) did not lead to complete cell stasis or tumor cell eradication (see graph in FIG. 8B). This was prominent when cells were cultured for an extra 10 days without drug and ~20-25 colonies outgrew. FIG. 8C shows images of representative culture plates when Compound A concentration was further lowered to 25 nM, 50 nM, or 100 nM and evaluated in combination with 50 nM trametinib. Complete tumor cell stasis or eradication to the limit of detection as visualized with 5× objective microscopy of tumor colony outgrowth was achieved with 100 nM Compound A in combination with trametinib following ten days of recovery (see arrow, FIG. 8C), nearly complete tumor cell stasis or near eradication (1% of vehicle control) was achieved with 50 nM Compound A in combination with trametinib (see arrow, FIG. 8C), and significant tumor cell stasis or killing was achieved with 25 nM Compound A (11% of vehicle control). In contrast, combination of 100 nM imatinib with 50 nM trametinib did not eradicate tumor colony outgrowth, achieving a modest tumor cell stasis or killing following ten days of recovery (60% of vehicle control).

FIG. 8D shows images of representative culture plates and graphical representation of the number of GIST-T1/T670I colonies counted from various treatments. It is noted that each of imatinib (500 nM) and Compound A (250 nM or 500 nM) as single agents demonstrate approximately a similar reduction of GIST T1/T670I colony outgrowth to approximately 44-49% of vehicle control. Treatment for 2 weeks with either 250 nM or 500 nM Compound A in combination with either 50 nM or 100 nM trametinib led to complete cell stasis or eradication of GIST T1/T670I colony outgrowth to the limit of detection as visualized with 5× objective microscopy, with no detectable colonies after removal of combination therapy for 10 days (note arrows in FIG. 8D). In contrast, treatment for 2 weeks with 500 nM imatinib in combination with either 50 nM or 100 nM trametinib did not lead to complete tumor cell stasis or tumor cell eradication after removal of combination therapy for 9 days.

Example 16. Combination Treatment of Compound B with Trametinib Prevents Colony Outgrowth in GIST-T1, GIST-T1/D816E and GIST-T1/T670I Imatinib Resistant Cells Studies explained in example 8 were also performed in combination treatment with Compound B and trametinib in 3 GIST cell lines.

Figure 9A:
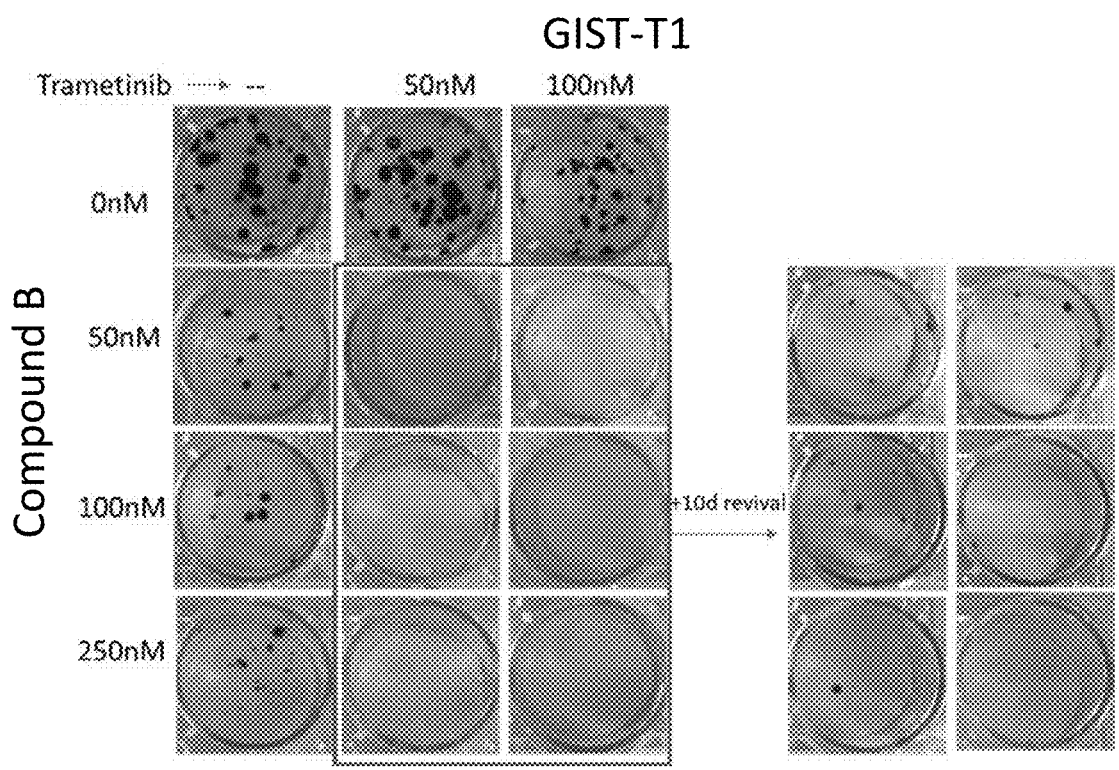
FIG. 9A shows images of representative culture plates and a graphical representation of the number of GIST-T1 colonies counted following various treatments with Compound B and trametinib for 2 weeks followed by a 10 day recovery period.
Figure 9A:
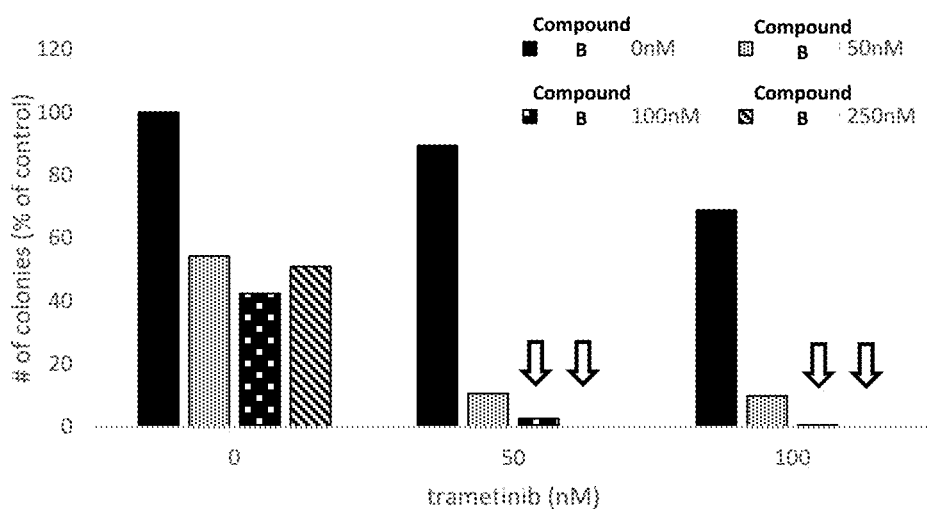

FIG. 9A shows images of representative culture plates and a graphical representation of the number of GIST-T1 colonies counted from various treatments. GIST T1 cells were sensitive to Compound B as single agents and showed a 42-54% reduction of GIST T1 colony outgrowth compared to vehicle control. Combination treatment for 2 weeks with 50 or 100 nM of Compound B and either 50 nM or 100 nM trametinib led to significant cell stasis with little colony outgrowth, while combination treatment with 250 nM of Compound A with either 50 nM or 100 nM trametninib led to complete cell stasis or eradication of GIST T1 colony outgrowth to the limit of detection as visualized with 5× objective microscopy, with no detectable colonies after removal of combination therapy for 10 days (note arrows in FIG. 9A). Outgrowth of colonies was prevented even after extended long term recovery for a total of 20 days.

FIG. 9B shows images of representative culture plates and graphical representation of the number of GIST-T1/D816E colonies counted from various treatments. It is noted that Compound B (50 nM, 100 nM or 250 nM) as a single agent demonstrate cytocidal efficacy of GIST T1/D816E with colony outgrowth of approximately 59-84% of vehicle control (FIG. 9B). Combination treatment for 2 weeks with Compound B (250 nM) and trametinib (50 nM) or with Compound B (100 nM or 250 nM) and trametinib (100 nM) led to >90% cell stasis or eradication of colony outgrowth in GIST-T1/D816E cells as visualized with 5× objective microscopy, following ten days of recovery (see arrows, FIG. 9B), Treatment with Compound B (250 nM) maintained cell stasis or cell killing in combination with trametinib (100 nM) even after extended long term of 20 days.

Figure 9C:
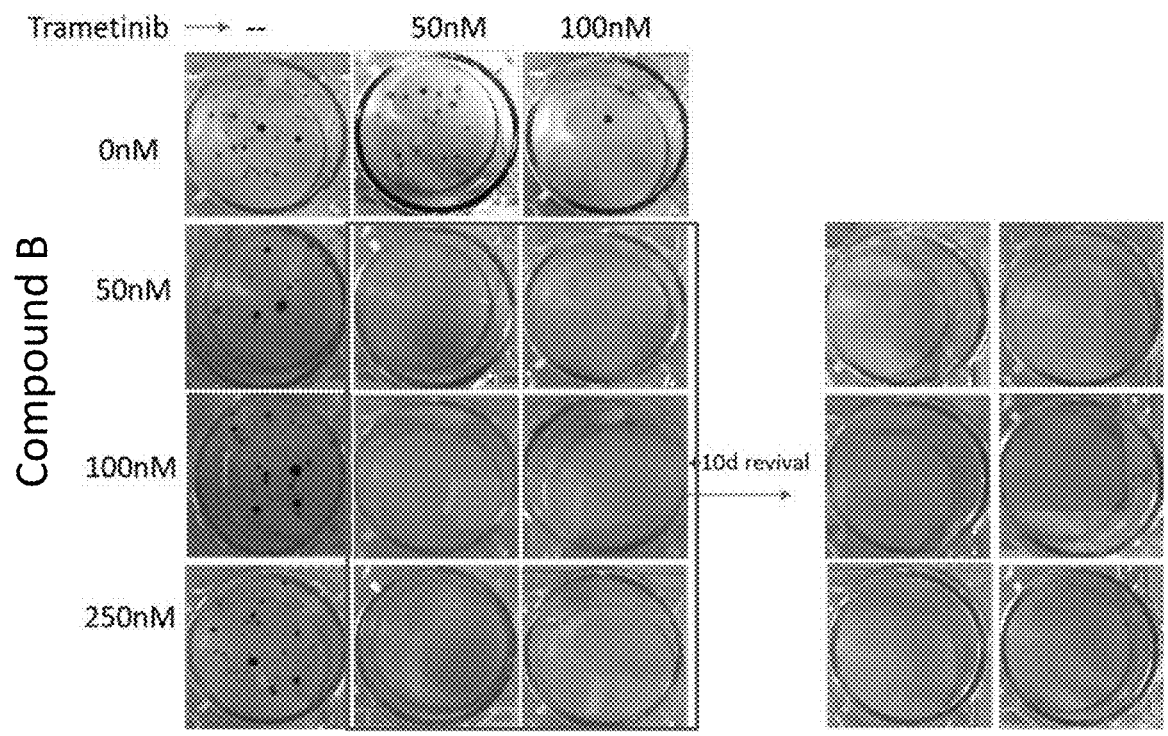
FIG. 9C shows images of representative culture plates showing the number of GIST-T1/T670I colonies counted following various treatments with Compound B and trametinib for 2 weeks followed by a 10 day recovery period.
Figure 9C:
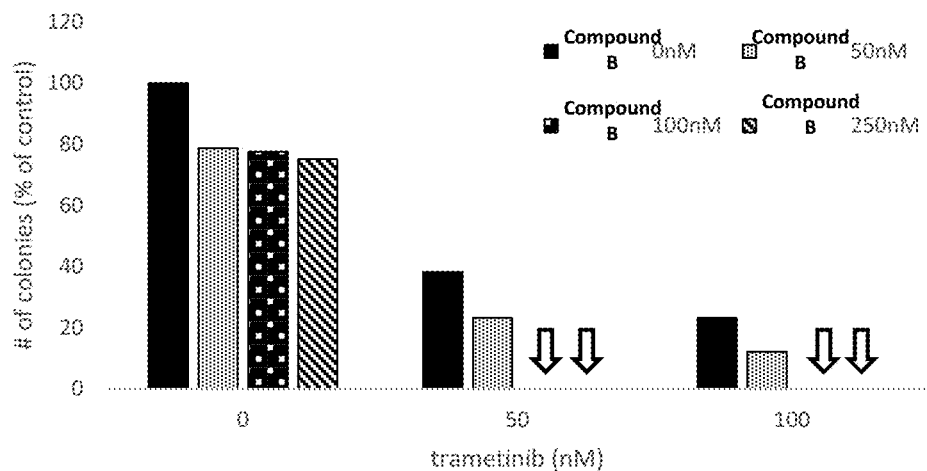

FIG. 9C shows images of representative culture plates and graphical representation of the number of GIST-T1/T670I colonies counted from various treatments. It is noted that Compound B (50 nM, 100 nM, 250 nM) as single agents demonstrate GIST T1/T670I colony outgrowth to approximately 75-78% of vehicle control. Treatment for 2 weeks with either 100 nM or 250 nM Compound B in combination with either 50 nM or 100 nM trametinib led to complete cell stasis or eradication of GIST T1/T670I colony outgrowth to the limit of detection as visualized with 5× objective microscopy, with no detectable colonies after removal of combination therapy for 10 days (note arrows in FIG. 9C). The inhibition of outgrowth was maintained even after extended term of 20 days without drug.

Example 17. Combination Treatment of Compound a with Binimetinib Prevents Colony Outgrowth in GIST-T1, GIST-T1/D816E and GIST-T1/T670I Imatinib Resistant Cells Studies were performed which demonstrate that combination treatment with Compound A and binimetinib prevents colony outgrowth in 3 GIST cell lines as explained in example 15.

Figure 10A:
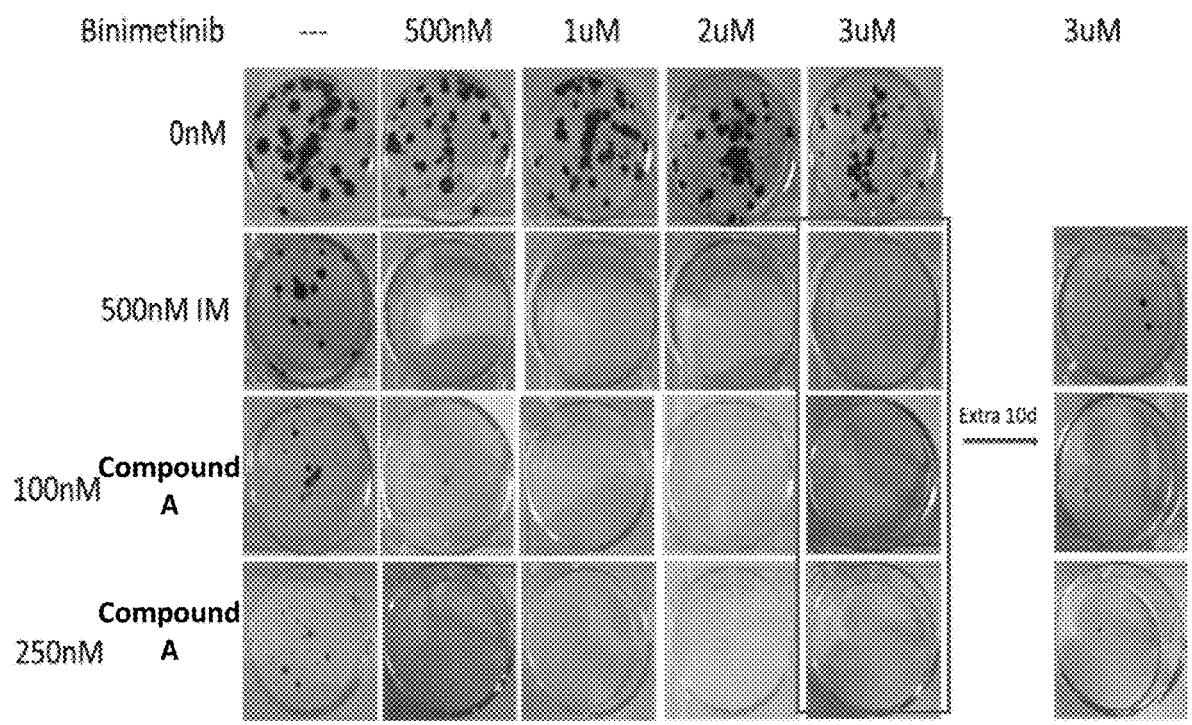
FIG. 10A shows images of representative culture plates and a graphical representation of the number of GIST-T1 colonies counted following various treatments with Compound A, imatinib, and binimetinib for 2 weeks followed by a 10 day recovery period. The right upper panel shows representative culture plates after additional 10 days of recovery.
Figure 10A:
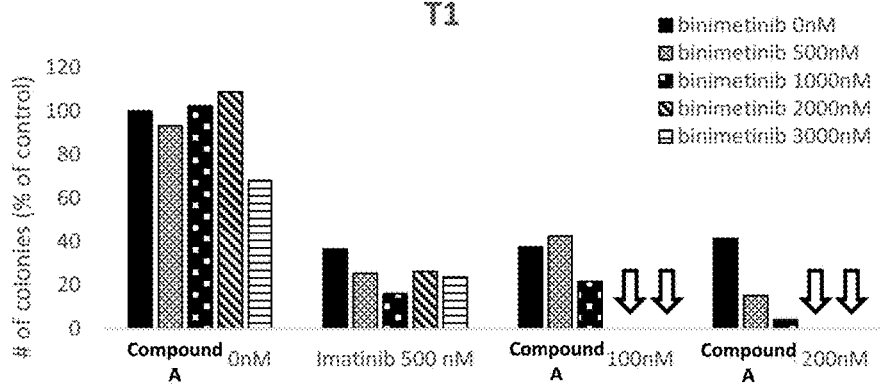

FIG. 10A shows images of representative culture plates and a graphical representation of the number of GIST-T1 colonies counted from various treatments. It is noted that each of imatinib and Compound A as single agents demonstrate approximately a similar reduction of GIST T1 colony outgrowth to 36-41% of vehicle control. Combination treatment for 2 weeks with 100 nM or 250 nM of Compound A and either 500 nM, 1 uM, 2 uM or 3 uM binimetinib was evaluated. Combination of Compound A (100 nM or 250 nM) with binimetinib (2 uM or 3 uM) led to complete cell stasis or eradication of GIST T1 colony outgrowth to the limit of detection as visualized with 5× objective microscopy, with no detectable colonies after removal of combination therapy for 10 days (note arrows in FIG. 10A). In contrast, combination treatment for 2 weeks with even 500 nM imatinib and either either 500 nM, 1 uM, 2 uM or 3 uM binimetinib did not lead to complete tumor cell stasis or eradication after removal of combination therapy for 10 days. The effect was more pronounced after incubation of extended period of time without drug, where ~10-15 colonies were visible with imatinib and no colony outgrowth was observed with Compound A.

Figure 10B:
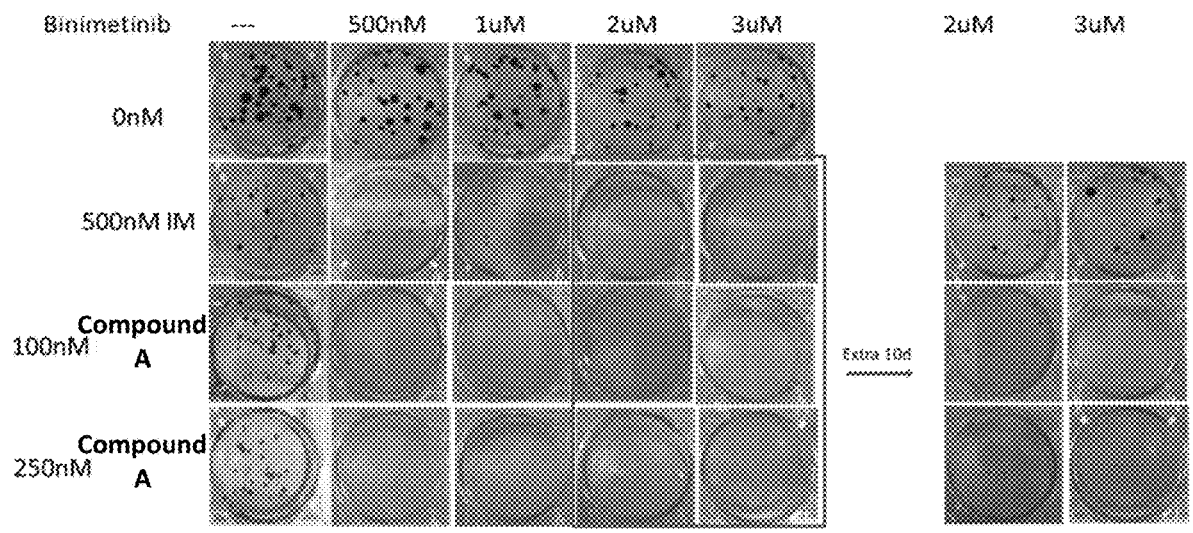
FIG. 10B shows images of representative culture plates and a graphical representation of the number of GIST-T1/D816E colonies counted following various treatments with Compound A, imatinib, and binimetinib for 2 weeks followed by a 10 day recovery period. The right upper panel shows representative culture plates after additional 10 days of recovery.
Figure 10B:
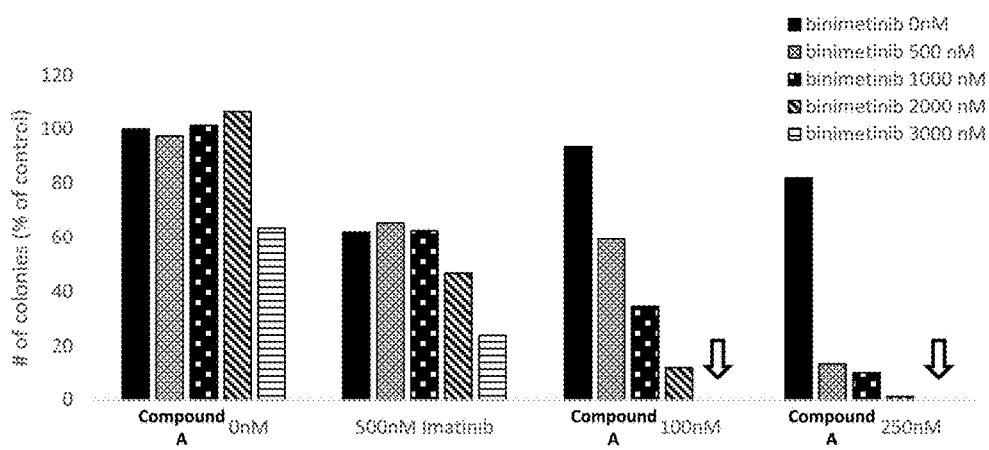

FIG. 10B shows images of representative culture plates and graphical representation of the number of GIST-T1/D816E colonies counted from various treatments. It is noted that each of imatinib (500 nM) and Compound A (100 nM or 250 nM) as single agents demonstrate a lack of cytocidal efficacy of GIST T1/D816E with colony outgrowth of approximately 60-95% of vehicle control (FIG. 10B). Combination treatment for 2 weeks with Compound A (100 nM or 250 nM) and binimetinib (500 nM, 1 uM, 2 uM or 3 uM) was evaluated. Combination of Compound A (100 nM or 250 nM) with binimetinib (3 uM) led to complete cell stasis or eradication of colony outgrowth in GIST-T1/D816E cells to the limit of detection as visualized with 5× objective microscopy, following ten days of recovery (see arrows, FIG. 10B), whereas combination treatment for 2 weeks with imatinib (500 nM) and binimetinib (500 nM, 1 uM, 2 uM or 3 uM) did not lead to complete cell stasis or tumor cell eradication. The effect was more pronounced after incubation of extended period of time where imatinib treatment did not lead to complete inhibition whereas Compound A showed maintained cell stasis or cell killing even after 20 days.

Figure 10C:
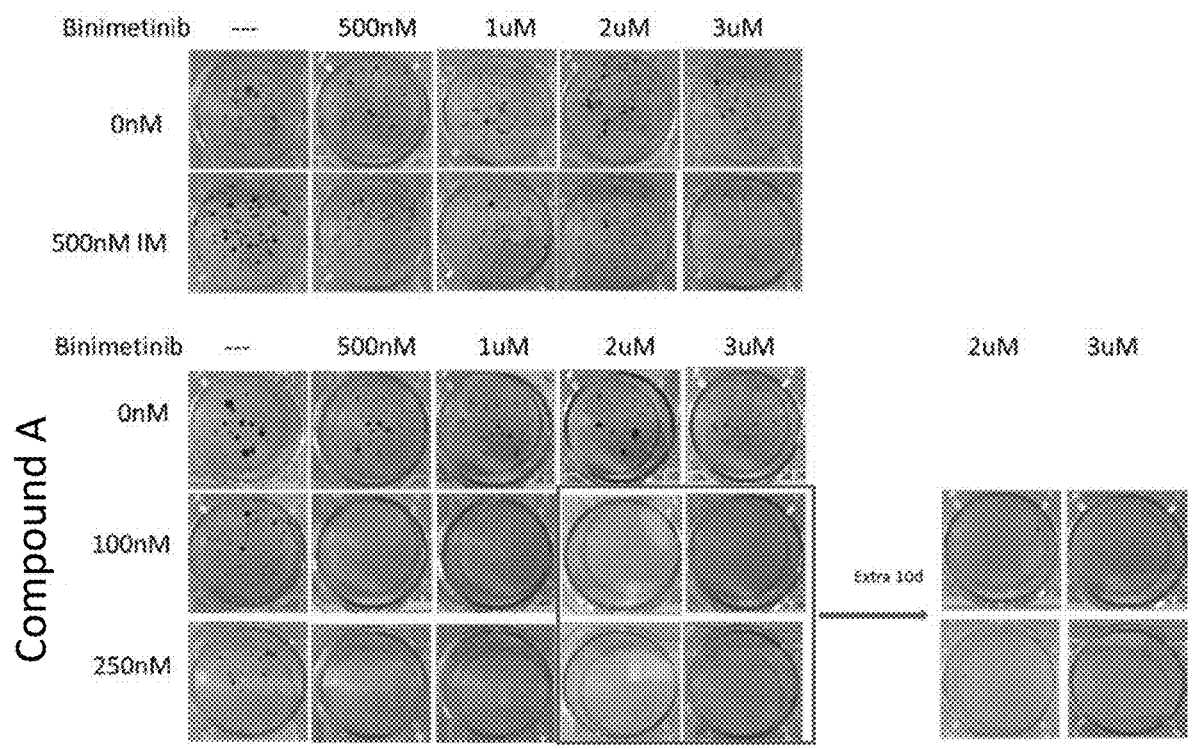
FIG. 10C shows images of representative culture plates and a graphical representation of the number of GIST-T1/T670I colonies counted following various treatments with Compound A, imatinib, and binimetinib for 2 weeks followed by a 10 day recovery period. The right upper panel shows representative culture plates after additional 10 days of recovery.
Figure 10C:
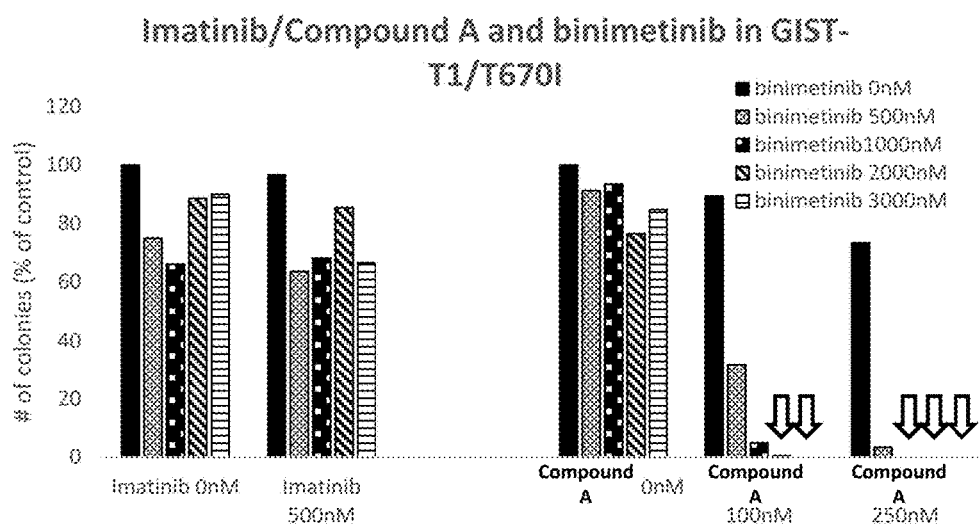

FIG. 10C shows images of representative culture plates and graphical representation of the number of GIST-T1/

T670I) colonies counted from various treatments. It is noted that imatinib (500 nM) as a single agent does not show any reduction of colonies whereas Compound A (100 nM or 250 nM) as single agents demonstrate a dose dependent reduction in colony outgrowth to about 78-89% of vehicle control. Treatment for 2 weeks with 250 nM Compound A in combination with 1 uM, 2 uM or 3 uM binimetinib led to complete cell stasis or eradication of GIST T1/T670I colony outgrowth to the limit of detection as visualized with 5× objective microscopy, with no detectable colonies after removal of combination therapy for 10 days (note arrows in FIG. 10C). Treatment for 2 weeks with 100 nM Compound A in combination with 3 uM binimetinib led to complete cell stasis or eradication of GIST T1/T670I colony outgrowth to the limit of detection as visualized with 5× objective microscopy, with no detectable colonies after removal of combination therapy for 10 days (note arrows in FIG. 10C). The cell stasis was maintained even after extended period of 20 days after drug removal. In contrast, treatment for 2 weeks with 500 nM imatinib in combination with either 500 nM, 1 uM, 2 uM or 3 uM binimetinib did not lead to complete tumor cell stasis or tumor cell eradication after removal of combination therapy for 10 days.

Example 18. Combination Treatment of Compound B with Binimetinib Prevents Colony Outgrowth in GIST-T1, GIST-T1/D816E and GIST-T/T670I Imatinib Resistant Cells Studies were performed which demonstrate that combination treatment with Compound B and binimetinib prevents colony outgrowth in 3 GIST cell lines as explained in Example 15.

Figure 11A:
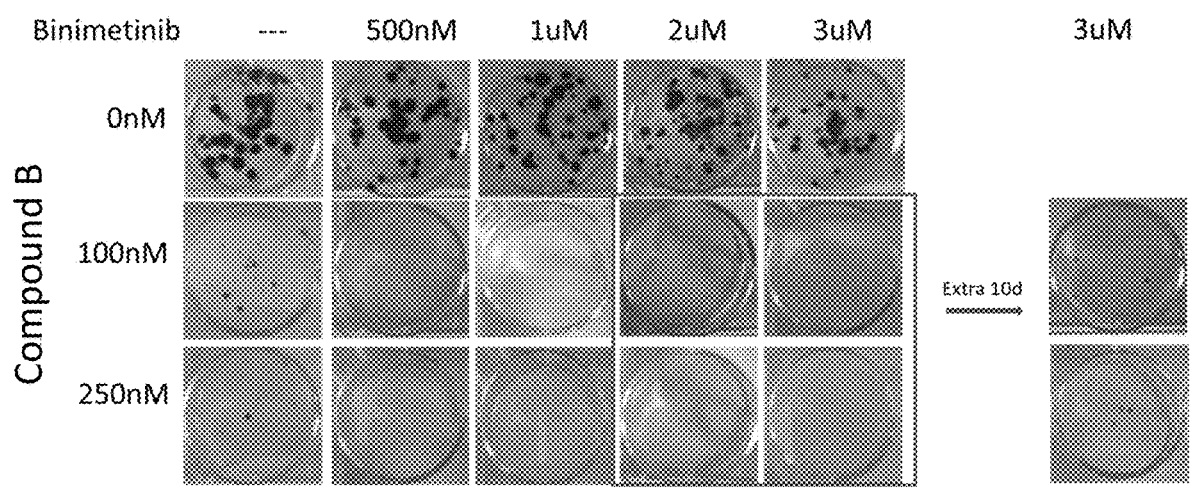
FIG. 11A shows images of representative culture plates and a graphical representation of the number of GIST-T1 colonies counted following various treatments with Compound B and binimetinib for 2 weeks followed by a 10 day recovery period. The right upper panel shows representative culture plates after additional 10 days of recovery.
Figure 11A:
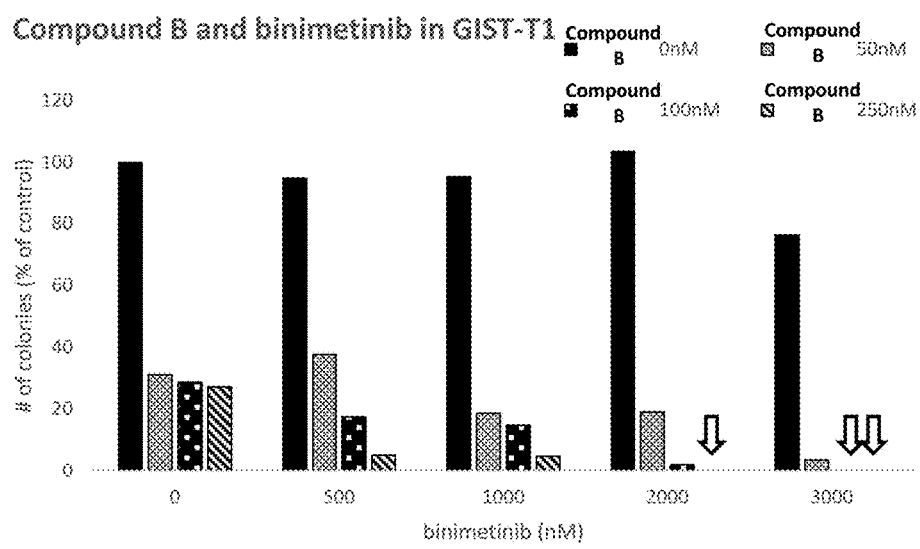

FIG. 11A shows images of representative culture plates and a graphical representation of the number of GIST-T1 colonies counted from various treatments. It is noted that each concentration of Compound B as a single agent demonstrates approximately a similar reduction of GIST T1 colony outgrowth to 27-31% of vehicle control. Combination treatment for 2 weeks with 250 nM of Compound B and 2 uM or 3 uM binimetinib led to complete cell stasis or eradication of GIST T1 colony outgrowth to the limit of detection as visualized with 5× objective microscopy, with no detectable colonies after removal of combination therapy for 10 days (note arrows in FIG. 11A) and maintained significant cell stasis or cell killing of GIST-T1 cells even after an extended long term recovery of 20 days (FIG. 11A upper right panel). Combination treatment for 2 weeks with 100 nM of Compound B and 3 uM binimetinib led to complete cell stasis or eradication of GIST T1 colony outgrowth to the limit of detection as visualized with 5× objective microscopy, with no detectable colonies after removal of combination therapy for 10 days (note arrows in FIG. 11A).

Figure 11B:
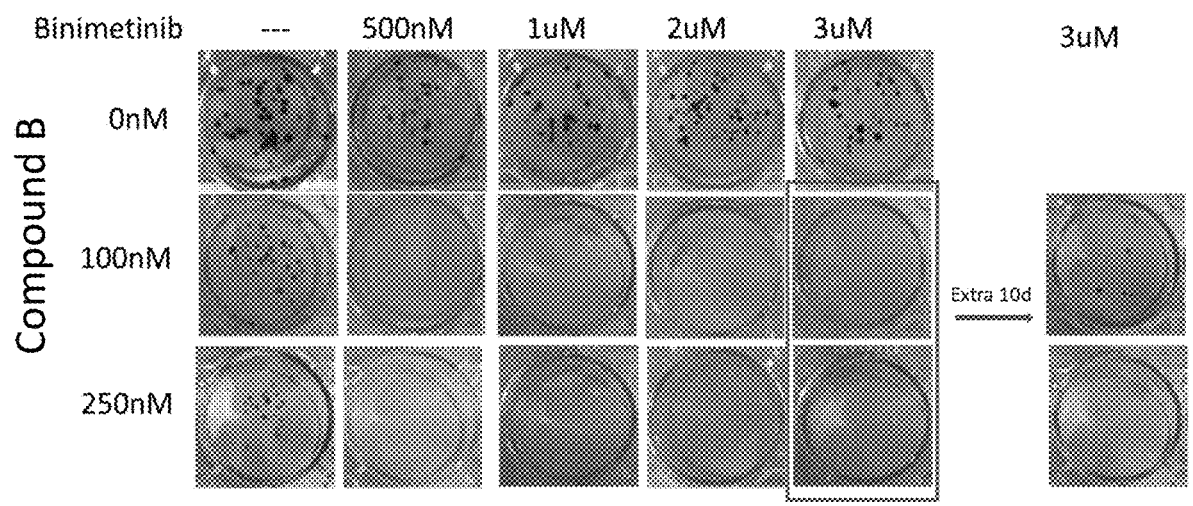
FIG. 11B shows images of representative culture plates and a graphical representation of the number of GIST-T1/D816E colonies counted following various treatments with Compound B and binimetinib for 2 weeks followed by a 10 day recovery period. The right upper panel shows representative culture plates after additional 10 days of recovery.
Figure 11B:
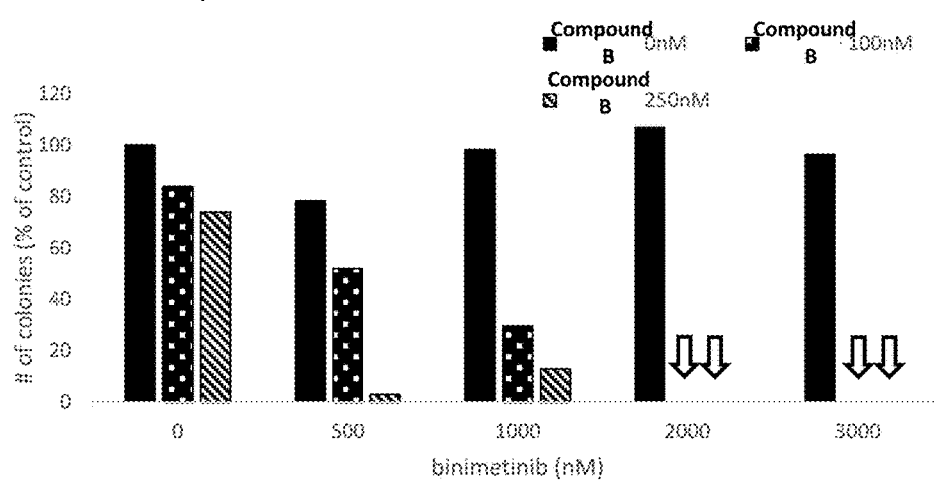

FIG. 11B shows images of representative culture plates and graphical representation of the number of GIST-T1/D816E colonies counted from various treatments. It is noted that Compound B (100 nM or 250 nM) as single agents demonstrate approximately a similar lack of cytocidal efficacy of GIST T1/D816E with colony outgrowth of approximately 74-83% of vehicle control (FIG. 11B). Combination treatment for 2 weeks with 100 nM or 250 nM of Compound B and either 2 uM or 3 uM binimetinib led to complete cell stasis or eradication of colony outgrowth in GIST-T1/D816E cells to the limit of detection as visualized with 5× objective microscopy, following ten days of recovery (see arrows, FIG. 11B) The cell stasis was maintained even after extended period of 20 days at higher concentration of Compound B.

FIG. 11C shows images of representative culture plates and graphical representation of the number of GIST-T1/T670I colonies counted from various treatments. It is noted that Compound B (100 nM or 250 nM) as single agent showed a reduction of GIST T1/T670I colony outgrowth to about 72-78% of vehicle control. Treatment for 2 weeks with either 100 nM or 250 nM of Compound B and 3 uM binimetinib unexpectedly led to complete cell stasis or eradication of GIST T1/T670I colony outgrowth to the limit of detection as visualized with 5× objective microscopy, with no detectable colonies after removal of combination therapy for 10 days (note arrows in FIG. 11C). Treatment for 2 weeks with 250 nM of Compound B and 2 uM binimetinib unexpectedly led to complete cell stasis or eradication of GIST T1/T670I colony outgrowth to the limit of detection as visualized with 5× objective microscopy, with no detectable colonies after removal of combination therapy for 10 days (note arrow in FIG. 11C). The cell stasis was maintained even after extended period of 20 days after drug removal.

Example 19. Combination Treatment of Compound a with Cobimetinib Prevents Colony Outgrowth in GIST-T1, GIST-T1/D816E and GIST-T1/T670I Imatinib Resistant Cells Studies were performed which demonstrate that combination treatment with Compound A and cobimetinib prevents colony outgrowth in 3 GIST cell lines as explained in Example 15.

Figure 12A:
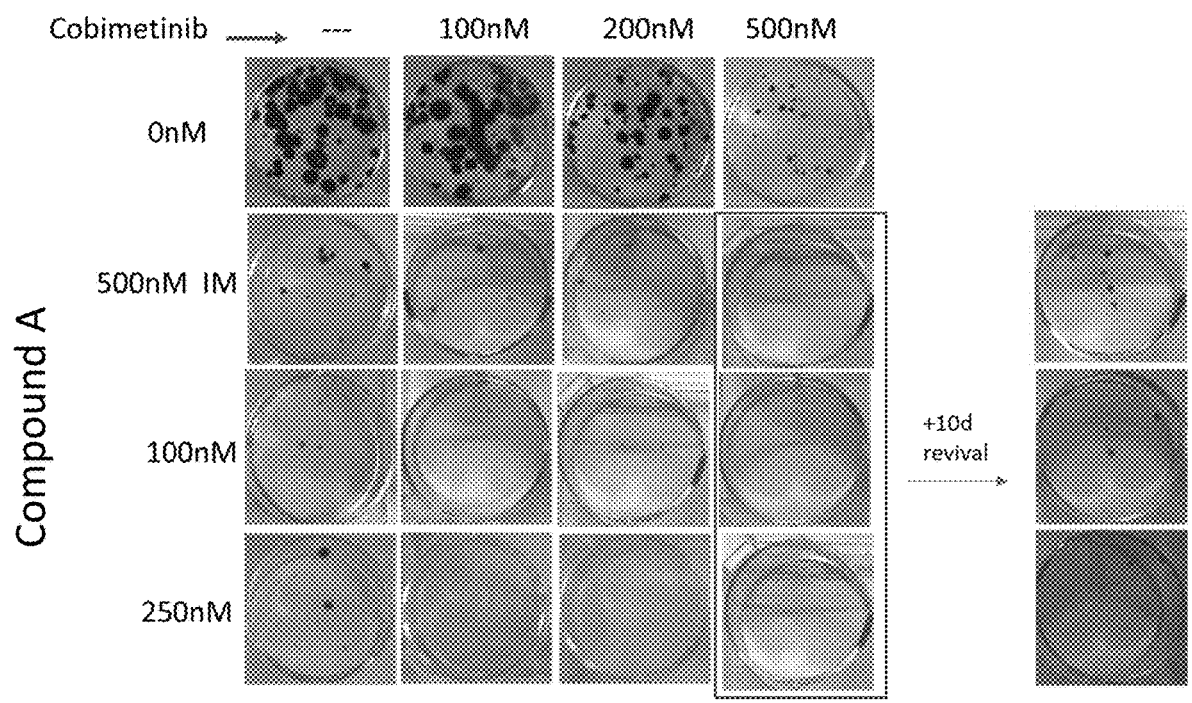
FIG. 12A shows images of representative culture plates and a graphical representation of the number of GIST-T1 colonies counted following various treatments with Compound A, imatinib, and cobimetinib for 2 weeks followed by a 10 day recovery period. The right upper panel shows representative culture plates after additional 10 days of recovery.
Figure 12A:
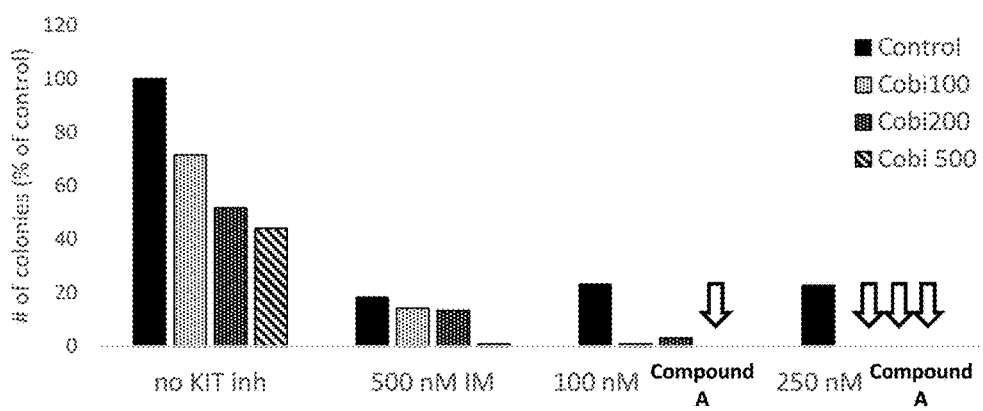

FIG. 12A shows images of representative culture plates and a graphical representation of the number of GIST-T1 colonies counted from various treatments. It is noted that each of imatinib and Compound A as single agents demonstrate approximately a similar reduction of GIST T1 colony outgrowth to 18-23% of vehicle control. Combination treatment for 2 weeks with 250 nM of Compound A and either 100 nM, 200 nM or 500 nM of cobimetinib led to complete cell stasis or eradication of GIST T1 colony outgrowth to the limit of detection as visualized with 5× objective microscopy, with no detectable colonies after removal of combination therapy for 10 days (note arrows in FIG. 12A). Combination treatment for 2 weeks with 100 nM of Compound A and 500 nM of cobimetinib led to complete cell stasis or eradication of GIST T1 colony outgrowth to the limit of detection as visualized with 5× objective microscopy, with no detectable colonies after removal of combination therapy for 10 days (note arrow in FIG. 12A). In contrast, combination treatment for 2 weeks with 500 nM imatinib and either 100 nM, 200 nM or 500 nM cobimetinib did not lead to complete tumor cell stasis or eradication after removal of combination therapy for 10 days.

The effect was more visible after incubation of extended period of time where ~10-15 colonies grew out with 500 nM imatinib and no colony out growth was observed with 500 nM of Compound A and 500 nM of cobimetinib.

Figure 12B:
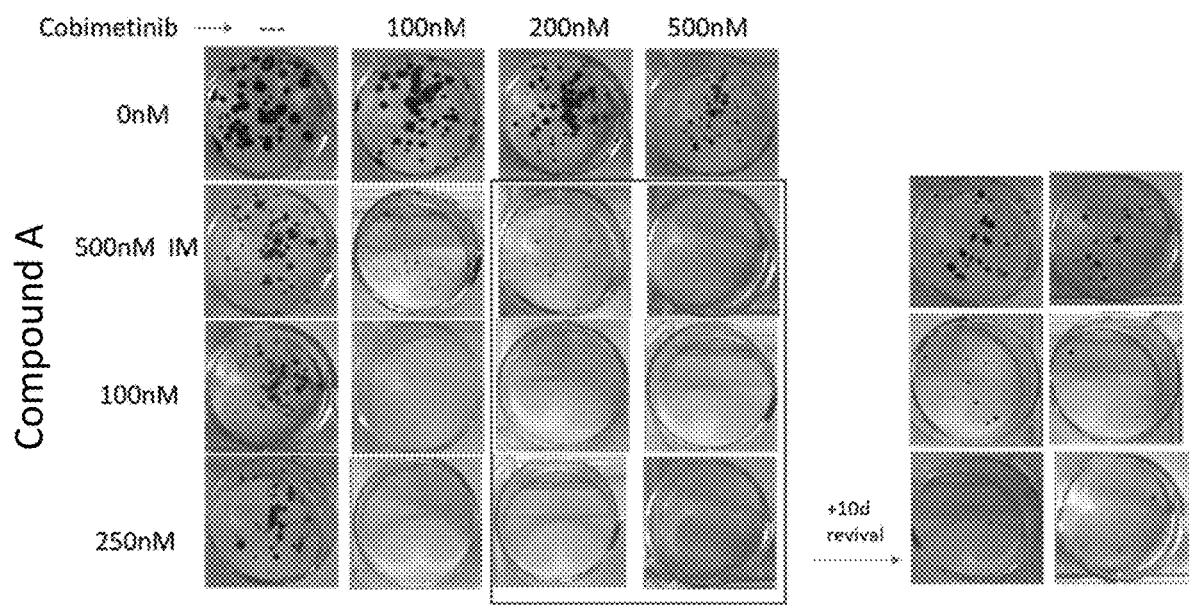
FIG. 12B shows images of representative culture plates and a graphical representation of the number of GIST-T1/D816E colonies counted following various treatments with Compound A, imatinib, and cobimetinib for 2 weeks followed by a 10 day recovery period. The right upper panel shows representative culture plates after additional 10 days of recovery.
Figure 12B:
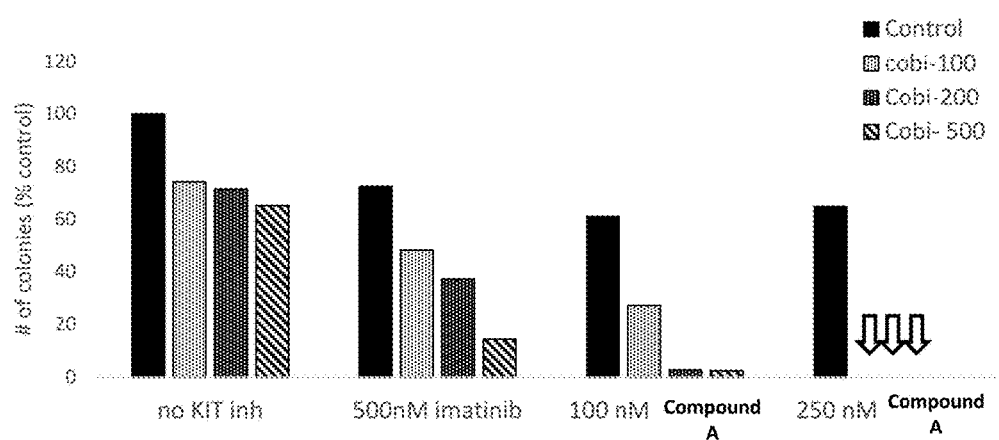

FIG. 12B shows images of representative culture plates and graphical representation of the number of GIST-T1/D816E colonies counted from various treatments. It is noted that each of imatinib (500 nM) and Compound A (100 nM or 250 nM) as single agents demonstrate approximately a similar lack of cytocidal efficacy of GIST T1/D816E with colony outgrowth of approximately 65-74% of vehicle control (FIG. 12B). Combination treatment for 2 weeks with Compound A (250 nM) and cobimetinib (100 nM, 200 nM or 500 nM) led to complete cell stasis or eradication of colony outgrowth in GIST-T1/D816E cells to the limit of detection as visualized with 5× objective microscopy, following ten days of recovery (see arrows, FIG. 12B), whereas combination treatment for 2 weeks with imatinib (500 nM) and cobimetinib (100 nM, 200 nM or 500 nM) did not lead to complete cell stasis or tumor cell eradication. The effect was more visible after incubation of extended period of time where imatinib treatment did not lead to complete inhibition whereas Compound A showed maintained significant cell stasis or cell killing even after 20 days after drug removal.

Figure 12C:
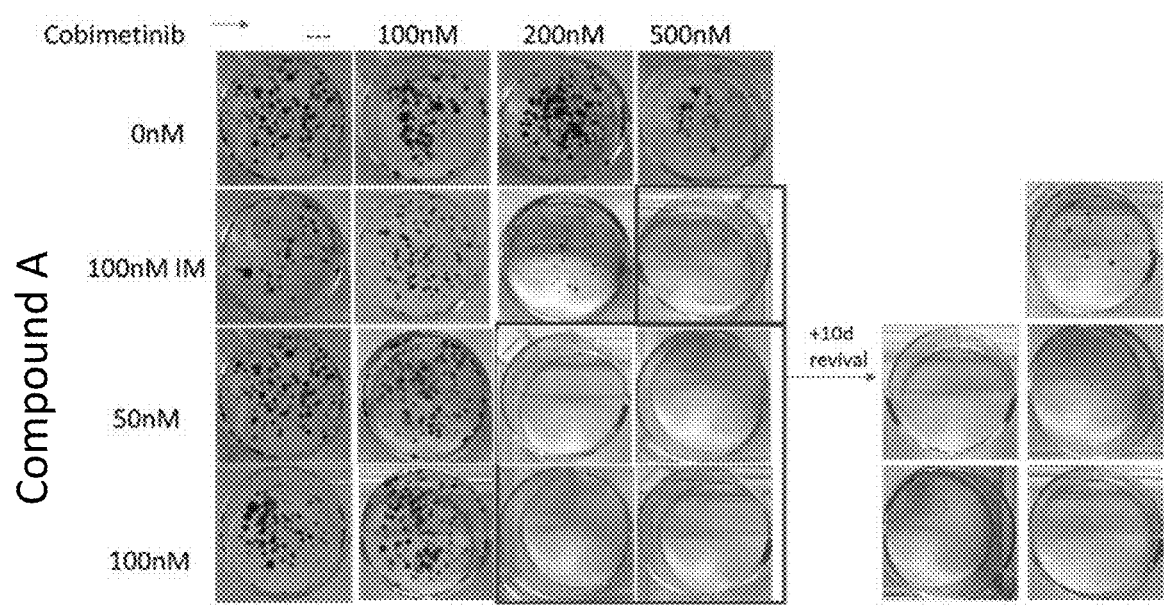
FIG. 12C shows images of representative culture plates and a graphical representation of the number of GIST-T1/T670I colonies counted following various treatments with Compound A, imatinib, and cobimetinib for 2 weeks followed by a 10 day recovery period. The right upper panel shows representative culture plates after additional 10 days of recovery.
Figure 12C:
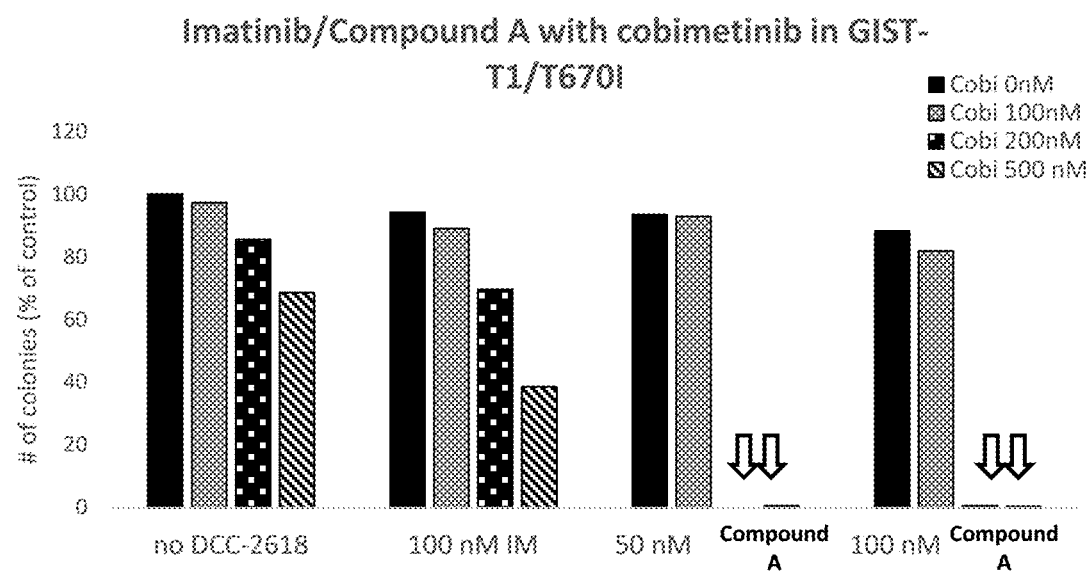

FIG. 12C shows images of representative culture plates and graphical representation of the number of GIST-T1/T670I colonies counted from various treatments. Treatment for 2 weeks with either 50 nM or 100 nM Compound A in combination with cobimetinib (200 nM or 500 nM) unexpectedly led to >99% inhibition of GIST T1/T670I colony outgrowth as visualized with 5× objective microscopy (note arrows in FIG. 12C). The cell stasis was maintained even after extended period of 20 days after drug removal. In contrast, treatment for 2 weeks with 500 nM imatinib in combination with up to 500 nM of cobimetinib did not lead to robust cell stasis or cell eradication after removal of combination therapy for 10 days.

Example 20. Combination Treatment of Compound B with Cobimetinib Prevents Colony Outgrowth in GIST-T1, GIST-T1/D816E and GIST-T1/T670I Imatinib Resistant Cells Studies were performed which demonstrate that combination treatment with Compound B and cobimetinib prevents colony outgrowth in 3 GIST cell lines as explained in example 15.

Figure 13A:
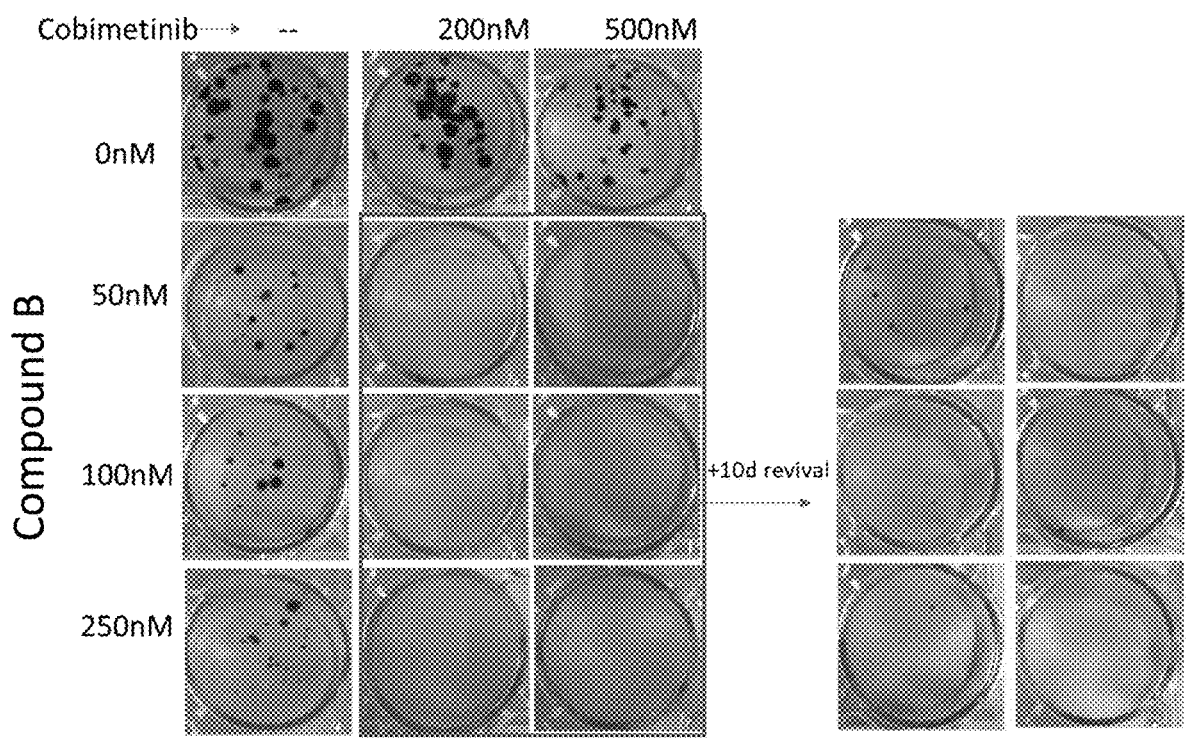
FIG. 13A shows images of representative culture plates and a graphical representation of the number of GIST-T1 colonies counted following various treatments with Compound B and cobimetinib for 2 weeks followed by a 10 day recovery period. The right upper panel shows representative culture plates after additional 10 days of recovery.
Figure 13A:
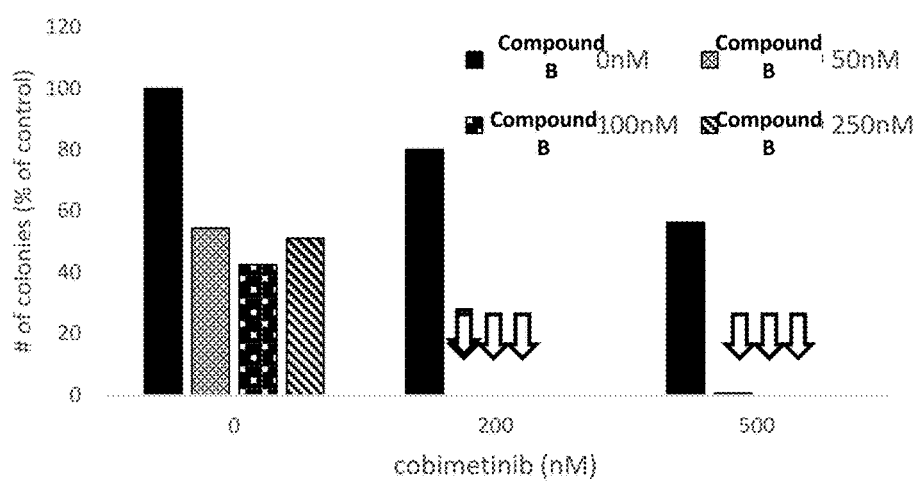

FIG. 13A shows images of representative culture plates and a graphical representation of the number of GIST-T1 colonies counted from various treatments. It is noted that Compound B as a single agent demonstrate approximately a similar reduction of GIST T1 colony outgrowth to 42-54% of vehicle control. Combination treatment for 2 weeks with 50 nM, 100 nM or 250 nM of Compound B and either 200 nM or 500 nM of cobimetinib led to complete or near complete cell stasis or eradication of GIST T1 colony outgrowth to the limit of detection as visualized with 5× objective microscopy, with no detectable colonies after removal of combination therapy for 10 days (note arrows in FIG. 13A). Combination treatment for 2 weeks with with 100 nM or 250 nM of Compound B and either 200 nM or 500 nM of cobimetinib maintained significant cell stasis or cell killing of GIST-T1 cells even after an extended long term recovery of 20 days.

FIG. 13B shows images of representative culture plates and graphical representation of the number of GIST-T1/D816E colonies counted from various treatments. It is noted that Compound B (100 nM or 250 nM) as a single agent demonstrates a lack of cytocidal efficacy of GIST T1/D816E with colony outgrowth of approximately 58-84% of vehicle control (FIG. 13B). Combination treatment for 2 weeks with 50 nM, 100 nM or 250 nM of Compound B and either 200 nM or 500 nM of cobimetinib led to >90 inhibition of colony outgrowth in GIST-T1/D816E cells as visualized with 5× objective microscopy, following ten days of recovery (see arrows, FIG. 13B). The cell stasis was significantly maintained even after extended period of 20 days at higher concentration of Compound B.

Figure 13C:
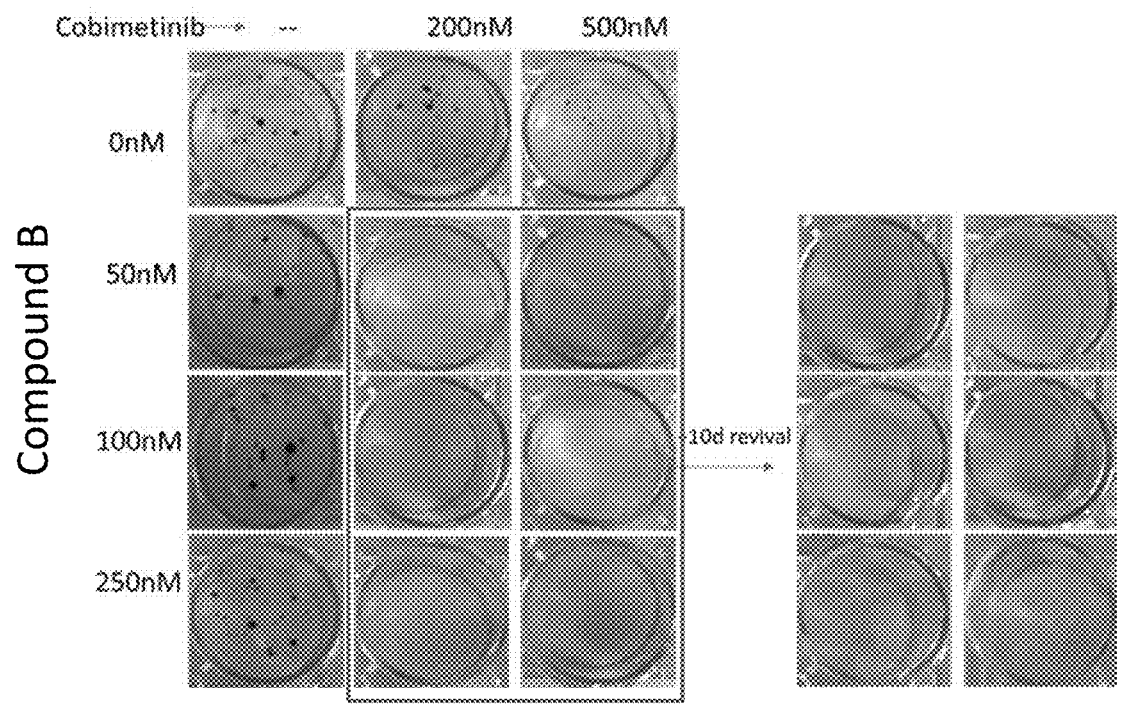
FIG. 13C shows images of representative culture plates showing the number of GIST-T1/T670I colonies counted following various treatments with Compound B and cobimetinib for 2 weeks followed by a 10 day recovery period. The right upper panel shows representative culture plates after additional 10 days of recovery.
Figure 13C:
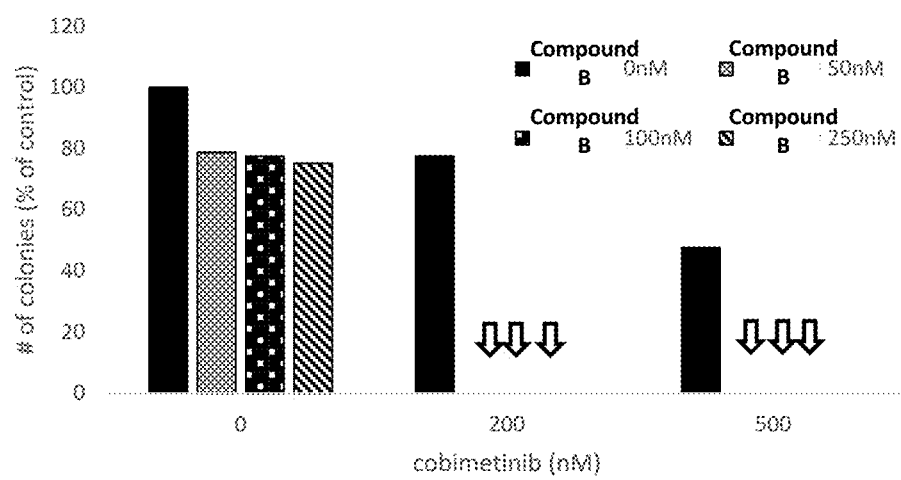

FIG. 13C shows images of representative culture plates and graphical representation of the number of GIST-T1/T670I colonies counted from various treatments. It is noted that Compound B (100 nM or 250 nM) as single showed a reduction of GIST T1/T670I colony outgrowth to about 75-78% of vehicle control. Treatment for 2 weeks with either 50 nM, 100 nM or 250 nM of Compound B and either 200 nM or 500 nM of cobimetinib led to complete cell stasis or eradication of GIST T1/T670I colony outgrowth to the limit of detection as visualized with 5× objective microscopy, with no detectable colonies after removal of combination therapy for 10 days (note arrows in FIG. 13C). The cell stasis was maintained even after extended period of 20 days after drug removal.

Example 21. Combination Treatment of Compound a with Ulixertinib Prevents Colony Outgrowth in GIST-T1, GIST-T1/D816E and GIST-T/T670I Imatinib Resistant Cells Studies were performed which demonstrate that combination treatment with Compound A and ulixertinib prevents colony outgrowth in 3 GIST cell lines as explained in example 15.

Figure 14A:
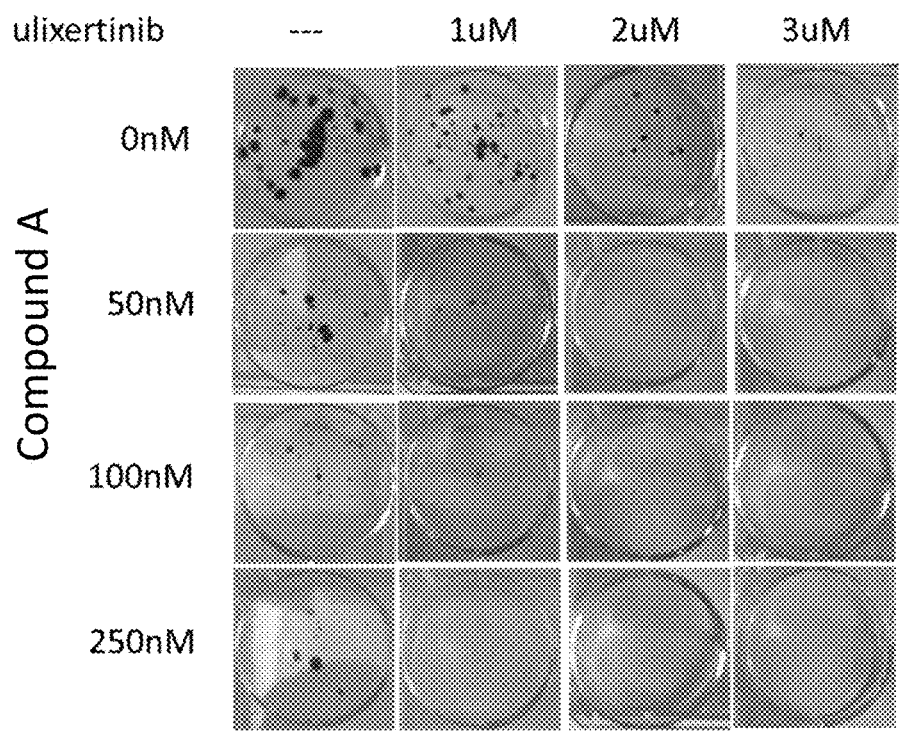
FIG. 14A shows images of representative culture plates and a graphical representation of the number of GIST-T1 colonies counted following various treatments with Compound A and the ERK inhibitor ulixertinib for 2 weeks followed by a 10 day recovery period.
Figure 14A:
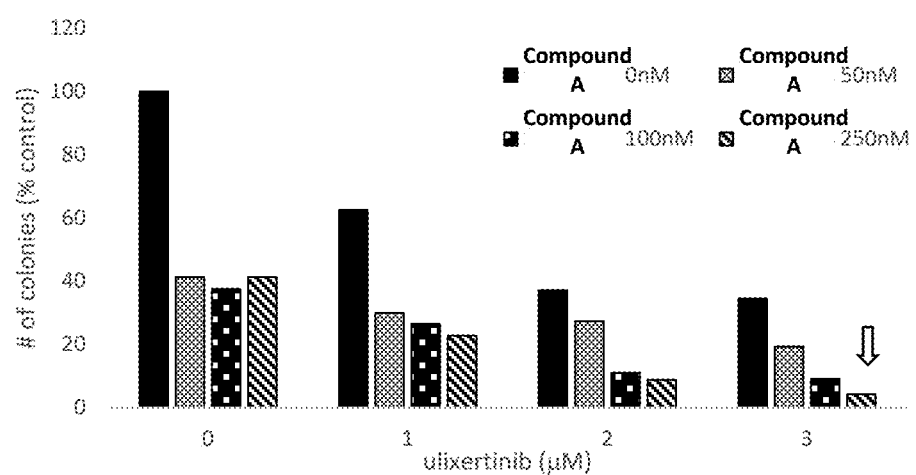

FIG. 14A shows images of representative culture plates and a graphical representation of the number of GIST-T1 colonies counted from various treatments. It is noted that Compound A as single agents demonstrate approximately a similar reduction of GIST T1 colony outgrowth to 37-41% of vehicle control. Combination treatment for 2 weeks with 50 nM, 100 nM or 250 nM of Compound A and either 1 uM, 2 uM or 3 uM of ulixertinib led to significant decrease in GIST T1 colony outgrowth as visualized with 5× objective microscopy (note arrows in FIG. 14A).

Figure 14B:
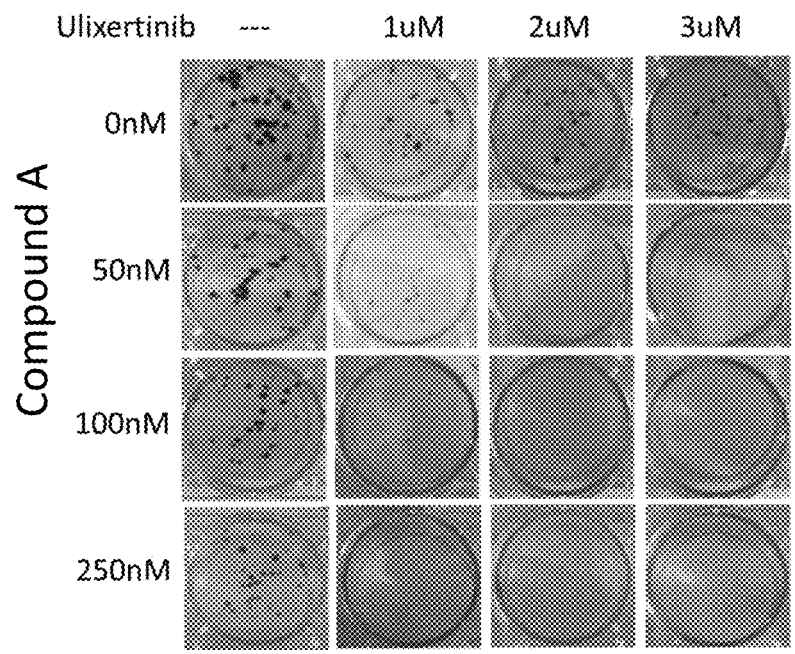
FIG. 14B shows images of representative culture plates and a graphical representation of the number of GIST-T1/D816E colonies counted following various treatments with Compound A and ulixertinib for 2 weeks followed by a 10 day recovery period.
Figure 14B:
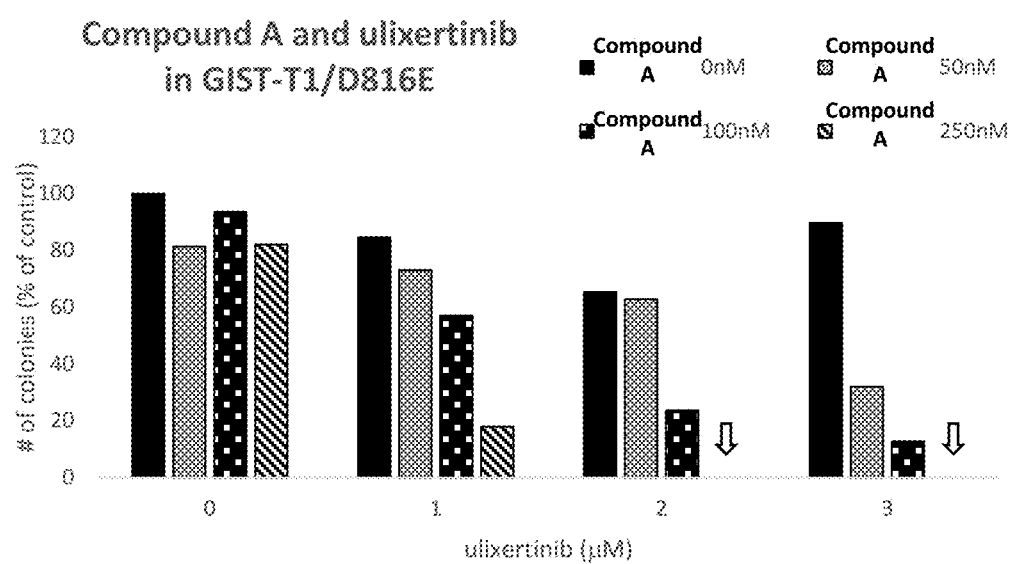

FIG. 14B shows images of representative culture plates and graphical representation of the number of GIST-T1/D816E colonies counted from various treatments. It is noted that Compound A (50 nM, 100 nM or 250 nM) as single agent demonstrate approximately a similar lack of cytocidal efficacy of GIST T1/D816E with colony outgrowth of approximately 81-93% of vehicle control (FIG. 14B). Combination treatment for 2 weeks with Compound A (250 nM) and ulixertinib (2 uM or 3 uM) led to complete cell stasis or eradication of colony outgrowth in GIST-T1/D816E cells to the limit of detection as visualized with 5× objective microscopy, following ten days of recovery (see arrows, FIG. 14B)

Figure 14C:
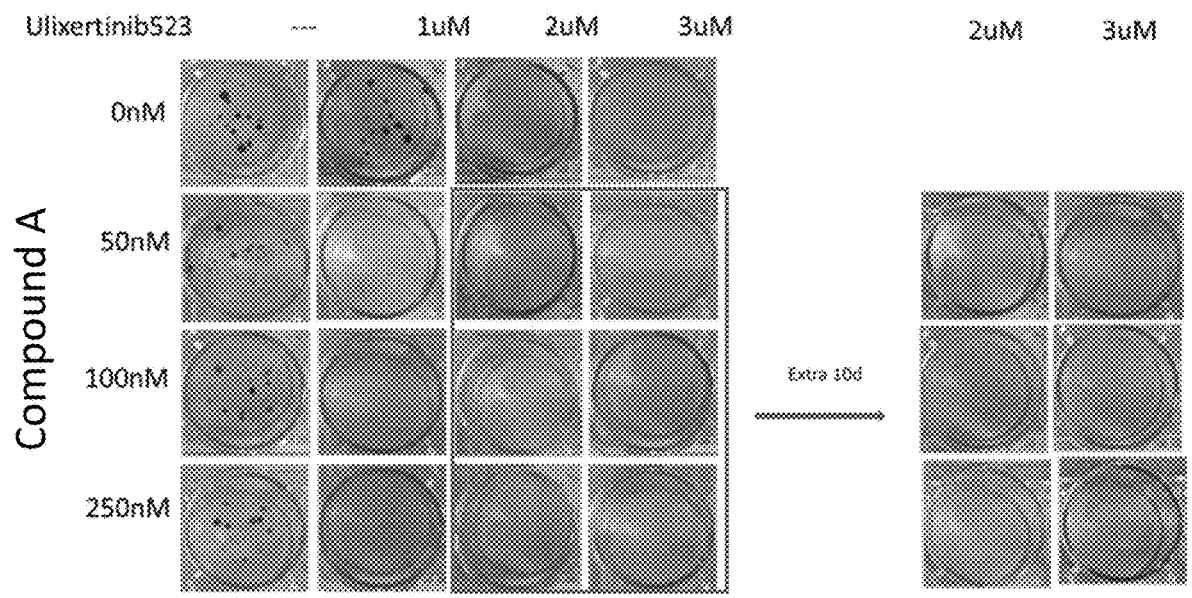
FIG. 14C shows images of representative culture plates and a graphical representation of the number of GIST-T1/T670I colonies counted following various treatments with Compound A and ulixertinib for 2 weeks followed by a 10 day recovery period. The right upper panel shows representative culture plates after additional 10 days of recovery.
Figure 14C:
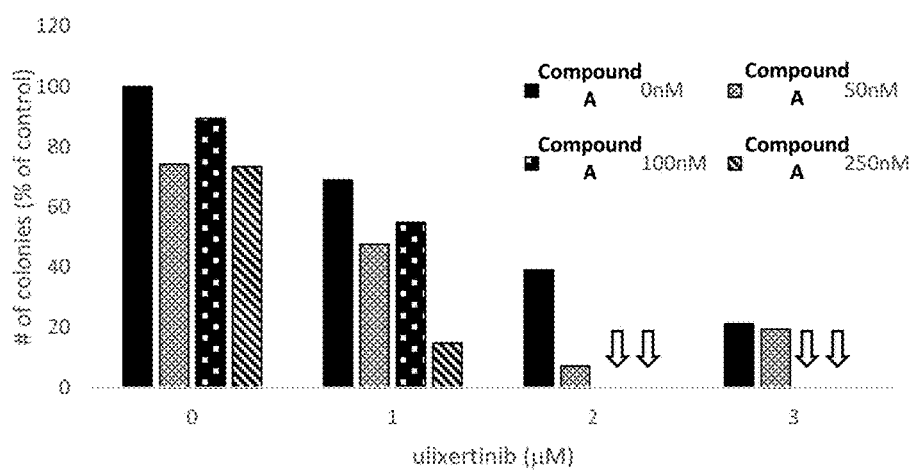

FIG. 14C shows images of representative culture plates and graphical representation of the number of GIST-T1/T670I colonies counted from various treatments. Treatment for 2 weeks with either 100 nM or 250 nM Compound A in combination with ulixertinib (2 uM or 3 uM) unexpectedly led to complete cell stasis or eradication of GIST T1/T670I colony outgrowth to the limit of detection as visualized with 5× objective microscopy, with no detectable colonies after removal of combination therapy for 10 days (note arrows in FIG. 14C). The cell stasis was maintained even after extended period of 20 days after drug removal.

Figure 15:
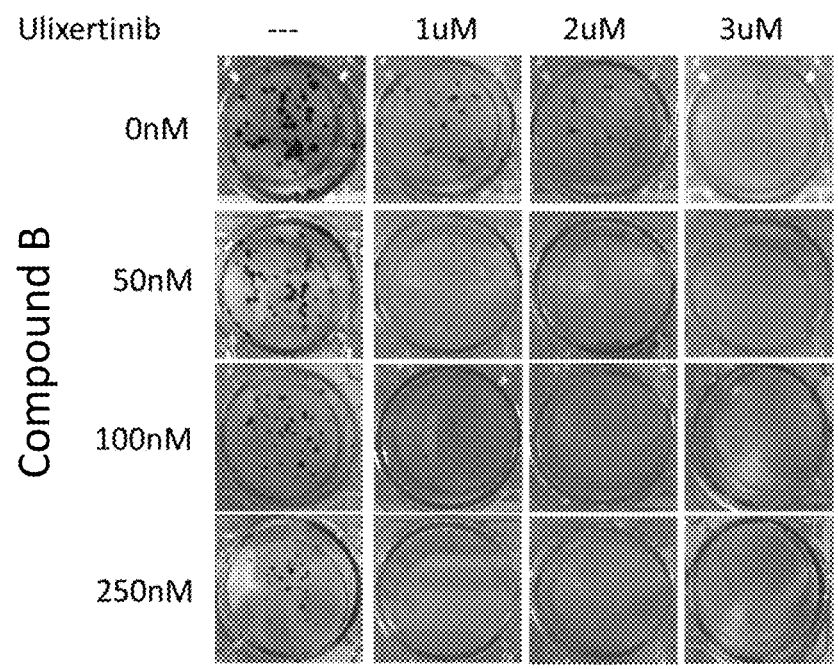
FIG. 15 shows images of representative culture plates and a graphical representation of the number of GIST-T1/D816E colonies counted following various treatments with Compound B and ulixertinib for 2 weeks.
Figure 15:
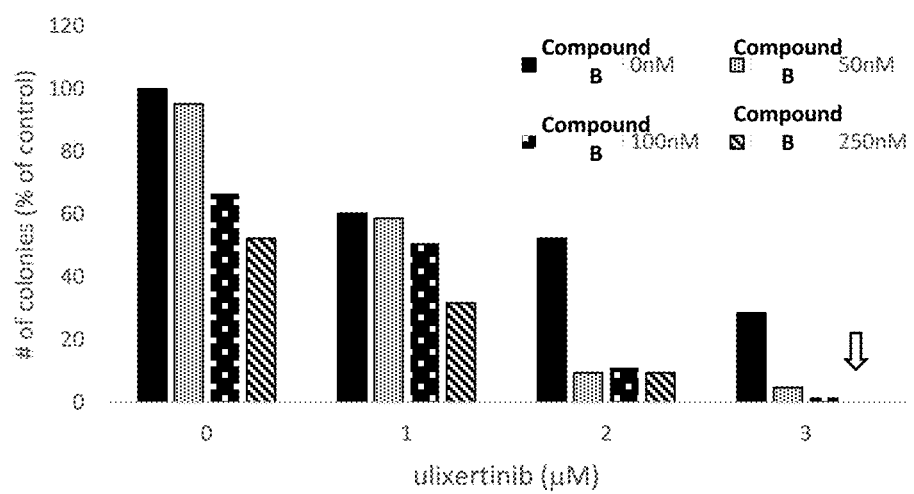

Example 22. Combination Treatment of Compound B with Ulixertinib Prevents Colony Outgrowth in GIST-T1/D816E Imatinib Resistant Cells FIG. 15 shows images of representative culture plates and graphical representation of the number of GIST-T1/D816E colonies counted from various treatments. It is noted that Compound B (50 nM, 100 nM or 250 nM) as a single agent demonstrated approximately a similar lack of cytocidal efficacy of GIST T1/D816E with colony outgrowth of approximately 52-95% of vehicle control (FIG. 15). Combination treatment for 2 weeks with Compound B (250 nM) and ulixertinib (3 uM) led to complete cell stasis or eradication of GIST T1/D816E colony outgrowth to the limit of detection as visualized with 5× objective microscopy, with no detectable colonies after removal of combination therapy for 10 days (note arrow in FIG. 15).

Example 23. Combination Treatment of Compound a and ERK Inhibitor SCH772984 Prevents Colony Outgrowth in GIST-T1/D816E Imatinib Resistant Cells The protocol outlined in Example 15 can be used to show synergy for Compound A and SCH772984 combination in preventing outgrowth of colonies in GIST-T1, GIST-T1/T670I and GIST-T1/D816E imatinib resistant cells.

Example 24. Combination Treatment of Compound B and ERK Inhibitor SCH772984 Prevents Colony Outgrowth in GIST-T1/D816E Imatinib Resistant Cells The protocol outlined in Example 15 can be used to show synergy for Compound B and SCH772984 combination in preventing outgrowth of colonies in GIST-T1, GIST-T1/T670I and GIST-T1/D816E imatinib resistant cells.

Example 25. Combination Treatment of Compound a and RAF Inhibitor LY3009120 Prevents Colony Outgrowth in GIST-T1/D816E Imatinib Resistant Cells The protocol outlined in Example 15 can be used to show synergy for Compound A and LY3009120 combination in preventing outgrowth of colonies in GIST-T1, GIST-T1/T670I and GIST-T1/D816E imatinib resistant cells.

Example 26. Combination Treatment of Compound B and RAF Inhibitor LY3009120 Prevents Colony Outgrowth in GIST-T1/D816E Imatinib Resistant Cells The protocol outlined in Example 15 can be used to show synergy for Compound B and LY3009120 combination in preventing outgrowth of colonies in GIST-T1, GIST-T1/T670I and GIST-T1/D816E imatinib resistant cells.

Example 27. Combination Treatment of Compound a and RAF Inhibitor Inhibitor Dabrafenib Prevents Colony Outgrowth in GIST-T1/D816E Imatinib Resistant Cells The protocol outlined in Example 15 can be used to show synergy for Compound A and dabrafenib combination in preventing outgrowth of colonies in GIST-T1, GIST-T1/T670I and GIST-T1/D816E imatinib resistant cells.

Example 28. Combination Treatment of Compound B and RAF Inhibitor Inhibitor Dabrafenib Prevents Colony Outgrowth in GIST-T1/D816E Imatinib Resistant Cells The protocol outlined in Example 15 can be used to show synergy for Compound B and dabrafanib combination in preventing outgrowth of colonies in GIST-T1, GIST-T1/T670I and GIST-T1/D816E imatinib resistant cells.

Example 29. Combination Treatment Induces Apoptosis in N-Ras G12D Transfected GIST-T1 Cells A study was performed which demonstrates that combination treatment of Compound A and trametinib induces apoptosis in empty vector control (EV) and mutant N-ras G12D transfected GIST-T1 cells. Assays were conducted in 96 well plates with 10,000 cells seeded/well for vector control or N-ras G12D transfected GIST-T1 cells. The cells were treated with vehicle control, Compound A, trametinib, or combinations thereof at varying concentrations, and the cells were allowed to grow for 48 hours. Apoptosis was assessed by measuring caspase 3/7 activity.

Figure 16A:
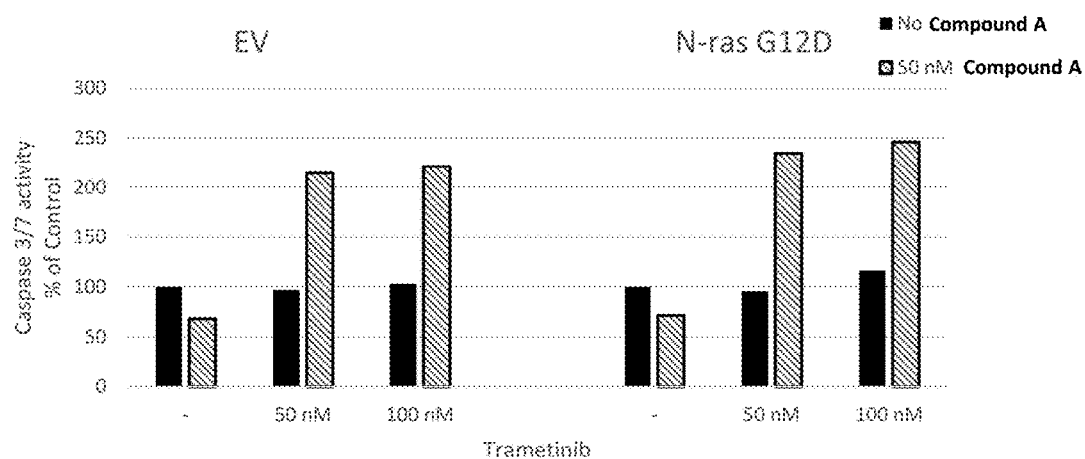
FIG. 16A shows graphical representations of Caspase activity from various treatments with Compound A and trametinib for 48 hours in vector control or N-ras G12D transfected GIST-T1 cells.

FIG. 16A provides graphical representations of caspase activity measure after the various treatments. Combination treatment for 48 hours with 50 nM Compound A and trametinib (50 nM or 100 nM) induced an increased apoptosis in mutant N-ras G12D transfected GIST-T1 cells compared to cells treated with either single agent Compound A or trametinib.

Example 30. Combination Treatment Prevents Colony Outgrowth in N-Ras G12D Transfected GIST-T1 Cells A study was performed which demonstrates that combination treatment of Compound A and trametinib prevents resistant colony outgrowth in empty vector control and mutant N-ras G12D transfected GIST-T1 cells. Assays were conducted in 6 well plates with 100 cells seeded per well. Cells were treated with vehicle control, 50 nM Compound A, 50 nM or 100 nM trametinb, or combinations thereof, and the cells were cultured for 2 weeks. In the same experiment, cells were treated with vehicle control, 100 nM imatinib, 50 nM or 100 nM trametinib, or combinations thereof. After 2 weeks, the drug was washed out, and the cells were cultured in normal media for 1-3 weeks. The colonies were stained with crystal violet and counted.

Figures 16B, 16C:
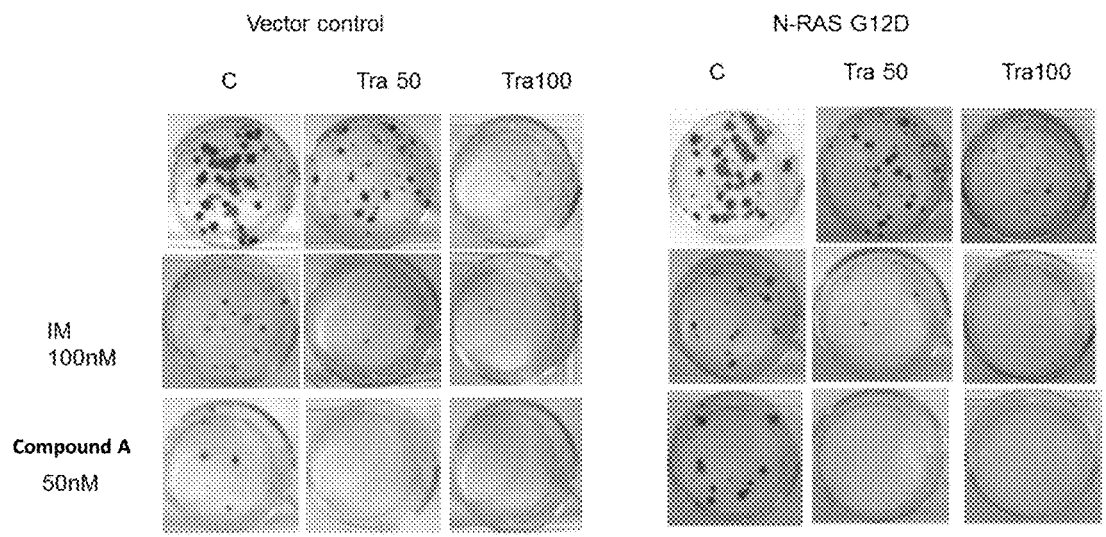
FIG. 16B shows images of representative culture plates of vector control transfected GIST-T1 colonies following various treatments with Compound A, imatinib, and trametinib and a subsequent 10 day recovery period.
FIG. 16C shows images of representative culture plates of N-ras G12D transfected GIST-T1 colonies following various treatments with Compound A, imatinib, and trametinib and a subsequent 10 day recovery period.

FIG. 16B and FIG. 16C show images of representative culture plates, and FIG. 16D and FIG. 16E show graphical representations of the number of vector control (FIG. 16B) and mutant N-ras G12D (FIG. 16C) transfected GIST-T1 colonies counted following various treatments. Quantitation of colony outgrowth in the vector control and N-ras G12D transfected GIST T-1 cells is shown in FIG. 16D and FIG. 16E, respectively. Combination treatment with 100 nM imatinib and 50 nM trametinib resulted in colony outgrowth (35% of vehicle control), and combination of 100 nM imatinib with 100 nM trametinib also resulted in colony outgrowth (19% of vehicle). In contrast, combinations of Compound A with trametinib unexpectedly resulted in superior cell stasis or cell killing compared to combination with imatinib. Combination treatment for 2 weeks with 50 nM Compound A and 50 nM trametinib led to almost complete cell stasis or cell killing (2% of vehicle control), and combination of 50 nM Compound A with 100 nM trametinib led to complete (0% of vehicle control colony outgrowth) cell stasis or cell killing to the limit of detection as visualized with 5× objective microscopy following ten days of drug washout and recovery (see arrow, FIG. 16E).

FIG. 16F shows images of representative culture plates of the number of mutant N-ras G12D transfected GIST-T1 colonies counted following an extended drug-free recovery period. Combination treatment for 2 weeks with 100 nM Compound A and 50 nM or 100 nM trametinib led to near complete blockade of colony outgrowth in N-ras G12D transfected GIST-T1 cells after an extended long term recovery period of 21 days.

Example 32. Combination Treatment Prevent Colony Outgrowth in Drug Resistant GIST Cells A saturation mutagenesis study was performed in Ba/F3 cells transformed with oncogenic KIT V560D mutant. DNA nicking was induced by N-ethyl-N-nitrosourea (ENU) for 18 hours to generate additional mutations in the KIT gene or other genes in a random fashion. Assays were conducted in 6 well plates with 100 cells seeded per well. After washout of ENU, wells were incubated with 100 nM or 250 nM or 500 nM imatinib, 100 nM or 250 nM or 500 nM imatinib in combination with 10 nM trametinib, 25 nM or 100 nM or 250 nM Compound A, or a combination of 25 nM, 100 nM, or 250 nM Compound A with 10 nM trametinib. Wells which exhibited resistance to drug treatments exhibited outgrowth of Ba/F3 cells. These cells were subjected to PCR and sequencing of the KIT gene to determine the presence of a resistant secondary mutation induced by the ENU treatment.

Figure 17A:
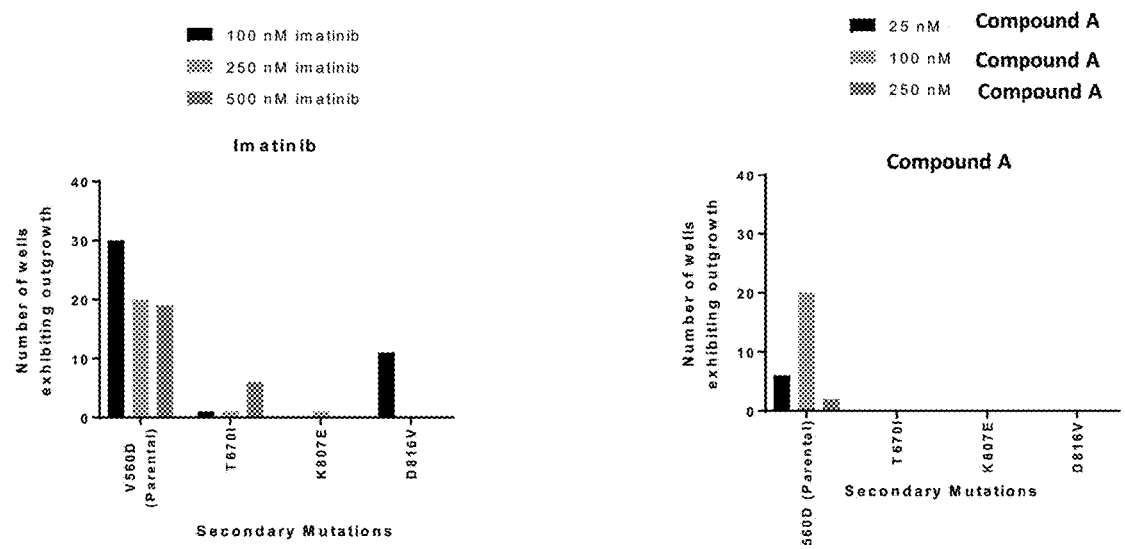
FIG. 17A provides graphical representations of Ba/F3 V560D KIT cell outgrowth of c-KIT secondary mutations in T670I, K807E, or D816V, or cell outgrowth retaining only the original c-KIT V560D mutation plus additional non-c-KIT resistance mechanisms upon saturation mutagenesis followed by single agent treatments with either imatinib (left panel) or Compound A (right panel).
Figure 17B:
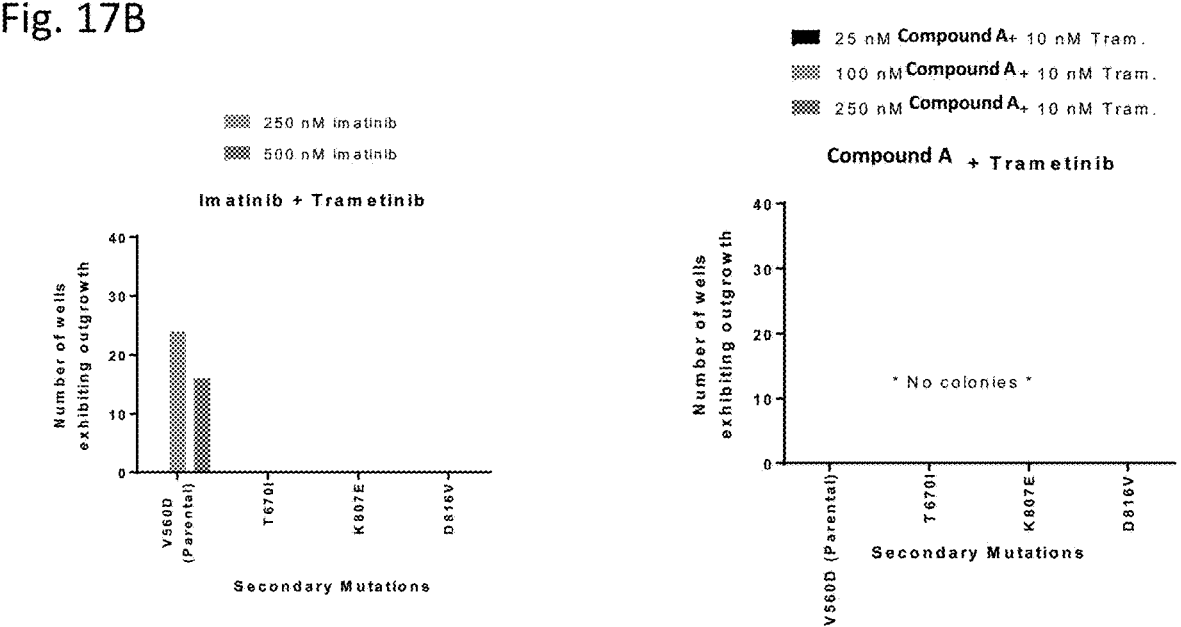
FIG. 17B provides graphical representations of Ba/F3 V560D KIT cell outgrowth of c-KIT secondary mutations in T670I, K807E, or D816V, or cell outgrowth retaining only the original c-KIT V560D mutation plus additional non-c-KIT resistance mechanisms upon saturation mutagenesis followed by combination treatments with either imatinib plus trametinib (left panel) or Compound A plus trametinib (right panel).

FIG. 17A is a graphical representation demonstrating the growth of Ba/F3 colonies resistant to imatinib. T670I, K807E, and/or D816V imatinib-resistant secondary KIT mutants were identified by PCR and DNA sequencing of genomic DNA in Ba/F3 cells exposed to 100 nM, 250 nM, or 500 nM imatinib as a single agent (FIG. 17A, left panel). FIG. 17A (right panel) is a graphical representation of the Ba/F3 cell saturation mutagenesis study with Compound A. Single agent treatment with 25 nM, 100 nM, or 250 nM Compound A did not lead to the outgrowth of any new secondary resistant mutation as determined by PCR and DNA sequencing. Only Ba/F3 cells containing the original V560D (parental) KIT mutation were shown to grow after exposure to Compound A, likely reflecting mutation in genes other than KIT (FIG. 17A, right panel). FIG. 17B is a graphical representation demonstrating the Ba/F3 cell colony outgrowth with imatinib in the presence of trametinib or Compound A in the presence of trametinib. Combination of imatinib at 250 nM or 500 nM with 10 nM trametinib did not lead to outgrowth of any new secondary resistant mutations but did lead to outgrowth of the original KIT V560D (parental) cells, likely reflecting mutation in genes other than KIT (FIG. 17B, left panel). Significantly, and in contrast to the combination study of imatinib with trametinib, combination of 25, 100, or 250 nM Compound A with 10 nM trametinib led to complete cell stasis or cell killing with no cell outgrowth to the limit of detection as determined by visual inspection in any wells (FIG. 17B, right panel).

Example 33. In Vivo Xenograft Study of Compound a in Combination with Trametinib The GIST T1 xenograft model was performed in compliance with all the laws, regulations and guidelines of the National Institutes of Health (NIH) and with the approval of the Animal Care and Use Committee of MI Bioresearch (Ann Arbor, MI), an AAALAC accredited facility. All mice had food and water ad libitum. All mice were observed for clinical signs at least once daily. Female Envigo nude mice (HsdCrl:Athymic Nude-NU-Foxn1nu; 6-7 weeks old) were inoculated subcutaneously just below the right high axilla with five million cells in Dulbecco's Phosphate Buffered Saline mixed with an equal volume of Matrigel, using a 27 gauge needle and syringe. When tumor burdens reached 117 mm$^3$ on average on day 10, mice were randomly assigned into groups such that the mean tumor burden for all groups was within 10% of the overall mean tumor burden for the study population. Groups were treated on days 10-27 as follows: vehicle control diet (n=10); Compound A formulated into the mouse diet to achieve approximately 100 mg/kg/day of Compound A (n=10); or Compound A formulated into mouse diet to achieve approximately 25 mg/kg/day of Compound A (n=10), trametinib dosed orally at 0.5 mg/kg BID and fed vehicle control diet (n=10), trametinib dosed orally at 0.5 mg/kg BID and fed Compound A-formulated diet (achieving treatment with approximately 100 mg/kg/day of Compound A) (n=10), or trametinib dosed orally at 0.5 mg/kg BID and fed Compound A-formulated diet (achieving treatment with approximately 25 mg/kg/day of Compound A (n=10). On Day 27, all animals were placed on control diet to monitor tumor regrowth. Tumor volume and body weight were measured thrice weekly. Tumor burden (mg) was estimated from caliper measurements by the formula: tumor burden (mg=mm$^3$)=(length×width$^2$)/2.

Figure 18A:
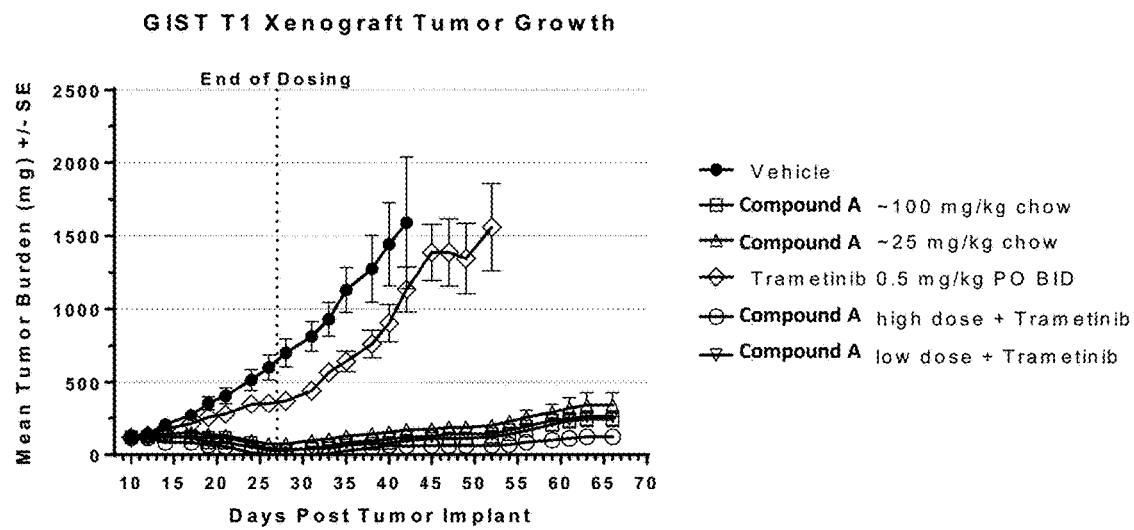
FIG. 18A provides a graphical representation of GIST T1 xenograft tumor growth following treatments with single agent Compound A, single agent trametinib, or with a combination of Compound A and trametinib.
Figure 18B:
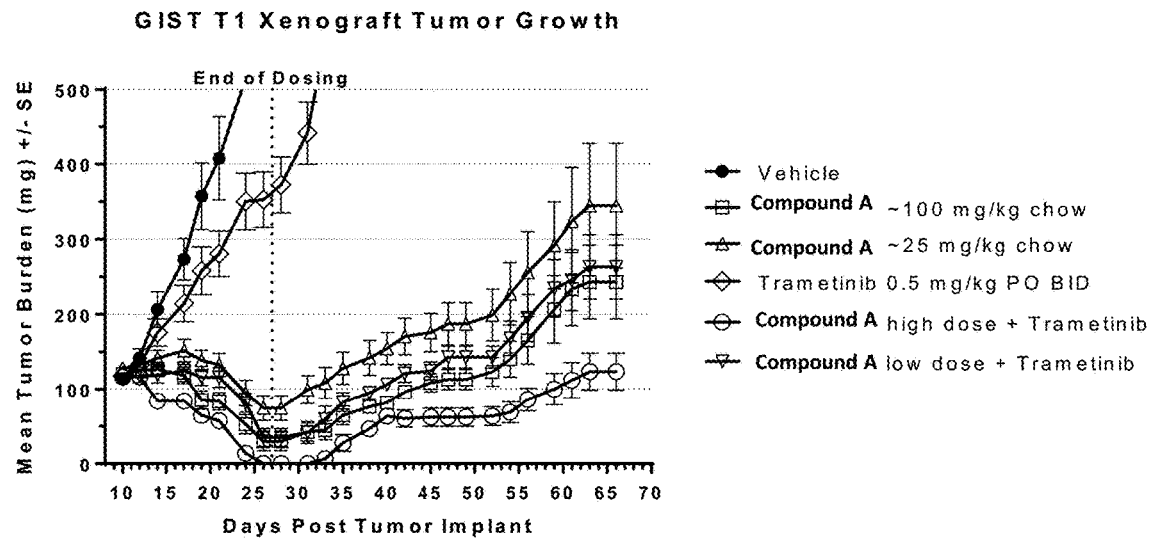
FIG. 18B is a blow up of the graphical representation from FIG. 18A, showing resolution of effects on tumor regression following treatments with single agent Compound A, single agent trametinib, or with a combination of Compound A and trametinib.

FIG. 18A and FIG. 18B are graphical representation demonstrating inhibition of tumor growth compared to vehicle control. FIG. 18B is the same data as FIG. 18A, but zoomed in to show differences among Compound A or Compound A/trametinib treated cohorts. Treatment with trametinib led to slight tumor growth inhibition compared to vehicle control. At the high dose of Compound A (approximately 100 mg/kg/day), 6/10 mice had complete tumor regression, with the remaining 4/10 mice having partial tumor regression during the dosing period. At the low dose of Compound A (approximately 25 mg/kg/day), 2/10 mice had complete tumor regression, and 6/10 had partial tumor regression. At the high dose of Compound A (approximately 100 mg/kg/day) combined with trametinib, 10/10 mice had complete tumor regression during the dosing period. At the low dose of Compound A (approximately 25 mg/kg/day) combined with trametinib, 5/10 mice had complete tumor regression, and 5/10 had partial tumor regression. In addition, after the dosing period, all Compound A treated cohorts had slower tumor regrowth than initial tumor growth of the vehicle control, indicating a prolonged effect on tumor cell growth through the end of the study on day 66. At the high dose of Compound A (approximately 100 mg/kg/day), 1/10 mice remained in partial tumor regression at the end of study. At the low dose of Compound A (approximately 25 mg/kg/day), 2/10 mice remained in partial tumor regression at the end of study. At the high dose of Compound A (approximately 100 mg/kg/day) combined with trametinib, 1/10 mice retained complete tumor regression and 4/10 mice remained in partial tumor regression at the end of the study. At the low dose of Compound A (approximately 25 mg/kg/day) combined with trametinib, 2/10 mice remained in partial tumor regression at the end of study. These data demonstrate that the combination of Compound A and trametinib induces cell death and/or prolonged cell stasis for at least 40 days after dosing was completed.

Example 34. Compound a is a Potent Inhibitor of the BCRP Efflux Transporter

To examine inhibition of the BCRP drug efflux transporter with Compound A, a vesicular transport inhibition assays was conducted using a low permeability probe substrate and inside-out membrane vesicles prepared from BCRP-expressing cells in the presence of ATP. The potential of Compound A to modify the uptake of the probe substrate into the transporter-containing vesicles was measured.

The in vitro interaction potential of Compound A with human efflux transporter BCRP was investigated at 7 concentrations in vesicular transport inhibition assays. Compound A potently inhibited the transport of the probe substrate of BCRP, where 44% inhibition was observed in the lowest concentration tested (0.04 μM). The IC50 value was estimated to be approximately 0.04 μM.

EQUIVALENTS

Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:

1. A method of treating a tumor having one or more c-KIT mutations in a patient in need thereof, comprising administering to the patient:
   an effective amount of 1-[4-bromo-5-[1-ethyl-7-(methylamino)-2-oxo-1,2-dihydro-1,6-naphthyridin-3-yl]-2-fluorophenyl1-3-phenylurea, or a pharmaceutically acceptable salt thereof; and
   an effective amount of one or more MAPKAP kinase inhibitors selected from the group consisting of trametinib, binimetinib, cobimetinib, and ulixertinib,
   wherein the tumor is gastrointestinal stromal tumor (GIST).

2. The method of claim 1, wherein the c-KIT mutation is a primary mutation in exon 9, exon 11, exon 13, or exon 17 of the c-KIT gene.

3. The method of claim 1, wherein the tumor has one or more secondary resistance mutations in the c-KIT gene.

4. The method of claim 3, wherein the secondary resistance mutation is in exon 13, exon 14, exon 17, or exon 18 of the c-KIT gene.

5. The method of claim 1, wherein the c-KIT mutation is a deletion mutation.

6. The method of claim 3, wherein the secondary resistance mutation is the substitution of aspartic acid in codon 816 or the substitution of asparagine in codon 822.

7. The method of claim 3, wherein the secondary resistance mutation is one of D816V, D816E, D816H, D820A, T670I, or N822V.

8. The method of claim 3, wherein the secondary resistance mutation is one of V654A or T670I.

9. The method of claim 3, wherein the secondary resistance mutation was acquired after previous administration of imatinib, sunitinib or regorafenib, or a pharmaceutically acceptable salt thereof to the patient.

10. The method of claim 1, wherein tumor was resistant to treatment with imatinib mesylate, sunitinib malate, or regorafenib.

11. The method of claim 1, wherein the tumor is selected from the group consisting of lung adenocarcinoma, squamous cell lung cancer, glioblastoma, pediatric glioma, astrocytoma, sarcoma, gastrointestinal stromal tumor (GIST), and melanoma.

* * * * *